(12) United States Patent
Misra

(10) Patent No.: US 10,736,842 B2
(45) Date of Patent: Aug. 11, 2020

(54) PHARMACEUTICAL OIL-IN-WATER NANO-EMULSION

(71) Applicant: SYNERGIA BIO SCIENCES PRIVATE LIMITED, Bangalore (IN)

(72) Inventor: Ambikanandan Misra, Vadodara (IN)

(73) Assignee: SYNERGIA BIO SCIENCES PRIVATE LIMITED, Bangalore (IN)

( * ) Notice: Subject to any disclaimer, the term of this patent is extended or adjusted under 35 U.S.C. 154(b) by 0 days.

(21) Appl. No.: 15/309,716

(22) PCT Filed: Jun. 25, 2015

(86) PCT No.: PCT/IN2015/000266
§ 371 (c)(1),
(2) Date: Nov. 8, 2016

(87) PCT Pub. No.: WO2015/198350
PCT Pub. Date: Dec. 30, 2015

(65) Prior Publication Data
US 2017/0143627 A1    May 25, 2017

(30) Foreign Application Priority Data

Jun. 25, 2014 (IN) .......................... 3077/CHE/2014

(51) Int. Cl.
| | | |
|---|---|---|
| *A61K 9/107* | (2006.01) | |
| *A61K 31/551* | (2006.01) | |
| *A61K 31/167* | (2006.01) | |
| *A61K 31/519* | (2006.01) | |
| *A61K 47/22* | (2006.01) | |
| *A61K 47/12* | (2006.01) | |
| *A61K 47/10* | (2017.01) | |
| *A61K 9/00* | (2006.01) | |
| *A61K 47/14* | (2017.01) | |
| *A61K 47/26* | (2006.01) | |
| *A61K 31/4178* | (2006.01) | |
| *A61K 47/44* | (2017.01) | |

(52) U.S. Cl.
CPC .......... *A61K 9/1075* (2013.01); *A61K 9/0043* (2013.01); *A61K 9/0048* (2013.01); *A61K 31/167* (2013.01); *A61K 31/4178* (2013.01); *A61K 31/519* (2013.01); *A61K 31/551* (2013.01); *A61K 47/10* (2013.01); *A61K 47/12* (2013.01); *A61K 47/14* (2013.01); *A61K 47/22* (2013.01); *A61K 47/26* (2013.01); *A61K 47/44* (2013.01)

(58) Field of Classification Search
CPC .... A61K 9/0043; A61K 9/0048; A61K 47/10; A61K 47/12; A61K 47/14; A61K 31/167; A61K 31/519
See application file for complete search history.

(56) References Cited

U.S. PATENT DOCUMENTS

| 5,929,070 A | 7/1999 | Shannon et al. |
| 5,993,846 A | 11/1999 | Friedman et al. |
| 6,284,268 B1 * | 9/2001 | Mishra ................ A61K 9/1075 424/455 |
| 2006/0210500 A1 * | 9/2006 | Bicard-Benhamou ...................... A61K 8/19 424/63 |
| 2010/0034880 A1 * | 2/2010 | Sintov ................ A61K 9/0014 424/484 |

FOREIGN PATENT DOCUMENTS

| CA | 2347032 A1 | 5/2000 |
| CN | 101524329 A | 9/2009 |
| CN | 101780037 A | 7/2010 |
| WO | 9956727 A2 | 11/1999 |
| WO | 03004015 A1 | 1/2003 |
| WO | 03017986 A1 | 3/2003 |
| WO | 03086392 A2 | 10/2003 |

OTHER PUBLICATIONS

Solans et al, Nano-emulsions; Current Opinion in colloid and Interface Science 10 (2005) 102-110.*
International Search Report for International Patent Application No. PCT/IN2015/000266 dated Nov. 26, 2015.
Mukesh Kumar et al, "Mucoadhesive nanoemulsion-based intranasal drug delivery system of olanzapine for brain targeting", Journal of Drug Targeting., vol. 16, No. 10, Jan. 2008 (Jan. 2008), p. 806-814, XP055229726 DOI: 10.1080/10611860802476504 external link ISSN:1061-186X.
Kumar M et al, "Intranasal nanoemulsion based brain targeting drug delivery system of risperidone", Jun. 24, 2008 (Jun. 24, 2008), vol. 358, No. 1-2, p. 285-291, XP022698740 DOI: 10.1016/J.IJPHARM. 2008.03.029 external link ISSN:0378-5173.
Gursoy R N et al, "Self-emulsifying drug delivery systems (SEDDS) for improved oral delivery of lipophilic drugs", Biomedicine and Pharmacotherapy, Elsevier, FR,vol. 58, No. 3, Apr. 2004 (Apr. 2004), p. 173-182, XP002500493 DOI: 10.1016/J.BIOPHA.2004. 02.001 external link ISSN:0753-3322.
Patel et al, "Formulation and Evaluation of Microemulsions-Based Drug Delivery System for Intranasal Administration of Olanzapine", International Journal of Biomedical and Pharmaceutical Sciences 7 (1), p. 20-27.
Mukesh Kumar et al "Composition and Characterization of Nanoemulsion of Olanzapine for Intranasal Delivery" PDA J Pharm Sci and Tech 2009, 63 p. 501-511.

* cited by examiner

*Primary Examiner* — Mina Haghighatian
(74) *Attorney, Agent, or Firm* — Katten Muchin Rosenman LLP

(57) ABSTRACT

Accordingly, the present invention provides a pharmaceutical oil-in-water nano-emulsion, with a pharmaceutically active substance. The selected pharmaceutically active substance is encased in monounsaturated fatty acid droplets with the droplets having an average particle size in the range of 60 to 200 nm. The nano-emulsion is also provided with a non-ionic surfactant system, which is a mixture of polyethers, macrogolglycerides and polysaccharides, along with pharmaceutically acceptable adjuvants. The present invention also provides a process for the preparation of pharmaceutical oil-in-water nano-emulsion.

19 Claims, 98 Drawing Sheets

PHARMACEUTICAL OIL-IN-WATER NANO-EMULSION

TECHNICAL FIELD

The present invention relates to a pharmaceutical oil-in-water nano-emulsion composition for an enhanced delivery of active pharmaceutical substances, particularly, lipophilic and partially lipophilic active pharmaceutical substances and a process for preparing the same.

BACKGROUND OF THE INVENTION

Drugs are often unable to reach the target site effectively and efficiently using conventional delivery systems, particularly to the brain and the central nervous system due to their inability to cross the blood/brain barrier. The delivery of pharmaceutically useful lipophilic substances is often challenging because of their low solubility in an aqueous environment. Though many advanced approaches have been developed for the delivery of these drugs, there are critical issues that need to be attended but not limited to thermodynamic instability, sedimentation, flocculation, administration of high dosage rates, side effects, and low absorption rates. Macro-emulsions are widely used to address some of the above issues; in particular, the size distribution and incompatibility of the components or excipients used in the emulsion, which makes it less efficient and tends to undergo separation before reaching the target site. Achieving enhanced bioavailability is a major problem faced while developing many delivery compositions, particularly for pharmaceutical compositions or agents that are poorly soluble in water. There is a need for improved compositions for lipophilic and partially lipophilic active substances that will promote stability in an aqueous environment and allow efficient delivery of such substances to a desired site of action.

Bioavailability depends on several factors, drug solubility in an aqueous environment and drug permeability through lipophilic membranes being important ones. Hence, it is important to improve the solubility and/or dissolution rate for lipophilic drugs. More than 40% of NCEs (new chemical entities) developed by the pharmaceutical industry recently are practically insoluble in water. These drugs are associated with slow drug absorption, leading to inadequate and variable bioavailability and mucosal toxicity. Micro-emulsions and nano emulsions offer several advantages, including improved drug solubility, enhanced bioavailability, protection of the drug from the environment, ease of manufacturing, and long shelf life.

When developing such compositions, it is to obtain systems with optimized drug loading and release properties, thermodynamic stability, long shelf-life, increased bioavailability and reduced toxicity. Though several micro and nanoemulsions of varied compositions have been described in the literature, they neither provide nanoparticle sized compositions having average particle size of less than 200 nm, nor do they provide compositions that are superior in at least one of the criteria i.e., higher drug loading, better in vivo performance, increased bioavailability, low viscosity, and rapid onset of action. These are achieved by the compositions of the present invention.

Many different strategies have been used in formulating micro-emulsions to make them suitable for the delivery of drugs requiring good solubility and stability. In patent applications no PCT/KR2002/001593 and PCT/US2003/010526, the use of oleic acid as the oil phase similar to the present invention for making a self-emulsifying drug delivery system was described. However, the composition contains high amounts of alcohol, which may cause irritancy to the absorption surface due to the drying effect. In addition, the drug loading and solubility described in the patent is much lower compared to the present invention.

PCT/GB2002/003005 discloses an emulsion comprising of an oil phase for delivery of benzodiazepine drug. The invention further limits the drug loading of the prototype benzodiazepine molecule (Midazolam) only to 10 mg/ml. However, it is well established in the literature that the drug loading capacity should be relatively high to allow for administration of the drug via different routes in order to be able to deliver the required therapeutic dose, as the dosing volume will be limited.

In CN 200810160956, a bicyclol submicroemulsion system having a particle size <500 nm and a drug loading capacity of 0.1 mg/ml has been described, whereas the current invention herein provides a highly stable composition having average particle size less than 150 nm and a high drug loading capacity.

Furthermore, U.S. Pat. No. 5,993,846 discloses oil-in-water emulsions having mucoadhesive properties which are primarily intended for administration of biologically active compounds to mucosal surfaces having particle diameter ranging from 10 nm to 600 nm. Further, the mucoadhesives prolong the residence time in situ. The invention disclosed herein describes compositions with a particle size between 10 to 150 nm and its immediate release. Another patent CA2347032 entitled 'O/w emulsion comprising a hydroxylated oil' describes an oil-in-water emulsion in which the oil phase comprises a hydroxylated oil preferably castor oil. This describes emulsions with particle size of 200 nm; the efficacy of the emulsions has not been established.

In CN101780037, a self emulsifying composition based on oliec acid is disclosed, however, oleic acid content is very high leading to greater viscocity and cause gelling problems upon the addition of water making it unstable unlike the instant invention.

Moreover, these compositions potentially are dependent on digestion prior to release of the drug. The drawbacks of this system include chemical instabilities of drugs and high surfactant concentrations in compositions. Early studies revealed that the selfemulsification process is specific to the nature of the oil/surfactant pair, the surfactant concentration and oil/surfactant ratio, the concentration and nature of co-surfactant and surfactant/co-surfactant ratio and the temperature at which self emulsification occurs. Due to presence of high surfactant and oil concentrations there may be chances of instabilities of drugs. Also the high content of surfactant in self emulsifying compositions irritates the GIT. This also causes less drug loading capabilty.

In Kumar et al. (2008) "Mucoadhesive nanoemulsion based intranasal drug delivery system of olanzapine for brain targeting" published on the Journal of Drug Targeting, contained 15% w/w Capmul MCM (medium-chain mono- and diglycerides) as oil, 35% Tween 80 (polysorbate 80) as a surfactant, 17.5% w/w of ethanol:polyethylene glycol 400 (1:1) mixture as co-surfactant, 32.5% water as aqueous phase and 0.5% chitosan as a muco-adhesive agent. However, this system has very low olanzapine loading i.e., only 8.5 mg/ml in the micro-emulsion was obtained. Furthermore, the aforementioned prior art has prolonged Tmax and achieves maximum concentration only after an hour in the case of brain and 2 hours in the case of blood plasma. This shows that the above said prior art fails in achieving the rapid onset of action when compared with the current invention.

In Patel et al entitled "Formulation and Evaluation of Microemulsions-Based Drug Delivery System for Intranasal Administration of Olanzapine", Olanzapine micro-emulsion described comprises of a system with 4%> oleic acid content, 30% of surfactant:co-surfactant mix containing Labrasol®, Cremophor RH40, and Transcutol P in ratio of 1:1:0.3 and 0.5% polycarbophil as a mucoadhesive agent. The drug loading of the micro-emulsion was only 8 mg/ml. Another similar system described by Mukesh Kumar et al. in "Composition and Characterization of Nanoemulsion of Olanzapine for Intranasal Delivery" contains 15% w/w Capmul MCM (medium-chain mono- and diglycerides) as oil, 35% Tween 80 (polysorbate 80) as a surfactant, 17.5% w/w of ethanol:polyethylene glycol 400 (1:1) mixture as co-surfactant, 32.5% water as co-surfactant and 0.5% chitosan as a muco-adhesive agent. Olanzapine loading in micro-emulsion was only 8.5 mg/ml. Furthermore, these inventions are highly viscous and cause gelling problems upon the addition of water making it unstable unlike the instant invention. Furthermore the instant invention showed no separation or phase separation on centrifugation, unlike the prior art.

One such drug which requires immediate attention is 2-Methyl-4-(4-methyl-1-piperazinyl)-10H-thieno[2,3-b][1,5]benzodiazepine, referred to by the International Nonproprietary Name (INN) olanzapine, is marketed as being useful for the treatment of schizophrenia, schizophreniform disorder, acute mania, bipolar disorder, mild anxiety states, and psychosis. U.S. Pat. No. 5,929,070A discloses that olanzapine is also useful in the control of pain associated with migraine. Presently, however, olanzapine must be administered orally in the form of tablets or capsules. This results in a substantial delay before the maximum concentration of active drug reaches the target site in the brain (long Tmax), with correspondingly slow onset of therapeutic effects.

It would be very desirable to have compositions for effective delivery of olanzapine and other therapeutic agents with a faster onset of action.

Accordingly, the present invention seeks to provide improved compositions with high therapeutic efficacy having an average particle size of less than 200 nm for pharmaceutical composition useful for the nasal, oral, intramuscular, ophthalmic, rectal or topical delivery of lipophilic or partially lipophilic drugs or as therapeutic, monitoring or diagnostic agents. Furthermore, the compositions address the aforementioned issues; particularly, they minimize drug degradation and loss, prevent harmful side-effects, increase drug bioavailability, improve solubility of some poorly soluble pharmaceutical components and provide a nano-sized low-viscose monophasic composition.

OBJECTS OF THE PRESENT INVENTION

The primary object of the present invention is to provide a pharmaceutical oil-in-water nano-emulsion composition for an enhanced delivery of active pharmaceutical substances, particularly, lipophilic and partially lipophilic active pharmaceutical substances.

An object of the present invention is to provide a a pharmaceutical oil-in-water nano-emulsion composition with a pharmaceutically active substance, encased in monounsaturated fatty acid droplets, the droplets having an average particle size in the range of 60 to 200 nm.

Another object of the present invention is to provide a pharmaceutical oil-in-water nano-emulsion composition with a pharmaceutically active substance, where a non-ionic surfactant system with a mixture of polyethers, macrogolglycerides and polysaccharides is provided.

SUMMARY OF THE INVENTION

Accordingly, the present invention provides a pharmaceutical oil-in-water nano-emulsion, with a pharmaceutically active substance. The selected pharmaceutically active substance is encased in monounsaturated fatty acid droplets with the droplets having an average particle size in the range of 60 to 200 nm. The nano-emulsion is also provided with a non-ionic surfactant system, which is a mixture of polyethers, macrogolglycerides and polysaccharides, along with pharmaceutically acceptable adjuvants.

BRIEF DESCRIPTION OF THE DRAWINGS

FIG. 1A depicts particles size distribution under conditions viz., a room temperature with a particle size of 66.36 nm and PDI of 0.408 and with a Zeta Potential of −0.0793

FIG. 1B depicts particles size distribution under conditions viz., a temperature 2-8° C. with a particle size of 82.76 nm and PDI of 0.286 and with a Zeta Potential of −0.152.

FIG. 1C depicts particles size distribution under conditions viz., 25° C./60% RH (Relative humidity); Particle size (nm): 83.37; PDI: 0.289; ZetaPotential: 0.0278

FIG. 1D depicts particles size distribution under conditions viz., 30° C./65% RH; Particle size (nm): 92.7; PDI: 0.285; ZetaPotential: 0.0657

FIG. 1E depicts particles size distribution under conditions viz., 30° C./75% RH; Particle size (nm): 75.02; PDI: 0.313; ZetaPotential: 0.0999

FIG. 1F depicts particles size distribution under conditions viz., 40° C./75% RH; Particle size (NM): 81.41; PDI: 0.29; ZetaPotential: 0.00659

FIG. 1G: depicts particles size distribution under conditions viz., Heat-Cool cycle; Particle size (nm): 59.78; PDI: 0.415; ZetaPotential: −0.180

FIG. 1H: depicts particles size distribution under conditions viz., Freeze-Thaw cycle; Particle size (nm): 70.69; PDI: 0.306; ZetaPotential: −0.234

FIG. 2A depicts particles size distribution under conditions viz., Initial (Room Temperature); Particle size (nm): 64.32; PDI: 0.372; ZetaPotential: −0.0981

FIG. 2B depicts particles size distribution under conditions viz., 2-8° C.; Particle size (nm): 64.57; PDI: 0.280; ZetaPotential: −0.301

FIG. 2C depicts particles size distribution under conditions viz., 25° C./60% RH (Relative humidity); Particle size (nm): 82.50; PDI: 0.284; ZetaPotential: −0.0702

FIG. 2D depicts particles size distribution under conditions viz., 30° C./65% RH; Particle size (nm): 80.25; PDI: 0.438; ZetaPotential: −0.214

FIG. 2E depicts particles size distribution under conditions viz., 30° C./75% RH; Particle size (nm): 68.05; PDI: 0.294; ZetaPotential: −0.0437

FIG. 2F depicts particles size distribution under conditions viz., 40° C./75% RH; Particle size (nm): 49.78; PDI: 0.424; ZetaPotential: 0.0591

FIG. 2G depicts particles size distribution under conditions viz., Heat-Cool cycle; Particle size (nm): 75.25; PDI: 0.367; ZetaPotential: −0.286

FIG. 2H depicts particles size distribution under conditions viz., Freeze-Thaw cycle; Particle size (nm): 94.31; PDI: 0.280; ZetaPotential: −0.535

FIG. 3A depicts particle size distribution under conditions viz., Room Temperature; Particle size (nm): 164.4; PDI: 0.418; ZetaPotential: 0.0991

FIG. 3B depicts particle size distribution under conditions viz., 2-8° C.; Particle size (NM): 164.6; PDI: 0.375; ZetaPotential: 0.0743

FIG. 3C depicts particle size distribution under conditions viz., 25° C./60% RH (Relative humidity); Particle size (nm): 162.0; PDI: 0.286; ZetaPotential: −0.0841

FIG. 3D depicts particle size distribution under conditions viz., 30° C./65% RH; Particle size (nm): 165.3; PDI: 0.289; ZetaPotential: 0.127

FIG. 3E depicts particle size distribution under conditions viz., 30° C./75% RH; Particle size (nm): 169.5; PDI: 0.293; ZetaPotential: 0.211

FIG. 3F depicts particle size distribution under conditions viz., 40° C./75% RH; Particle size (nm): 147.3; PDI: 0.252; ZetaPotential: 0.209

FIG. 3G depicts particle size distribution under conditions viz., Heat-Cool cycle; Particle size (nm): 215.4; PDI: 0.474; ZetaPotential: 0.141

FIG. 3H depicts particle size distribution under conditions viz., Freeze-Thaw cycle; Particle size (nm): 239.2; PDI: 0.485; ZetaPotential: −0.107

FIG. 4A depicts particle size distribution under conditions viz., Initial (Room Temperature); Particle size (NM): 73.55; PDI: 0.304; ZetaPotential: −0.4

FIG. 4B depicts particle size distribution under conditions viz., 2-8° C.; Particle size (NM): 71.1; PDI: 0.322; ZetaPotential: 0.175

FIG. 4C depicts particle size distribution under conditions viz., 25° C./60% RH (Relative humidity); Particle size (NM): 84.47; PDI: 0.283; ZetaPotential: 0.0954

FIG. 4D depicts particle size distribution under conditions viz., 30° C./65% RH; Particle size (nm): 97.15; PDI: 0.276; ZetaPotential: 0.0148

FIG. 4E depicts particle size distribution under conditions viz., 30° C./75% RH; Particle size (nm): 77.79; PDI: 0.289; ZetaPotential: 0.129

FIG. 4F depicts particle size distribution under conditions viz., 40° C./75% RH; Particle size (nm): 80.43; PDI: 0.293; ZetaPotential: 0.0134

FIG. 4G depicts particle size distribution under conditions viz., Heat-Cool cycle; Particle size (nm): 77.02; PDI: 0.410; ZetaPotential: −0.184

FIG. 4H depicts particle size distribution under conditions viz., Freeze-Thaw cycle; Particle size (nm): 91.33; PDI: 0.307; ZetaPotential: −0.186

FIG. 5A depicts particle size distribution under conditions viz., 25° C./60% RH (Relative humidity); Particle size (NM): 98.77; PDI: 0.408; ZetaPotential: −0.198

FIG. 5B depicts particle size distribution under conditions viz., 30° C./75% RH; Particle size (NM): 87.18; PDI: 0.31; ZetaPotential: 0.24

FIG. 5C depicts particle size distribution under conditions viz., 40° C./75% RH; Particle size (NM): 84.34; PDI: 0.349; ZetaPotential: 0.0726

FIG. 5D depicts particle size distribution under conditions viz., Heat-Cool cycle; Particle size (NM): 61.73; PDI: 0.410; ZetaPotential: −0.169

FIG. 5E depicts particle size distribution under conditions viz., Freeze-Thaw cycle; Particle size (NM): 77.47; PDI: 0.291; ZetaPotential: 0.006

FIG. 6A depicts particle size distribution under conditions viz., 25° C./60% RH (Relative humidity); Particle size (NM): 79.66; PDI: 0.418; ZetaPotential: −0.111

FIG. 6B depicts particle size distribution under conditions viz., 30° C./75% RH; Particle size (NM): 87.65; PDI: 0.311; ZetaPotential: −0.0981

FIG. 6C depicts particle size distribution under conditions viz., 40° C./75% RH; Particle size (NM): 86.37; PDI: 0.351; ZetaPotential: 0.0412

FIG. 6D depicts particle size distribution under conditions viz., Heat-Cool cycle; Particle size (NM): 78.76; PDI: 0.461; ZetaPotential: −0.158

FIG. 6E depicts particle size distribution under conditions viz., Freeze-Thaw cycle; Particle size (NM): 90.76; PDI: 0.290; ZetaPotential: −0.358

FIG. 7A depicts particle size distribution under conditions viz., Initial (Room Temperature); Particle size (nm): 143.5; PDI: 0.266; ZetaPotential: 0.0327

FIG. 7B depicts particle size distribution under conditions viz., −8° C.; Particle size (nm): 144.9; PDI: 0.255; ZetaPotential: −0.0155

FIG. 7C depicts particle size distribution under conditions viz., 25° C./60% RH (Relative humidity); Particle size (NM): 158.6; PDI: 0.276; ZetaPotential: 0.0863

FIG. 7D depicts particle size distribution under conditions viz., 30° C./65% RH; Particle size (nm): 163.8; PDI: 0.276; ZetaPotential: 0.28

FIG. 7E depicts particle size distribution under conditions viz., ° C./75% RH; Particle size (nm): 170.4; PDI: 0.306; ZetaPotential: 0.495

FIG. 7F depicts particle size distribution under conditions viz., 40° C./75% RH; Particle size (nm): 156.5; PDI: 0.282; ZetaPotential: −0.0123

FIG. 8A depicts particle size distribution under conditions viz., Initial (Room Temperature); Particle size (NM): 98.72; PDI: 0.243; ZetaPotential: −0.101

FIG. 8B depicts particle size distribution under conditions viz., 2-8° C.; Particle size (nm): 97.17; PDI: 0.31; ZetaPotential: −0.526

FIG. 8C depicts particle size distribution under conditions viz., 25° C./60% RH (Relative humidity); Particle size (nm): 109.4; PDI: 0.412; ZetaPotential: −0.376

FIG. 8D depicts particle size distribution under conditions viz., 40° C./75% RH; Particle size (nm): 107.2; PDI: 0.438; ZetaPotential: −0.298

FIG. 8E depicts particle size distribution under conditions viz., Heat-Cool cycle; Particle size (nm): 86.24; PDI: 0.400; ZetaPotential: −0.136

FIG. 8F depicts particle size distribution under conditions viz., Freeze-Thaw cycle; Particle size (nm): 92.71; PDI: 0.390; ZetaPotential: −0.0462

FIG. 9A depicts particle size distribution under conditions viz., Initial (Room Temperature); Particle size (NM): 96.11; PDI: 0.245; ZetaPotential: −0.00741

FIG. 9B depicts particle size distribution under conditions viz., 2-8° C.; Particle size (NM): 87.26; PDI: 0.306; ZetaPotential: −0.0881

FIG. 9C depicts particle size distribution under conditions viz., 25° C./60% RH (Relative humidity); Particle size (NM): 74.91; PDI: 0.284; ZetaPotential: −0.432

FIG. 9D depicts particle size distribution under conditions viz., 40° C./75% RH; Particle size (NM): 91.65; PDI: 0.388; ZetaPotential: −0.0307

FIG. 9F depicts particle size distribution under conditions viz., Freeze-Thaw cycle; Particle size(NM): 82.68; PDI: 0.239; ZetaPotential: −0.0868.

FIG. 9E depicts particle size distribution under conditions viz., Freeze-Thaw cycle; Particle size (NM): 82.68; PDI: 0.239; ZetaPotential: −0.0868

FIG. 10A depicts particle size distribution under conditions viz., Initial (Room Temperature); Particle size (NM): 79.6; PDI: 0.279; ZetaPotential: 0.161

FIG. 10B depicts particle size distribution under conditions viz., 2-8° C.; Particle size (NM): 84.8; PDI: 0.292; ZetaPotential: 0.00795

FIG. 10C depicts particle size distribution under conditions viz., 25° C./60% RH (Relative humidity); Particle size (NM): 55.79; PDI: 0.241; ZetaPotential: −0.2

FIG. 10D depicts particle size distribution under conditions viz., 40° C./75% RH; Particle size (NM): 88.8; PDI: 0.315; ZetaPotential: 0.00409

FIG. 10E depicts particle size distribution under conditions viz., Heat-Cool cycle; Particle size (NM): 70.13; PDI: 0.298; ZetaPotential: 0.0311

FIG. 10F depicts particle size distribution under conditions viz., Freeze-Thaw cycle; Particle size (NM): 74.27; PDI: 0.363; ZetaPotential: −0.106

FIG. 11A depicts particle size distribution under conditions viz., Initial (Room Temperature); Particle size (NM): 87.53; PDI: 0.242; ZetaPotential: −0.176

FIG. 11B depicts particle size distribution under conditions viz., 2-8° C.; Particle size (NM): 87.68; PDI: 0.295; ZetaPotential: −0.0151

FIG. 11C depicts particle size distribution under conditions viz., 25° C./60% RH (Relative humidity); Particle size (NM): 85.85; PDI: 0.298; ZetaPotential: −0.506

FIG. 11D depicts particle size distribution under conditions viz., 40° C./75% RH; Particle size (NM): 87.61; PDI: 0.395; ZetaPotential: −0.112

FIG. 11E depicts particle size distribution under conditions viz., Heat-Cool cycle; Particle size (NM): 78.52; PDI: 0.268; ZetaPotential: 0.0101

FIG. 11F depicts particle size distribution under conditions viz., Freeze-Thaw cycle; Particle size (NM): 77.41; PDI: 0.281; ZetaPotential: −0.0777

FIG. 13A depicts particle size distribution under conditions viz., Initial (Room Temperature); Particle size (NM): 121.5; PDI: 0.252; ZetaPotential: −0.592

FIG. 13B depicts particle size distribution under conditions viz., 2-8° C.; Particle size (NM): 135.3; PDI: 0.431; ZetaPotential: −0.583

FIG. 13C depicts particle size distribution under conditions viz., 25° C./60% RH (Relative humidity); Particle size (NM): 146.3; PDI: 0.407; ZetaPotential: −0.309

FIG. 13D depicts particle size distribution under conditions viz., 40° C./75% RH; Particle size (NM): 136.8; PDI: 0.287; ZetaPotential: −0.361

FIG. 14A depicts particle size distribution under conditions viz., Initial (Room Temperature); Particle size (NM): 125.3; PDI: 0.311; ZetaPotential: −0.341

FIG. 14B depicts particle size distribution under conditions viz., 2-8° C.; Particle size (NM): 123.6; PDI: 0.387; ZetaPotential: −0.219

FIG. 14C depicts particle size distribution under conditions viz., 25° C./60% RH (Relative humidity); Particle size (NM): 127.7; PDI: 0.317; ZetaPotential: −0.00259

FIG. 14D depicts particle size distribution under conditions viz., 40° C./75% RH; Particle size (NM): 130.2; PDI: 0.319; ZetaPotential: −0.364

FIG. 15A depicts particle size distribution under conditions viz., Initial (Room Temperature); Particle size (NM): 117.5; PDI: 0.274; ZetaPotential: −0.588

FIG. 15B depicts particle size distribution under conditions viz., 2-8° C.; Particle size (NM): 161; PDI: 0.488; ZetaPotential: 0.0531

FIG. 15C depicts particle size distribution under conditions viz., 25° C./60% RH (Relative humidity); Particle size (NM): 148.3; PDI: 0.446; ZetaPotential: 0.115

FIG. 15D depicts particle size distribution under conditions viz., 40° C./75% RH; Particle size (NM): 158.3; PDI: 0.514; ZetaPotential: 0.157

FIG. 16A depicts particle size distribution under conditions viz., Initial (Room Temperature); Particle size (NM): 103.5; PDI: 0.194; ZetaPotential: −0.139

FIG. 16B depicts particle size distribution under conditions viz., 2-8° C.; Particle size (NM): 107; PDI: 0.251; ZetaPotential: 0.139

FIG. 16C depicts particle size distribution under conditions viz., 25° C./60% RH (Relative humidity); Particle size (NM): 100.6; PDI: 0.233; ZetaPotential: 0.00712

FIG. 16D depicts particle size distribution under conditions viz., 40° C./75% RH; Particle size (NM): 107.9; PDI: 0.228; ZetaPotential: 0.973

FIG. 17A depicts particle size distribution under conditions viz., Initial (Room Temperature); Particle size (NM): 146.6; PDI: 0.332; ZetaPotential: −0.254

FIG. 17B depicts particle size distribution under conditions viz., 2-8° C.; Particle size (NM): 166.7; PDI: 0.522; ZetaPotential: −0.175

FIG. 17C depicts particle size distribution under conditions viz., 25° C./60% RH (Relative humidity); Particle size (NM): 151.5; PDI: 0.462; ZetaPotential: −0.233

FIG. 17D depicts particle size distribution under conditions viz., 40° C./75% RH; Particle size (NM): 154.3; PDI: 0.318; ZetaPotential: −0.0449

FIG. 18A depicts particle size distribution under conditions viz., Initial (Room Temperature); Particle size(NM): 142.5; PDI: 0.449; ZetaPotential: −0.248

FIG. 18B depicts particle size distribution under conditions viz., 2-8° C.; Particle size(NM): 146.7; PDI: 0.405; ZetaPotential: −0.389

FIG. 18C depicts particle size distribution under conditions viz., 25° C./60% RH(Relative humidity); Particle size(NM): 131.4; PDI: 0.447; ZetaPotential: −0.361

FIG. 18D depicts particle size distribution under conditions viz., 40° C./75% RH; Particle size(NM): 144.9; PDI: 0.331; ZetaPotential: −0.229

DETAILED DESCRIPTION OF THE INVENTION

Figure 1:
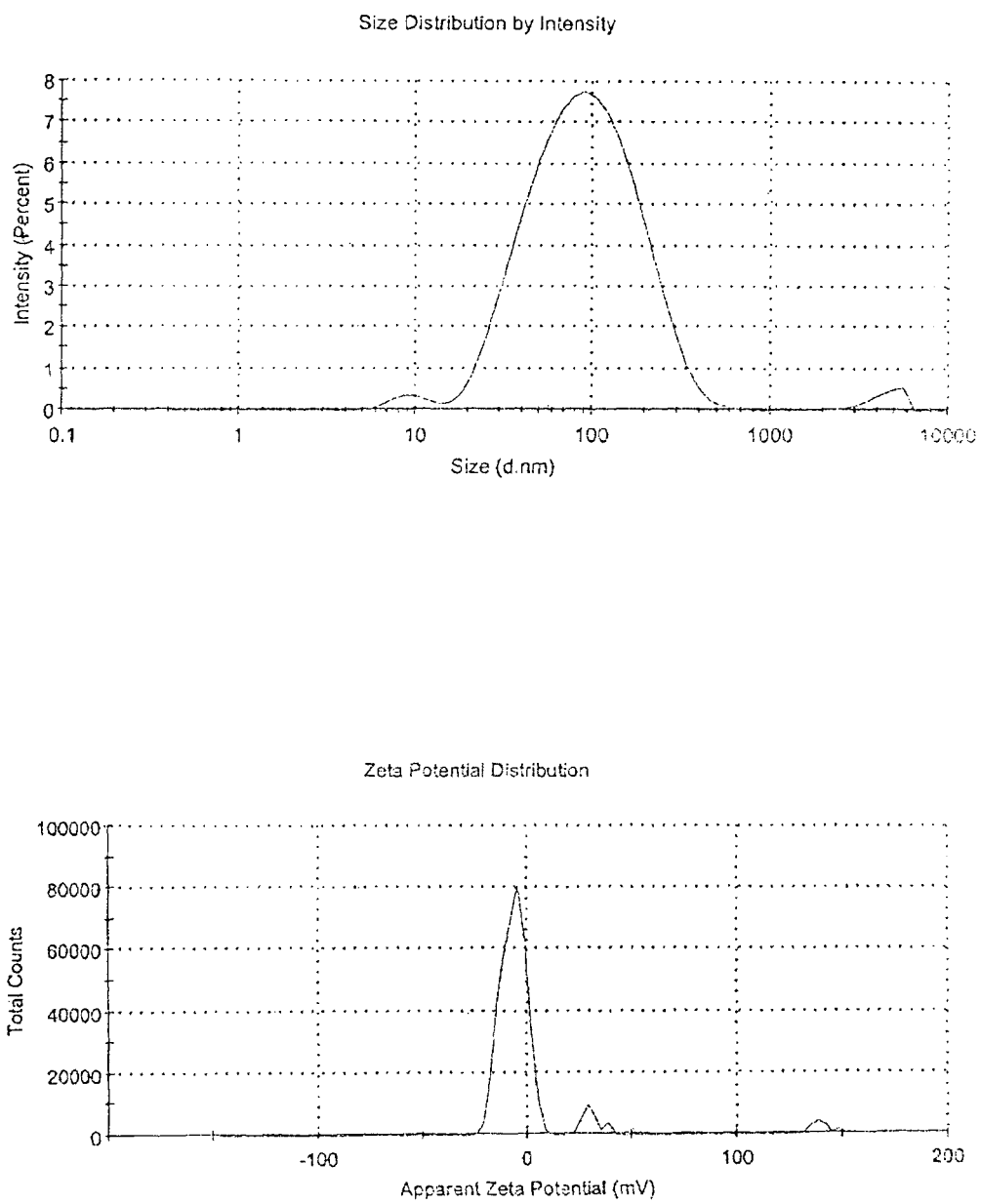
FIG. 1A to FIG. 1H illustrate particle size distribution in nanometre (nm), polydispersity index (PDI) and zeta potential (MV) of an exemplary composition No. 1 of the present invention, under various conditions.
Figure 1:
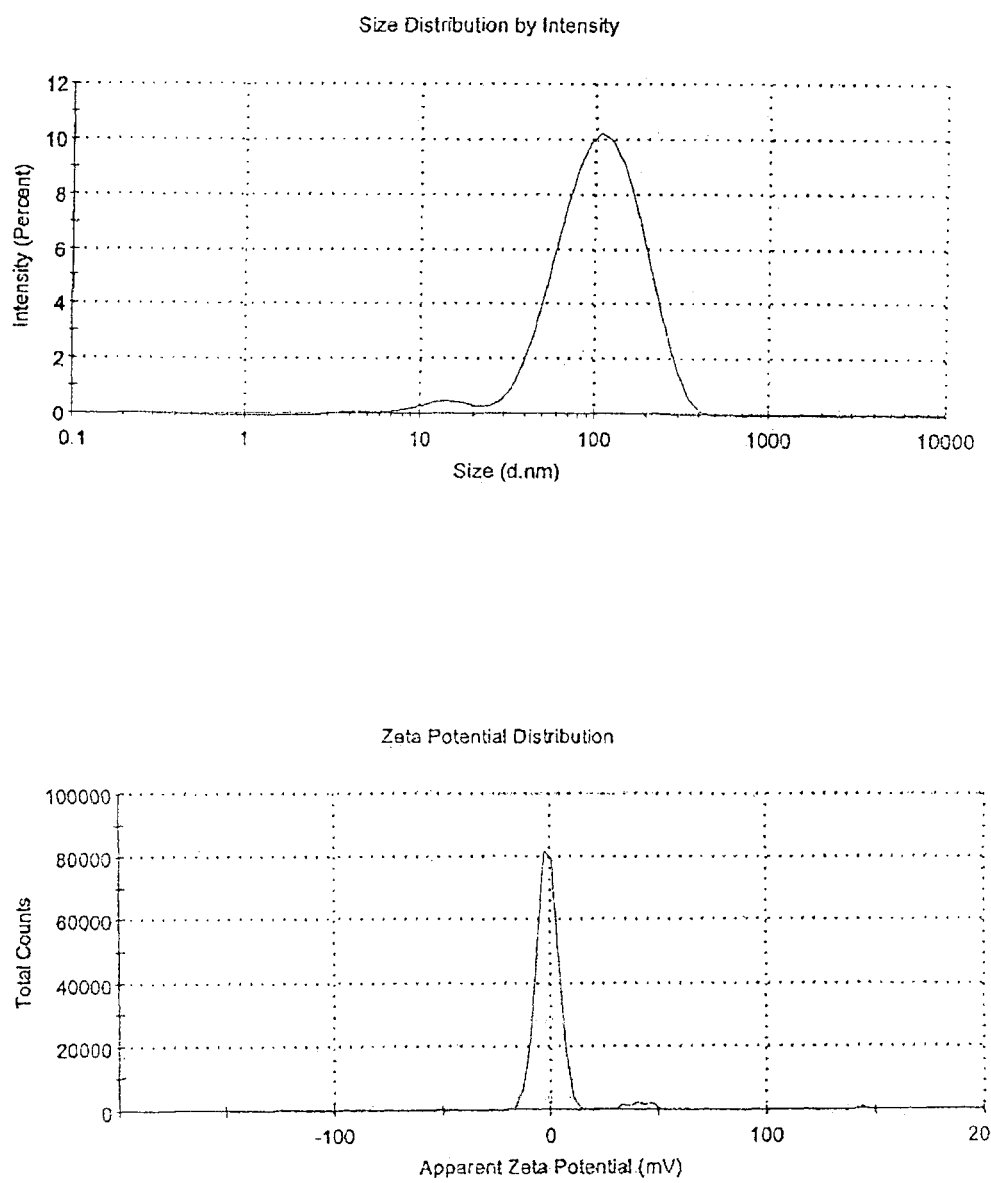
Figure 1:
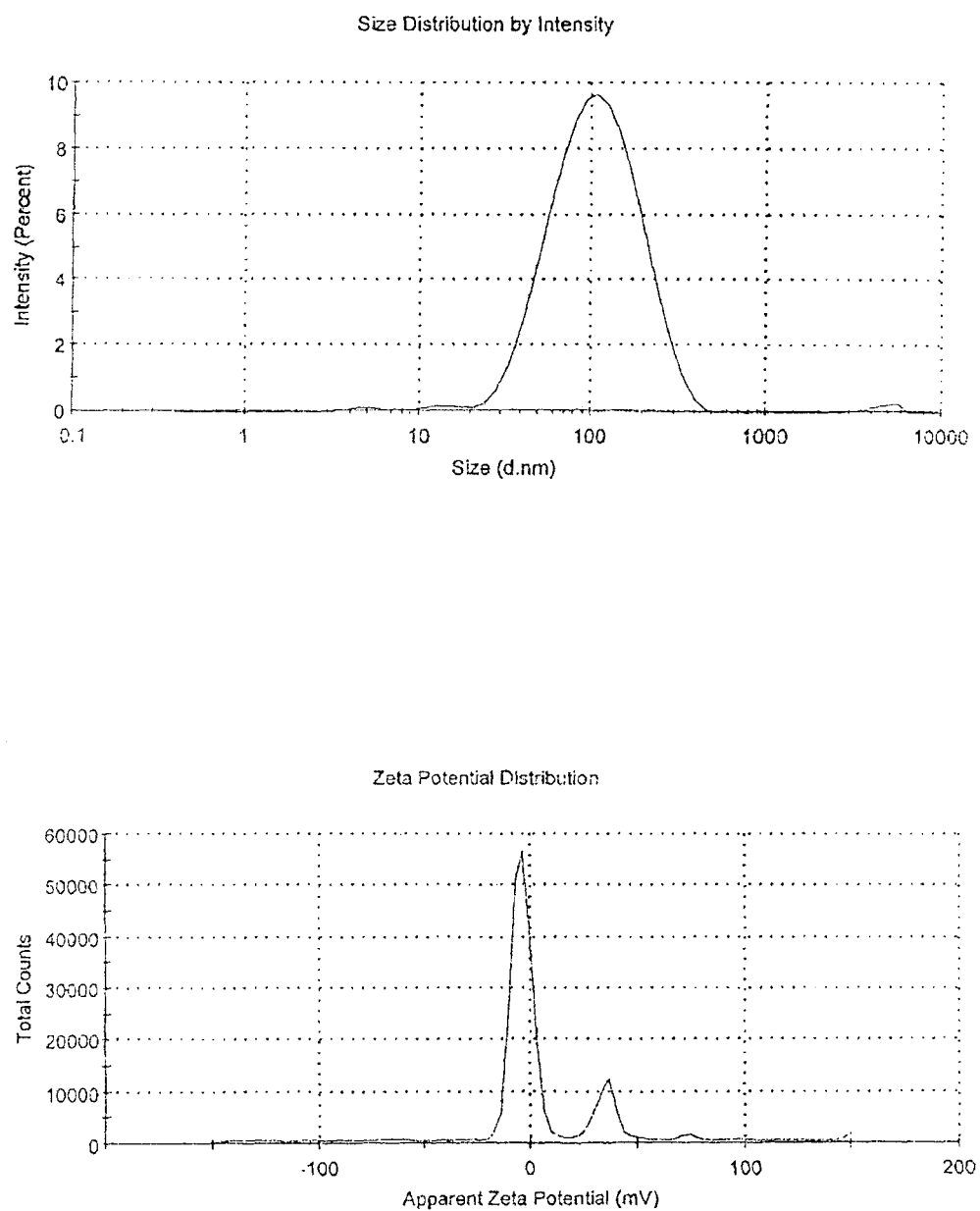
Figure 1:
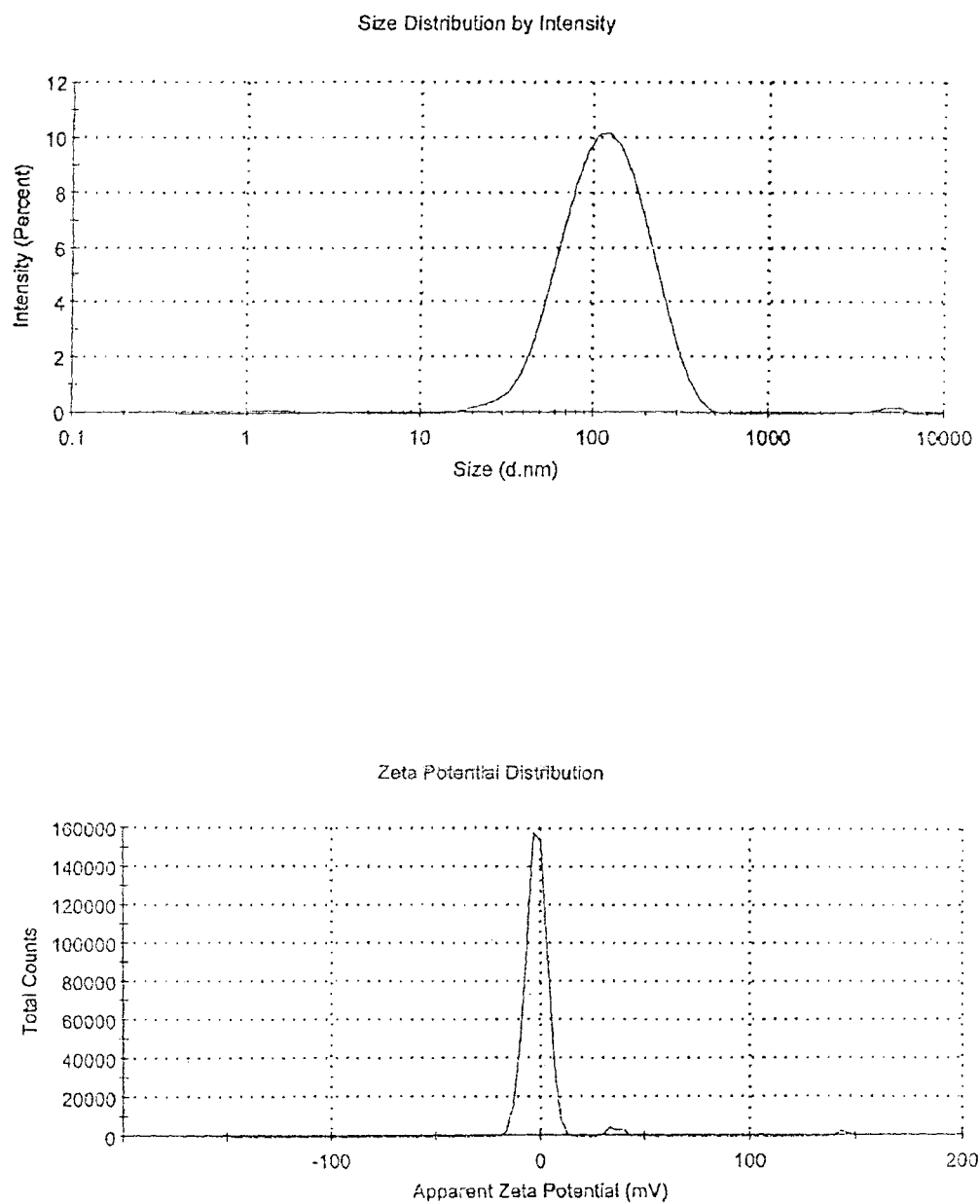
Figure 1E:
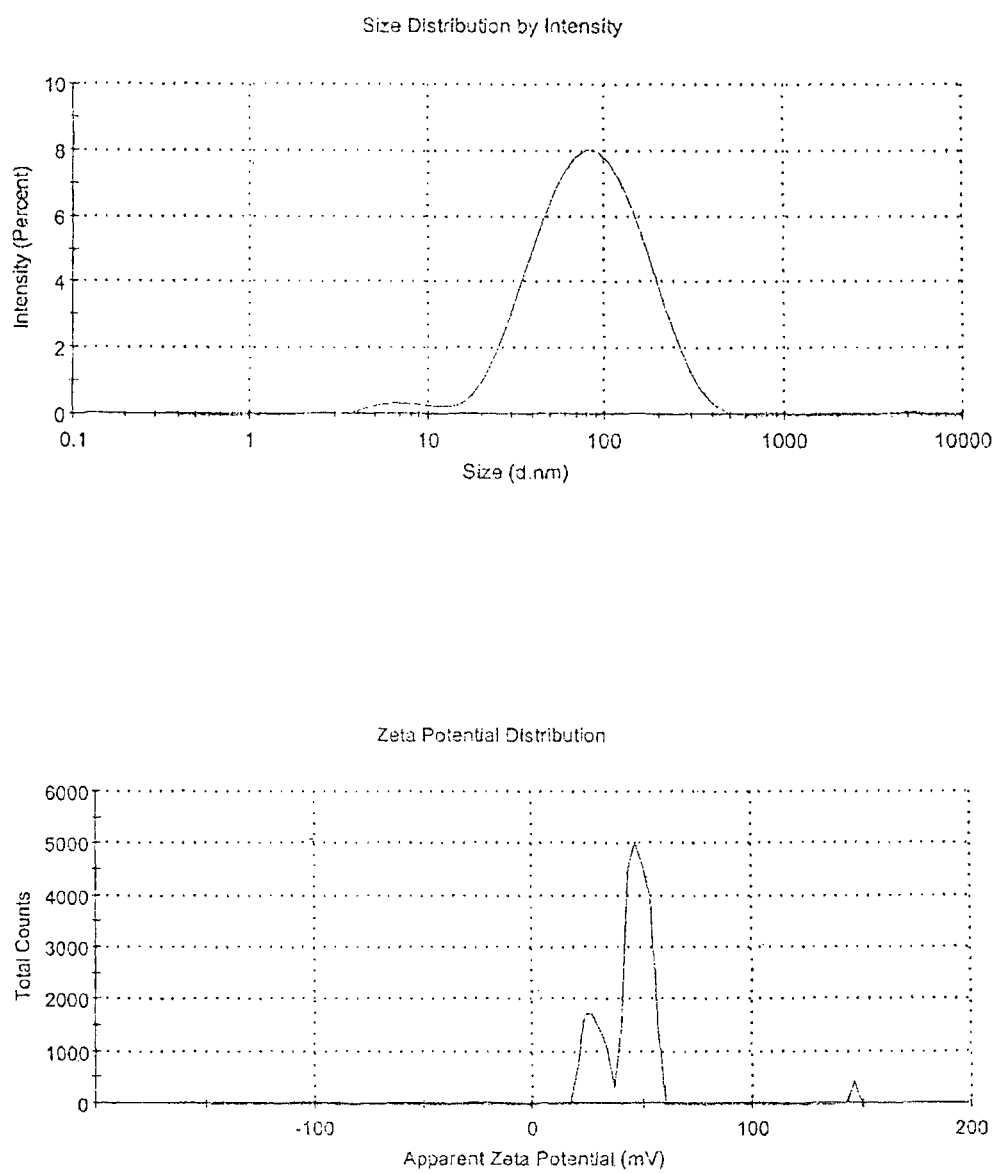
Figure 1:
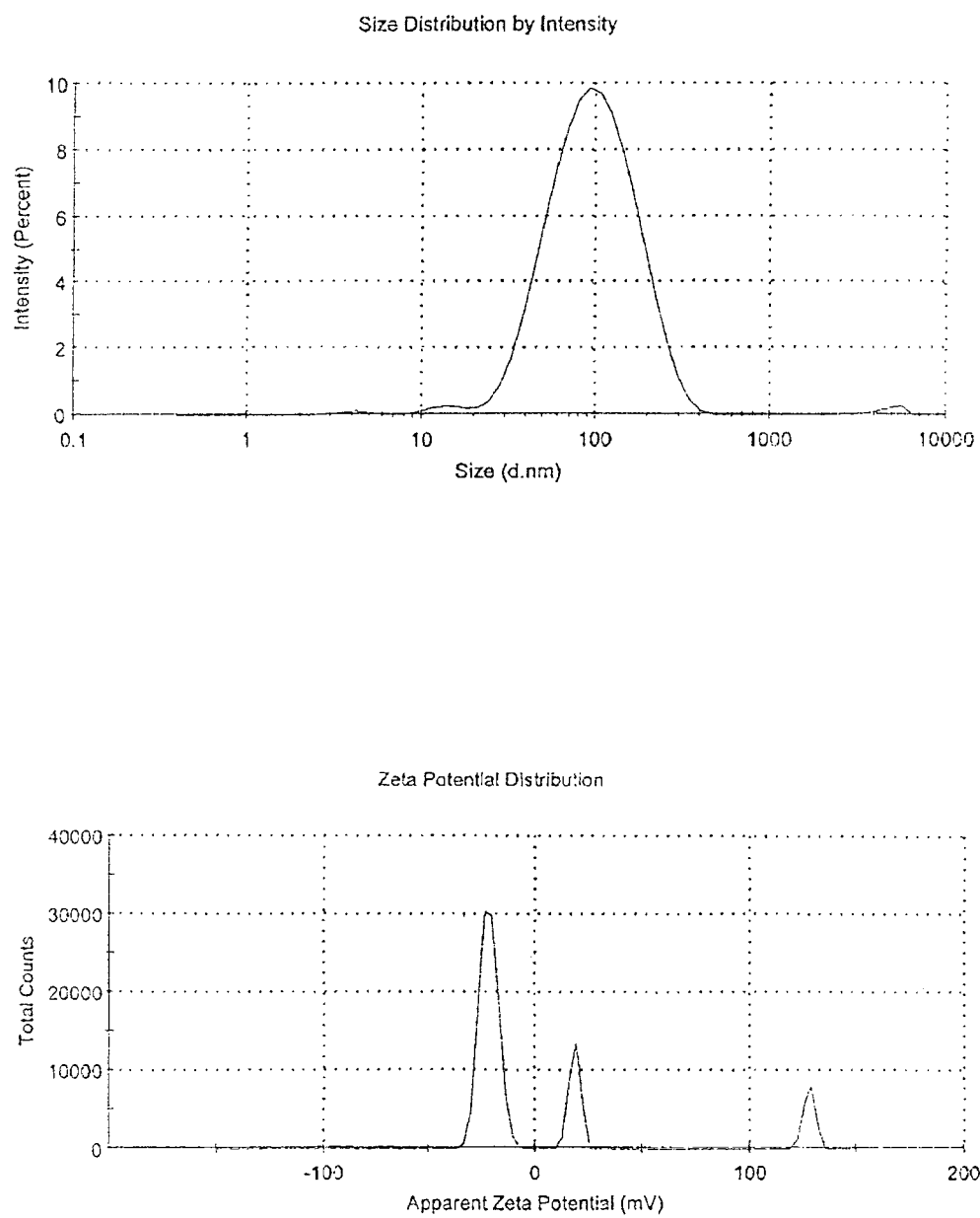
Figure 1G:
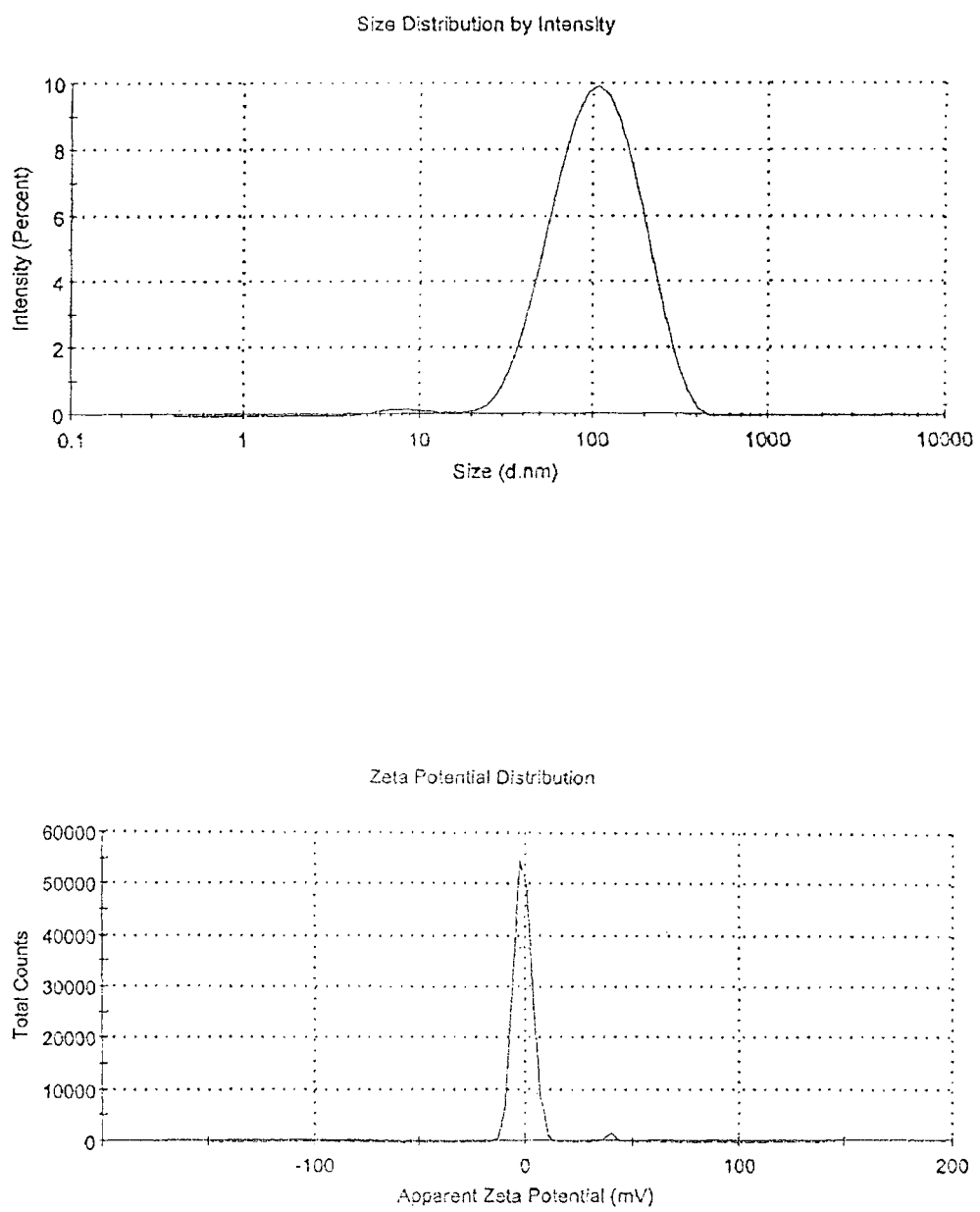
Figure 1H:
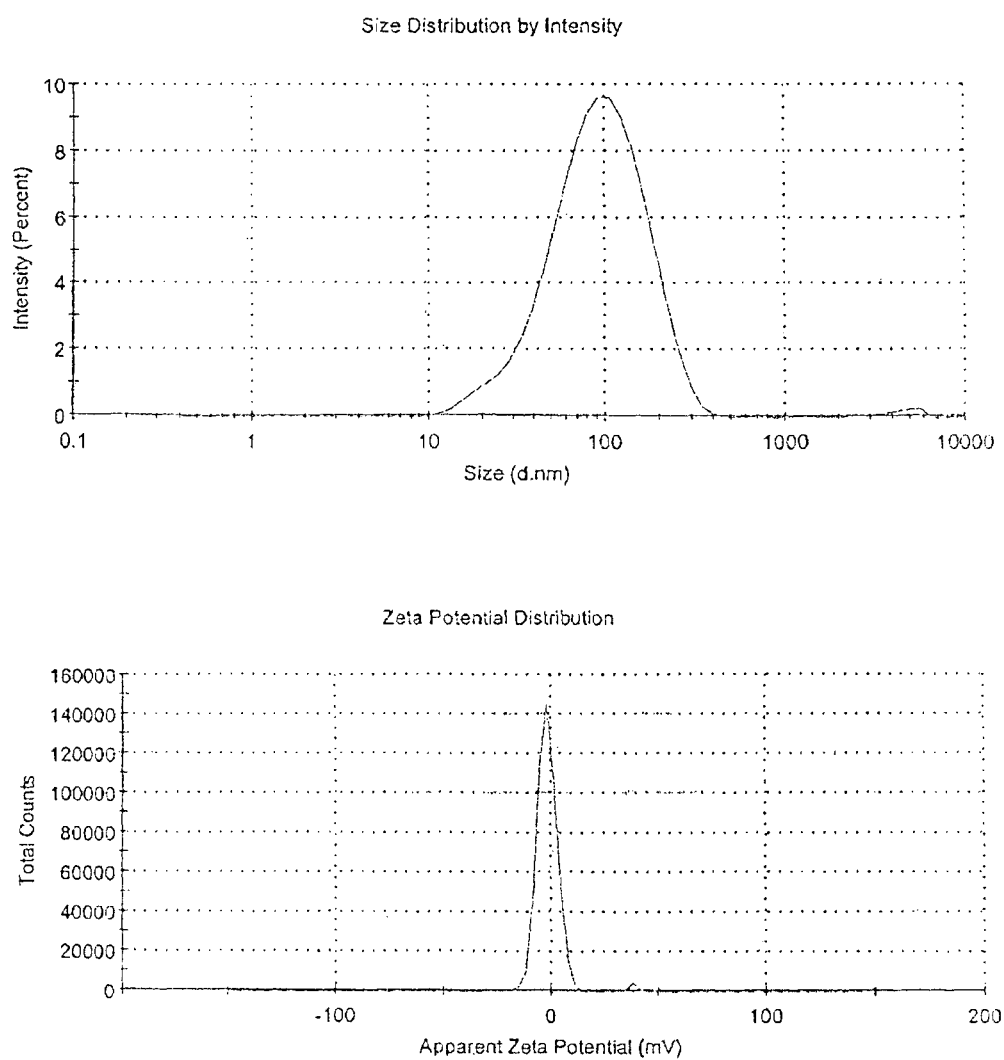
Figure 2:
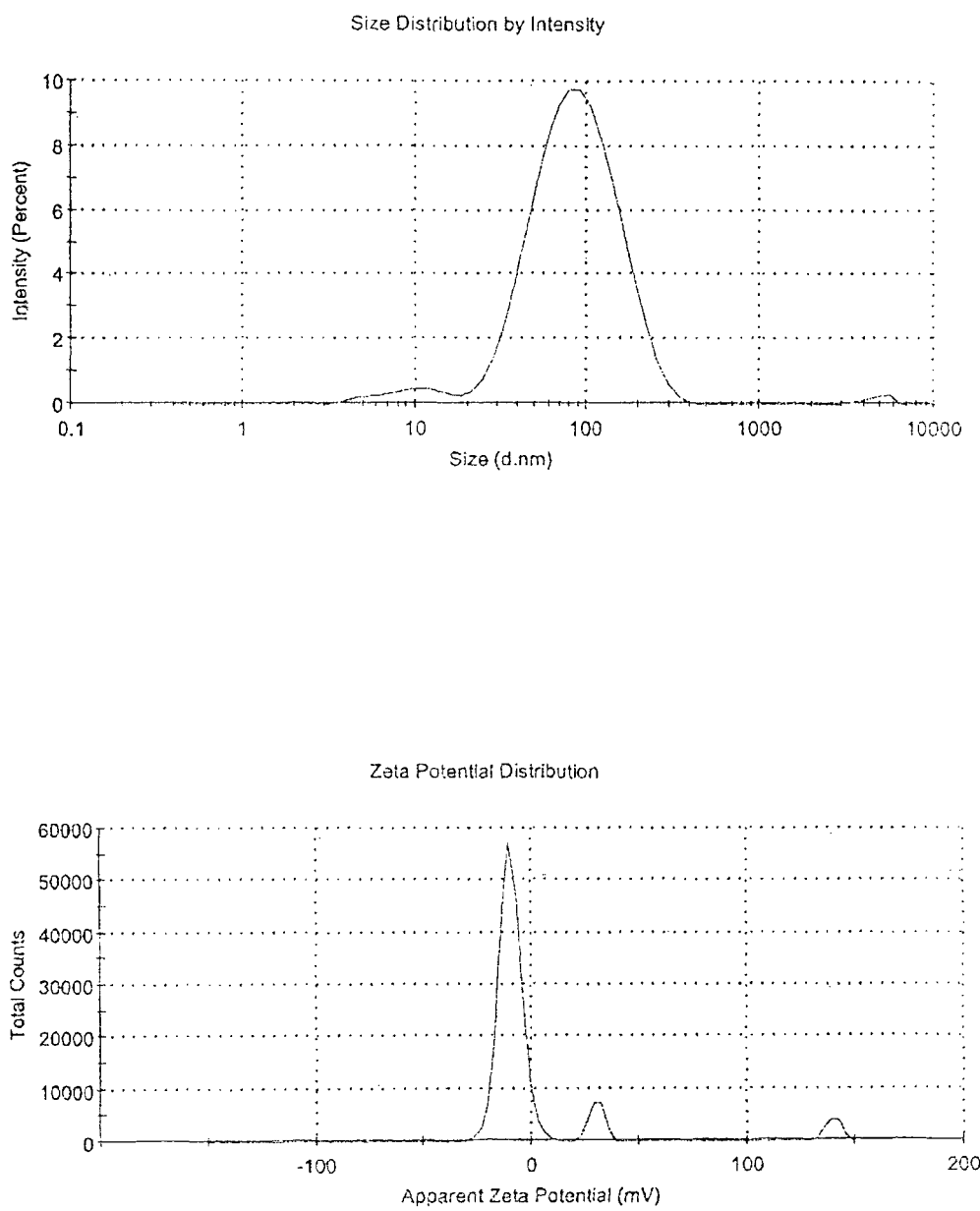
FIG. 2A to FIG. 2H depict particle size distribution in nanometre (nm), polydispersity index (PDI) and zeta potential (MV) of the exemplary composition No. 2 under various conditions.
Figure 2B:
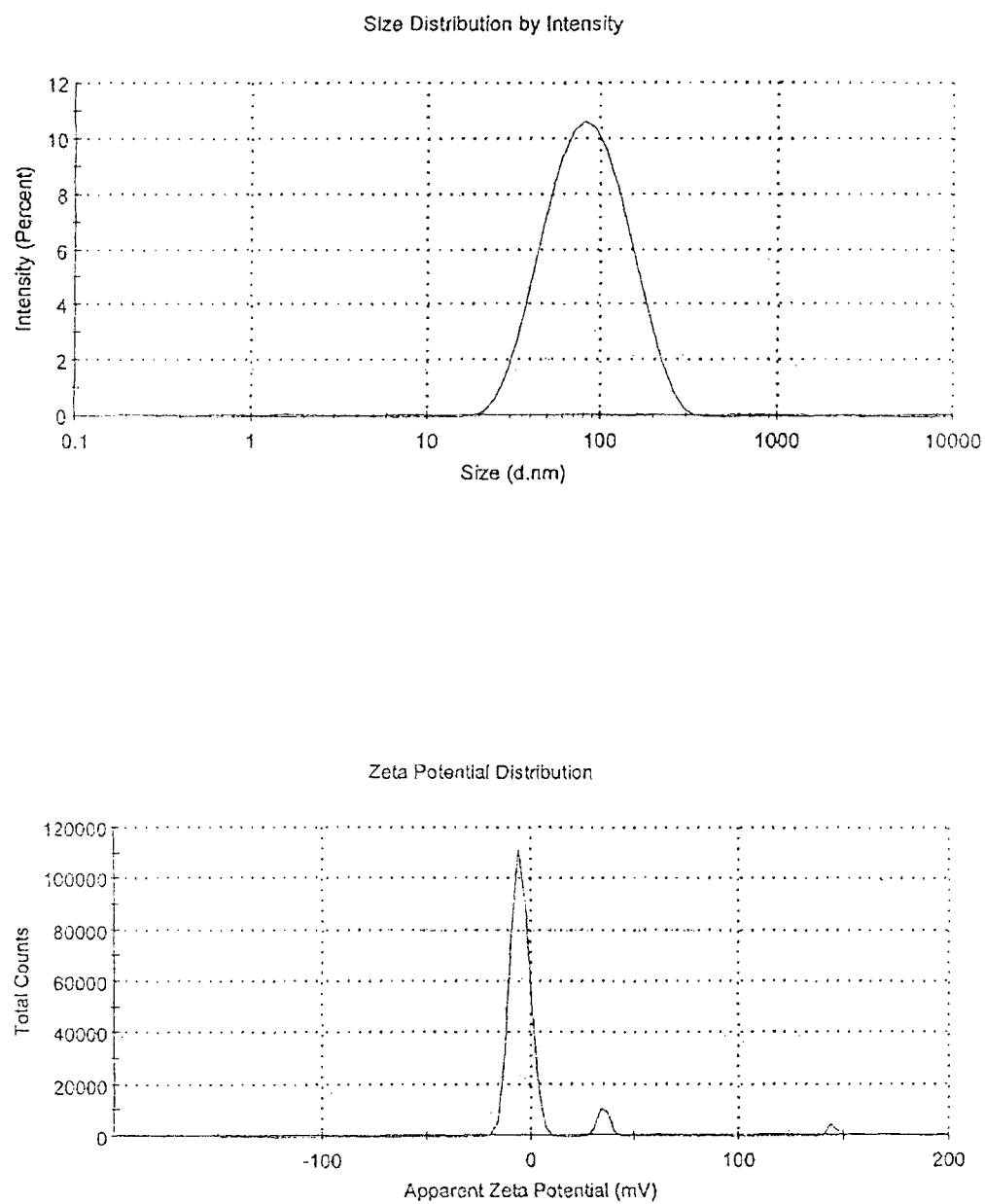
Figure 2C:
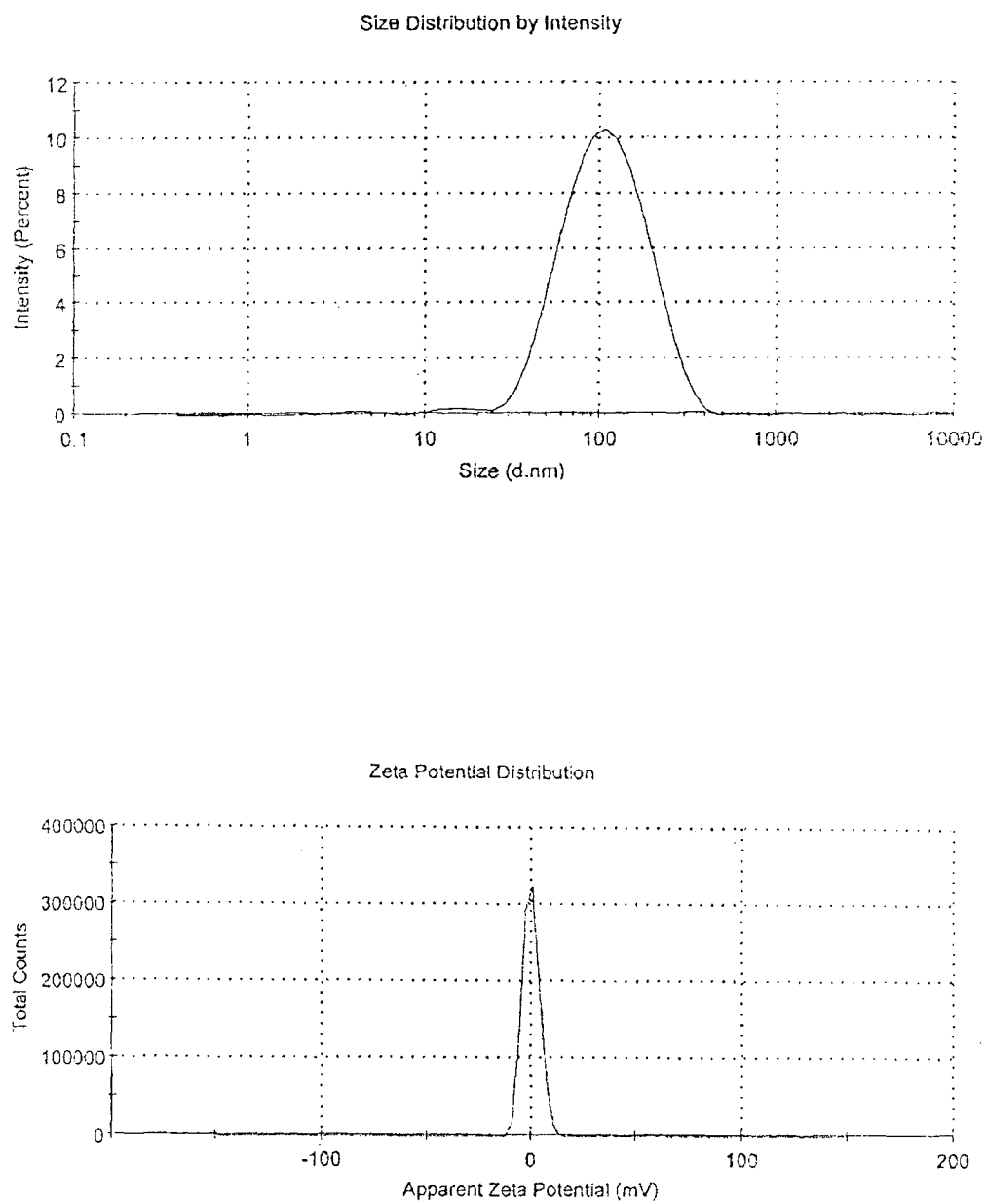
Figure 2D:
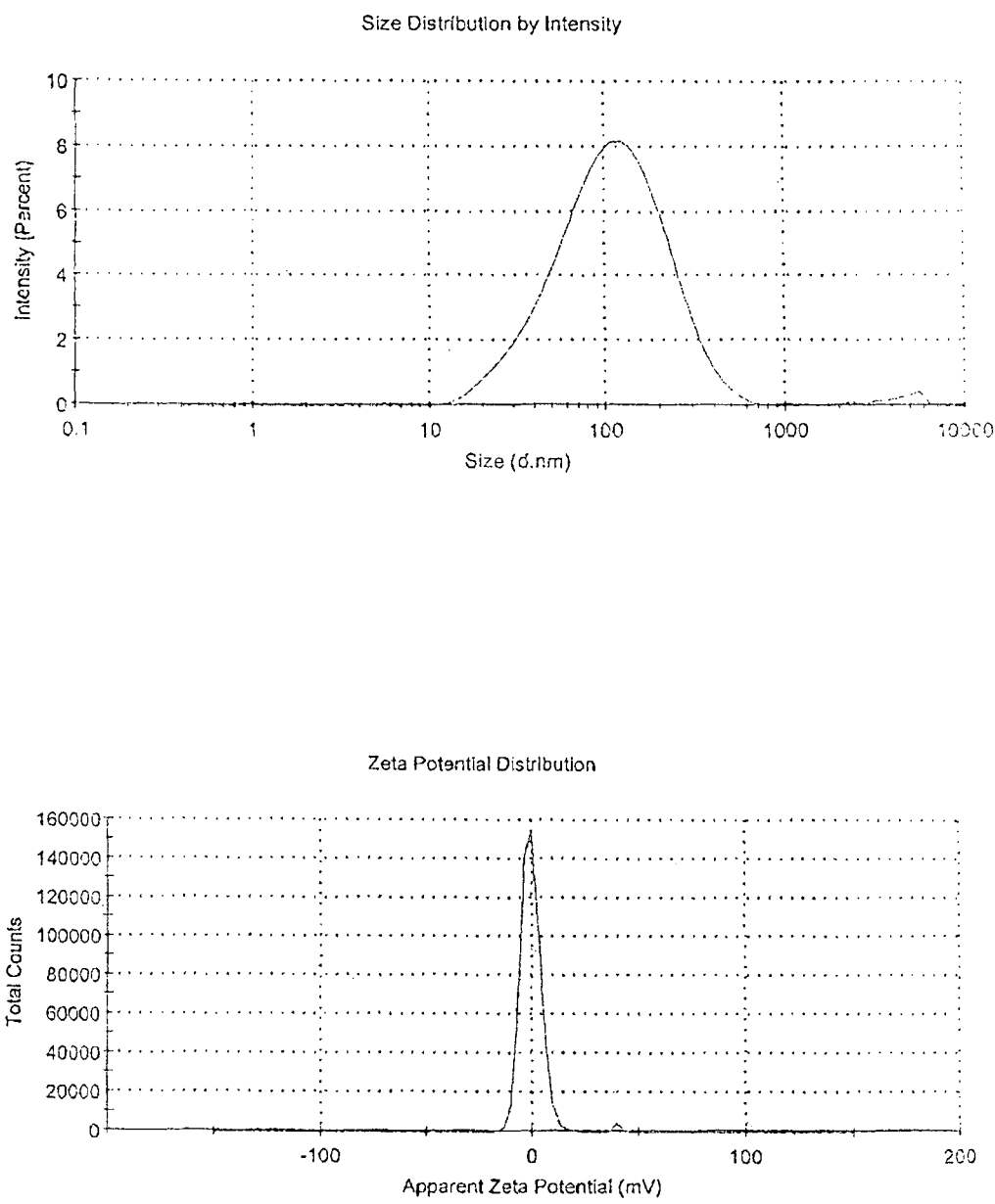
Figure 2:
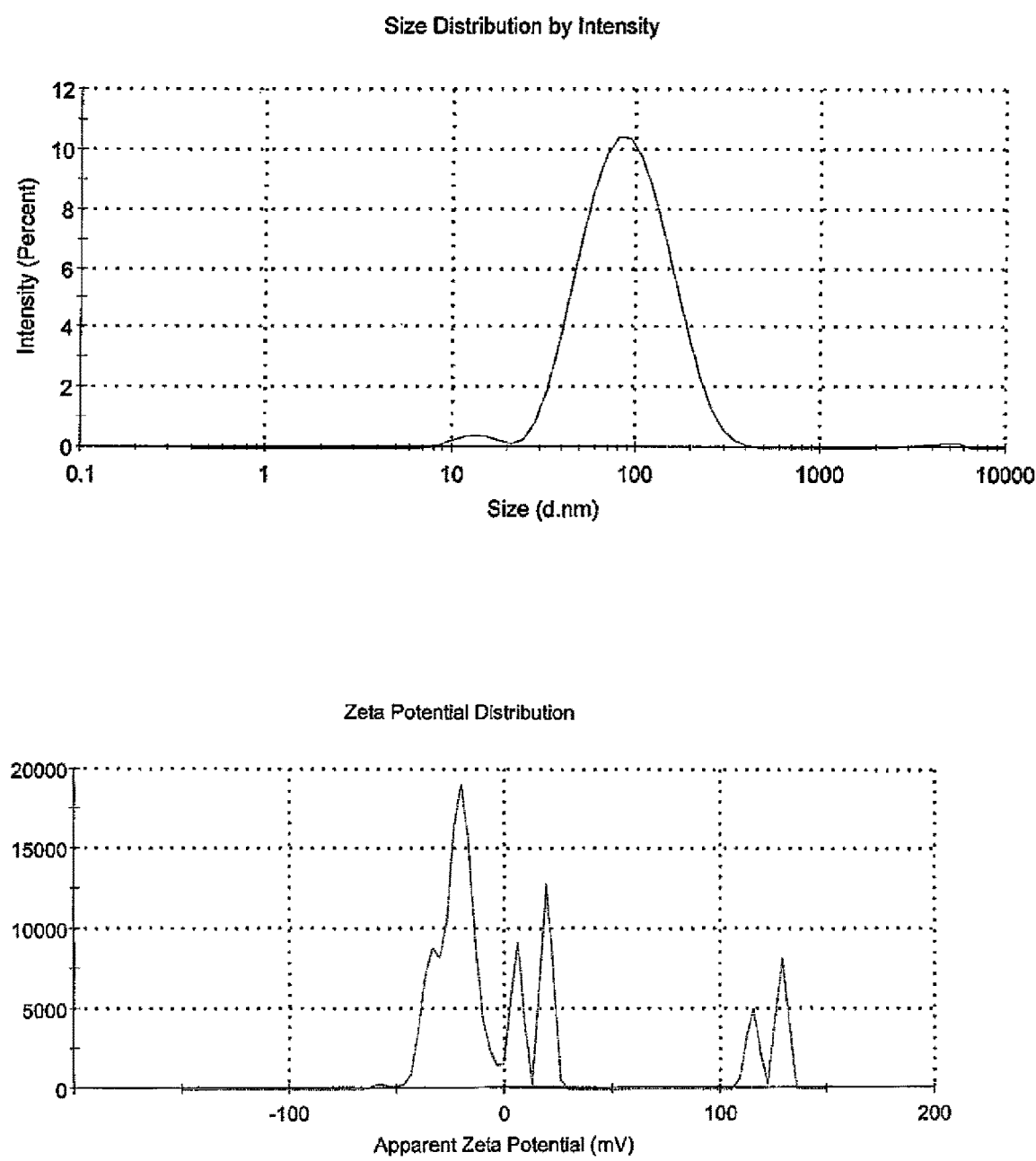
Figure 2F:
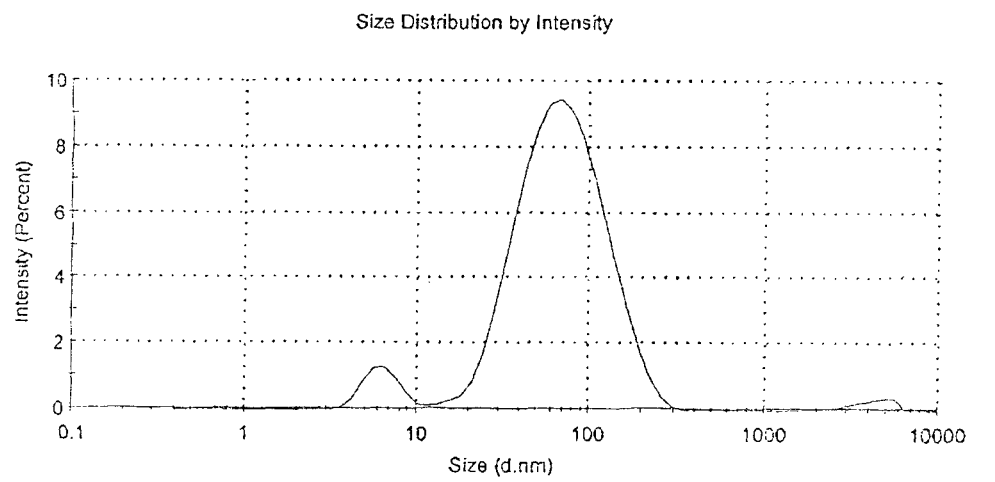
Figure 2F:
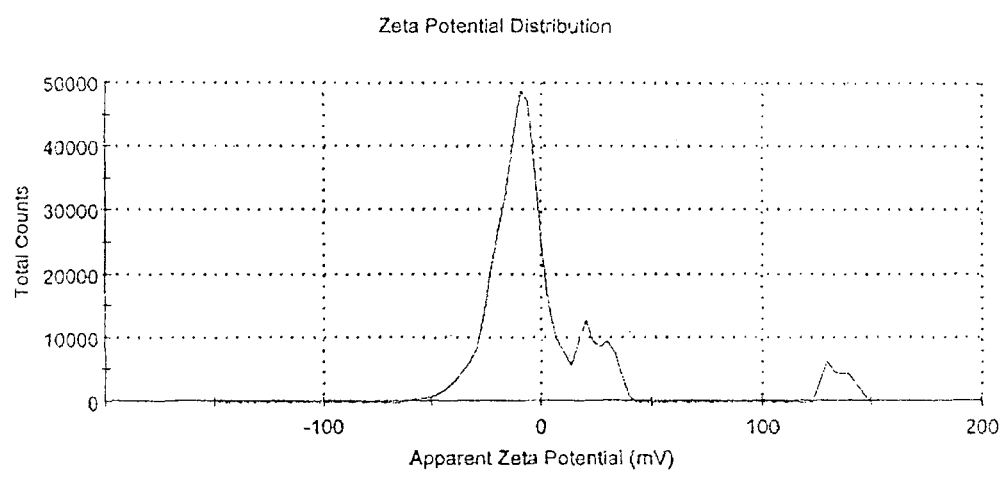
Figure 2G:
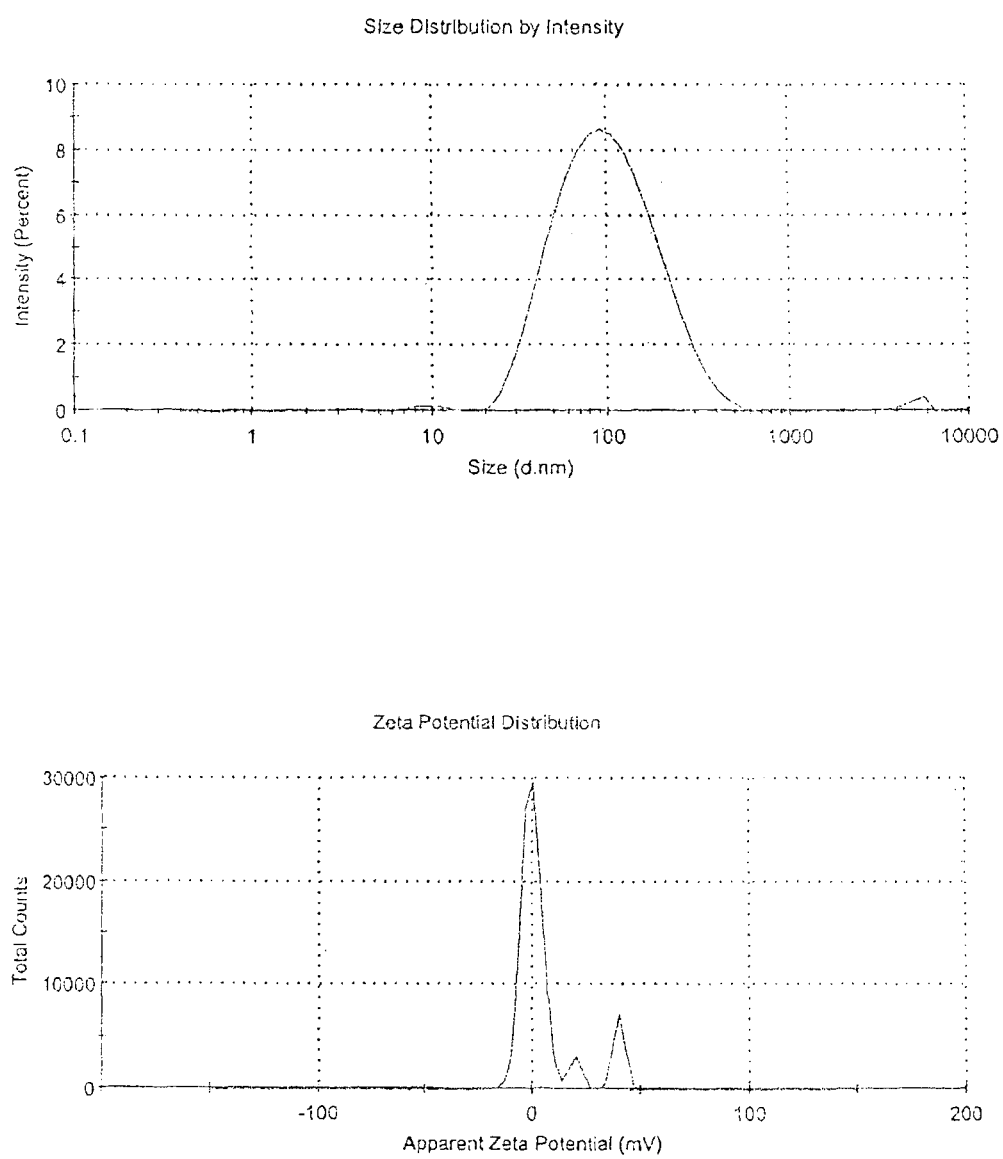
Figure 2H:
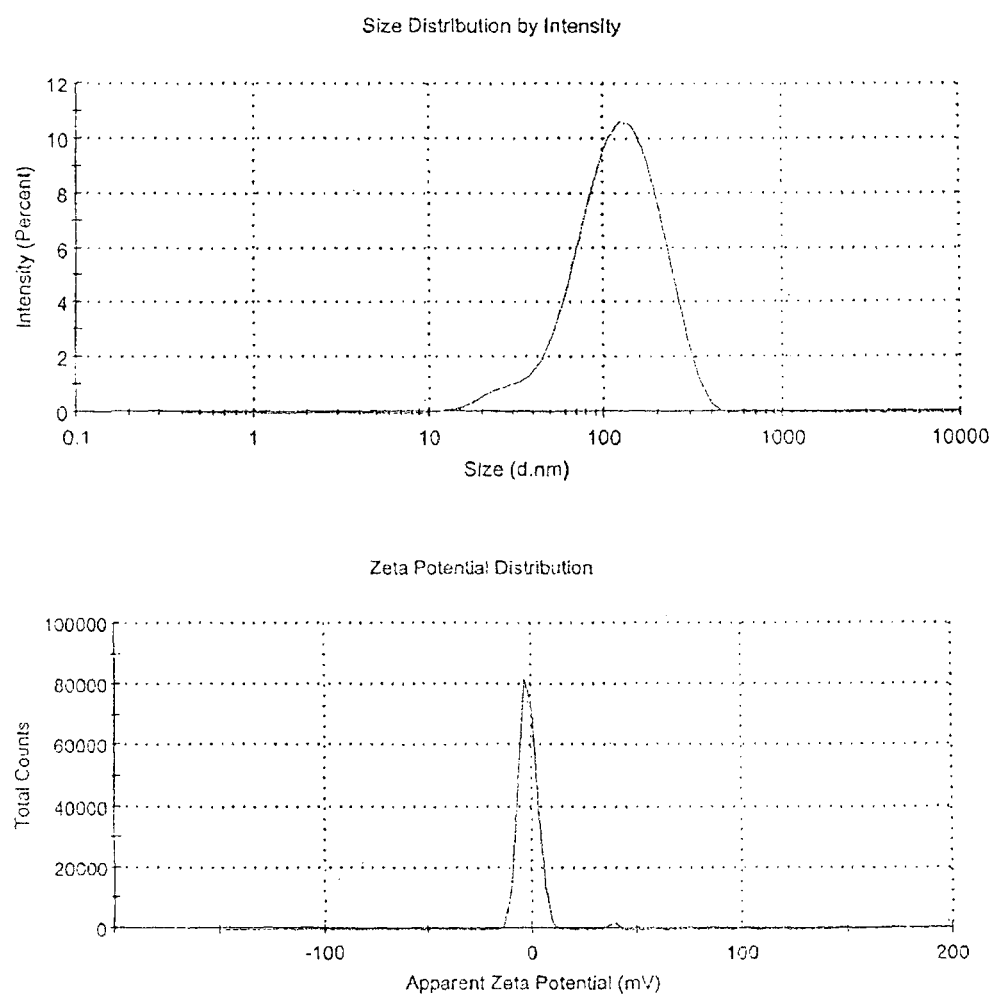
Figure 3A:
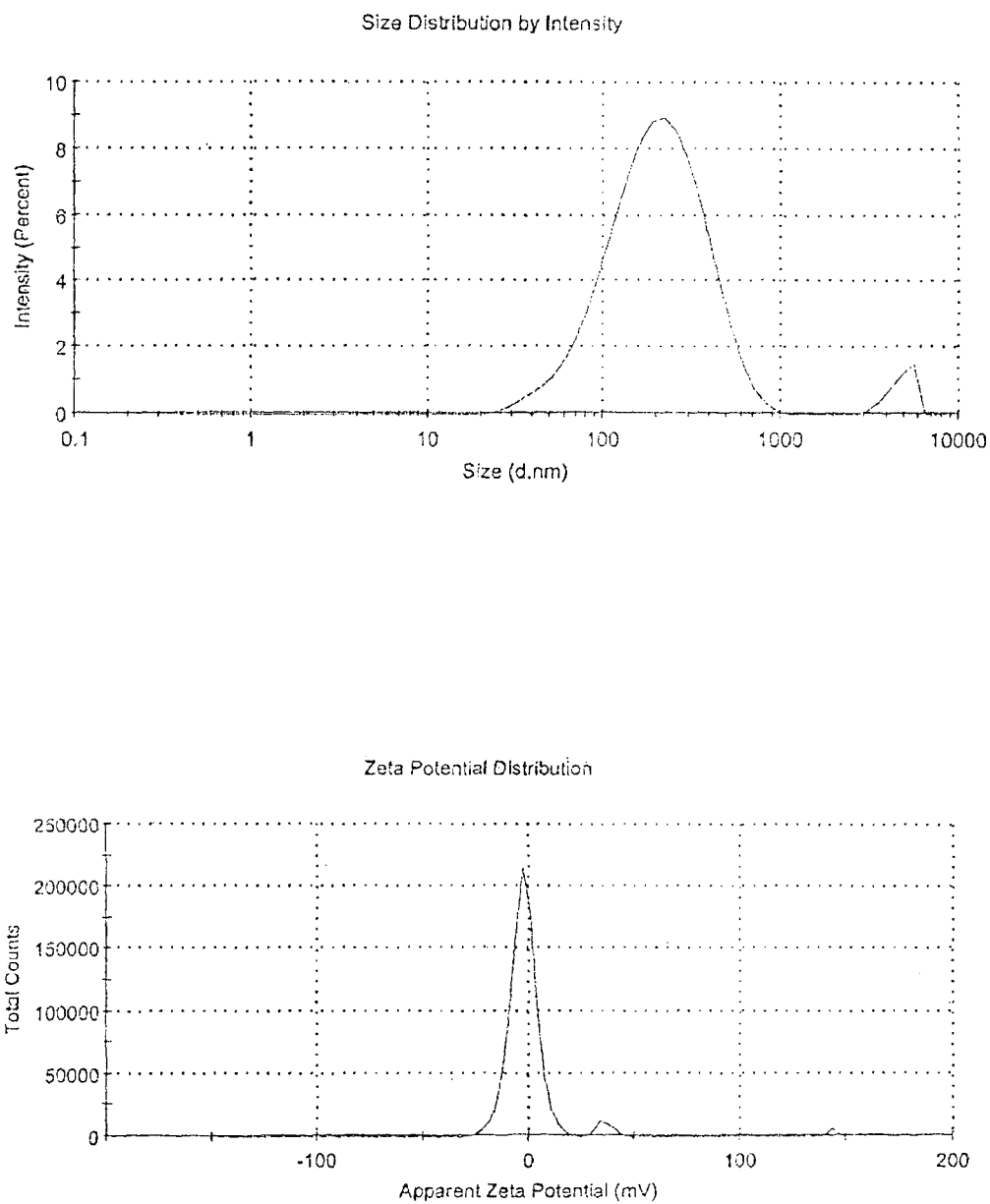
FIG. 3A to FIG. 3H depict particle size distribution in nanometre (nm) polydispersity index (PDI) and zeta potential (MV) of the exemplary composition No. 3 of the present invention under conditions.
Figure 3B:
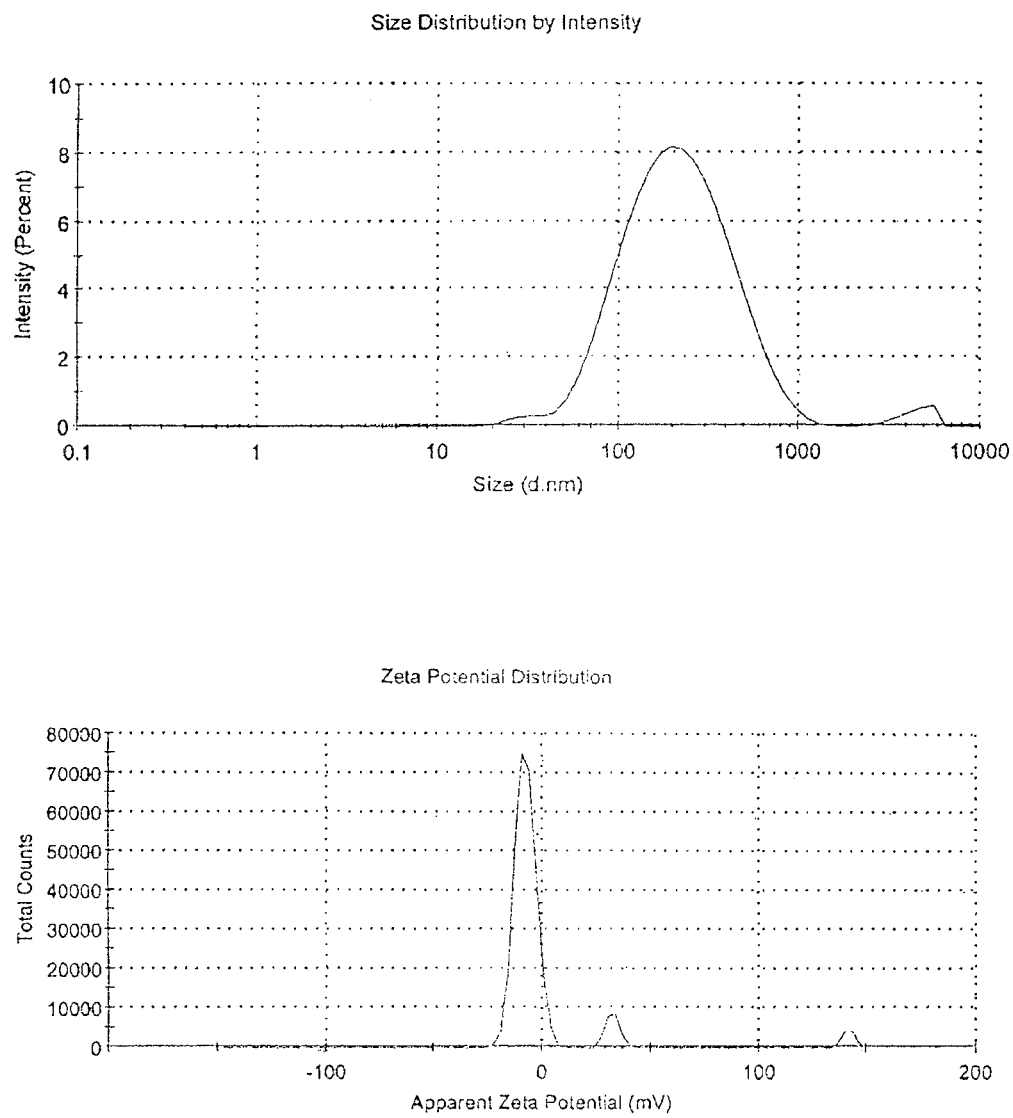
Figure 3C:
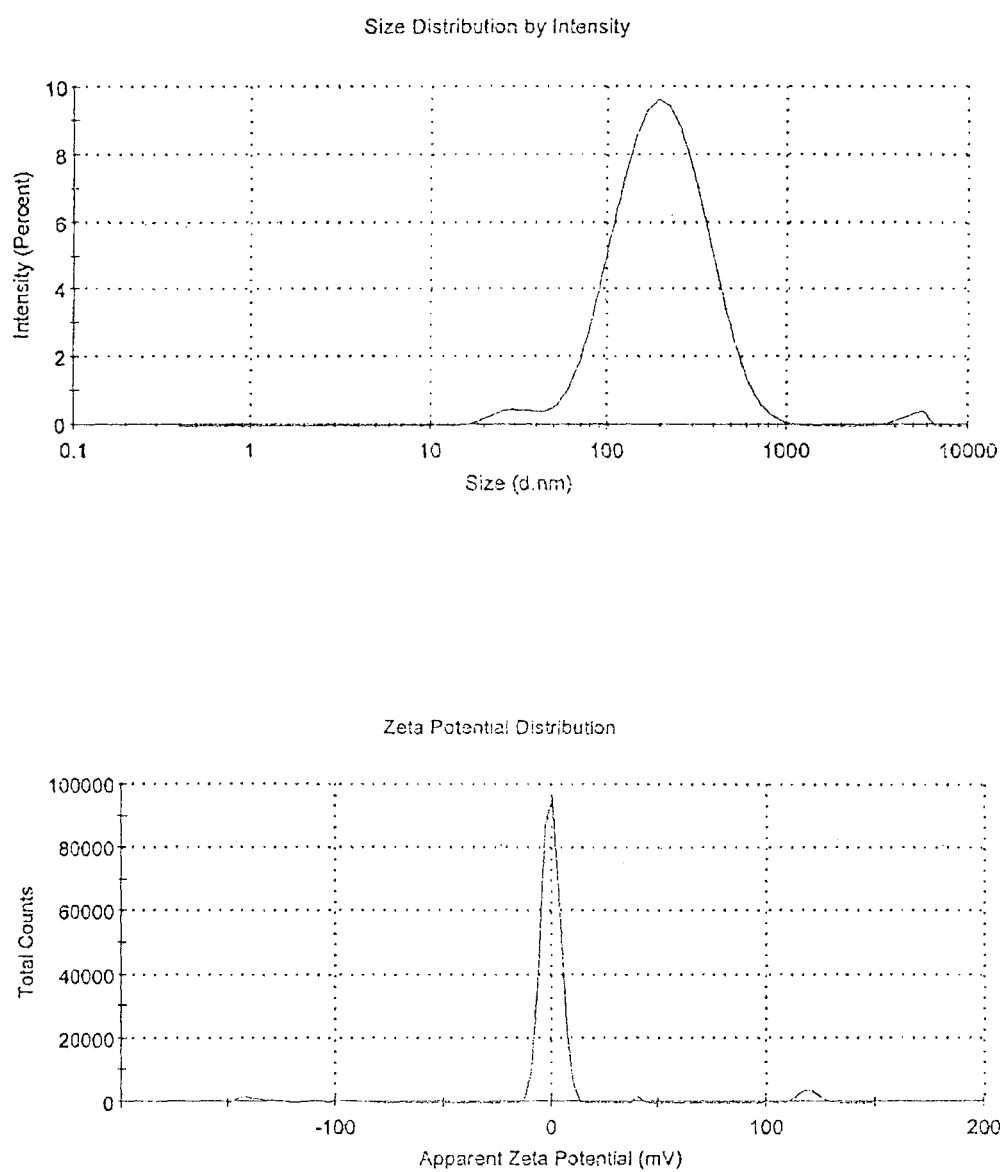
Figure 3D:
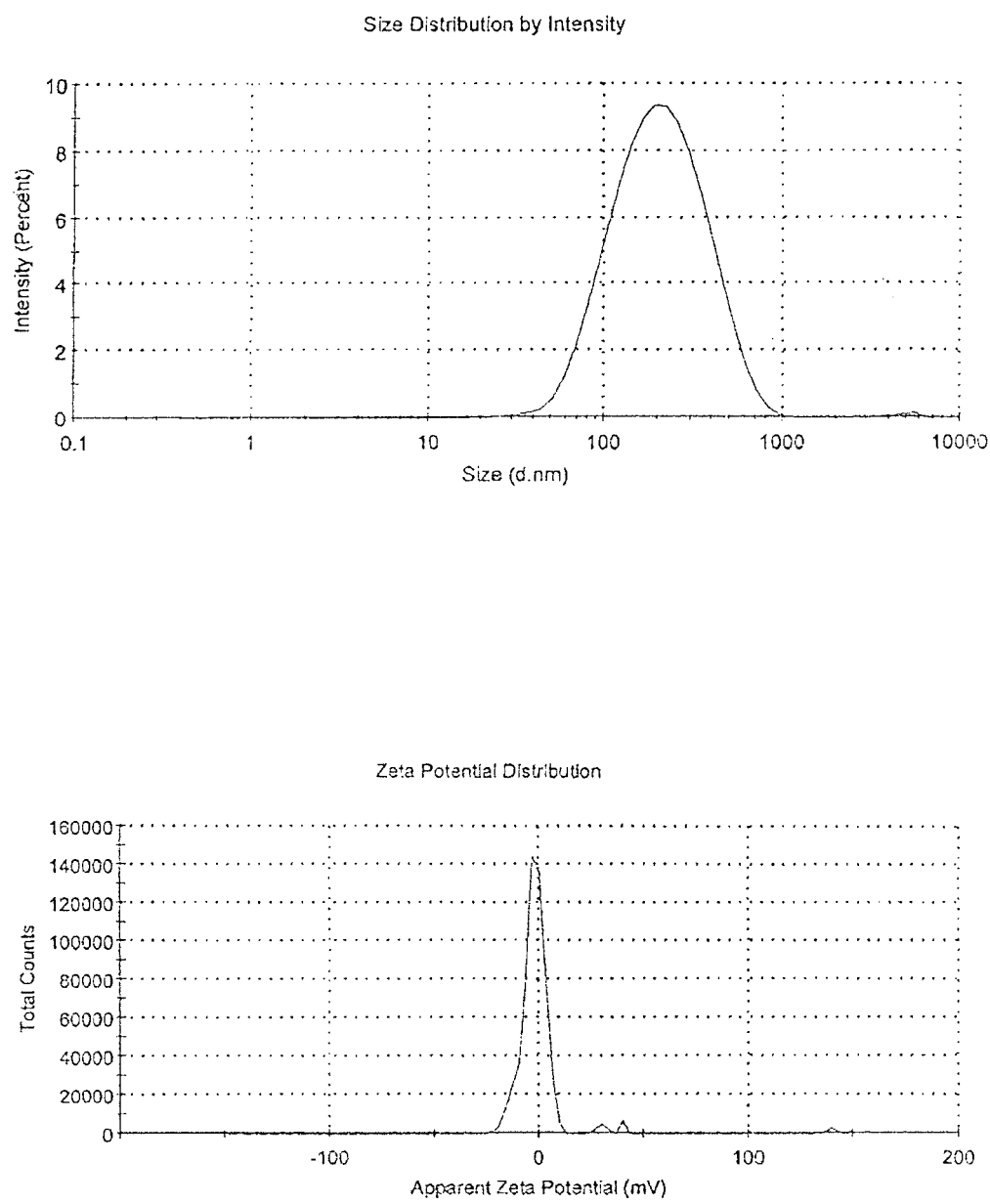
Figure 3:
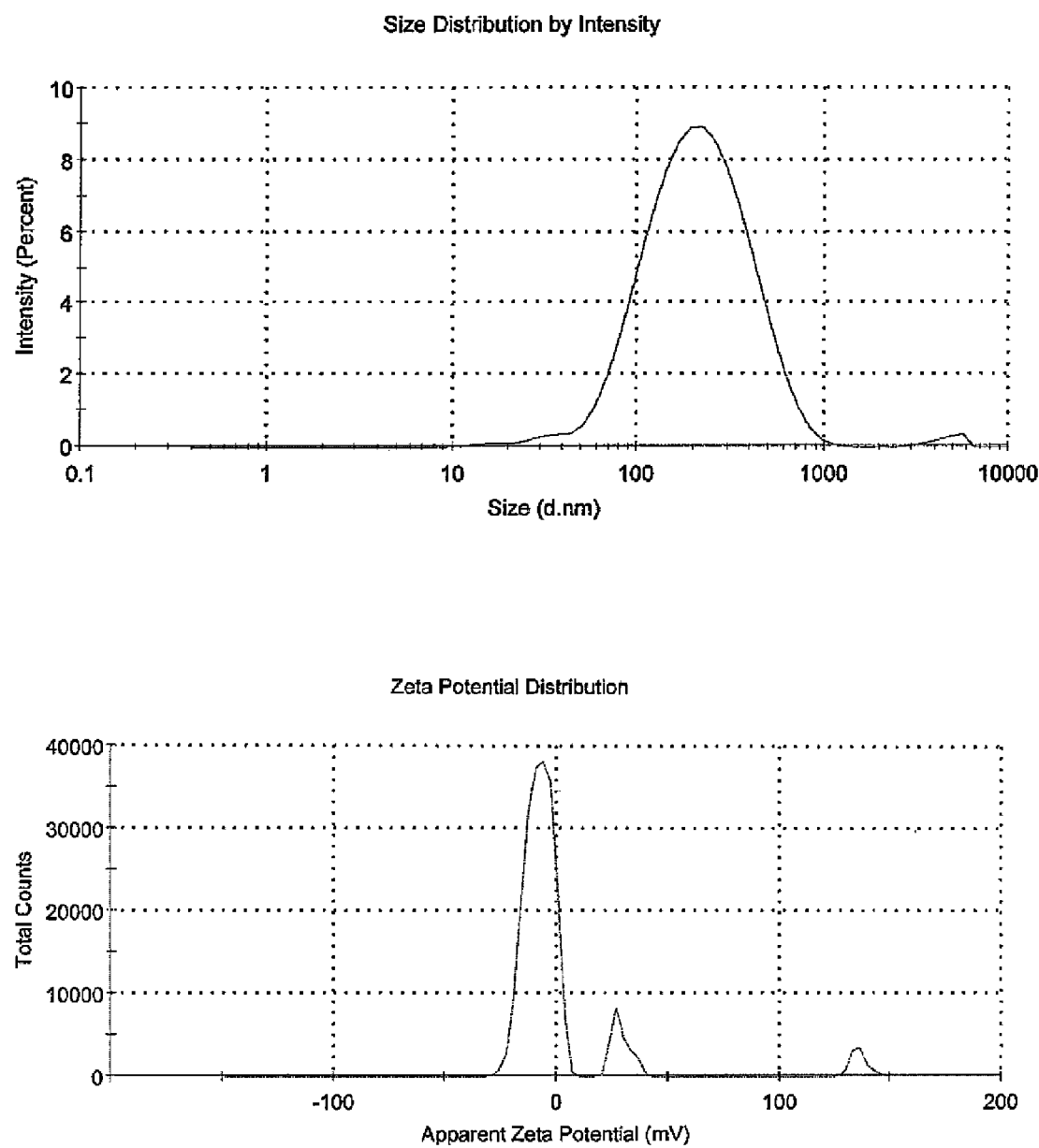
Figure 3F:
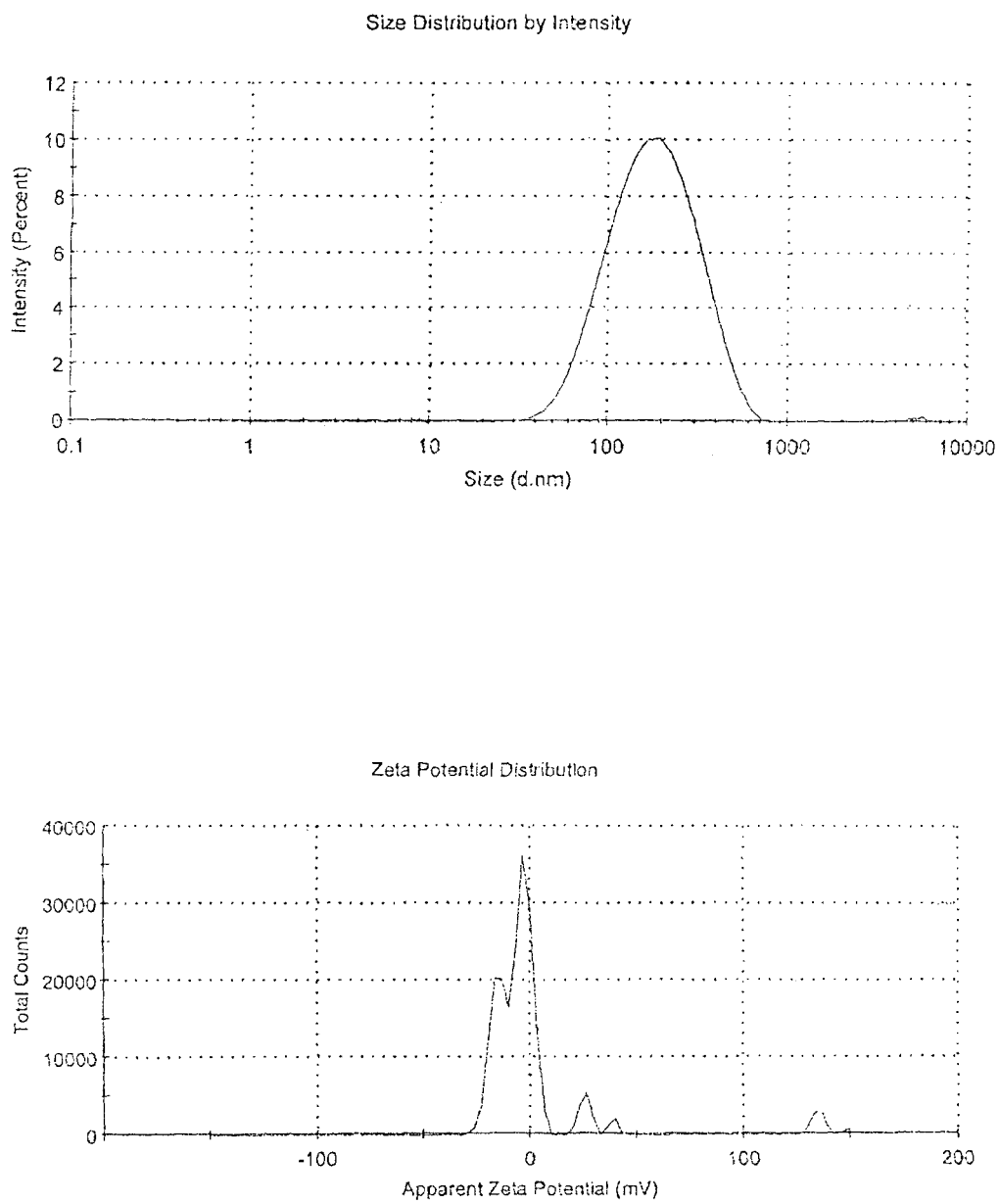
Figure 3G:
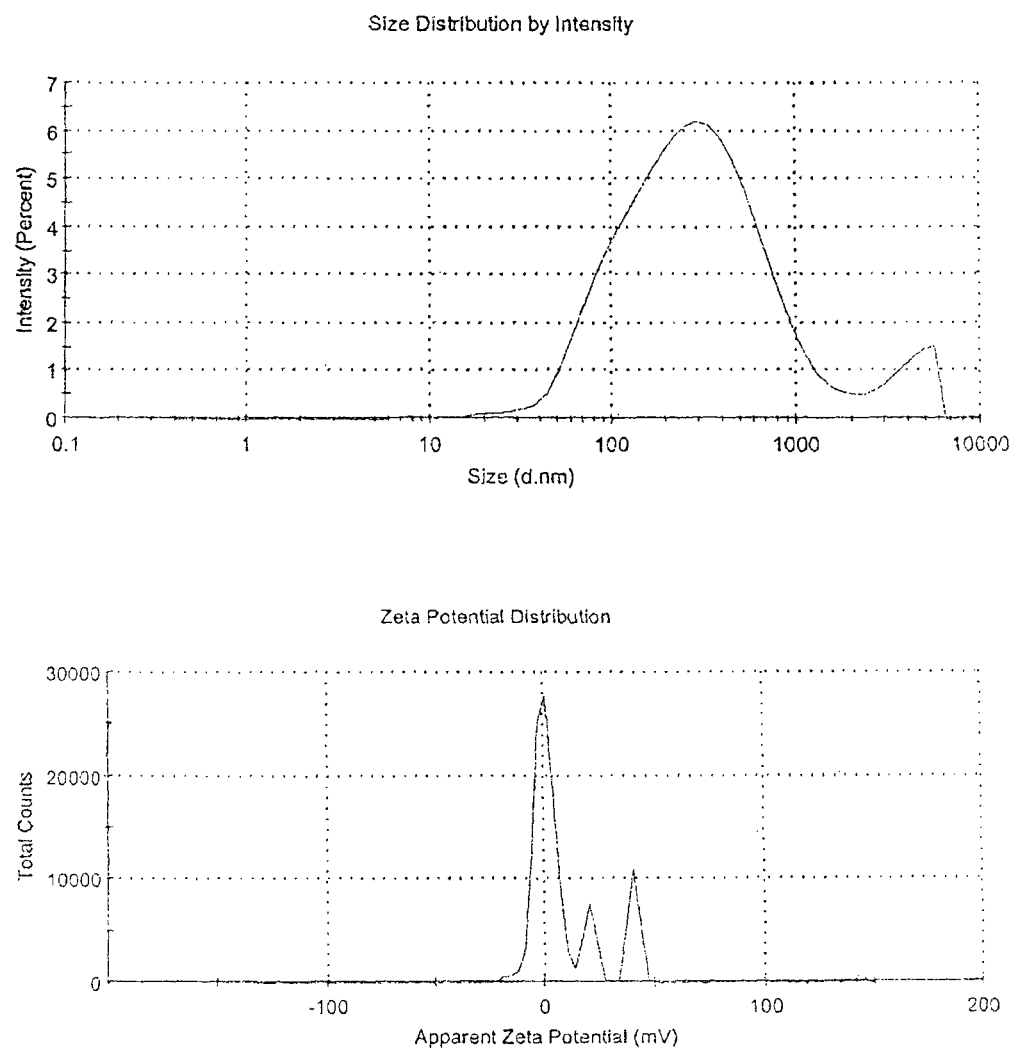
Figure 3H:
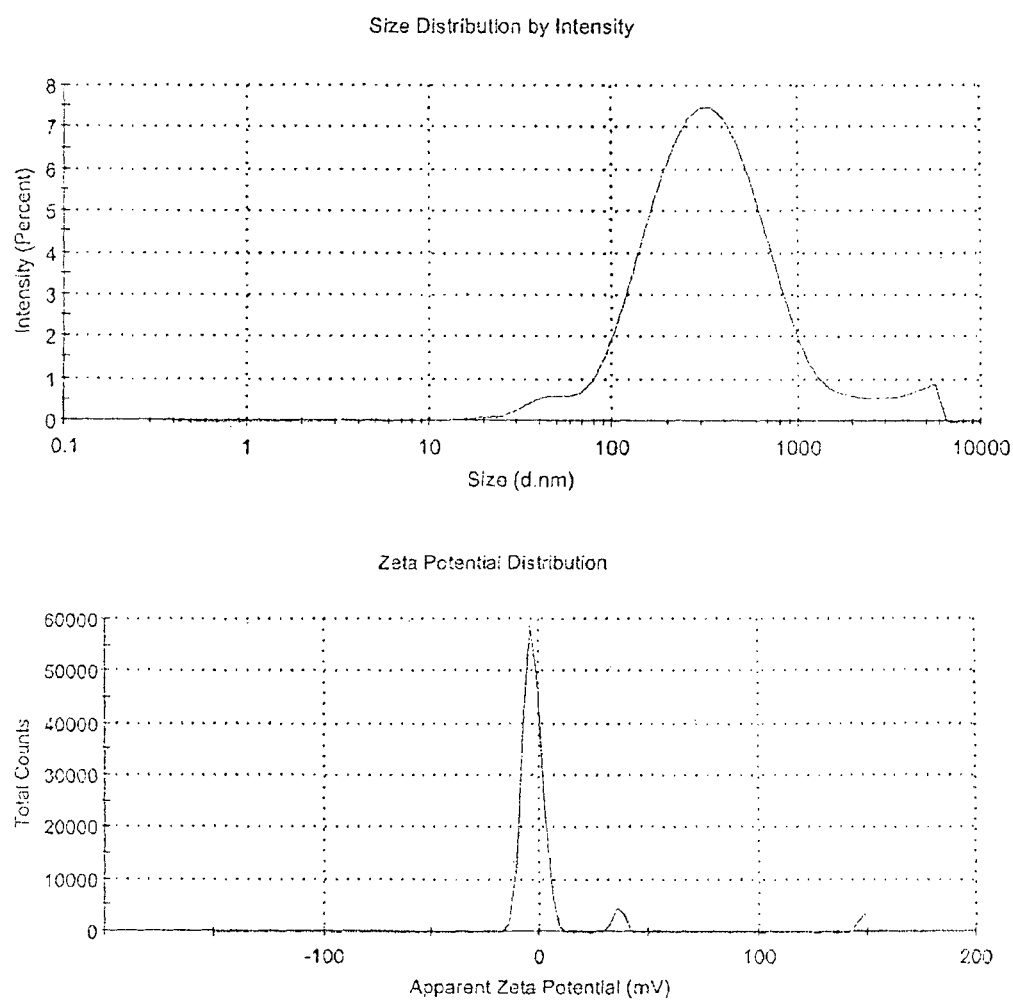
Figure 4A:
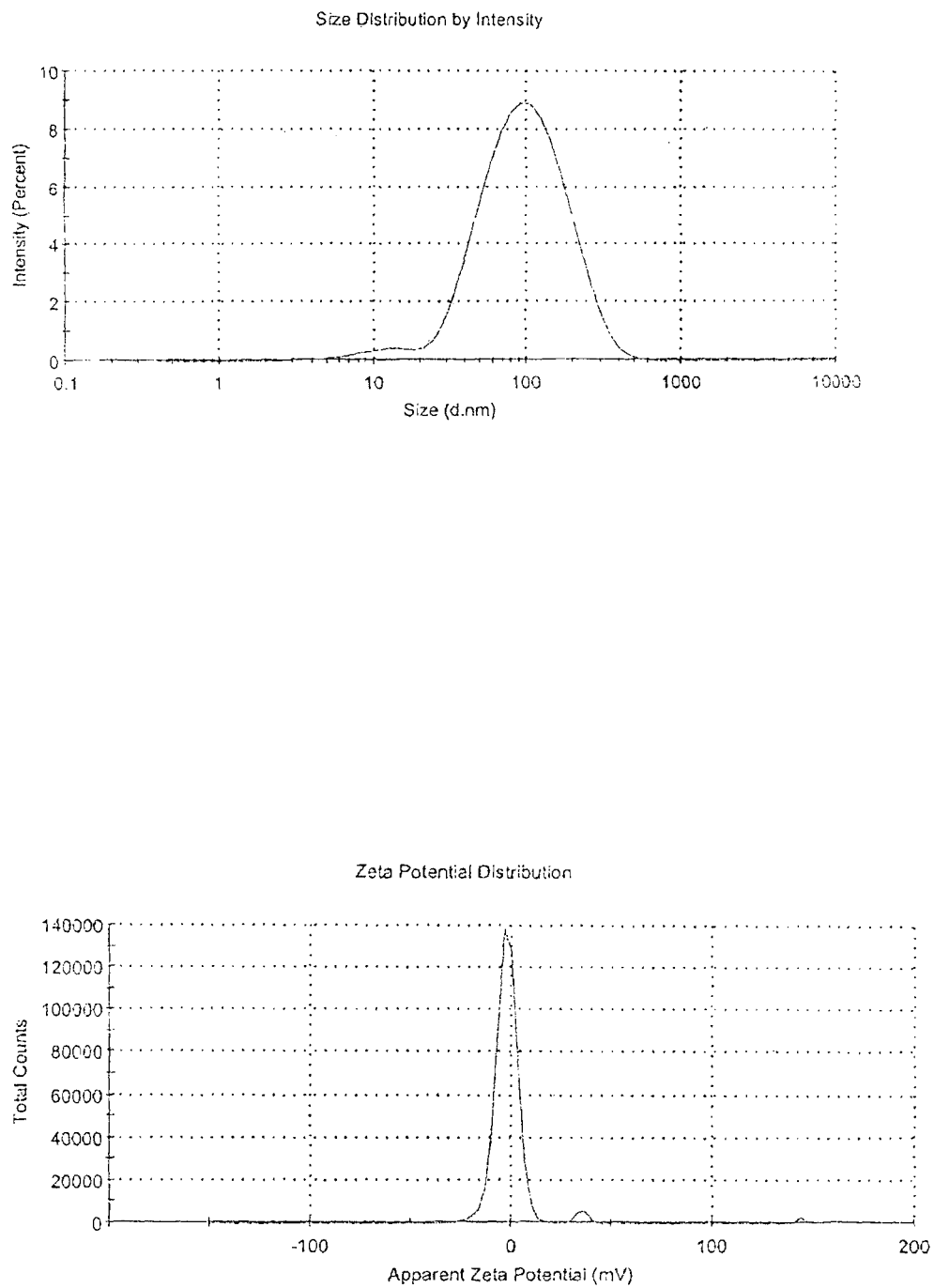
FIG. 4A to FIG. 4H depict particle size distribution in nanometre (nm), polydispersity index (PDI) and zeta potential (MV) of the exemplary composition No. 4 under various conditions.
Figure 4B:
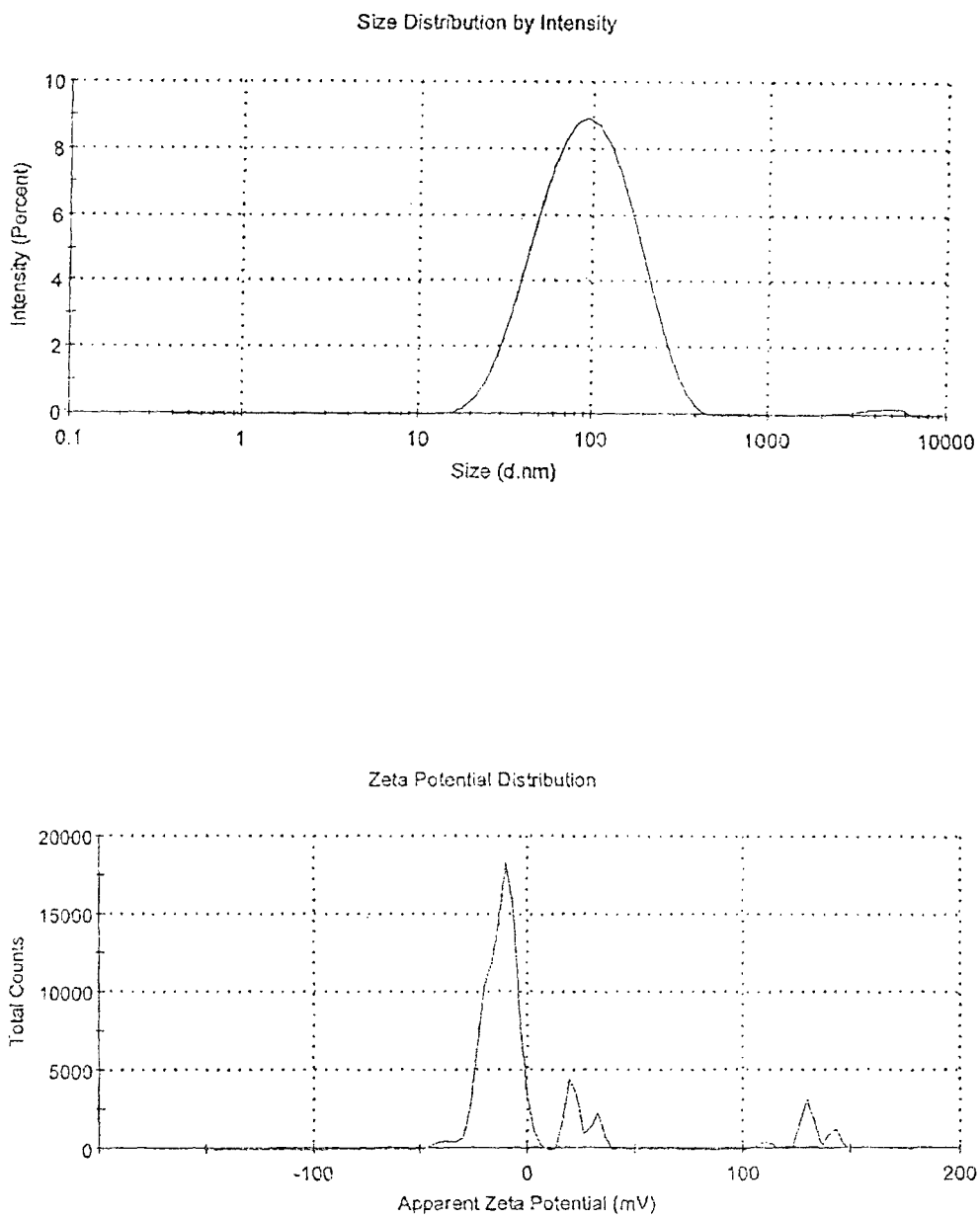
Figure 4C:
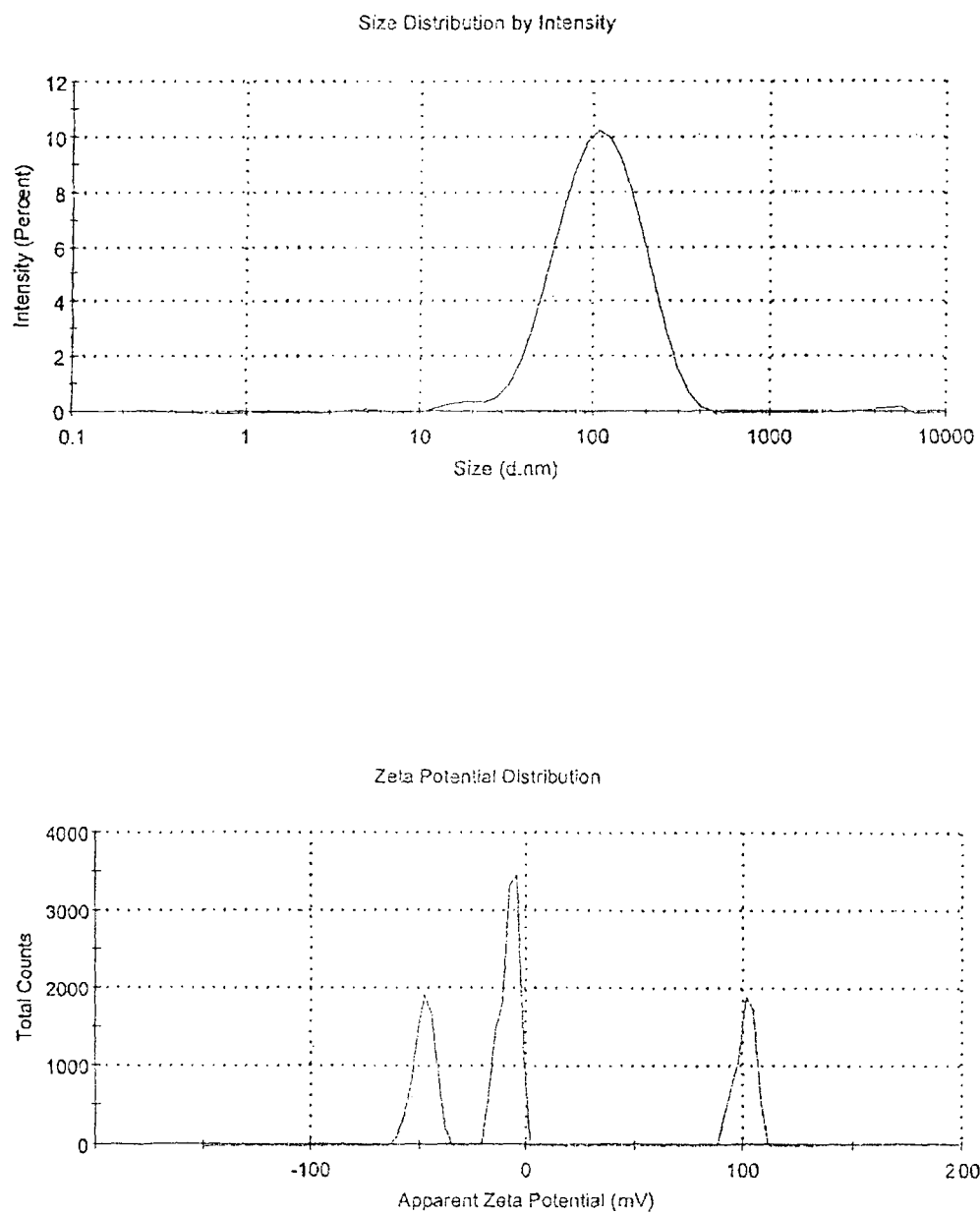
Figure 4D:
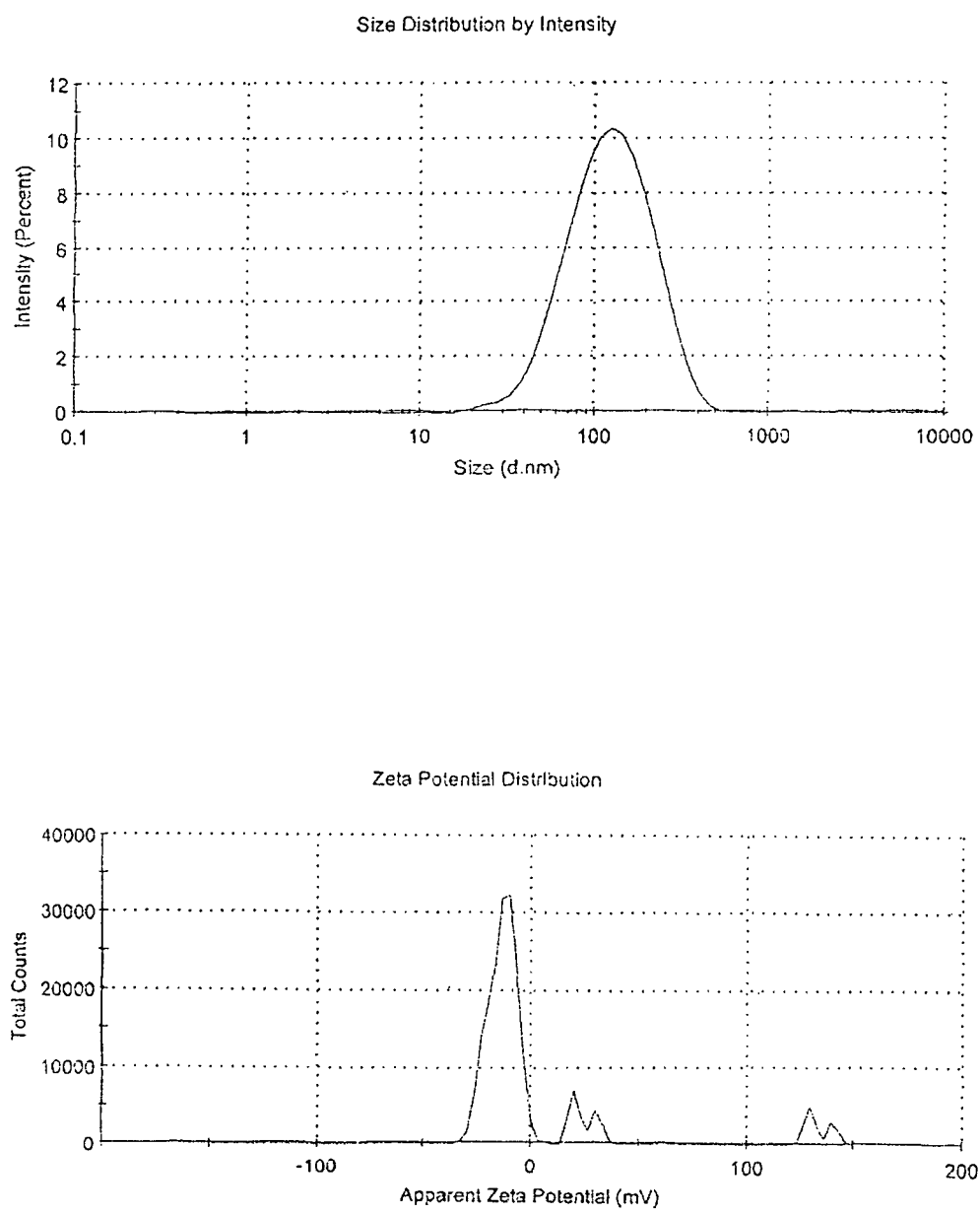
Figure 4:
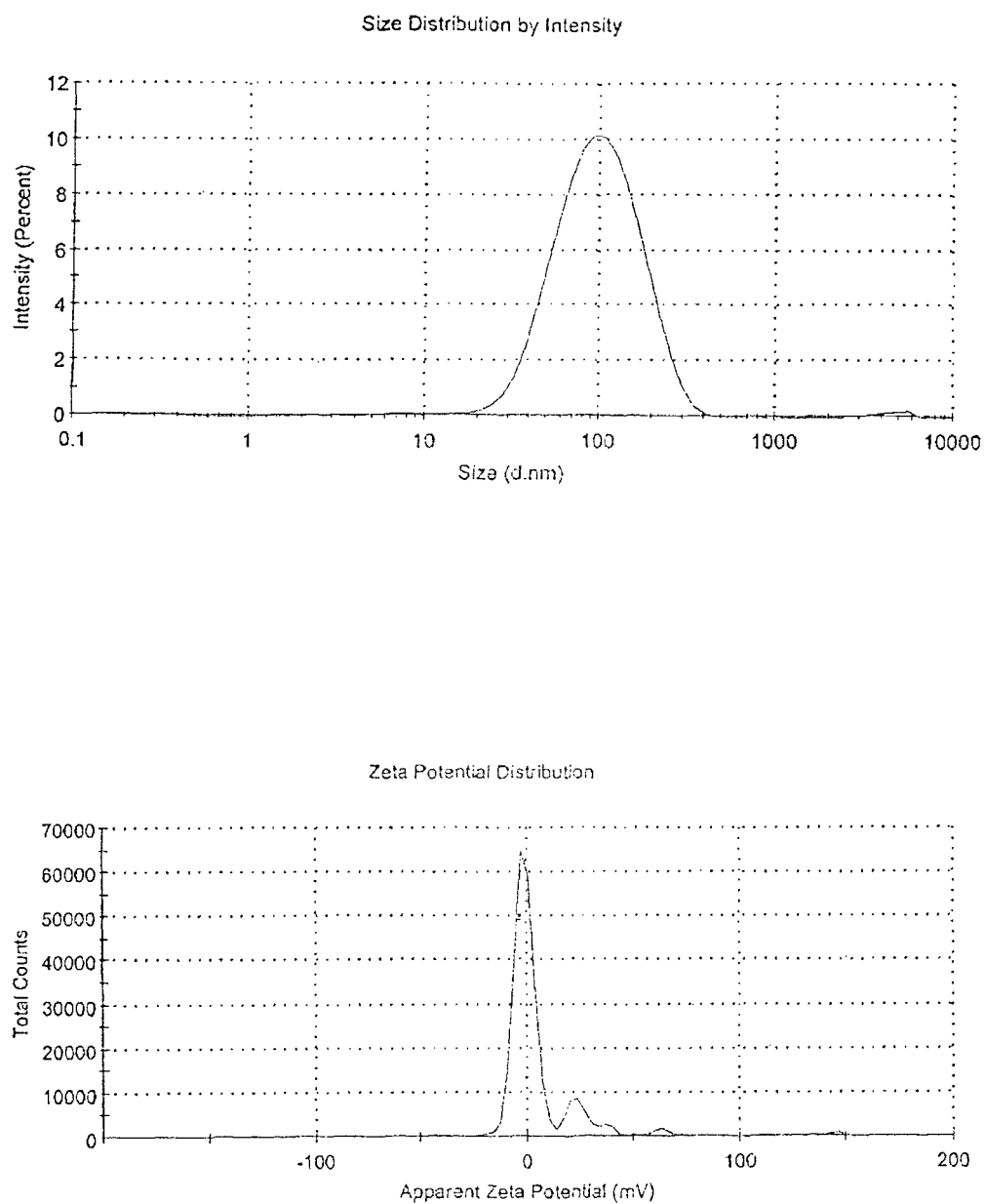
Figure 4F:
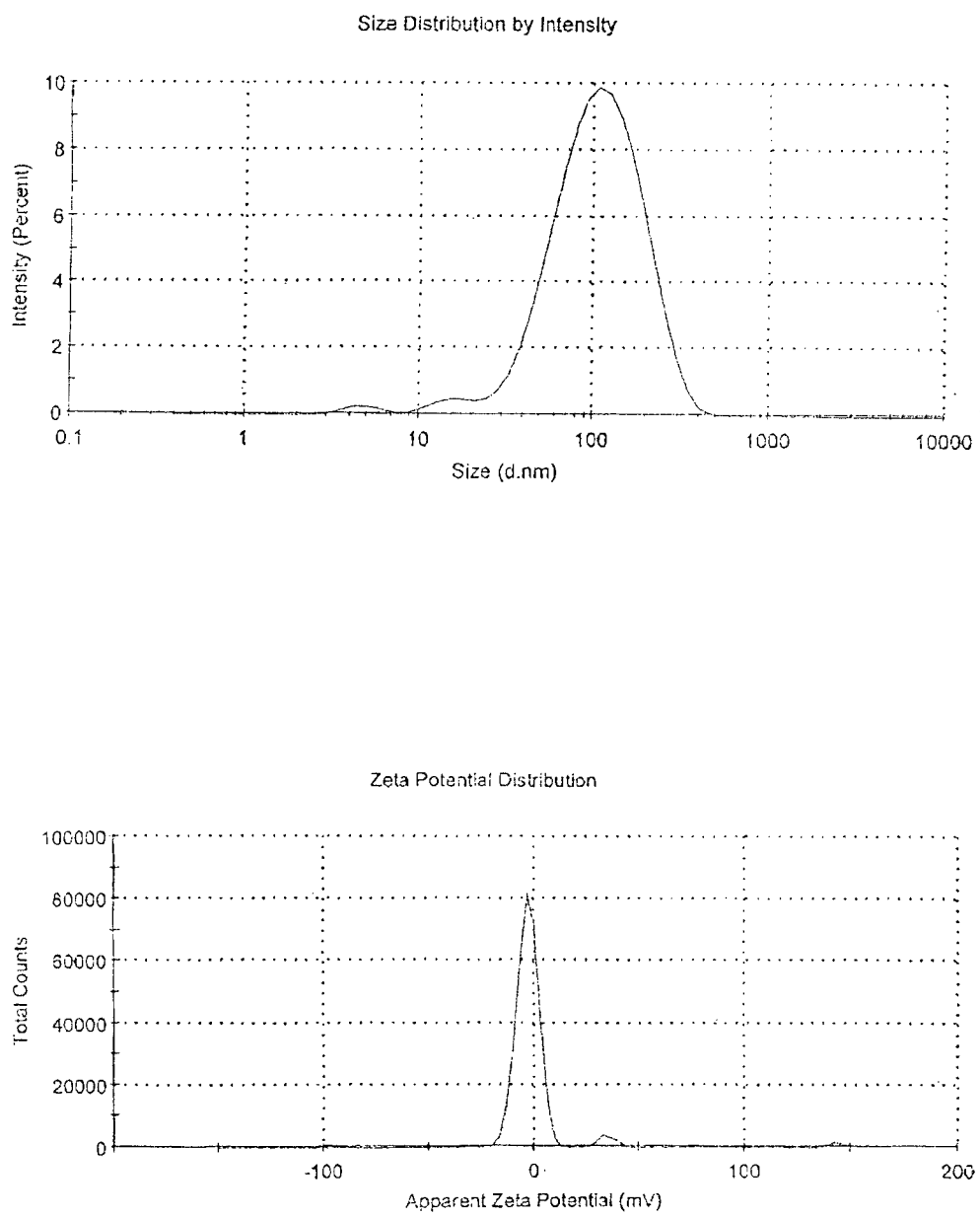
Figure 4G:
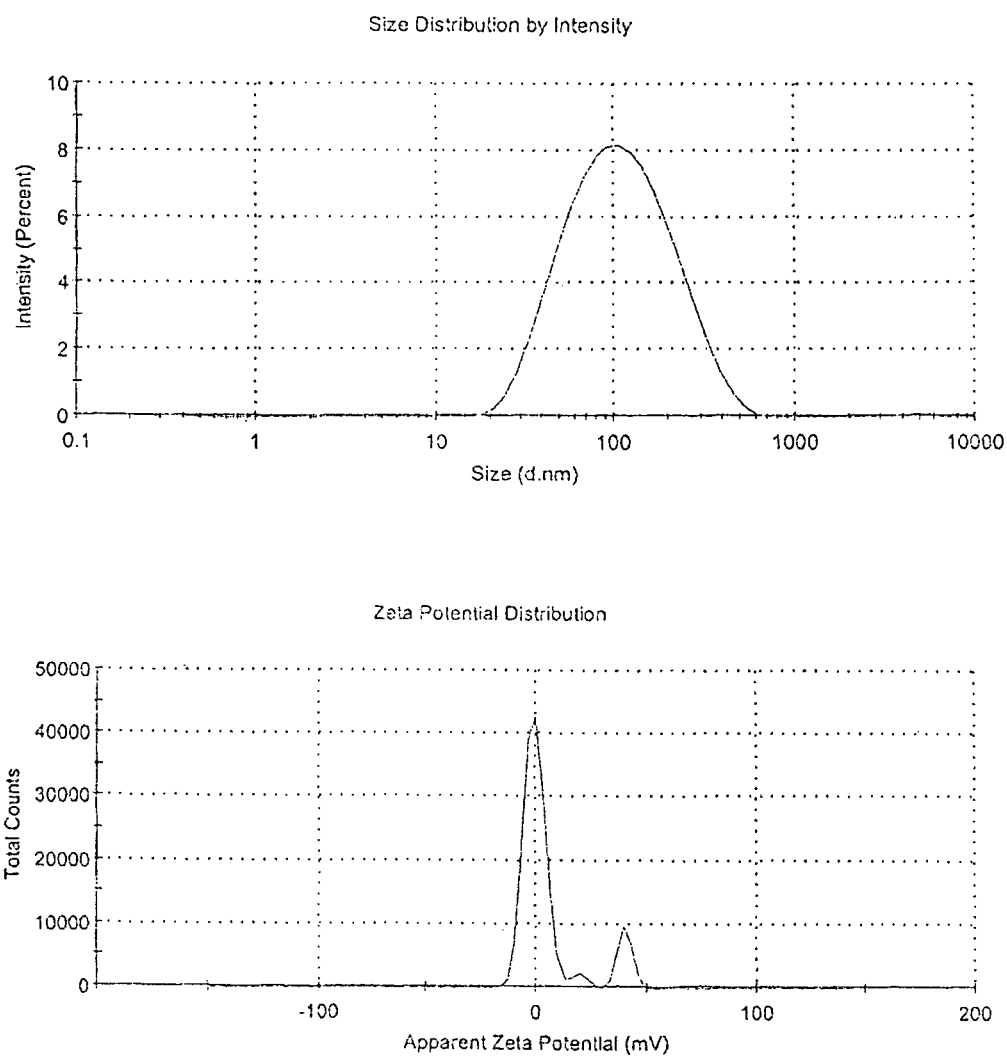
Figure 4H:
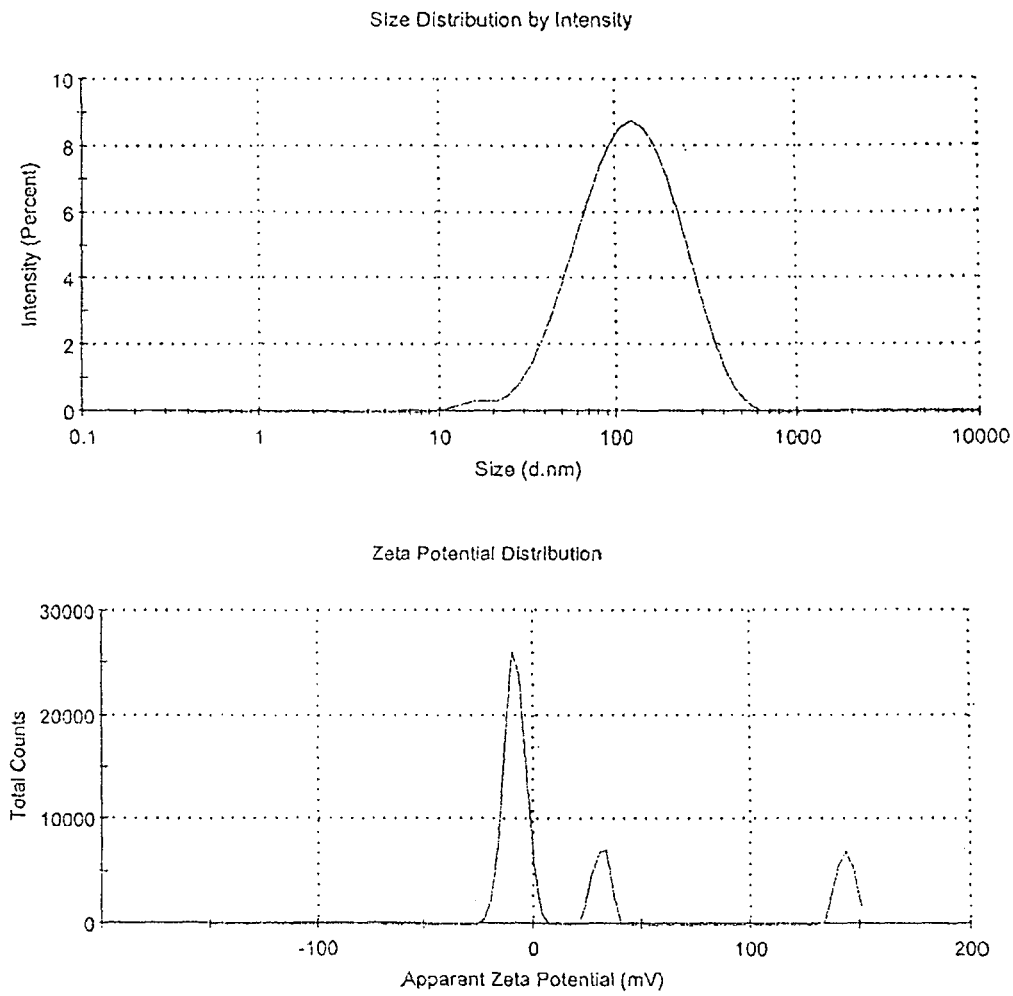
Figure 5A:
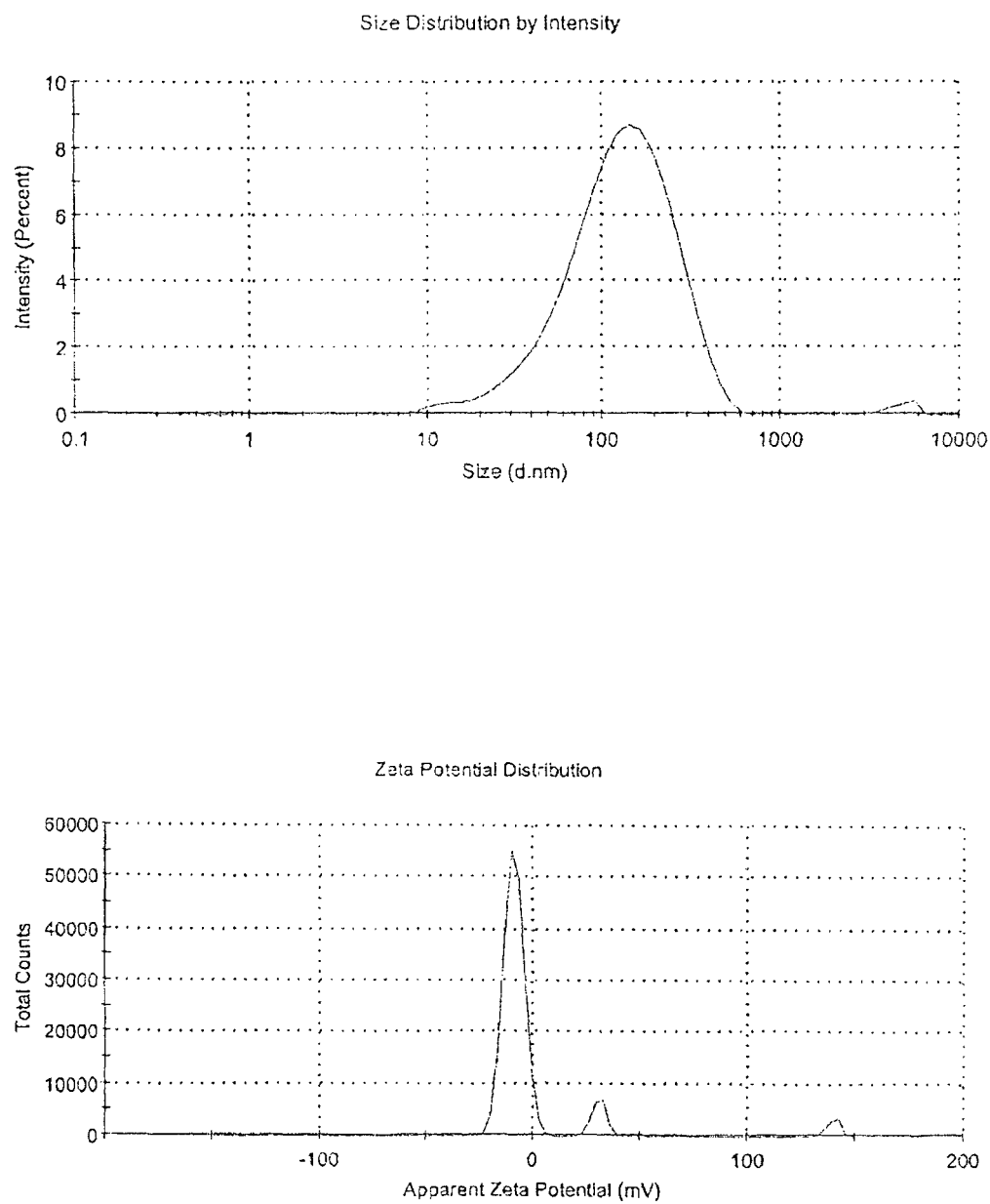
FIG. 5A to FIG. 5E depict particle size distribution in nanometre (nm), polydispersity index (PDI) and zeta potential (MV) of the exemplary composition No. 5 of the present invention under various conditions.
Figure 5B:
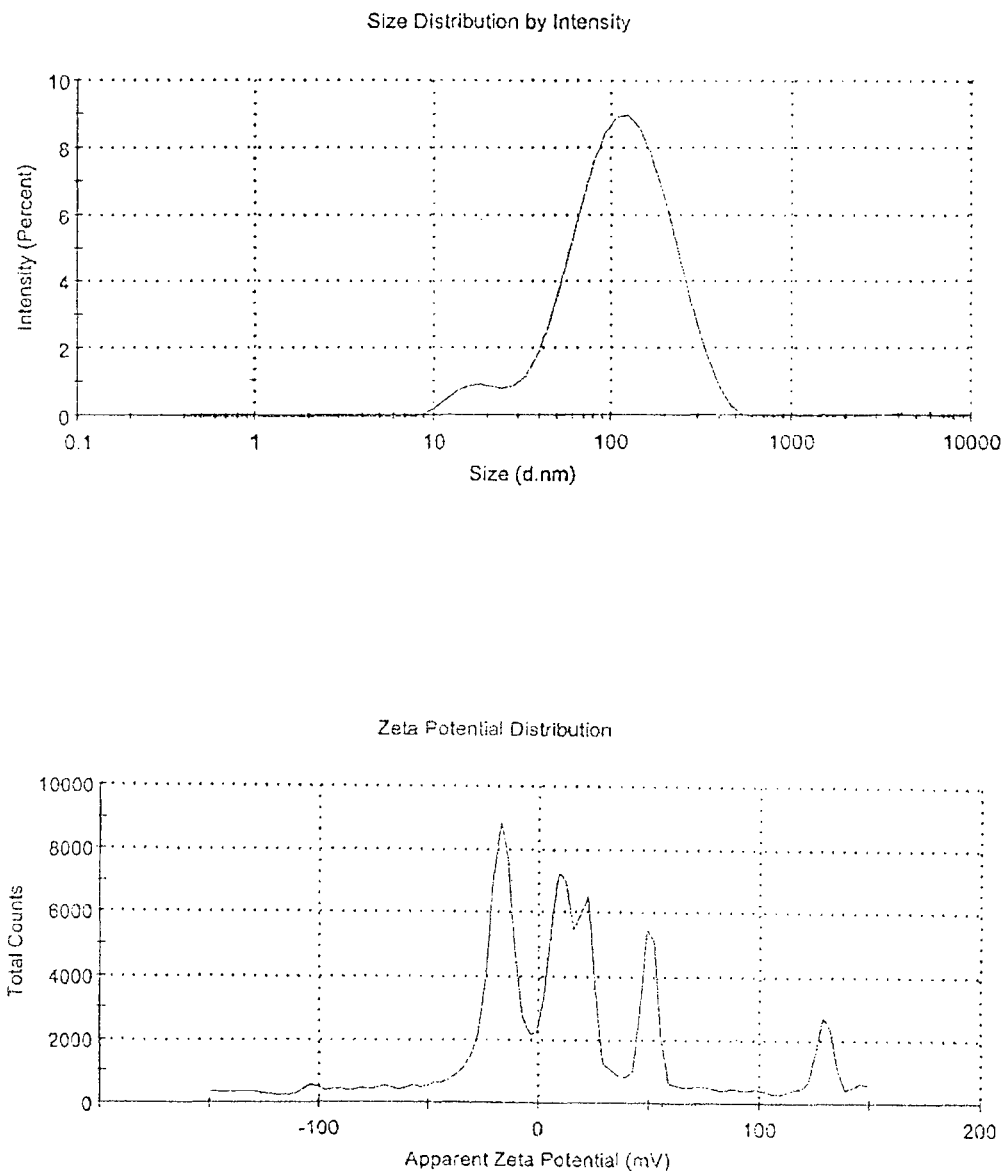
Figure 5C:
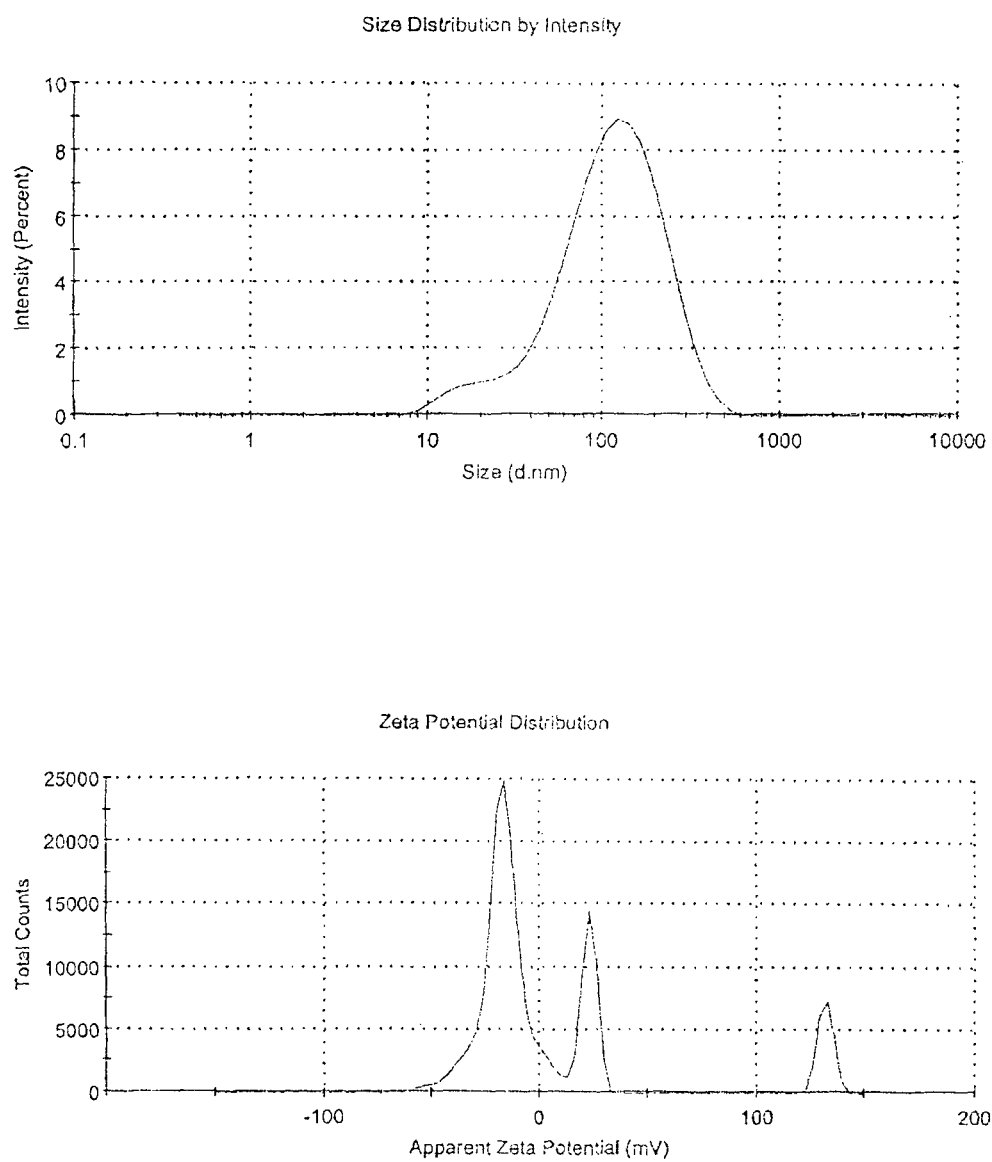
Figure 5:
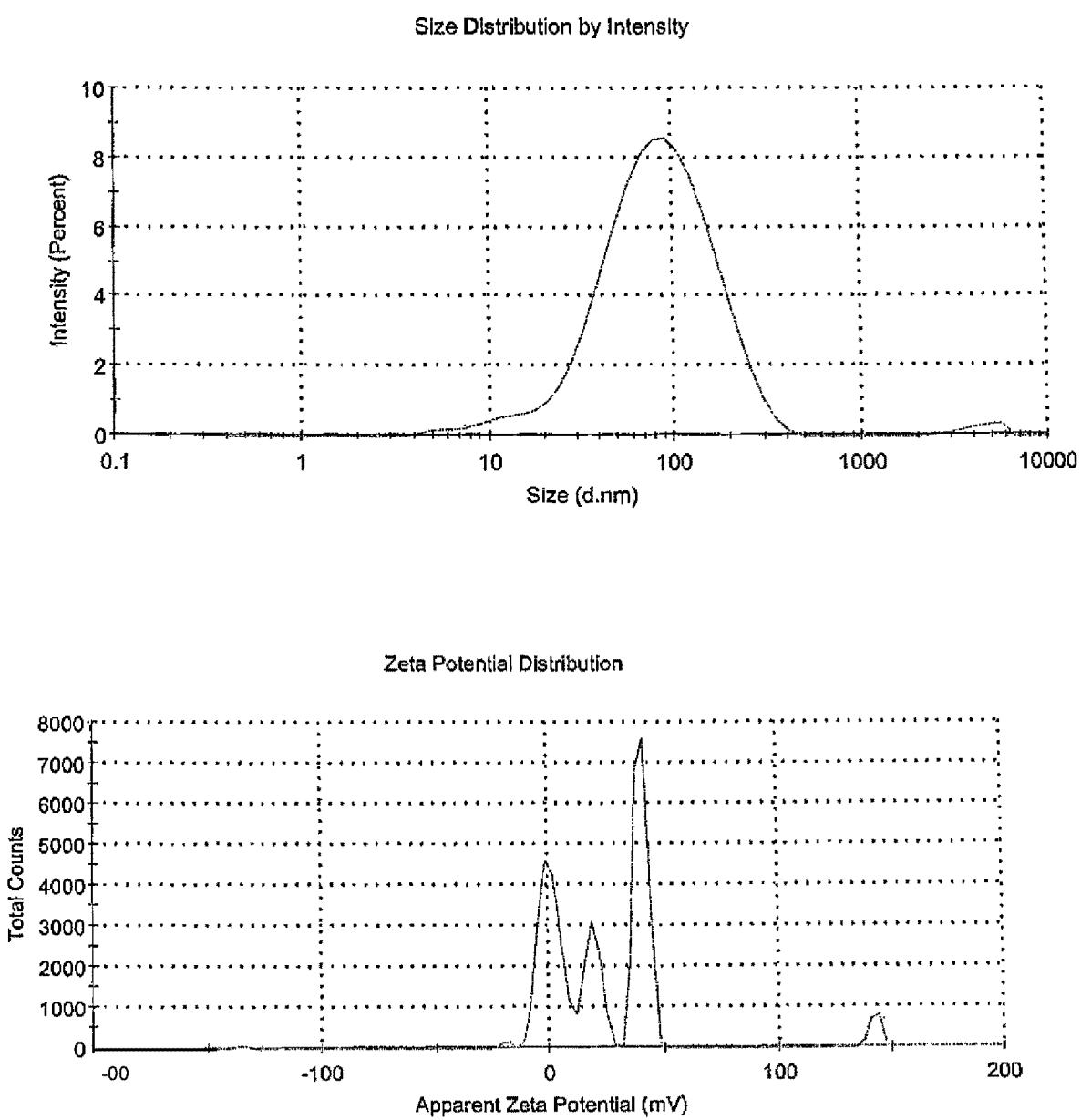
Figure 5E:
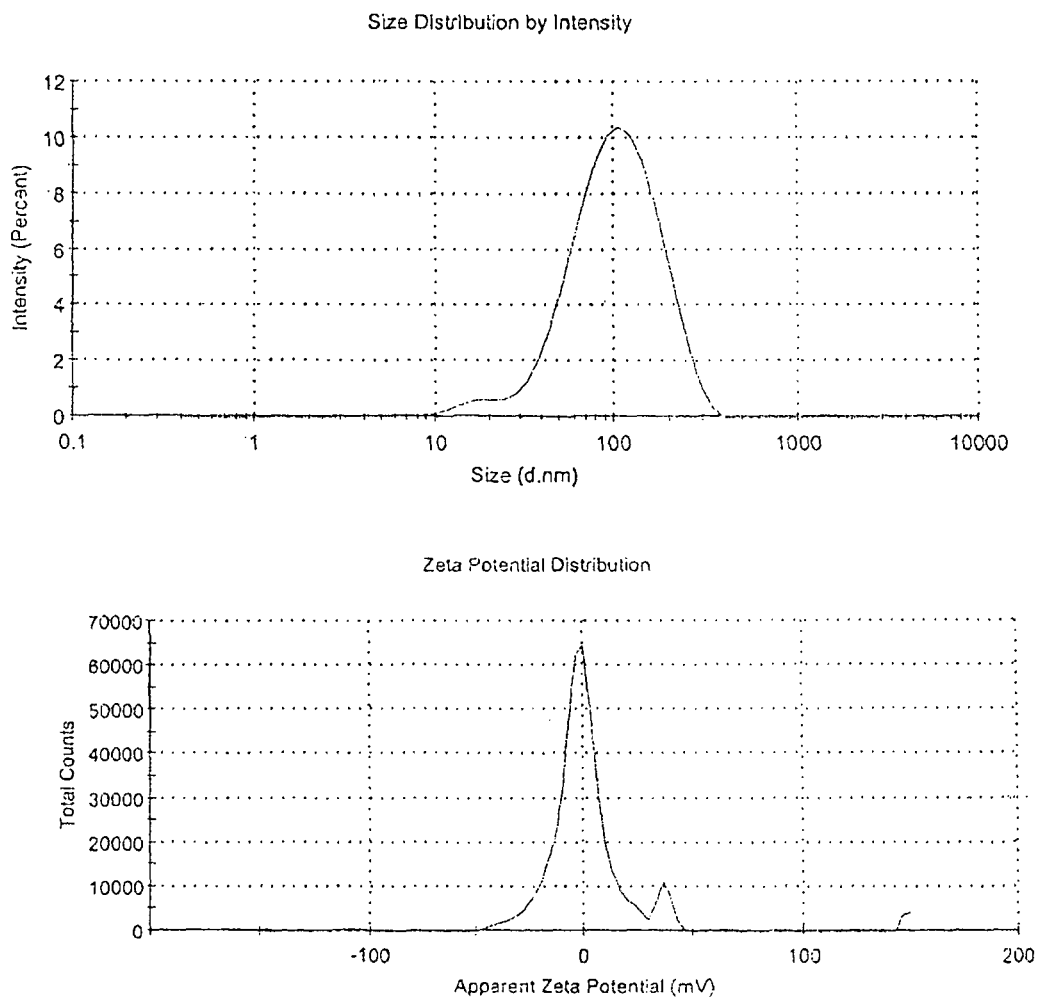
Figure 6A:
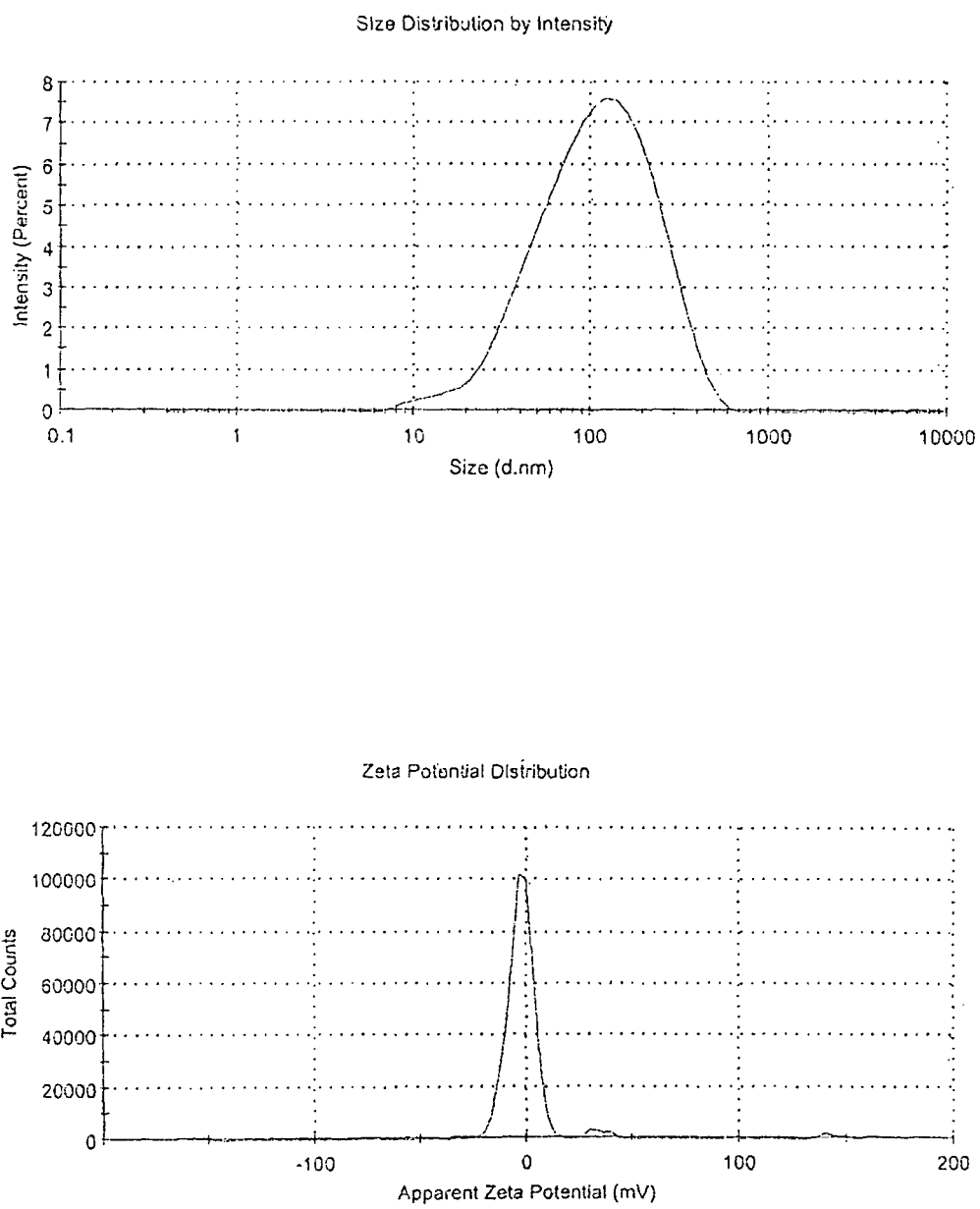
FIG. 6A to FIG. 6E depict particle size distribution in nanometre (nm), polydispersity index (PDI) and zeta potential (MV) of the exemplary composition No. 6 of the present invention under various conditions.
Figure 6B:
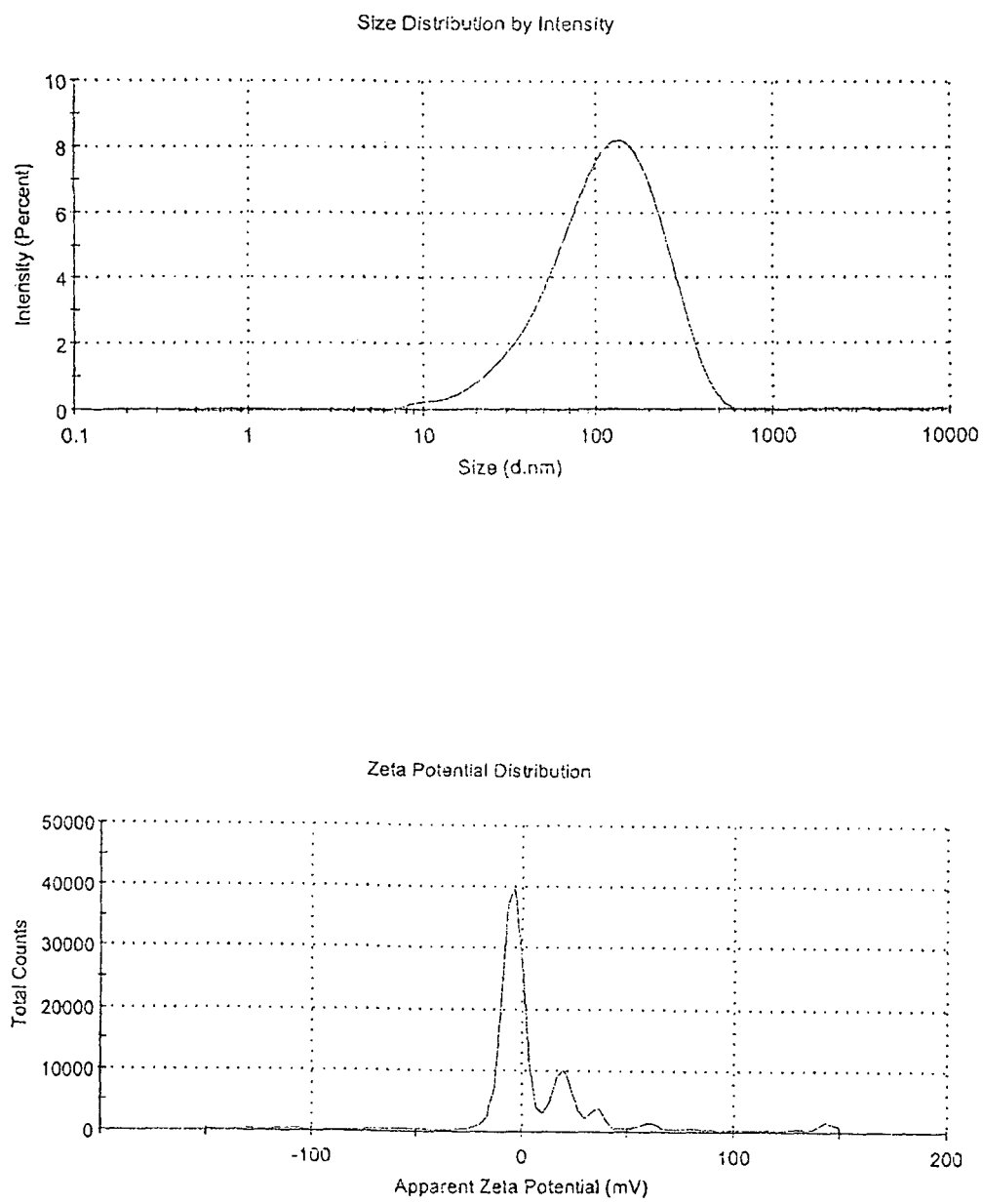
Figure 6C:
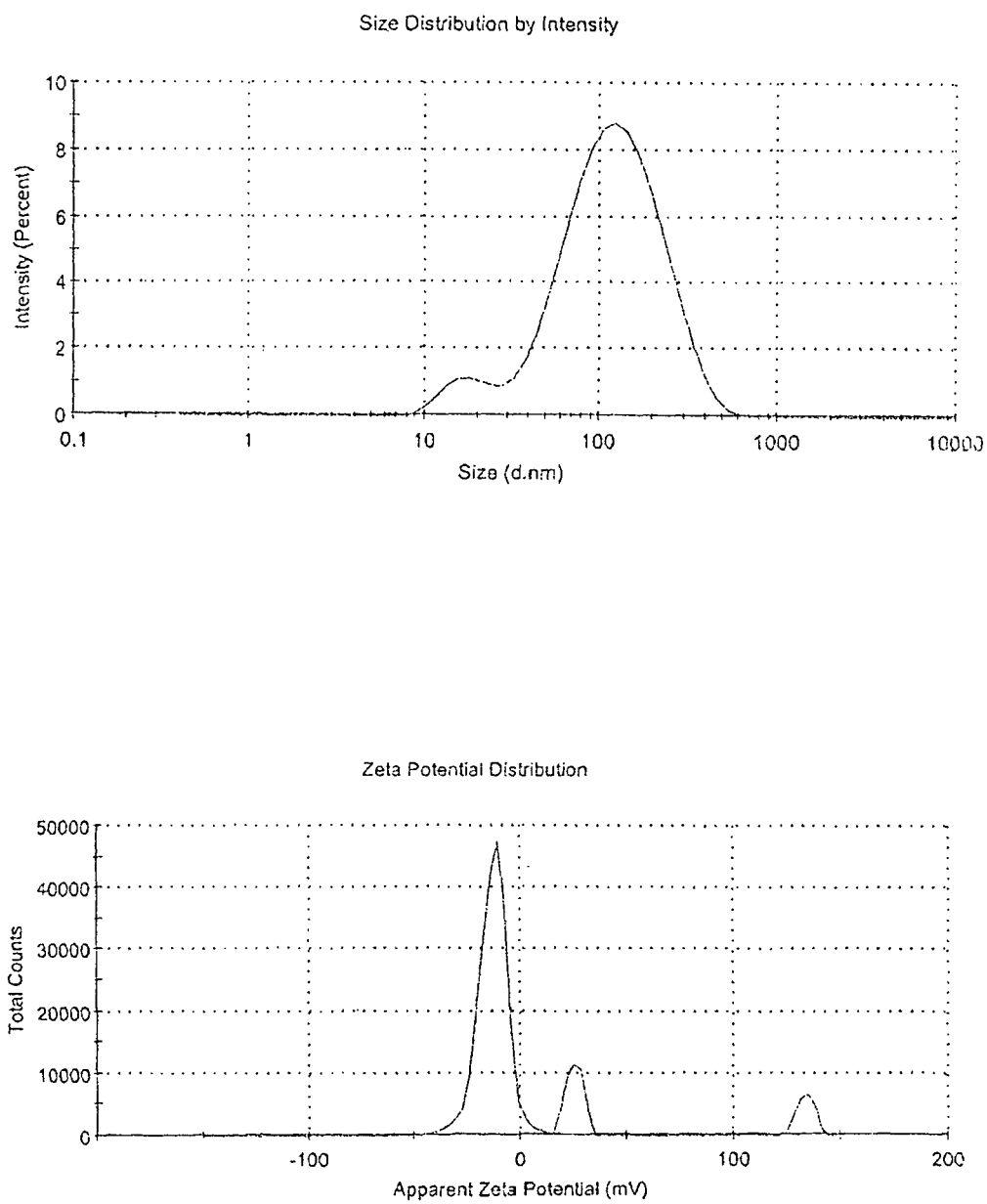
Figure 6D:
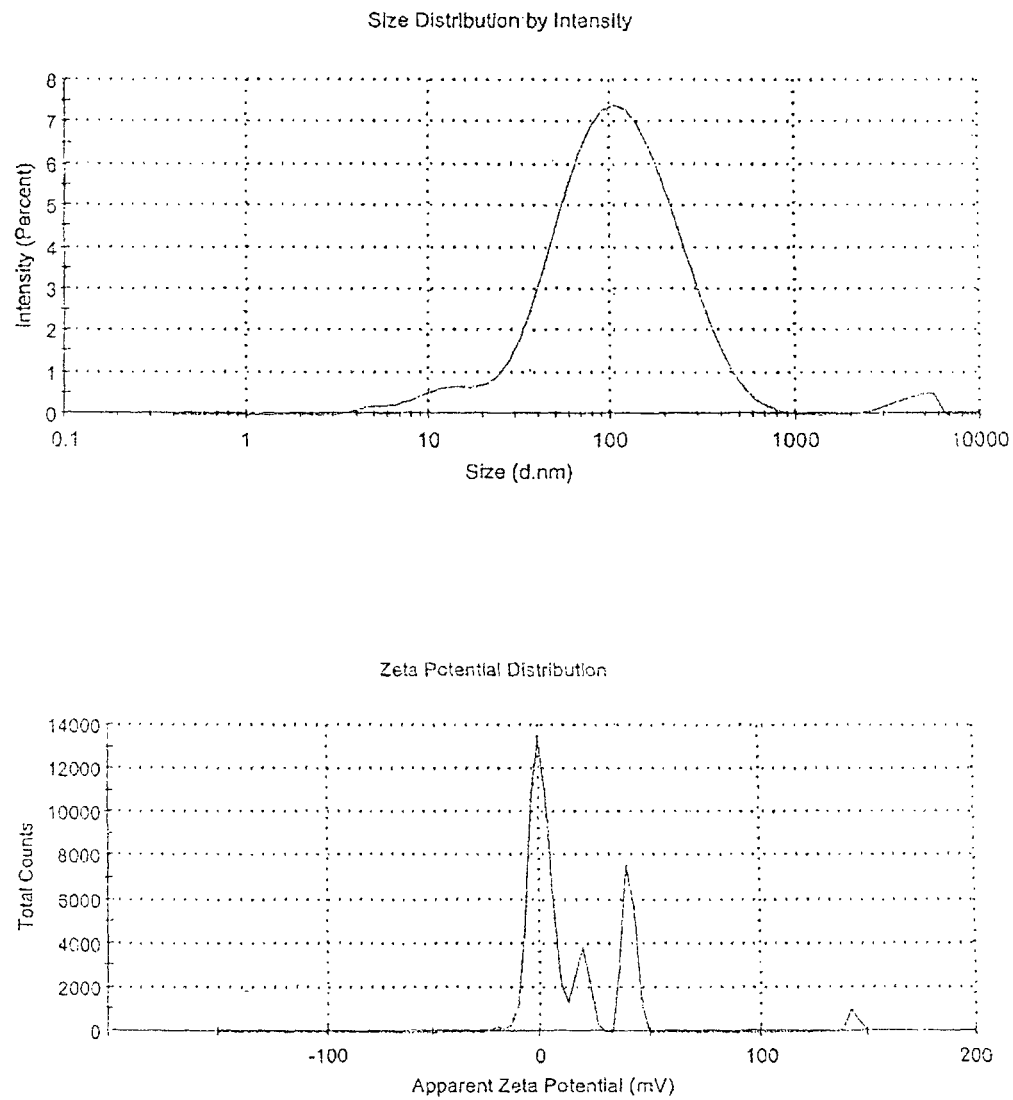
Figure 6E:
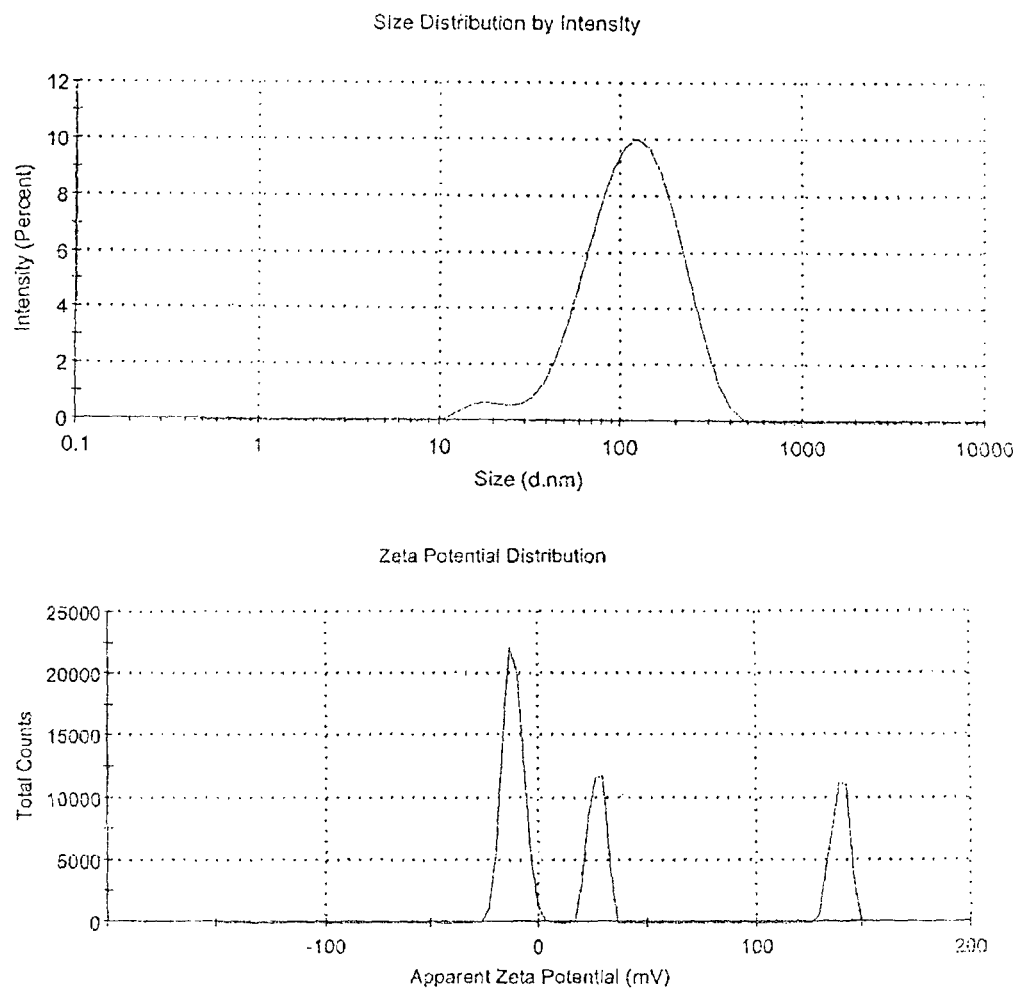
Figure 7A:
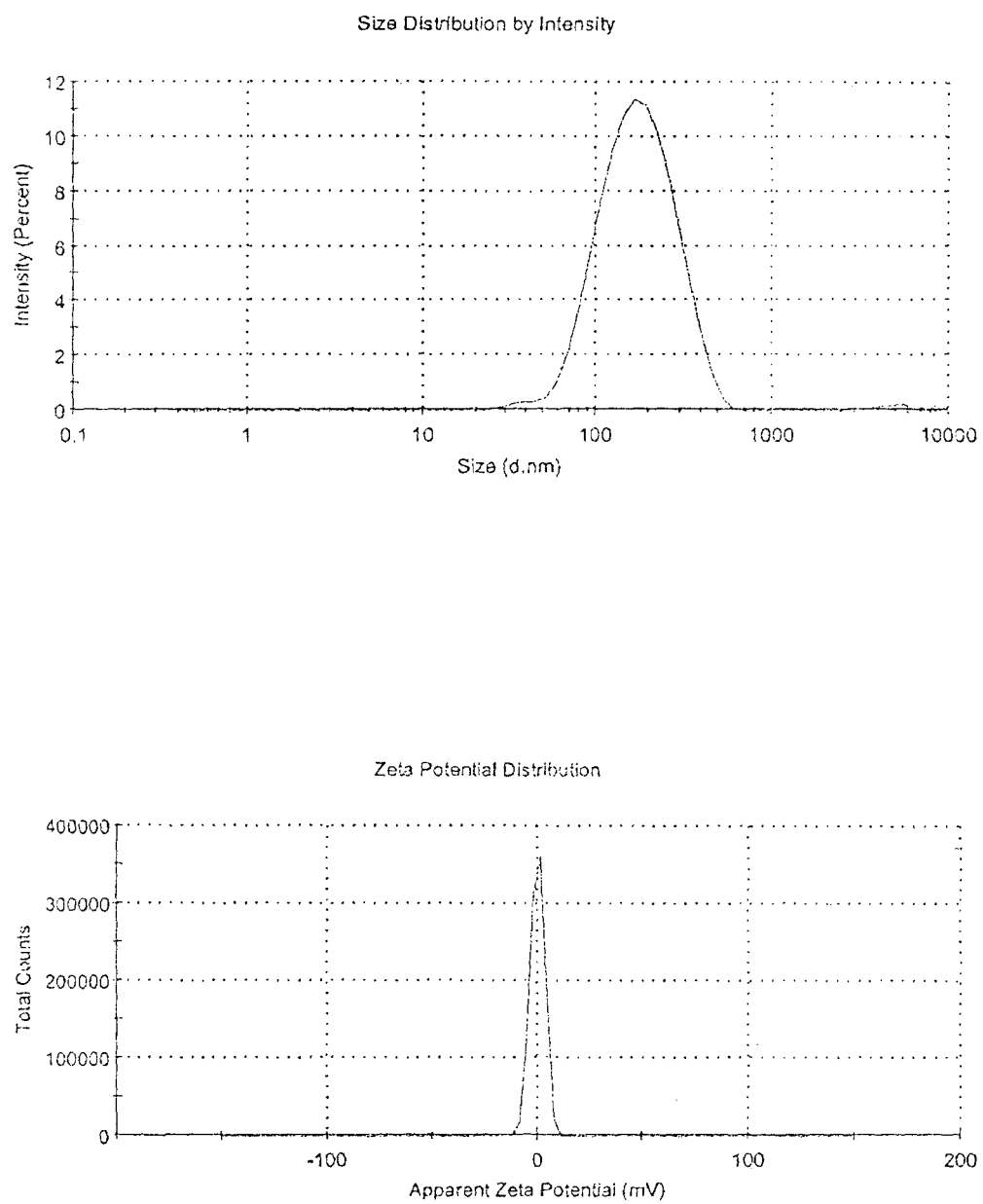
FIG. 7A to FIG. 7F depict particle size distribution in nanometre (nm), polydispersity index (PDI) and zeta potential (MV) of the exemplary composition No. 7 of the present invention under various conditions.
Figure 7B:
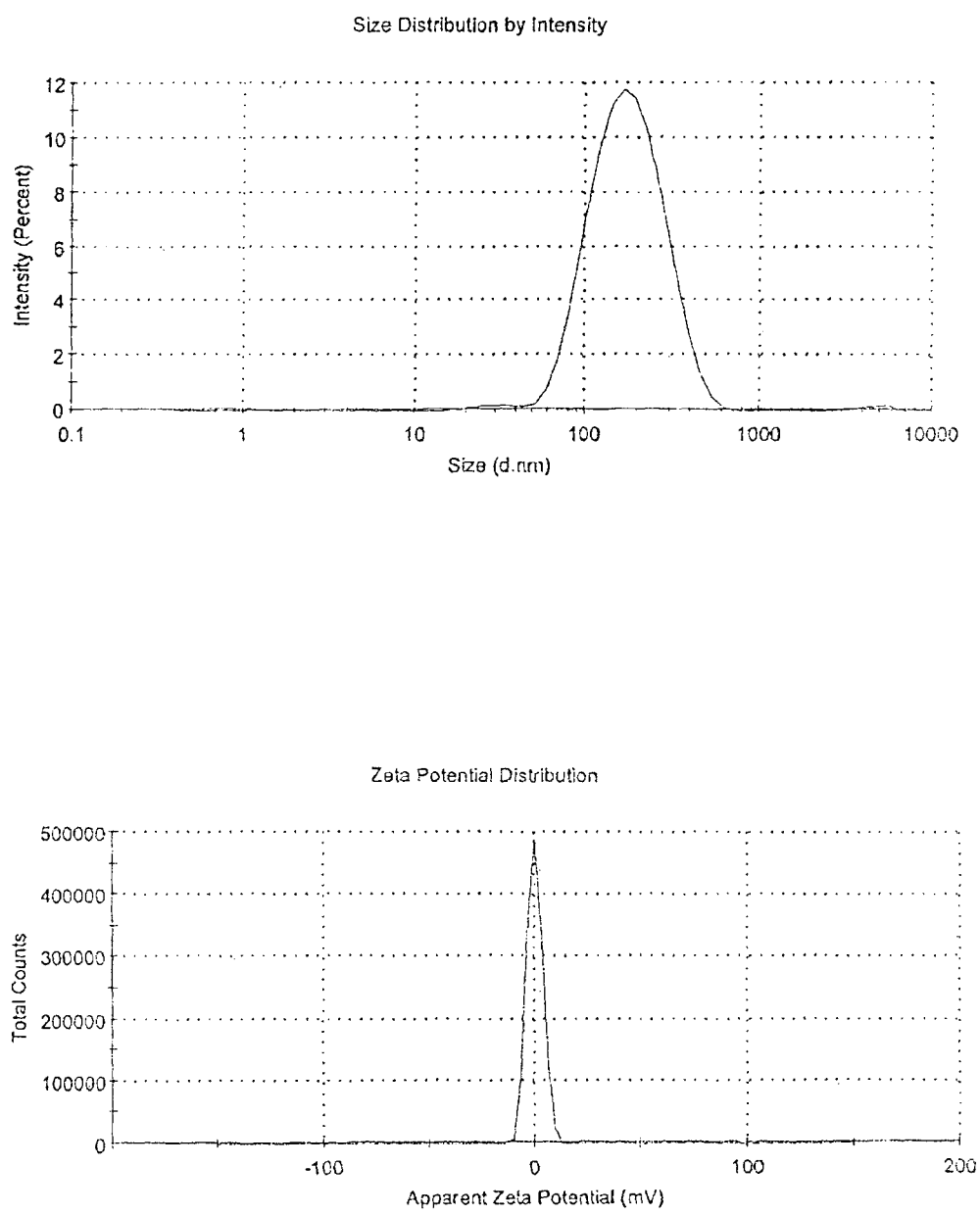
Figure 7C:
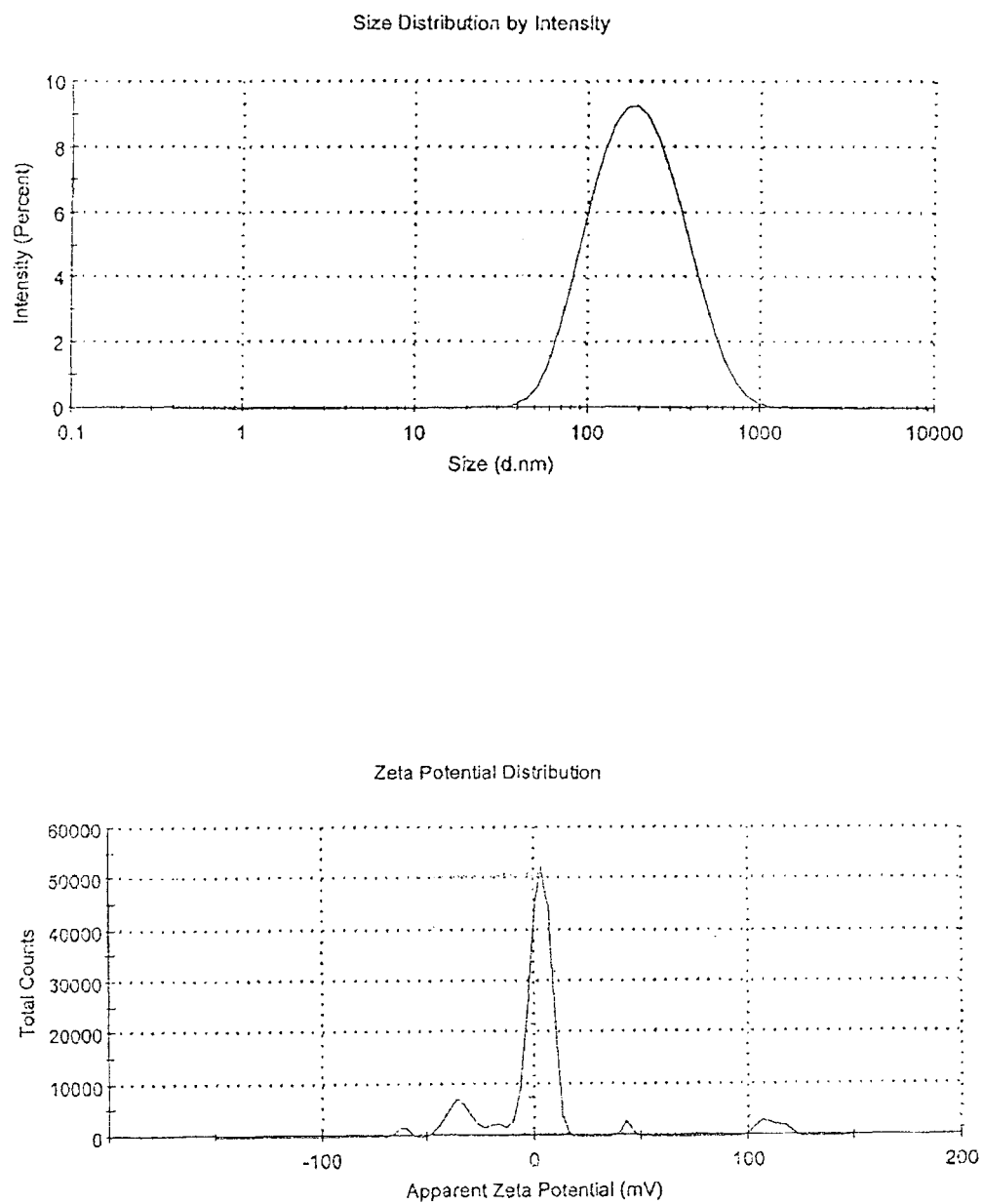
Figure 7D:
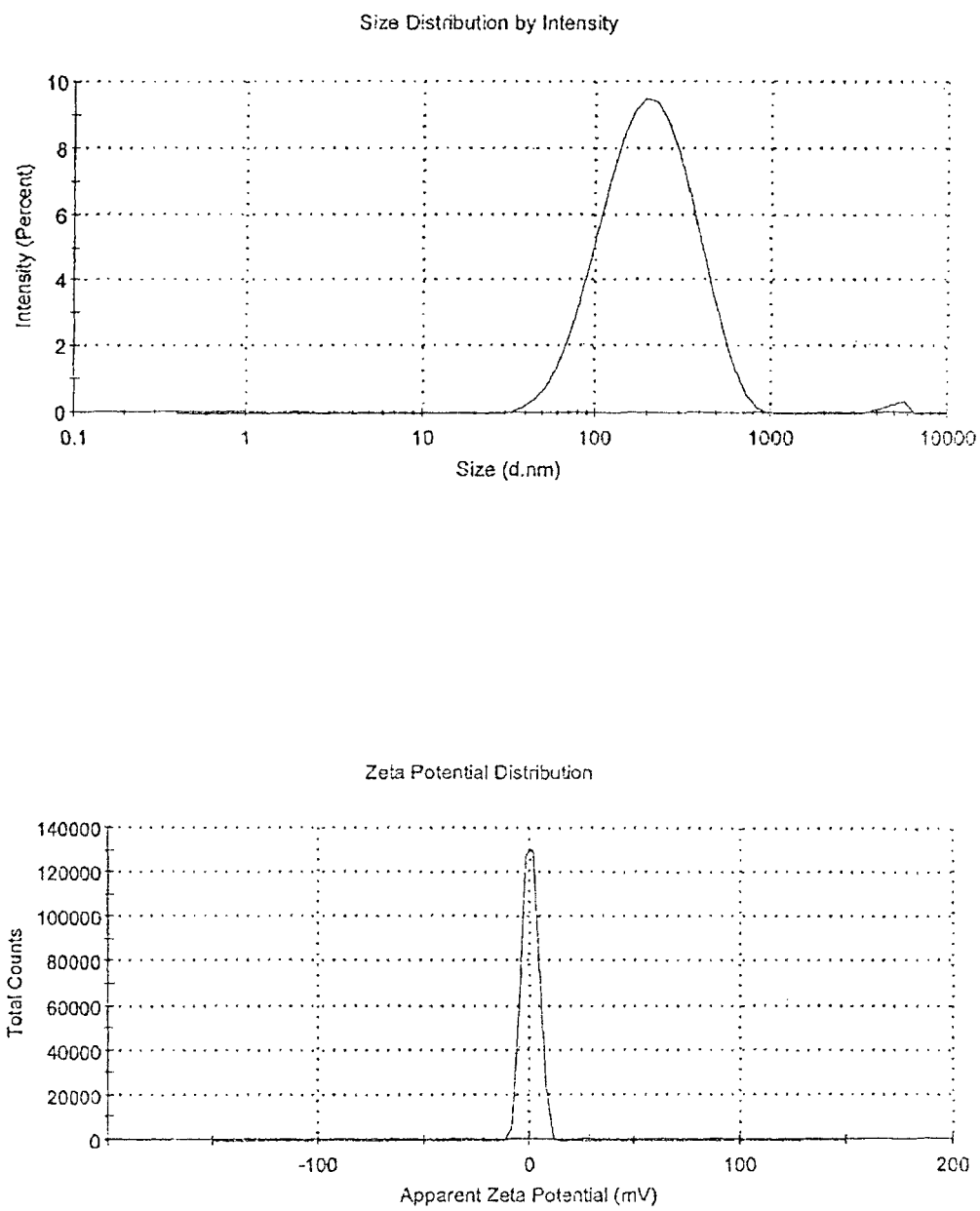
Figure 7E:
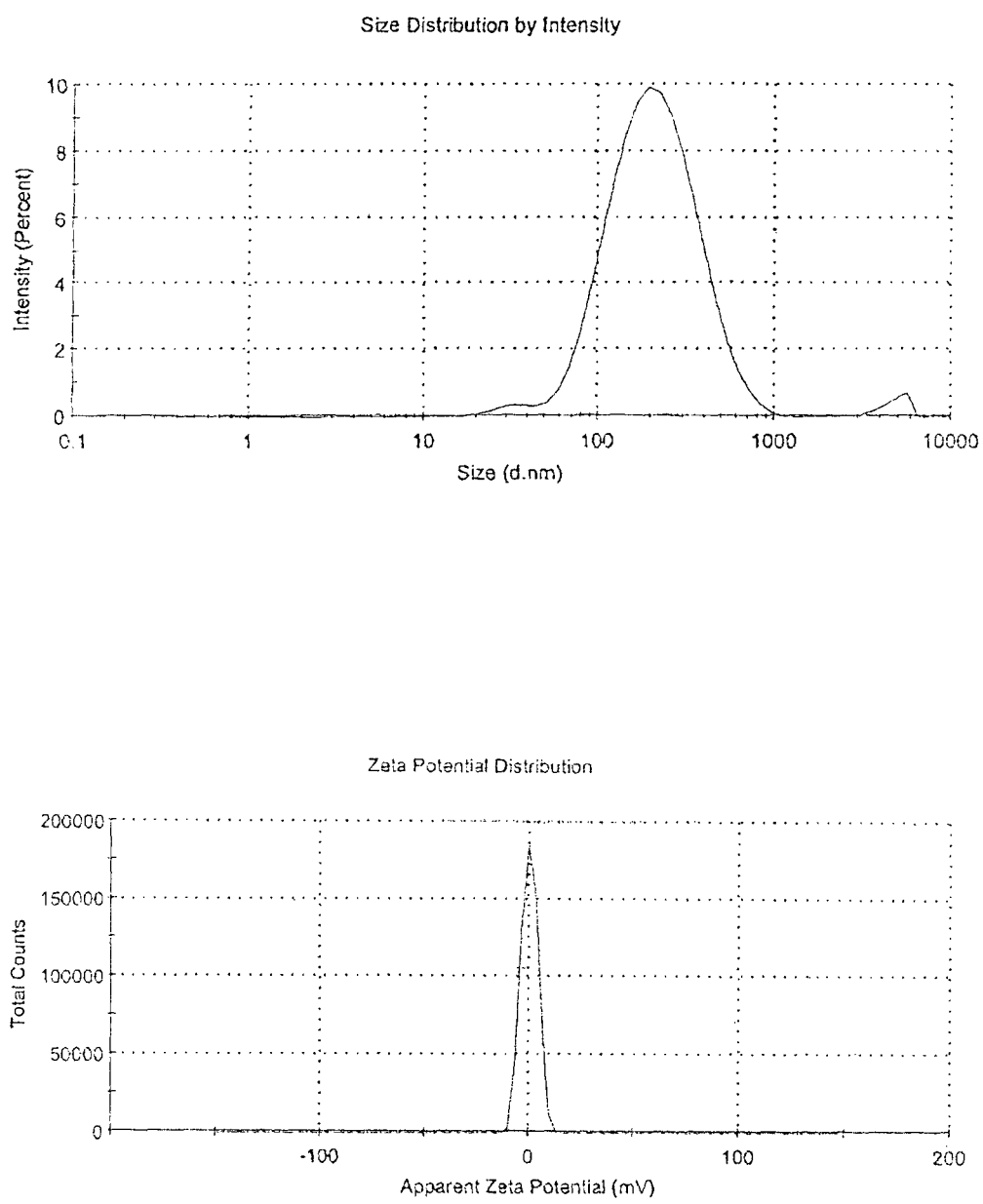
Figure 7F:
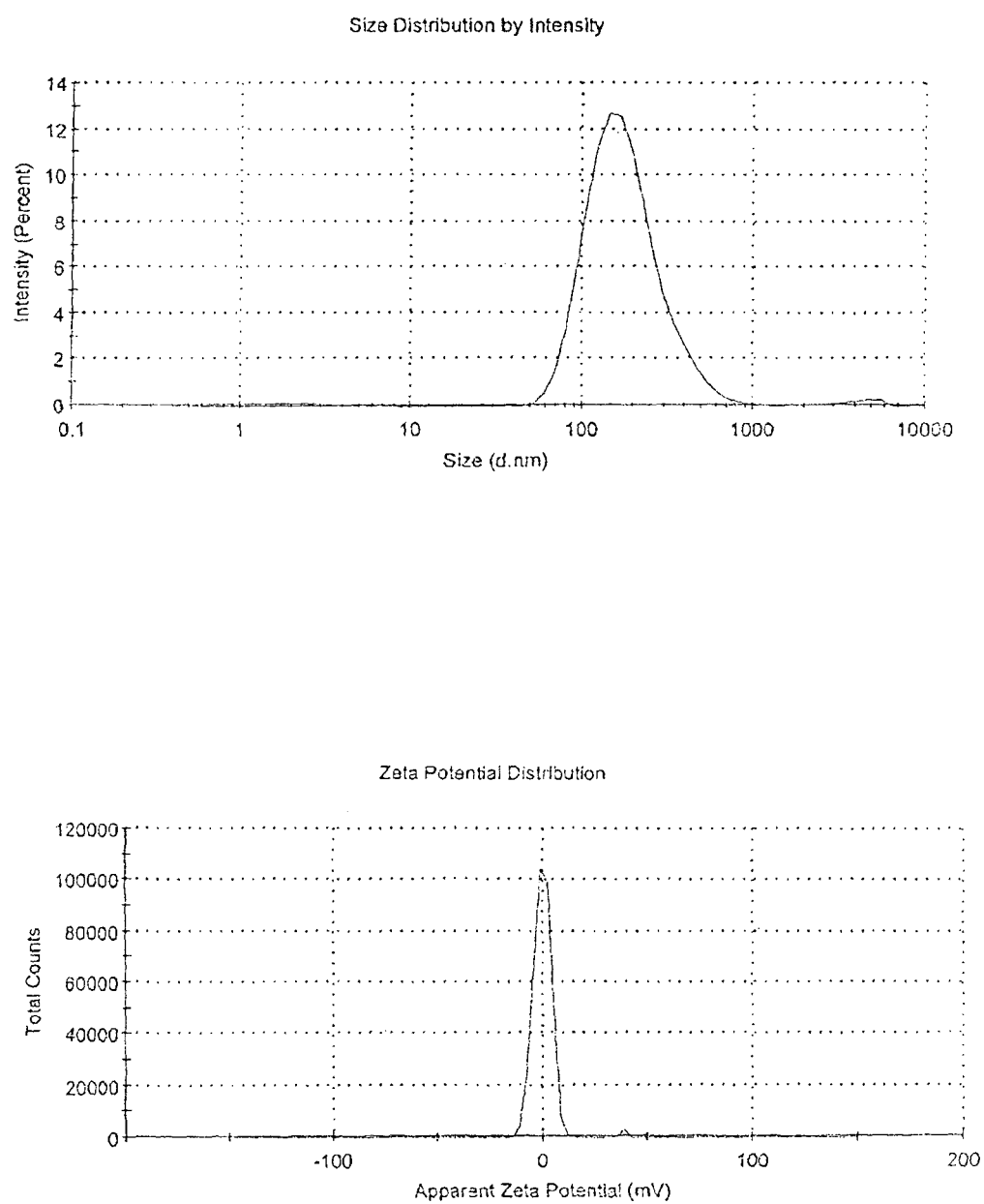
Figure 8A:
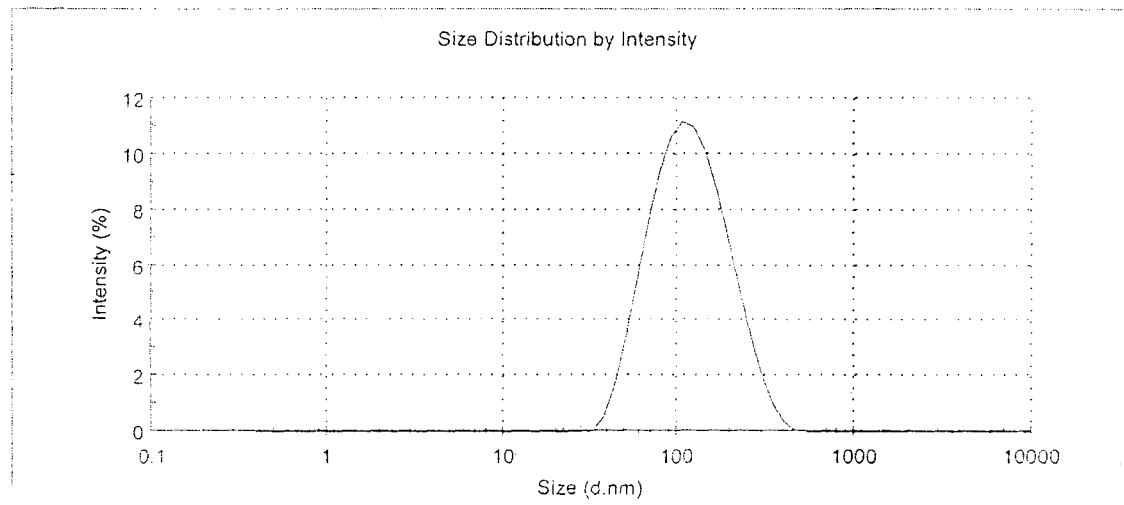
FIG. 8A to FIG. 8F depict particle size distribution in nanometre (nm), polydispersity index (PDI) and zeta potential (MV) of the exemplary composition No. 8 of the present invention under various conditions.
Figure 8A:
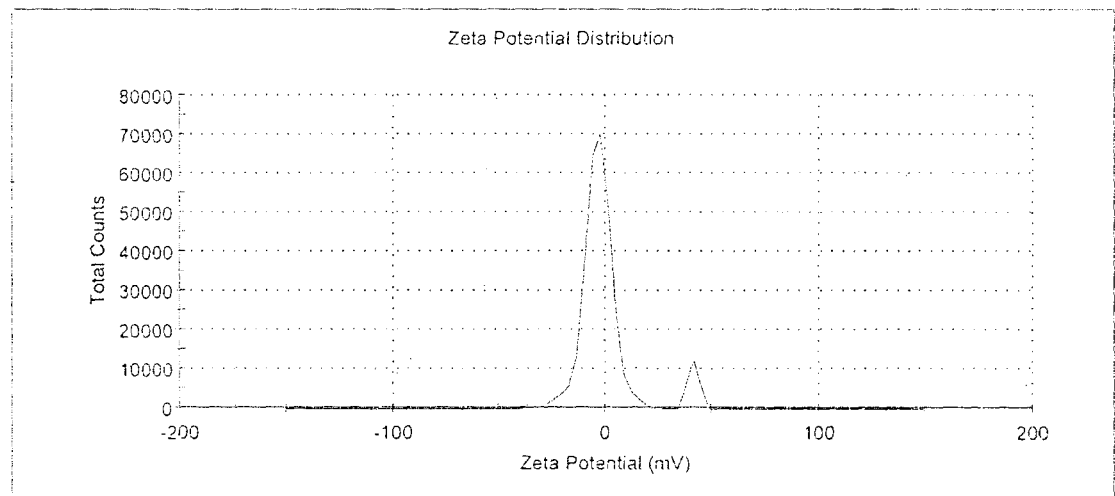
Figure 8B:
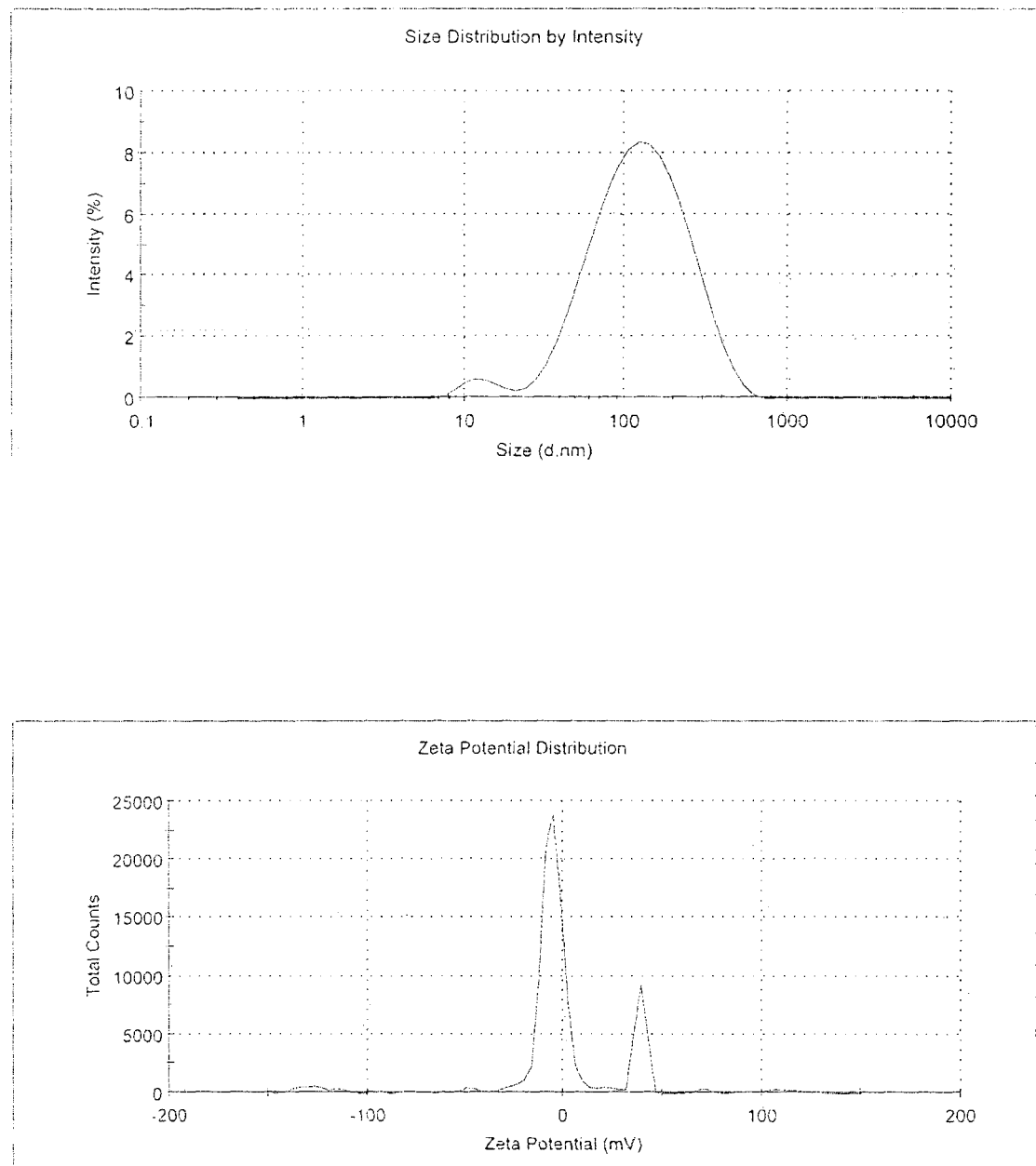
Figure 8C:
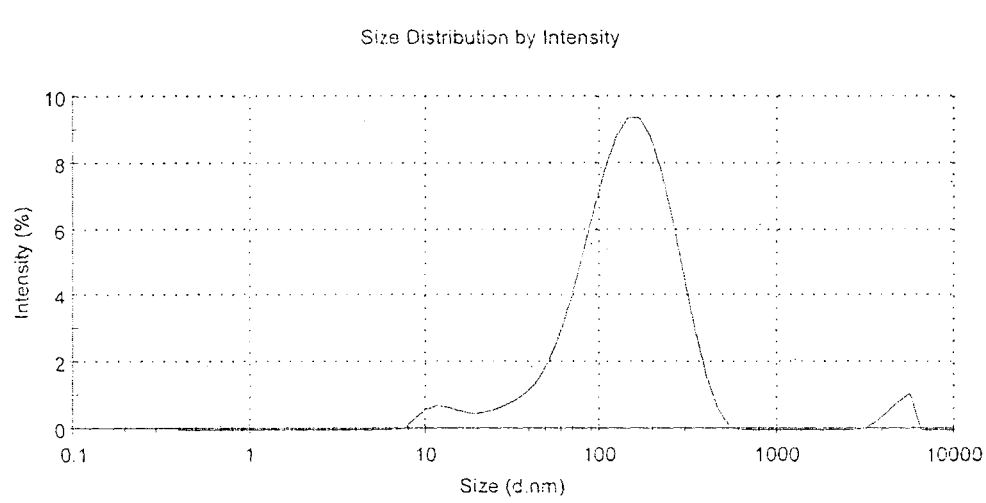
Figure 8C:
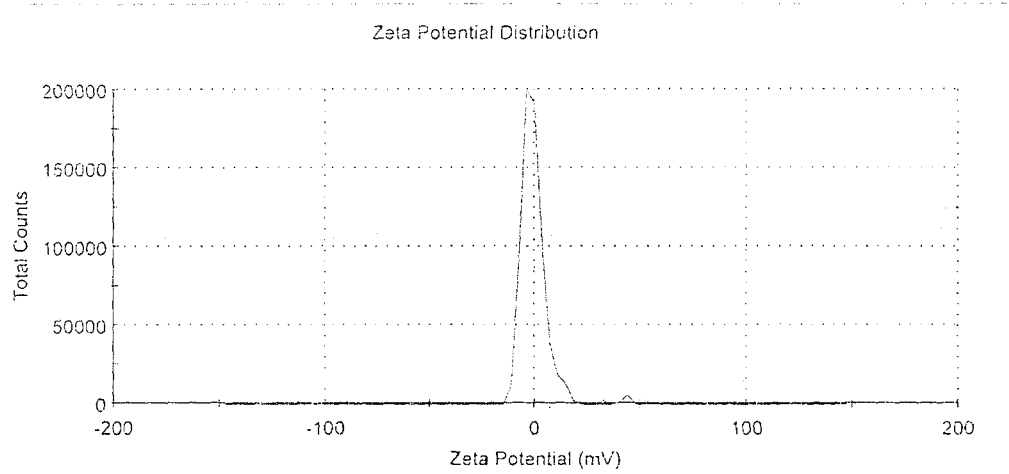
Figure 8D:
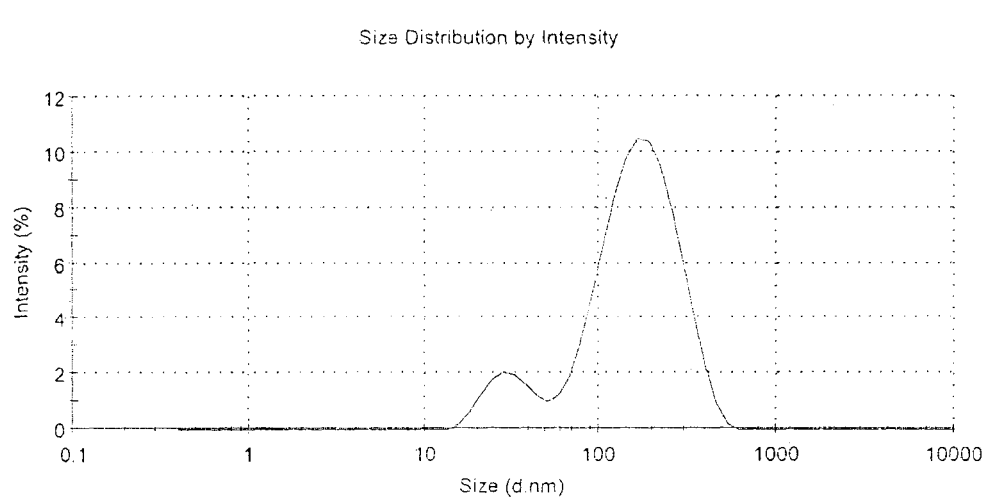
Figure 8D:
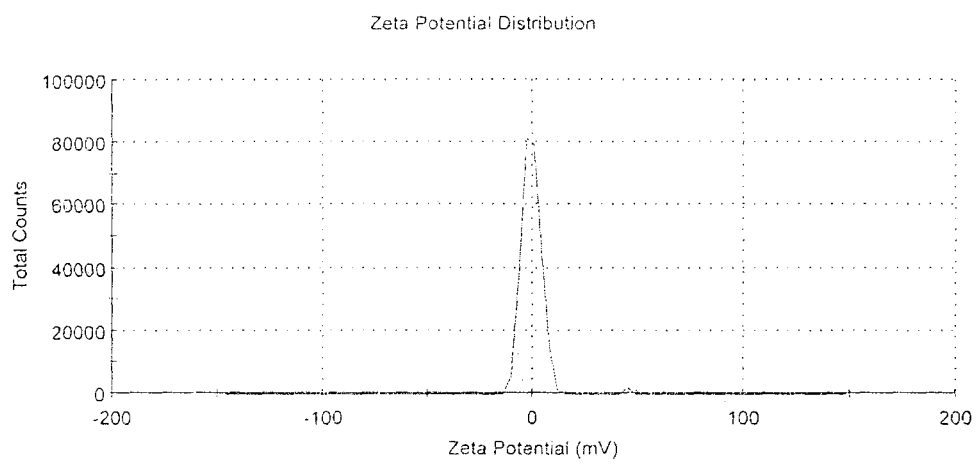
Figure 8E:
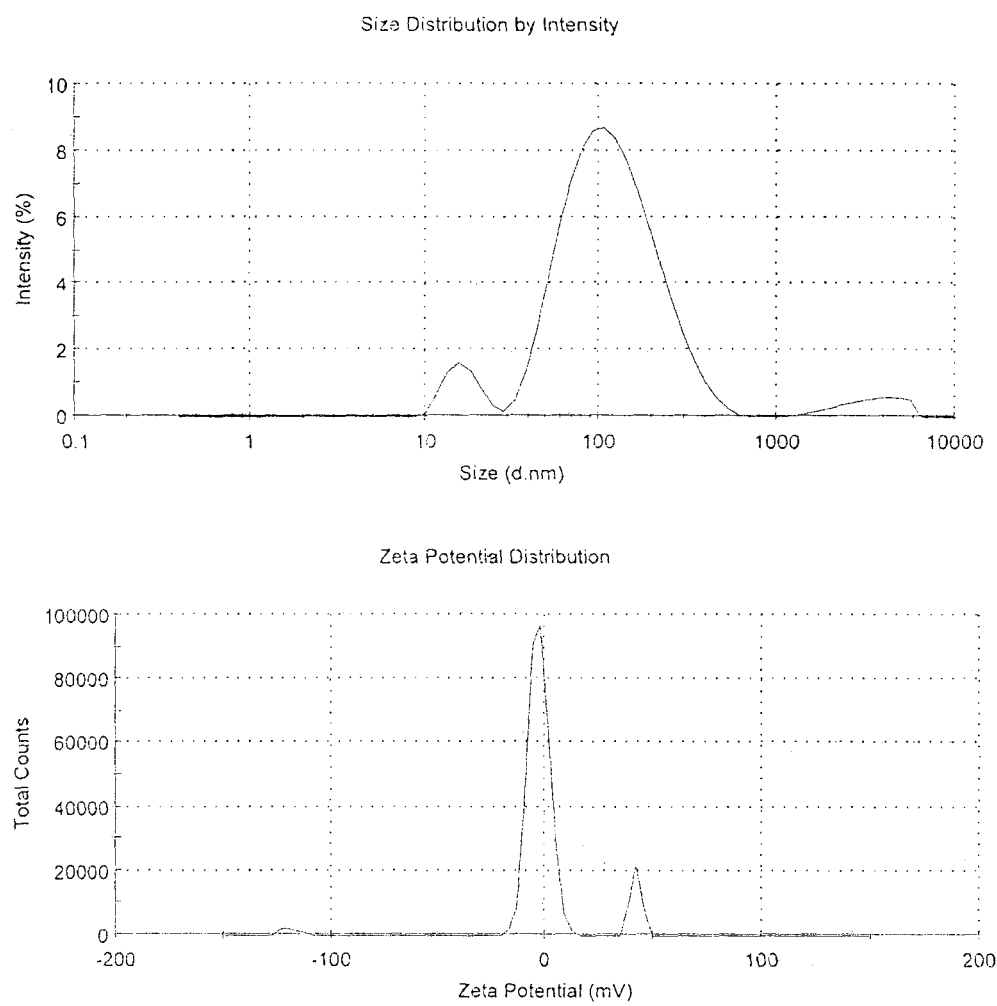
Figure 8F:
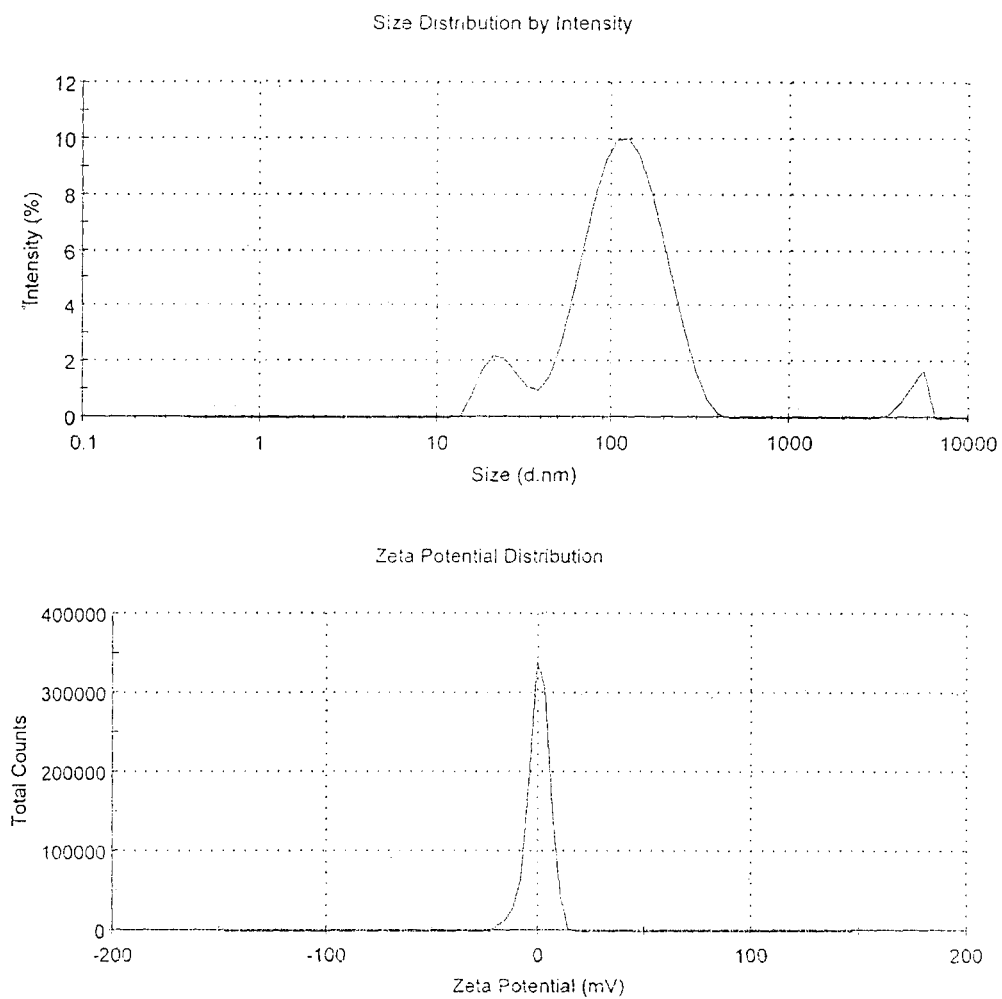
Figure 9A:
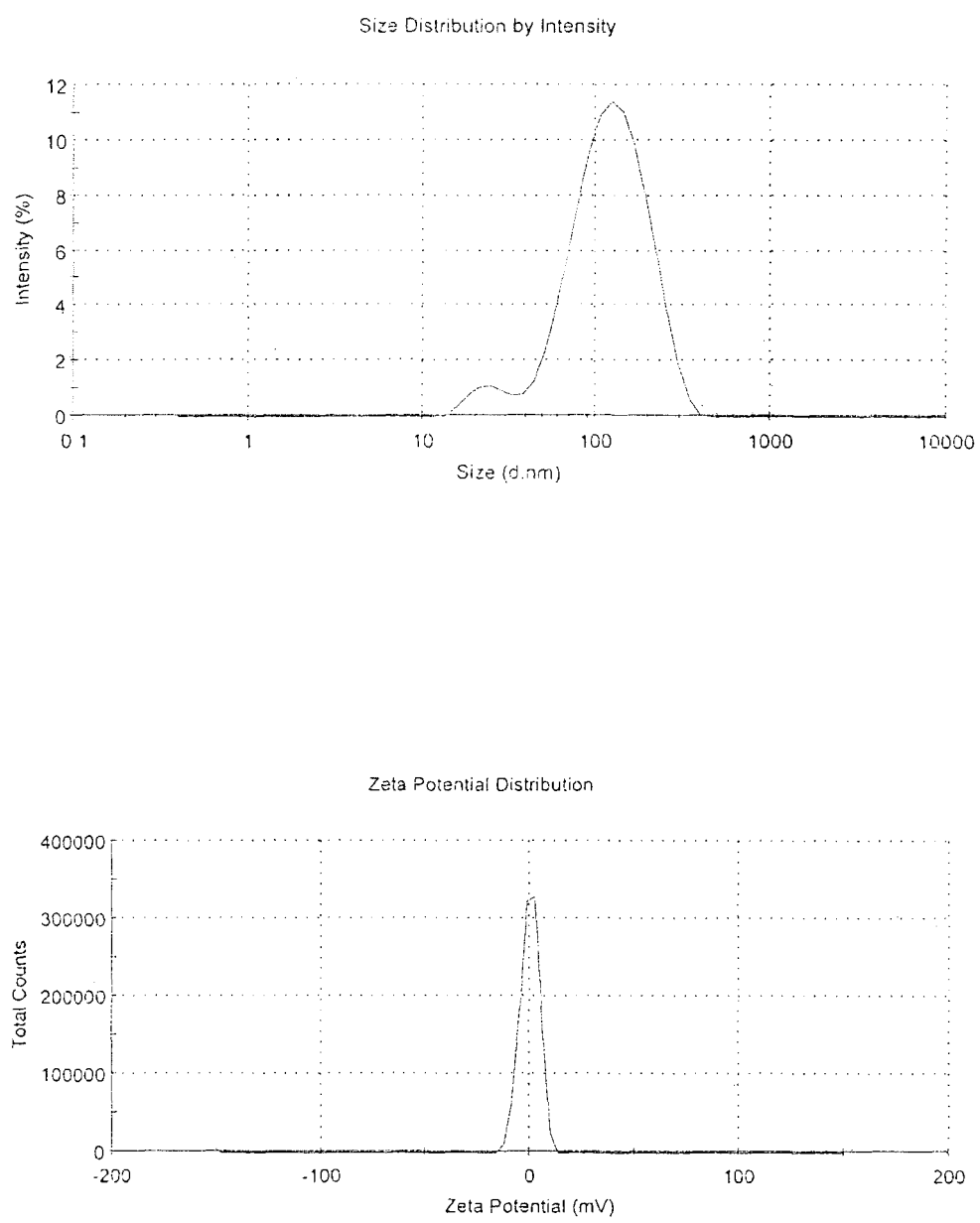
FIG. 9A to FIG. 9F depict particle size distribution in nanometre (nm), polydispersity index (PDI) and zeta potential (MV) of the exemplary composition No. 9 of the present invention under various conditions.
Figure 9B:
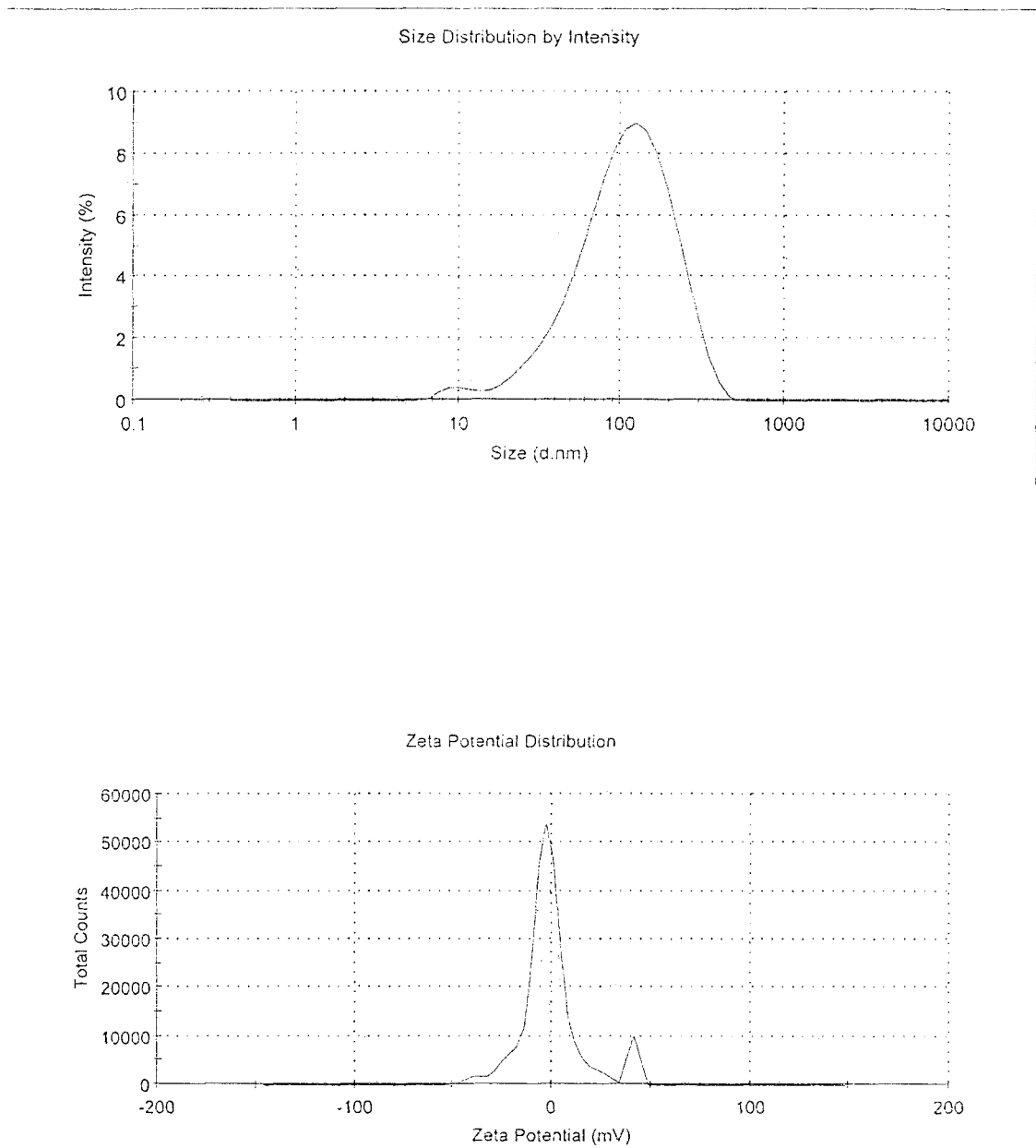
Figure 9C:
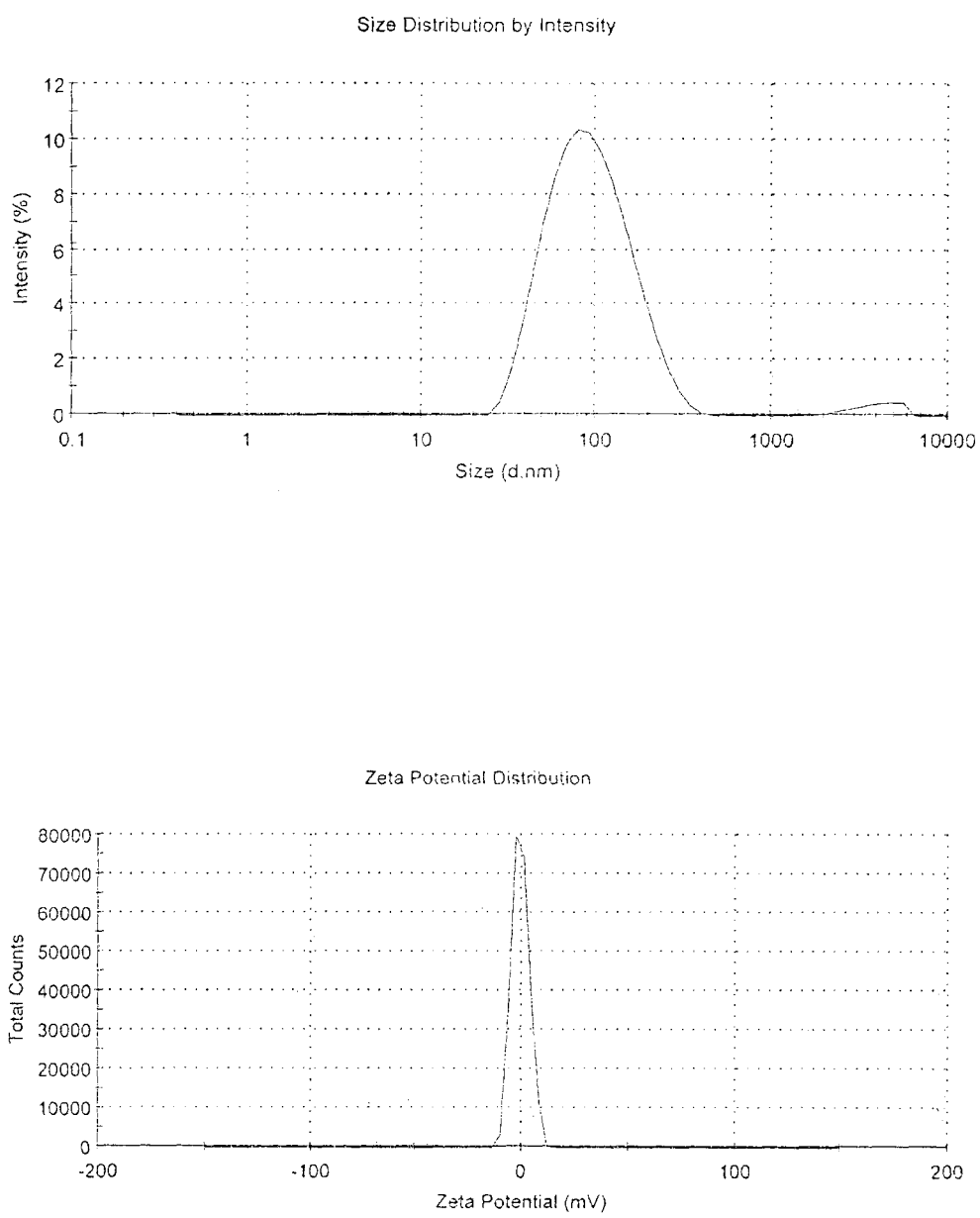
Figure 9D:
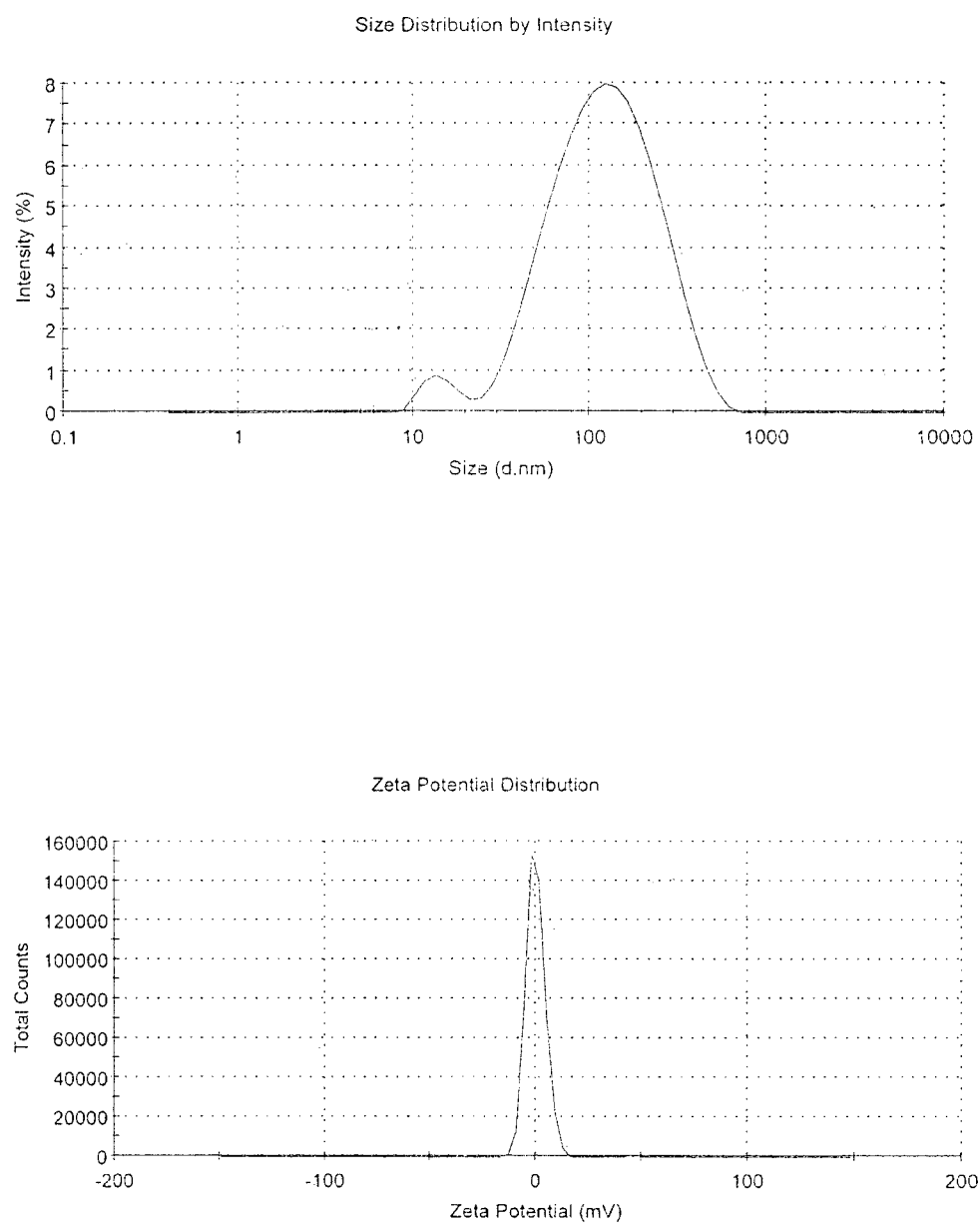
Figure 9E:
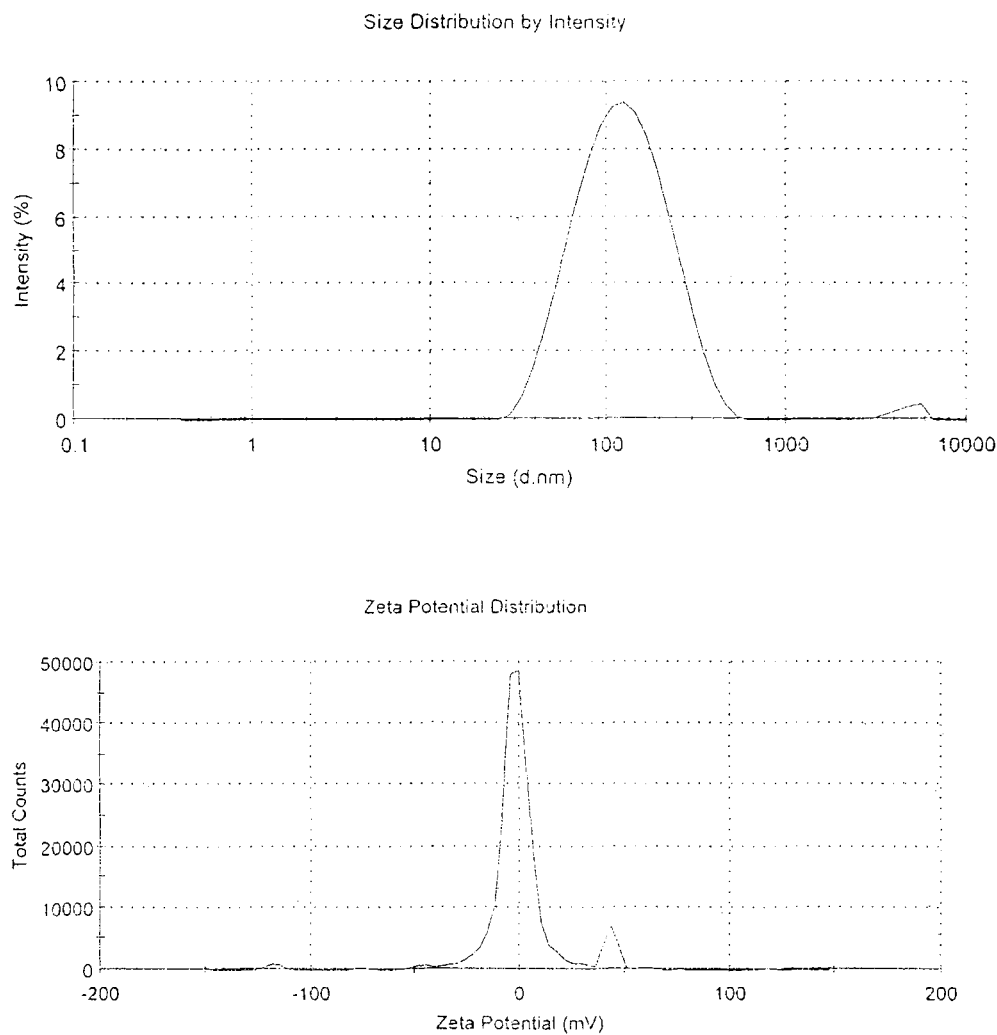
Figure 9F:
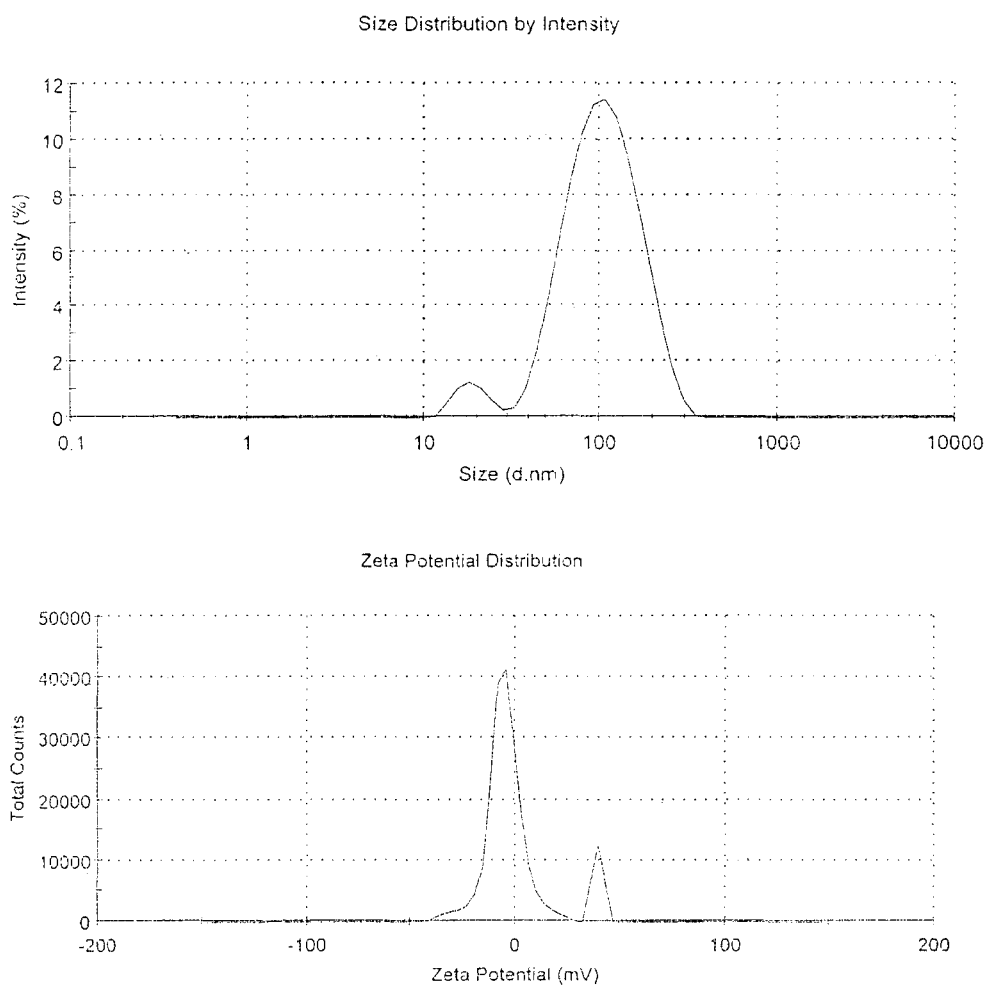
Figure 10A:
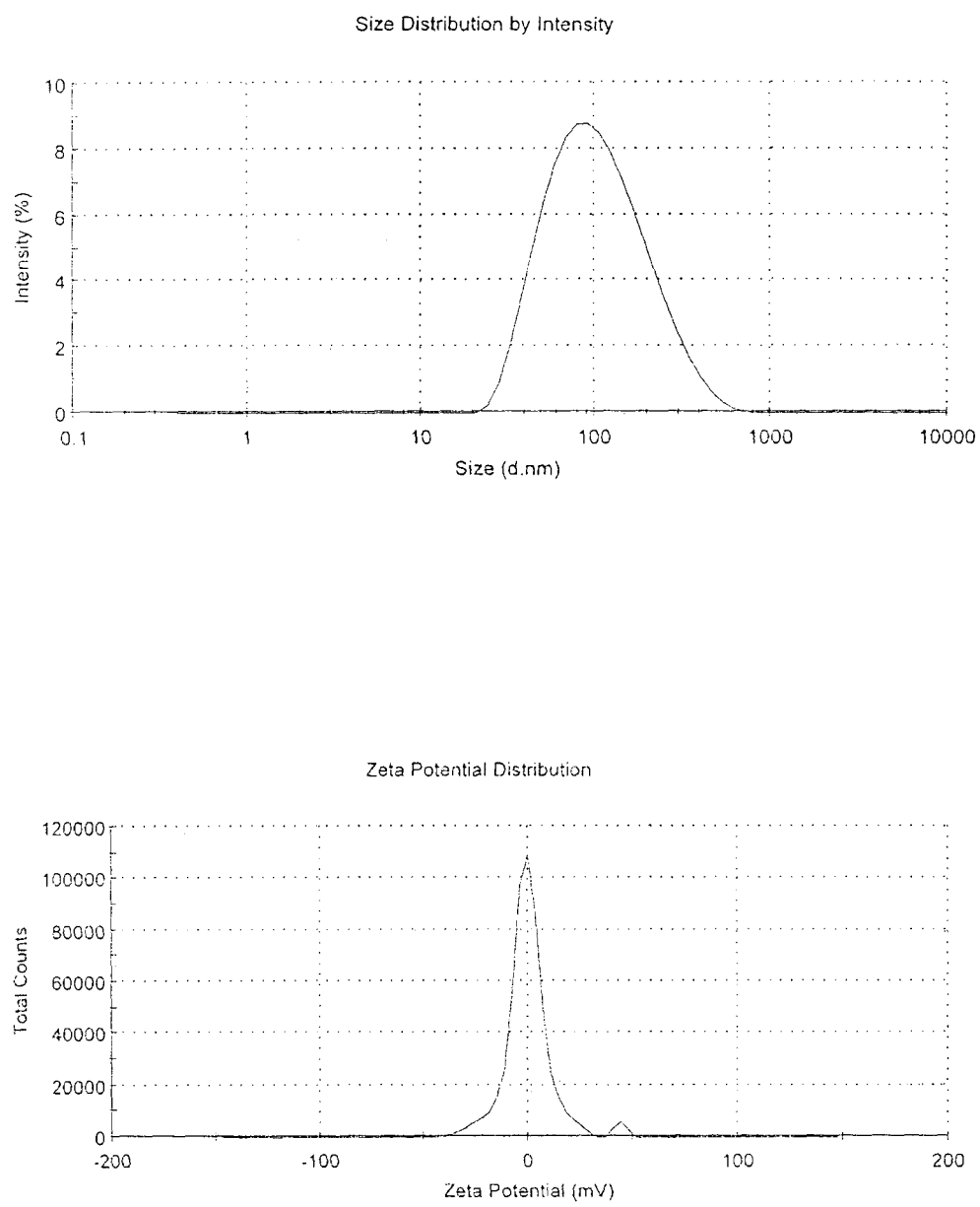
FIG. 10A to FIG. 10F depict particle size distribution in nanometre (nm), polydispersity index (PDI) and zeta potential (MV) of the exemplary composition No. 10 of the present invention under various conditions.
Figure 10B:
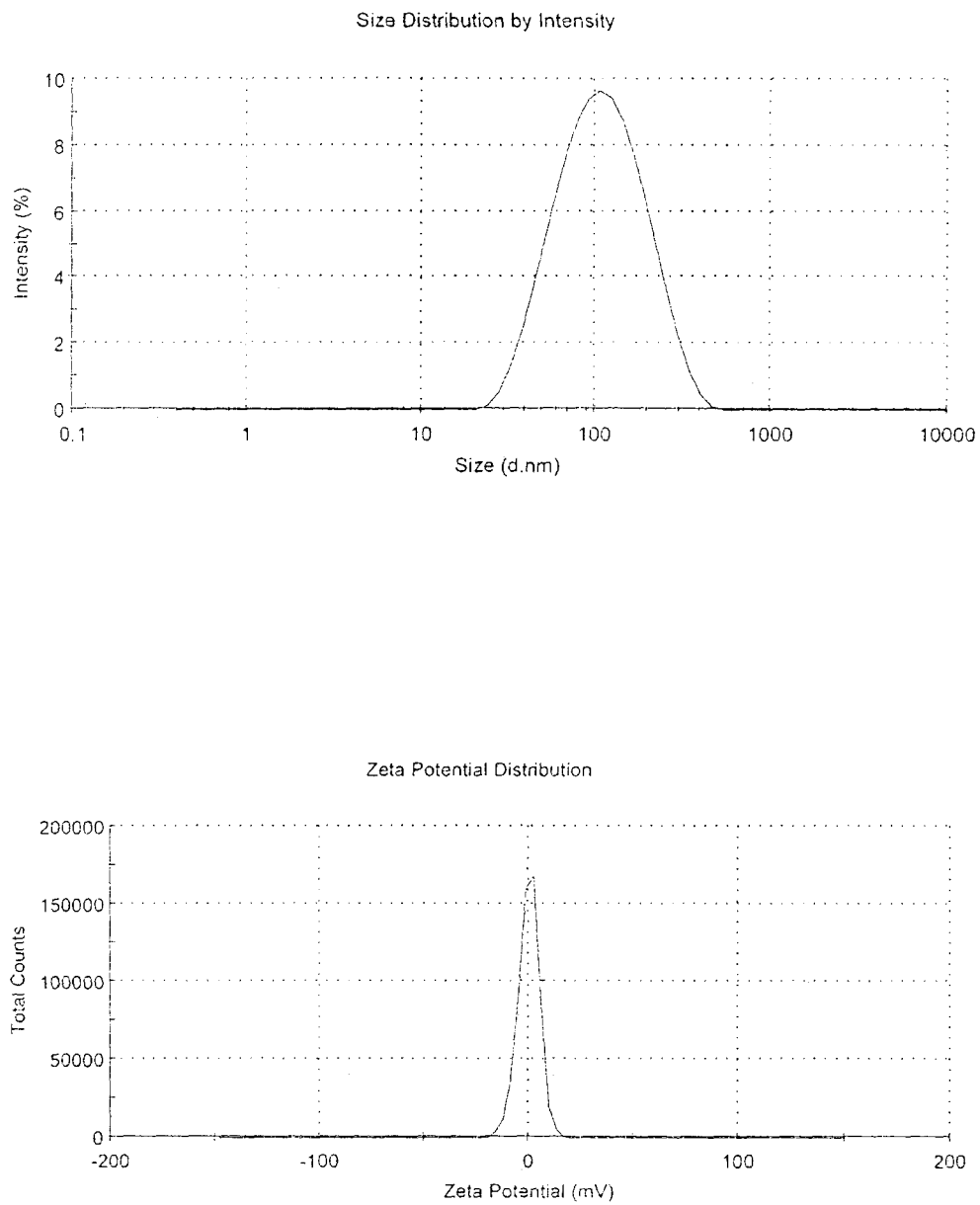
Figure 10C:
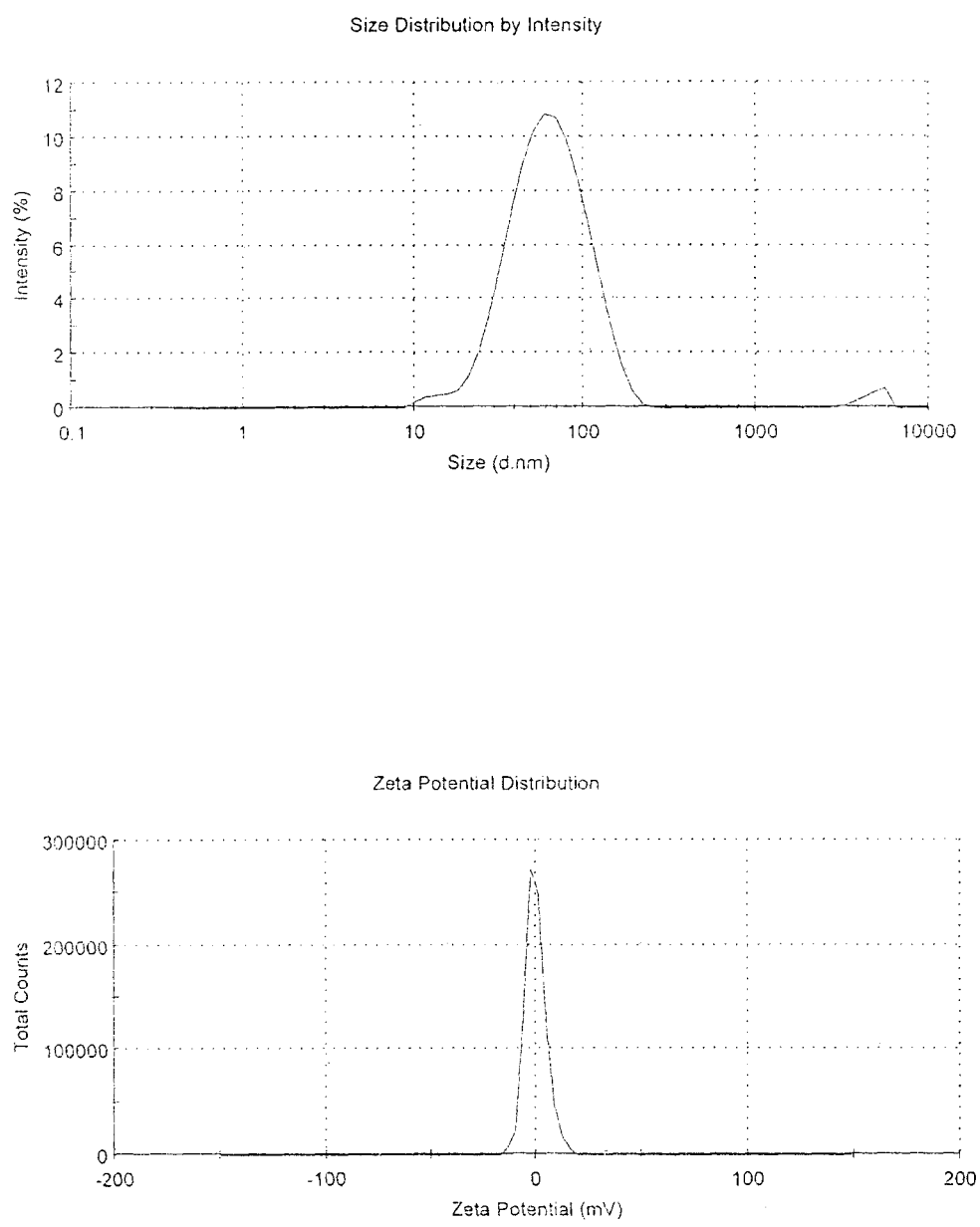
Figure 10D:
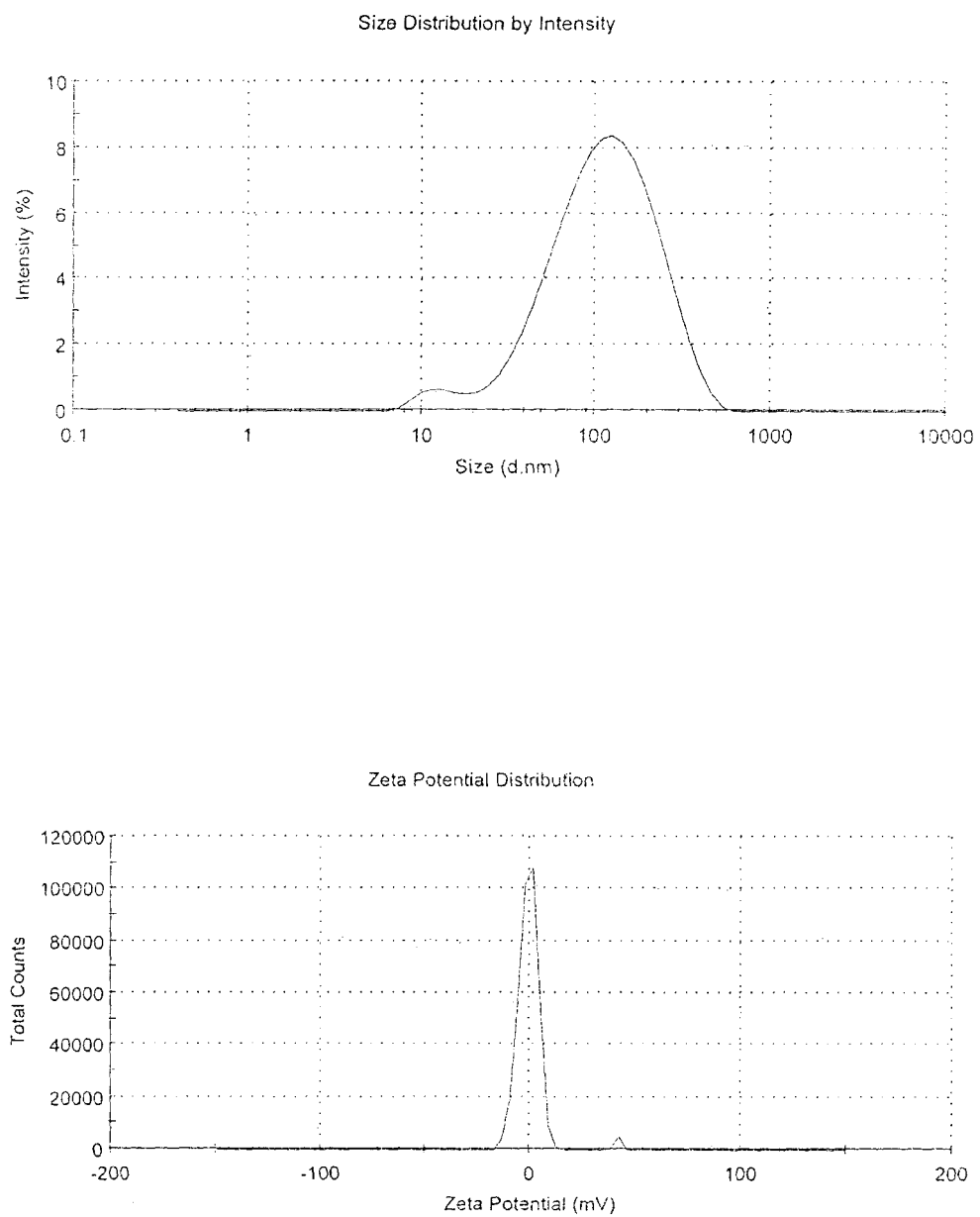
Figure 10E:
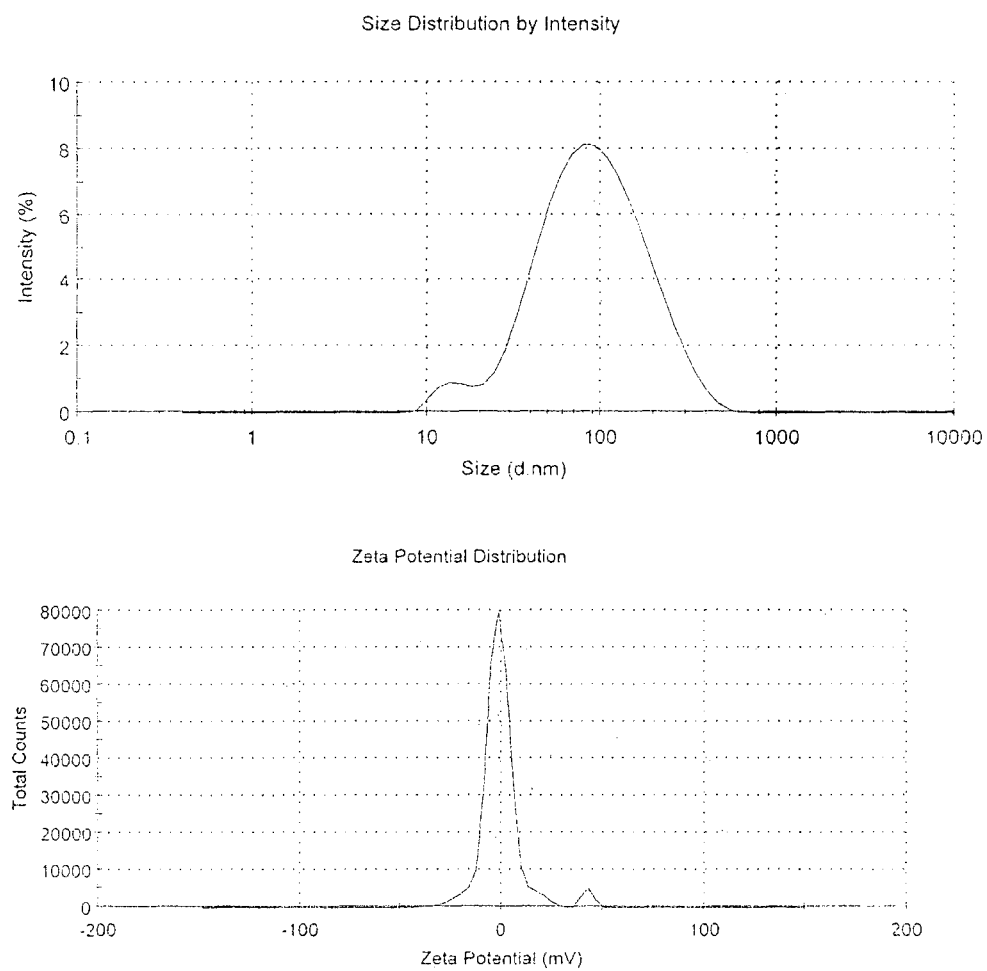
Figure 10F:
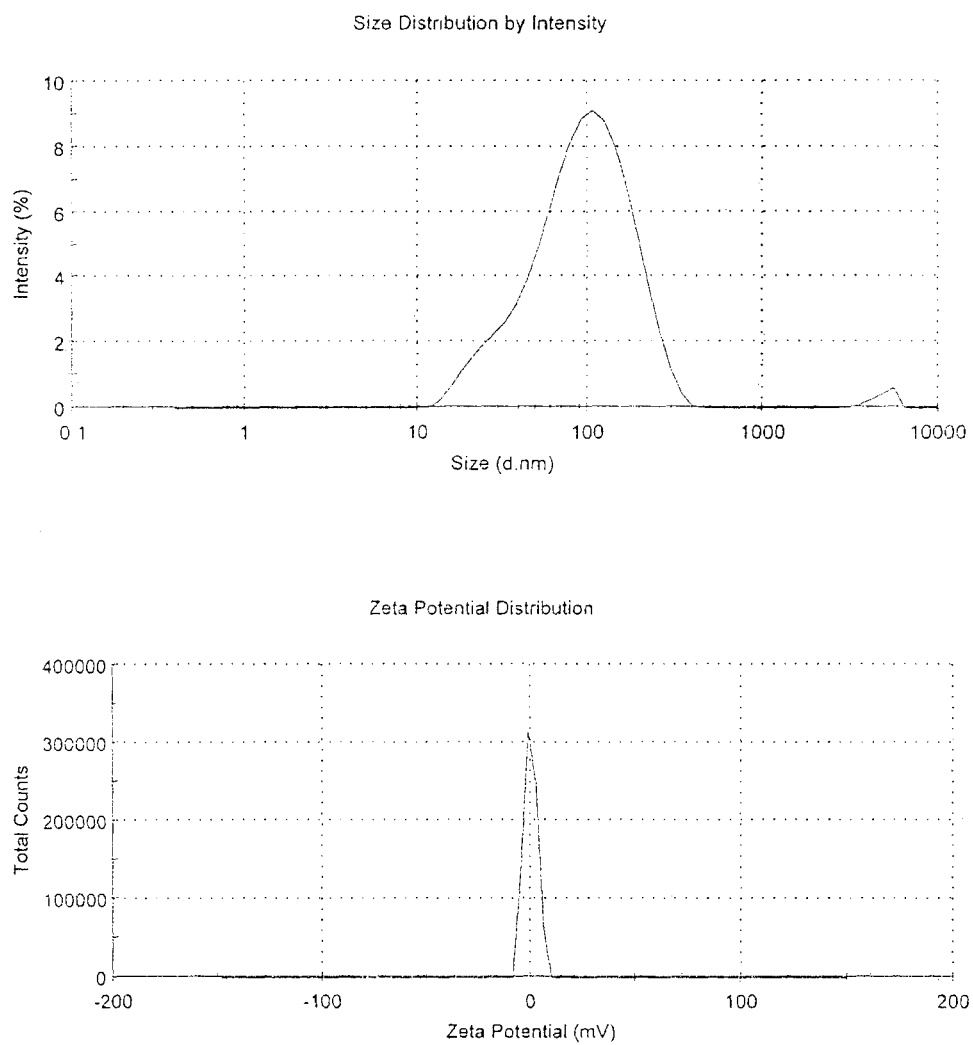
Figure 11A:
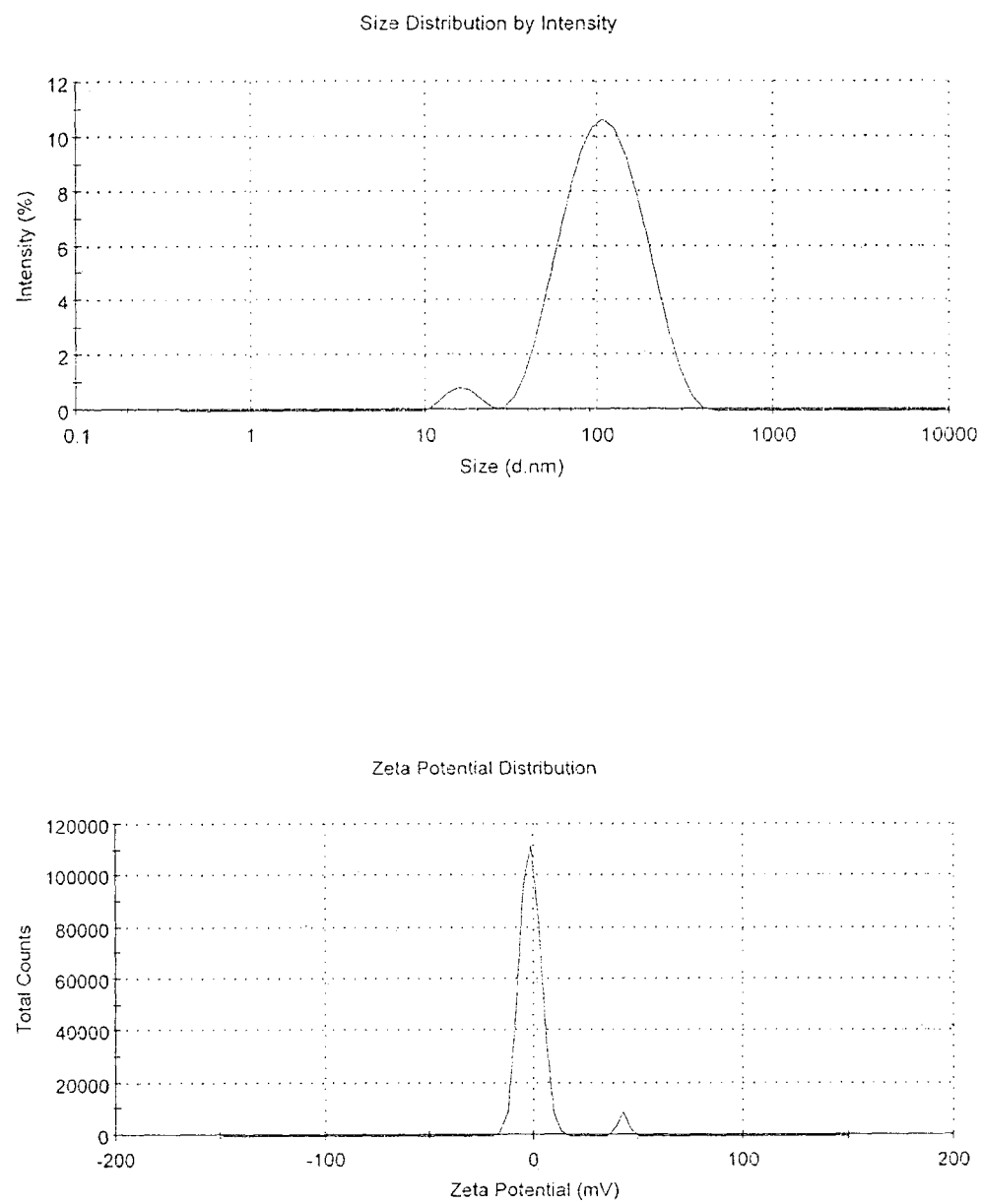
FIG. 11A to FIG. 11F depict particle size distribution in nanometre (nm), polydispersity index (PDI) and zeta potential (MV) of the exemplary composition No. 11 of the present invention under various conditions.
Figure 11B:
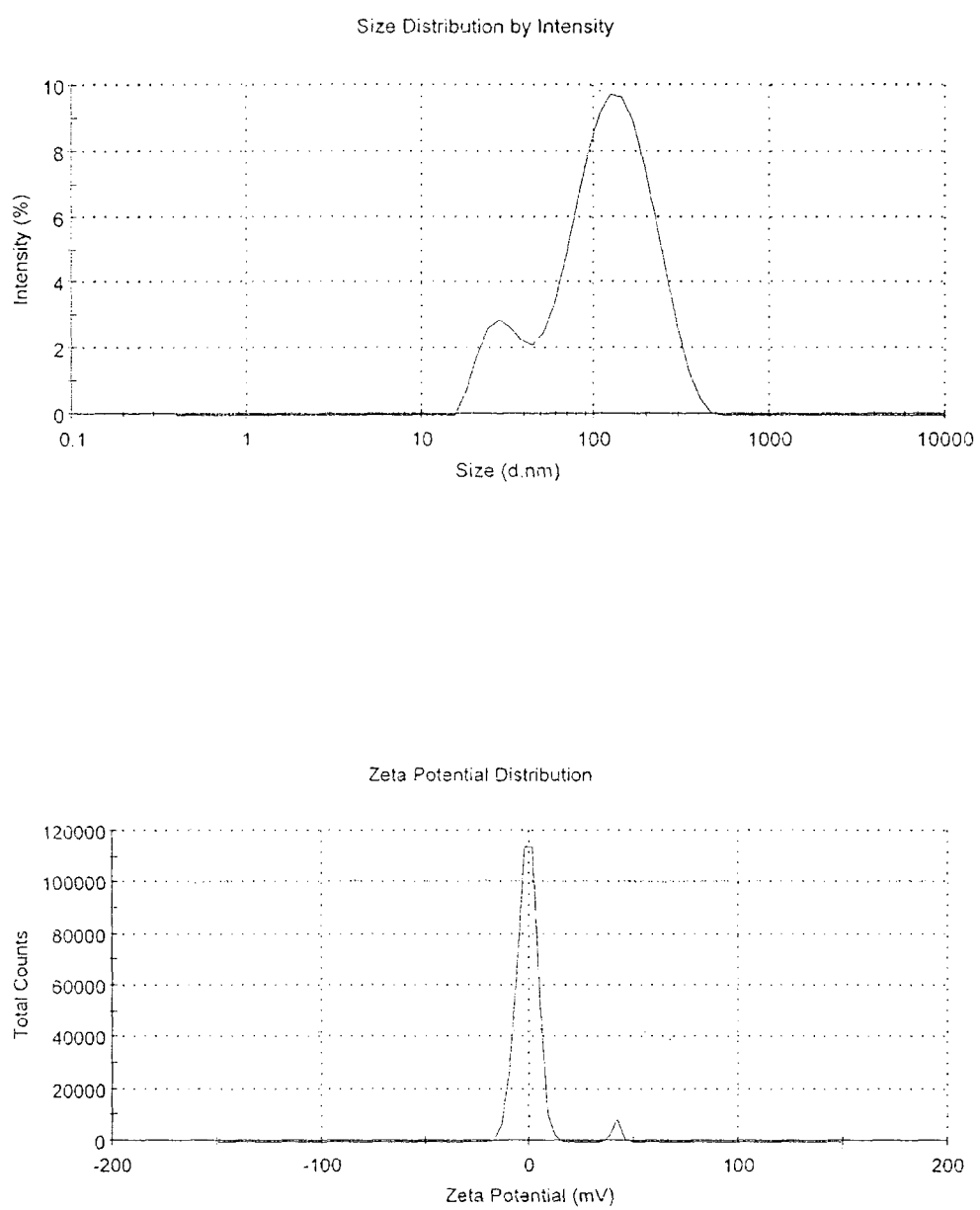
Figure 11C:
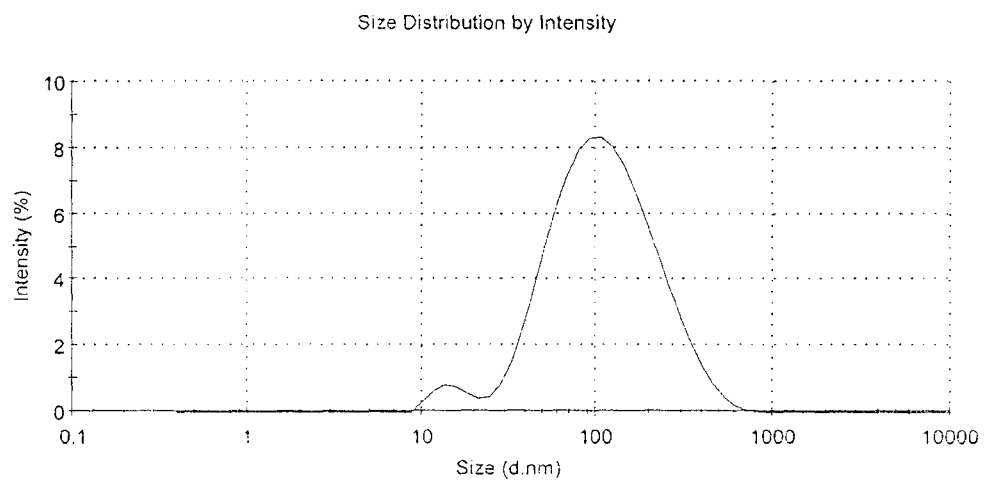
Figure 11C:
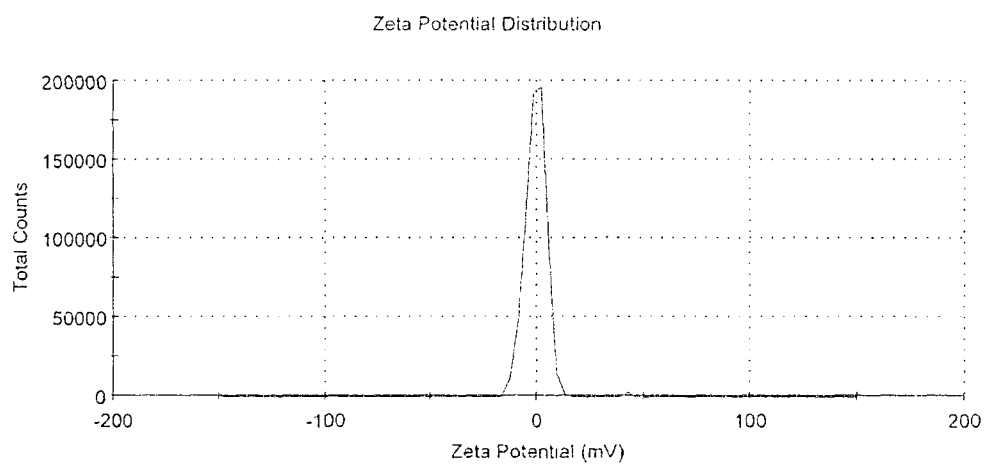
Figure 11D:
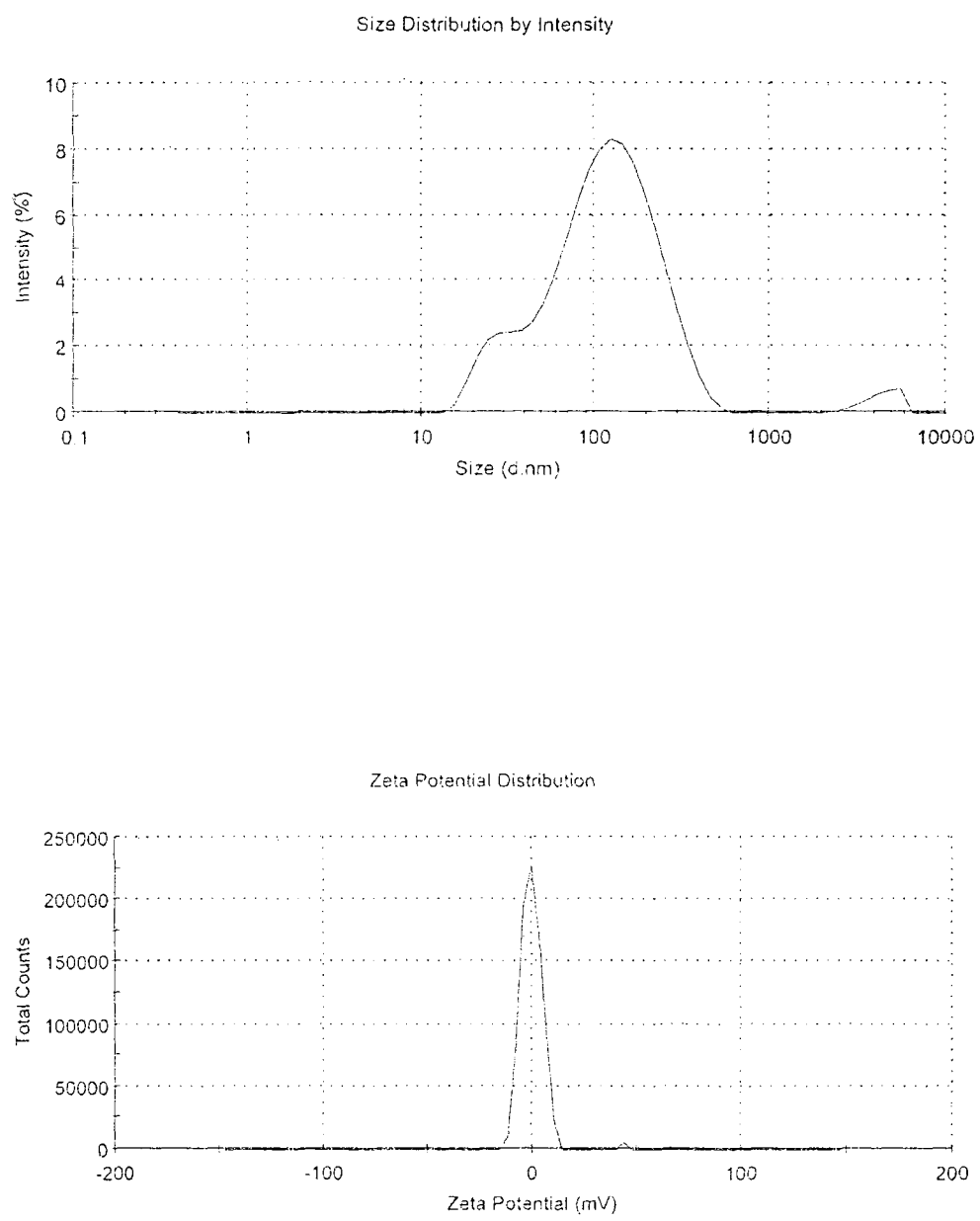
Figure 11E:
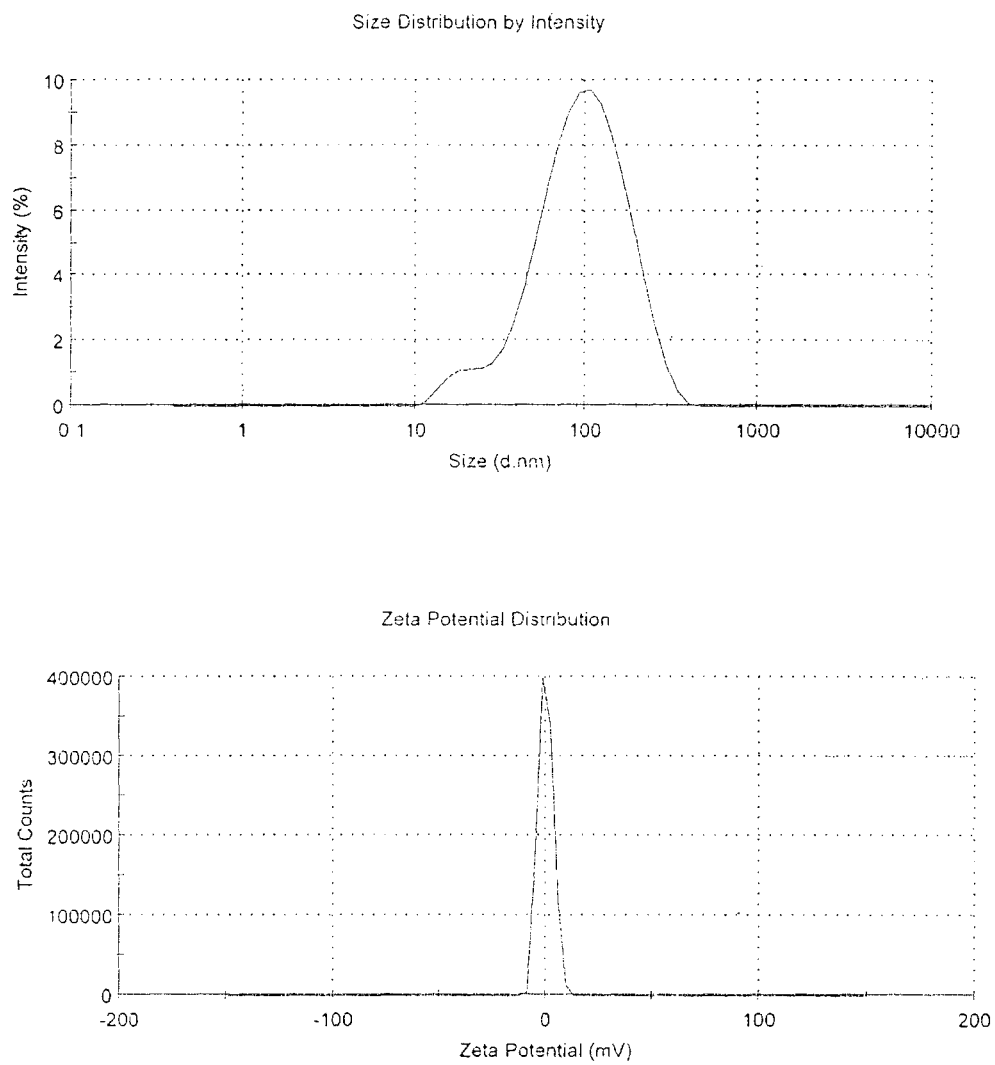
Figure 11F:
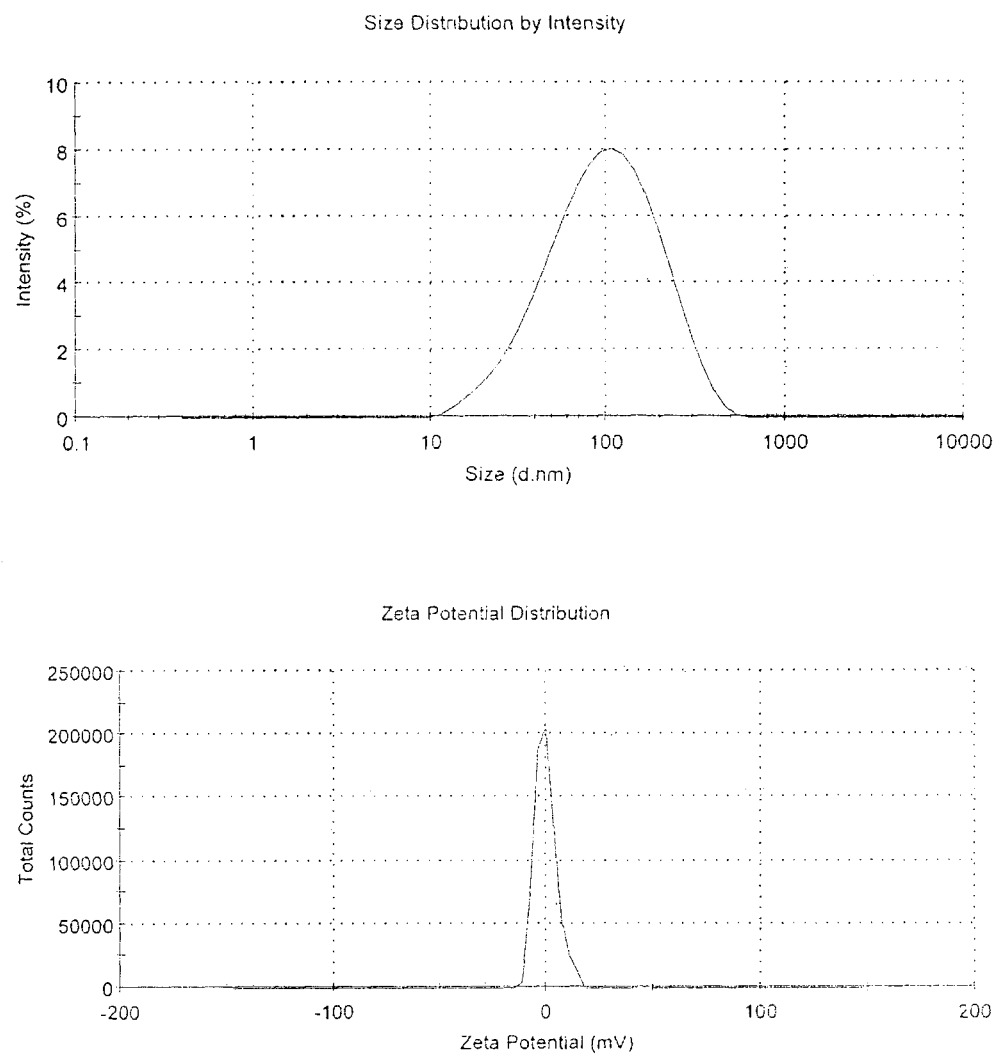
Figure 12:
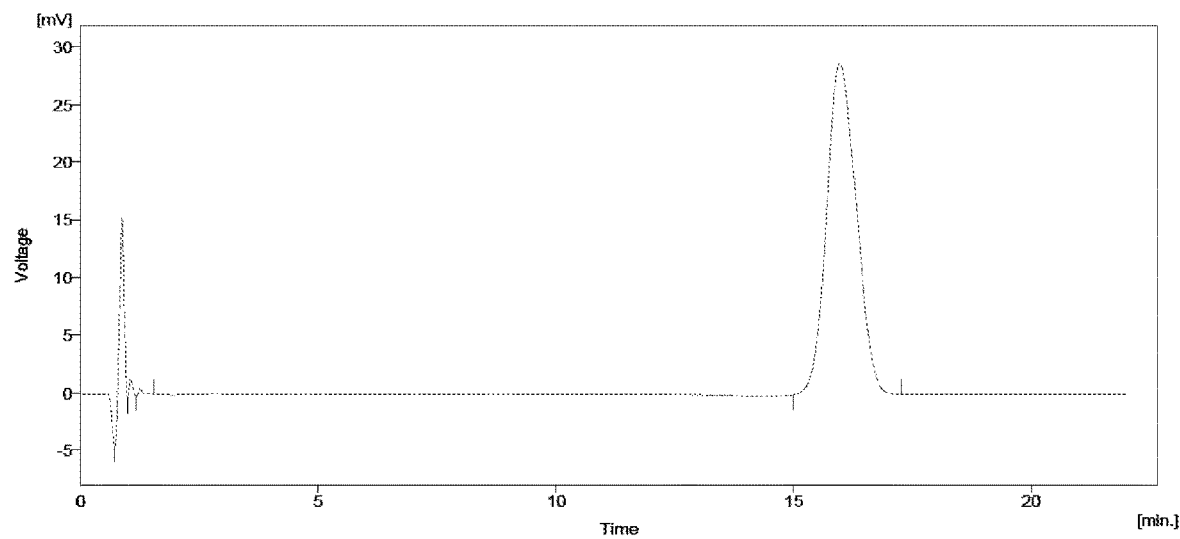
FIG. 12A and FIG. 12B depict HPLC assay results to determine the percentage of drug content in the exemplary composition of the present invention.
Figure 12:
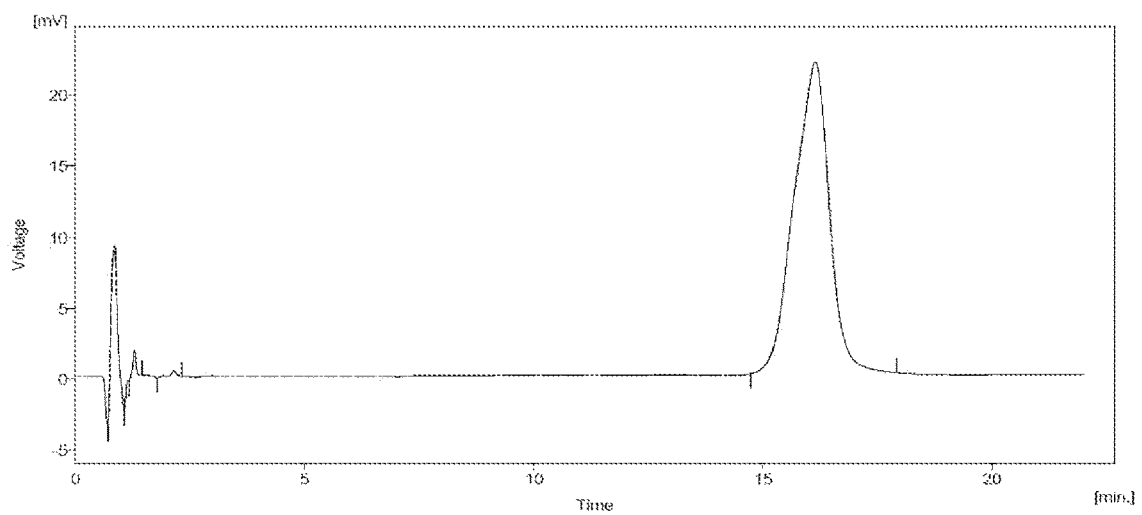
Figure 12:
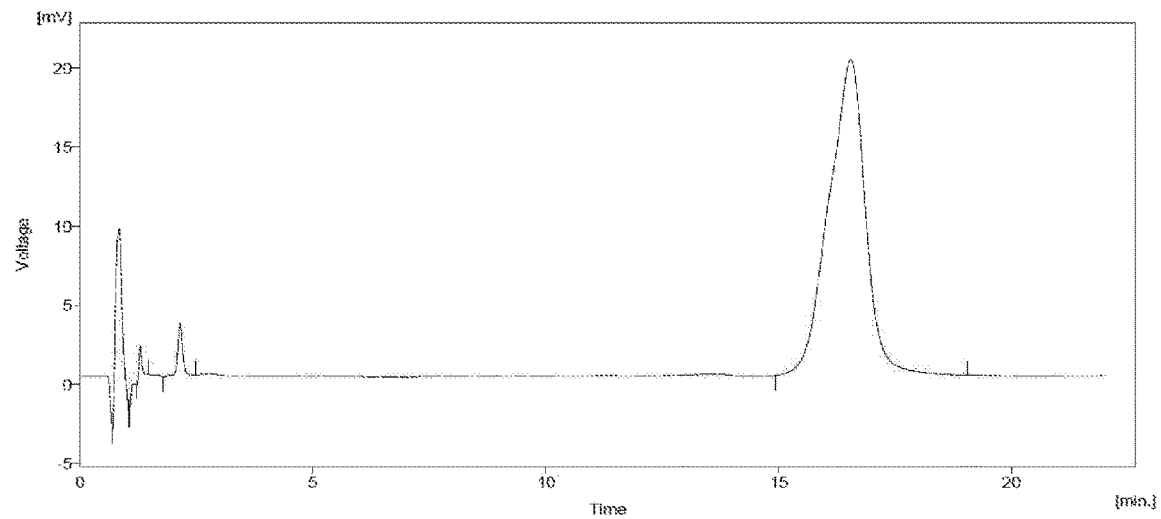
Figure 12:
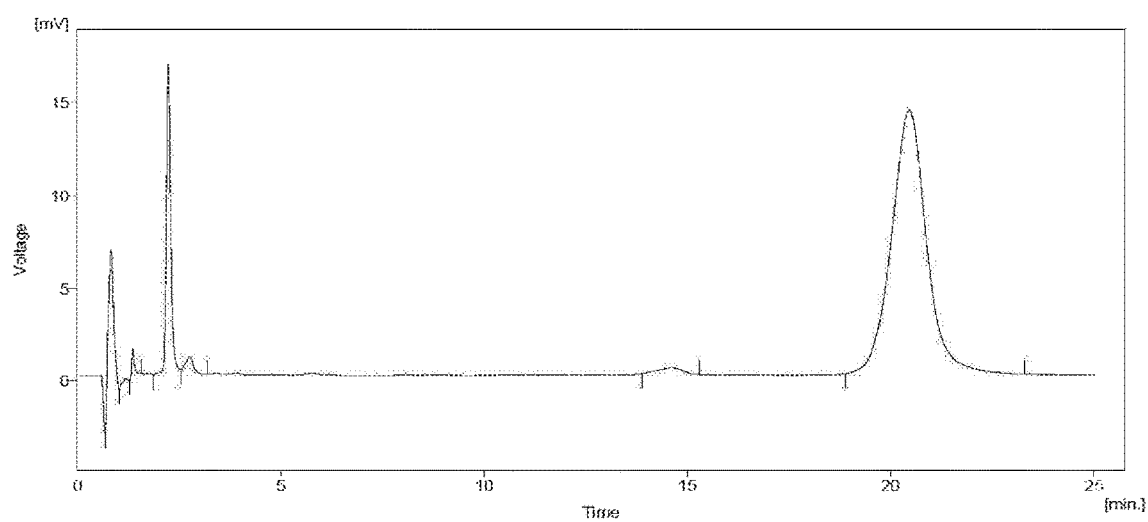
Figure 13A:
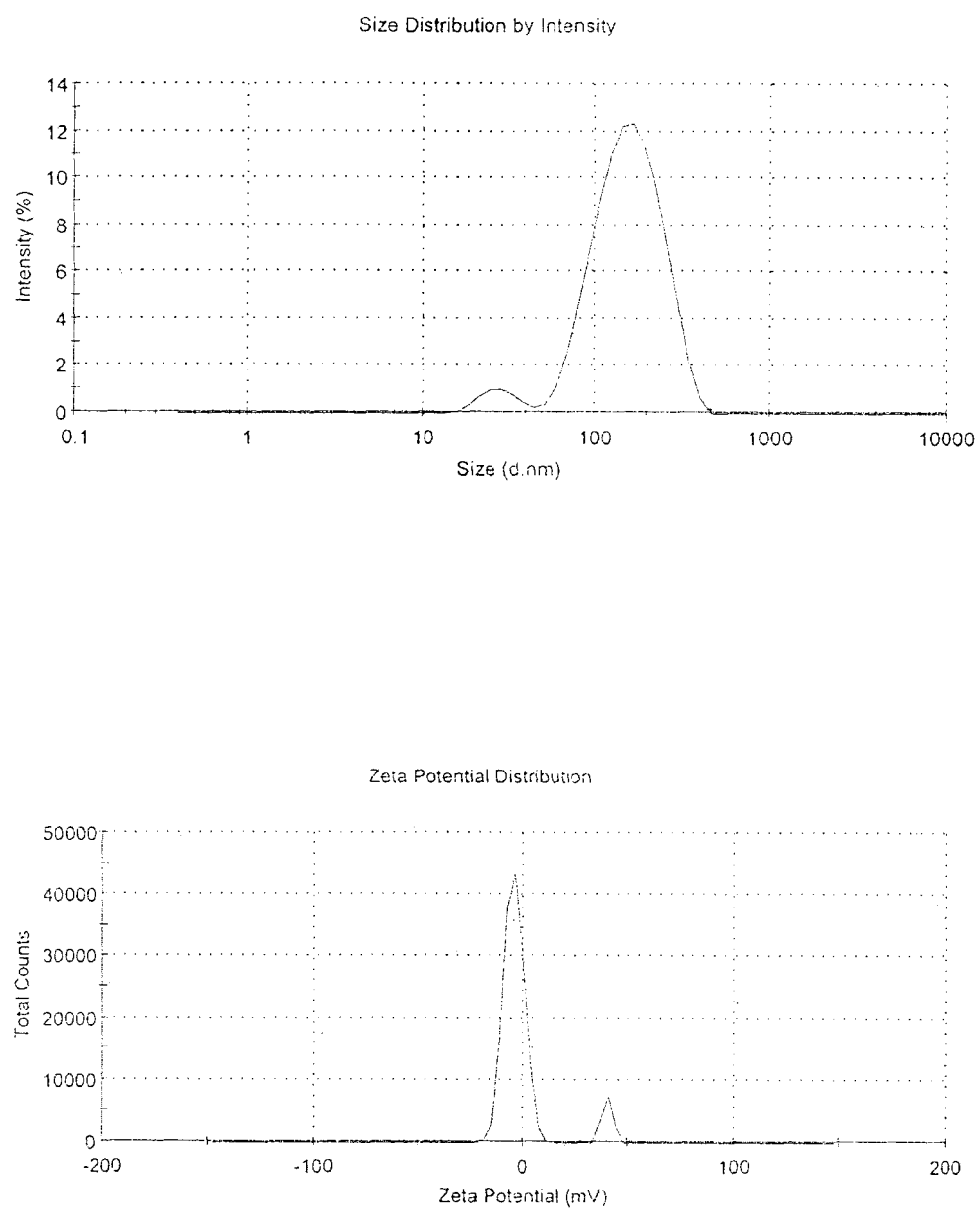
FIG. 13A to FIG. 13D depict particle size distribution in nanometre(nm), polydispersity index(PDI) and zeta potential (MV) of the exemplary composition No. 13 of the present invention under various conditions.
Figure 13B:
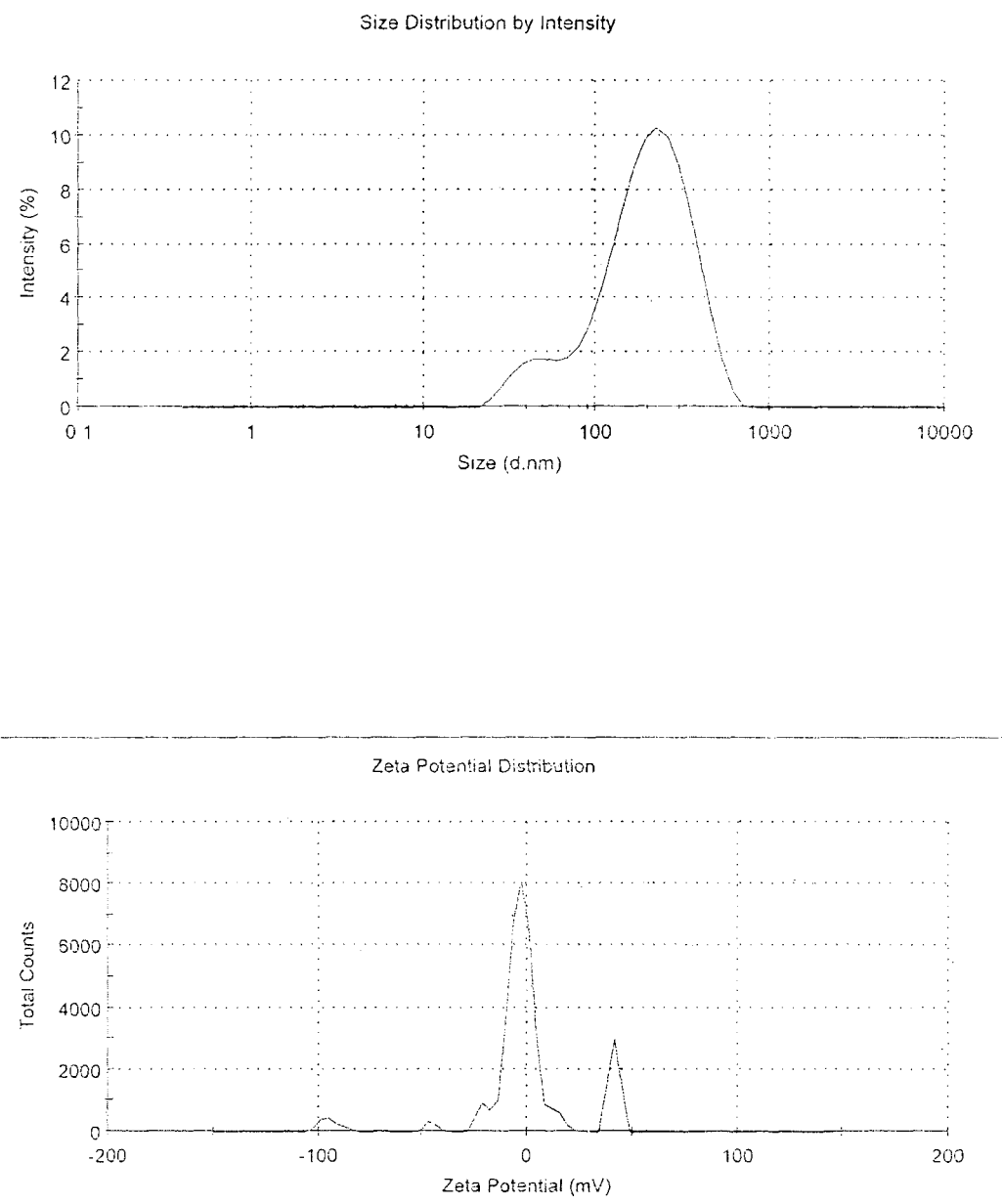
Figure 13C:
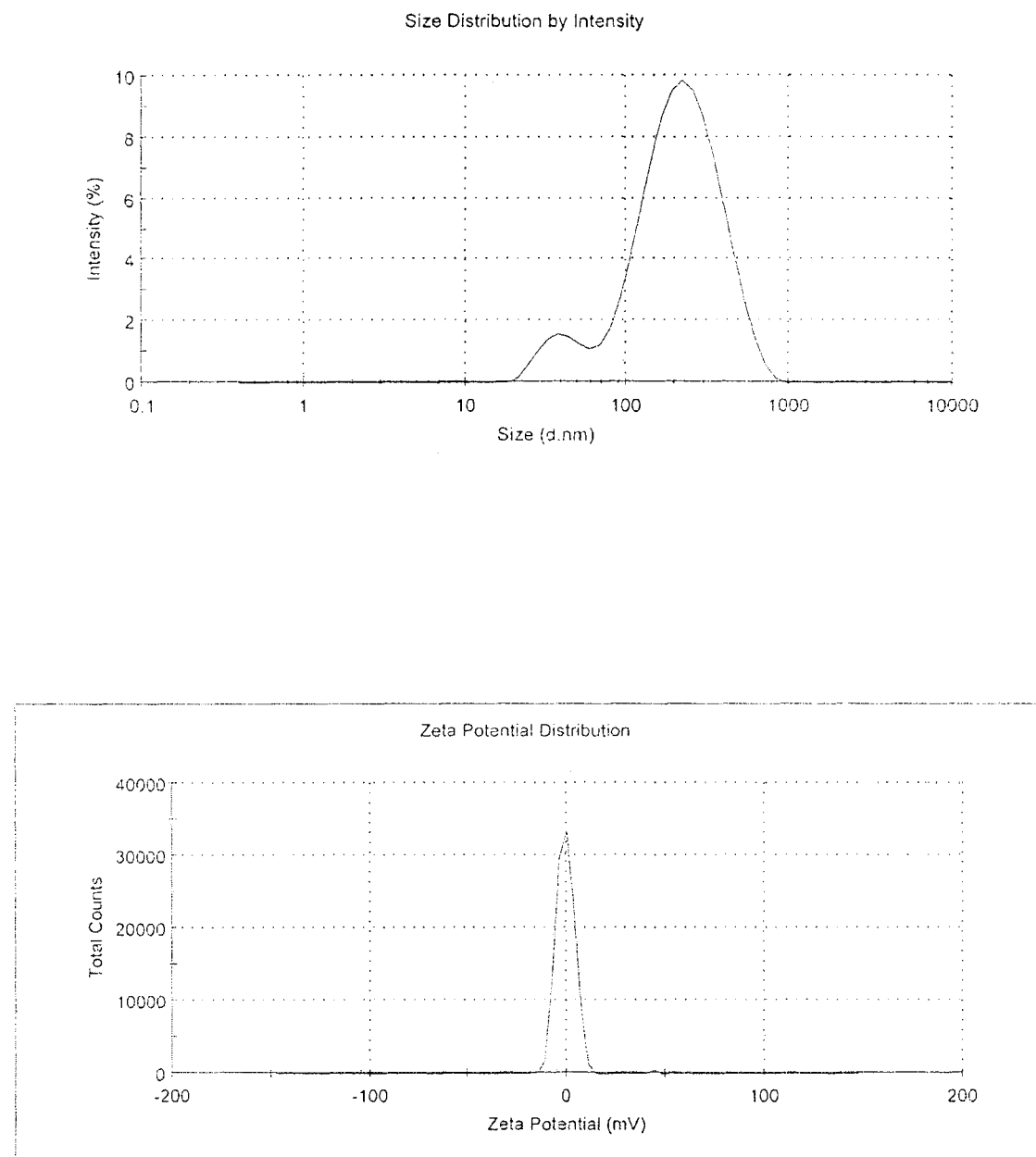
Figure 13D:
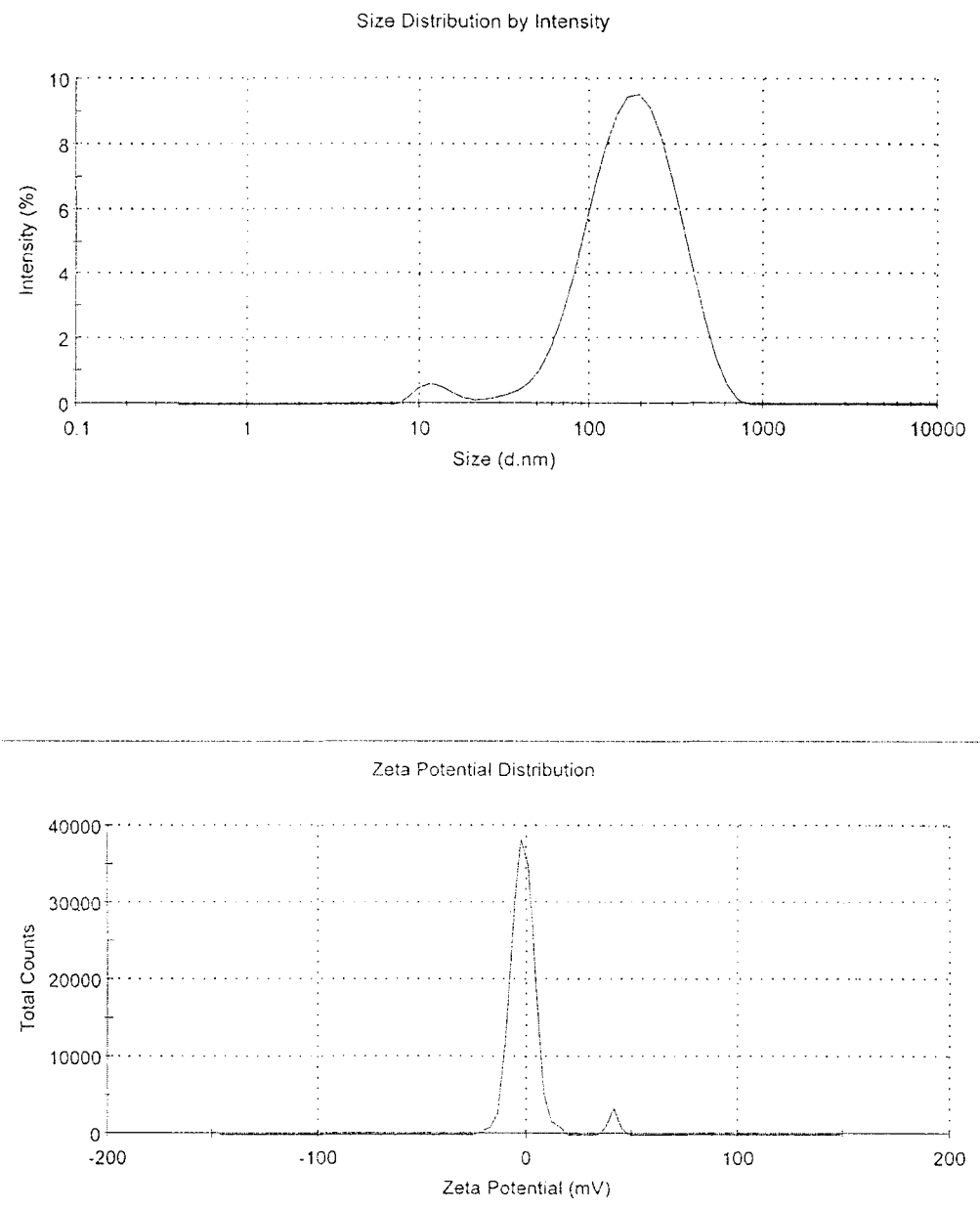

A composition for delivery of lipophilic or partially lipophilic based active pharmaceutical substance and a method for preparing the same, is disclosed.

In one embodiment, the present invention relates to an oil-in-water emulsion comprising an oil phase, the average particle size of which is in the range of 60 to 200 nm, a method for preparing the composition and the use of the composition for the delivery of the active pharmaceutical substance. The composition demonstrates favourable dilution properties without being affected by the solubility characteristics of individual components of the composition. Furthermore, the composition exhibits a stable state throughout its shelf life.

The emulsion of the present invention comprises at least an active pharmaceutical substance, a surfactant, or a mixture of surfactants and additives, wherein the average particle size of the emulsion of the composition is less than 200 nm.

In a further embodiment, the invention provides pharmaceutical compositions comprising such compositions and methods of making and using such compositions.

The active pharmaceutical substance referred herein may also be referred to herein as "drug", "active pharmaceutical ingredient" or "therapeutic agent". These terms are used interchangeably refer to chemical material or compound which, when administered to a species (human or animal), is generally bioavailable and induces the desired pharmacologic effect.

In one embodiment the invention provides composition comprising of a lipophilic or partially lipophilic based drugs, an oil phase, surfactants, co-surfactants, adjuvants or other excipients comprising of one or more of stabilizers, antioxidants, preservatives, mucoadhesive agents, buffering agents, absorption enhancers and pH adjusting agents;

In an embodiment of the invention, the active pharmaceutical substance is selected from a group of substances that are soluble in oil or partially soluble in water, such as angiotensin-converting enzyme (ACE) inhibitors, antipsychotics, anti-emetics, analgesics and anti-inflammatory drugs including olanzapine, risperidone, ondansetron and paracetamol. The active pharmaceutical substance can be entrapped in the composition and incorporated into the composition to maintain its stability and to increase its bioavailability. Olanzapine, risperidone, ondansetron and paracetamol is preferred.

The term "Partially soluble in water" referred herein includes sparingly soluble (1 gram drug gets dissolved in 30 to 100 ml solute) slightly soluble (1 gram drug gets dissolved in 100 to 1000 ml solute) and/or very slightly soluble (1 gram drug gets dissolved in 1000 to 10000 ml solute) as provided under European Pharmacopeia definitions and as described in biopharmaceutics classification system under class II and class IV.

The oil phase of the inventive composition comprises one or more fatty acids. Preferably, these are selected from fatty acids having 6 to 22 carbon atoms, more preferably 13 to 21 carbon atoms, more preferably 16 to 20 carbon atoms, most preferably 18 carbon atoms. The fatty acids may be saturated, monounsaturated or polyunsaturated.

Monounsaturated fatty acids are preferred. Preferred fatty acids are myristoleic acid, palmitoleic acid, sapienic acid, oleic acid, elaidic acid, and vaccenic acid. Oleic acid is especially preferred. Mixtures of fatty acids are also contemplated, although use of a single fatty acid remains favoured.

The amount of fatty acid present in the inventive emulsions is in the range of 5 to 25% w/w. More preferably, the fatty acid is present in the range of 5 to 15% w/w, and still more preferably in the amount of 7.5 to 10% w/w.

In a further embodiment, the composition further comprises of various surfactants selected from a group of polyether sufactants, macroglyceride surfactants and/or polysaccharide sufactants. Suitable polyethers are paraformaldehyde, polyethylene glycol, polypropylene glycol, Diethylene glycol monoethyl ether (Transcutol) and polytetramethylene glycol. Polyethylene glycol and/or transcutol is preferred. The polyether suitably has a molecular weight in the range of from 50 gmol-1 to 1000 gmol-1, more preferably from 100 gmol-1 to 500 gmol-1, still more preferably from 150 gmol-1 to 400 gmol-1, such as about 200 gmol-1 (PEG 200) and/or 400 gmol-1 (PEG 400). The polyether may optionally be end-capped.

The polyether is present in the emulsion in an amount of from 2.0 to 25% w/w, preferably from 2.5% to 20% w/w, for example about 15 w/w of PEG 200 or 400 and most preferably from 2.5% of Transcutol.

The oil phase further comprises of a macrogolglyceride surfactant. The term "macrogolglyceride" refers to saturated polyglycolized glycerides such as stearoyl-, lauroyl-, oleoly-, lineoyl-, and caprylocaproyl-macrogol glycerides. A preferred macrogolglyceride is caprylocaproyl macrogol-8 glycerides, commercially available under the trade name Labrasol® and Acconon® CC6. The macrogolglyceride is present in the emulsion in an amount of from 10 to 30% w/w, preferably from 12 to 25% w/w. most preferably 15% to 22.5% w/w of labrasol and 15% w/w of acconon CC 6.

The oil phase further comprises a polysaccharide surfactant. Preferred polysaccharide surfactants are polyoxyethylene sorbitan fatty acid esters or sorbitan monooleate. Particularly preferred are polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), and polysorbate 80 (polyoxyethylene (20) sorbitan monooleate), with polysorbate 20 (polyoxyethylene (20) sorbitan monolaurate) and polysorbate 80 (polyoxyethylene (80) sorbitan monooleate) being most preferred. Polysorbate 20 (polyoxyethylene (20) sorbitan monolaurate) and polysorbate 80 (polyoxyethylene (20) sorbitan monooleate) is commercially available as Tween 20® and Tween 80® and sorbitan monooleate is commercially available as Span 80®

The polysaccharide surfactant is present in the emulsion in an amount of from 2 to 30% w/w, preferably from 5 to 25% w/w and most preferably 5% of span 80 and 15% to 22.5% w/w of tween.

In a further embodiment, the composition in accordance with the present invention can contain one or more additives such as stabilisers, antioxidants, preservatives, mucoadhesive agents, in-situ gelling agents, buffering agents, absorption enhancers and pH adjusting agents in order to improve the physical and chemical stability of the composition. These additives are preferably chosen from the group comprising of butylated hydoxytoulene, butylated hydroxyanisole, Kolliphor® HS, Benzyl alcohol, tocopherol, EDTA and ascorbic acid to prevent oxidation, and to form a stable composition.

In another embodiment, the said antioxidants are selected from a group comprising of one or more of butylated hydroxytoluene, butylated hydroxyanisole and ascorbic acid. The amount of antioxidants in the composition of the invention can preferably range from 0.01% to 5% by weight and more preferably from 0.01% to 0.2% by weight with respect to the total weight of the composition.

In one embodiment, the said absorption enhancers are also optionally added to this invention to improve the mucous absorption and bioavailability. Preferred absorption enhancers are selected from the group consisting of macrogol fatty acid esters, bile salts, and salts of medium-chain fatty acids. Amongst macrogol fatty acid esters, macrogol-15-hydroxystearate, is commercially available as Kolliphor® HS. Amongst bile salts, sodium glycocholate is preferred. Amongst salts of medium-chain fatty acids, sodium caprylate is preferred. The amount of absorption enhancers in the composition of the invention can preferably range from 0.1% to 10% by weight and more preferably from 1% to 5% by weight with respect to the total weight of the composition.

In a further embodiment, to improve the residence time of the dosage form at the site of absorption, mucoadhesive agents may also optionally be added to this invention. Preferred mucoadhesive agents are selected from the group comprising of Synthetic polymers including Cellulose derivatives like hydroxy propyl methylcellulose, sodium carboxy methylcellulose, Poly (vinyl pyrrolidone), Poly (vinyl alcohol); natural polymers like tragacanth, sodium alginate, guar gum, xanthan gum; hydrophilic Polymers: carbomers, chitosan; hydrogels: sodium alginate, guar gum and modified guar gum, etc.

In one embodiment, the different buffering agents that can be used for maintaining the pH are acetate buffer solution, phosphate buffer solution, maleate buffer solution, preferably sodium acetae tryhydarte with glacial acetic acid buffer solution and potassium dihydrogen phosphate with sodium hydroxide buffer solution was used.

The dispersed phase particles and other ingredients of the composition of the invention have an average size of less than 200 nm and preferably ranging from 40 to 170 nm. The composition of the present invention are notable for their low and uniform particle size.

The decrease in the size of the particles makes it possible to promote the penetration of the drug into the target site more effectively and improves the bioavailability. The composition has an excellent stability rate by virtue of the optimum zeta potential, preferably in the range −30 mV to +30 mV, preferably in the range −10 mV to +10 mV most preferably in the range −05 mV to +05 mV.

In an embodiment, the invention provides highly stable composition having drug loading capacity of up to 100 mg/ml, preferably up to 80 mg/ml and leads to quick release of drug to the target site in less than 30 minutes preferably less than 10 minutes.

The composition of the present invention are further notable for their low viscosity, and a desired degree of dispersibility can be obtained to increase the (dispersed) inner phase content to deliver the active ingredient effectively which makes them suitable for administration via e.g. the nasal route. Preferably, the viscosity of the emulsions is less than 250 cP or lower, more preferably less than 150 cP, or lower In another embodiment of the invention, the composition is a transparent and clear monophasic system with high stability.

In one embodiment, the composition of the invention is substantially free of co-solvents, including monohydric alcohols. However, if required co-solvents may be added in less quantities. The preferred co-solvents are benzyl alcohol, phenyl ethyl alcohol, chlorobutanol. In this context, "substantially free" or less quantities means less than 1% w/w.

The composition of the present invention is further notable for their high stability.

In one embodiment, the composition of the invention provides an advantage of higher drug loading capability in the range of 10 to 80 mg/ml as evidenced in the examples below. Preferably, the drug loading for olanzapine is in the range of 35 to 45 mg/ml, preferably 40 mg/ml, and most preferably 38.46 mg/ml. The drug loading for ondansetron is in the range of 10 to 15 mg/ml, preferably 12 mg/ml, the drug loading for paracetamol is between 60 to 80 mg/ml, preferably 75 mg/ml; and for resperidone it is between 20 to 30 mg/ml preferably 25 mg/ml. This property of the invention enables improvement of drug bioavailability and reduction of the dosing frequency also suitable for highly potent low-dose drugs. Even with higher drug content, the invention showed stable and favorable physicochemical characteristics. The higher drug loading and the reduction in the particle size indicate the solubility of the lipophilic and partially lipophilic drugs in the instant invention leading to high bioavailability.

The emulsion of the invention comprises an aqueous phase. Preferably, the aqueous phase is present in an amount greater by weight than any other single component. The aqueous phase is present in an amount of between 15 and 50% w/w.

In yet another embodiment, the compositions of the present invention are prepared by conventional methods well known to those skilled in the art. The composition of the composition of the invention can be obtained by a process of subjecting the oleic acid, surfactants and co-surfactants or a mixture thereof to homogenization using magnetic stirrer. The oil and surfactant mixture is then mixed with a solution containing the required drug and the additives are added and subjected to vigorous stirring at controlled room temperature ranging between 20° C. to 25° C. (68 to 77° F.) using any suitable mixing apparatus known to those skilled in the art for about 30 minutes or until the entire amount of drug is dissolved. The homogenized mixture is then subjected to water phase preferably containing ascorbic acid and mixed well to get clear transparent composition, which indicates that the drug has dissolved/incorporated successfully.

In further embodiment, the composition can be used in any pharmaceutical field where this type of composition is useful. While various embodiments herein describe nasal and ocular route of delivery, most preferably nasal delivery of compositions containing the drug, it is further envisaged that the delivery of the drug can be performed by any suitable delivery mechanism that provides therapeutically effective levels of the drug. Accordingly, the system is particularly useful for non-parenteral modes of administration such as buccal, sublingual, rectal, transdermal, topical, nasal, urethral, vaginal, and ocular. When administered by such non-parenteral modes the methods and composition of the present invention can deliver drug both locally and systemically as desired including oral, intramuscular and transcutaneous routes.

In one embodiment, the invention provides composition for intra nasal delivery or ophthalmic route; preferably composition comprises drops, gel composition or aerosol composition. In an embodiment, the invention provides composition comprising an emulsion as disclosed herein can be administrated preferably as a spray or aerosol or ocular route. By aerosol we refer to an airborne mist of liquid particles. The dispensing system for such a composition may typically be a can or bottle that contains a liquid pressurized by compressed, propellant gas. Similarly, sprays of liquid particles may be produced by devices in which the liquid is pressurized by a hand-operated pump and forced through an atomizer nozzle. A typical nasal spray composition consists of the therapeutic agent suspended or dissolved in an aqueous medium, which is filled into a bottle with a metered spray pump. Pump actuation by the patient delivers the drug in fine droplets into the nasal cavity. Furthermore, the composition of ocular suspension consists of the therapeutic agent suspended or dissolved in aqueous medium, which is filled in a bottle for use as eye drops.

In still a further embodiment of the invention, the aforesaid composition confers a synergistic therapeutic effect of high bioavailability compared to the therapeutic effect when a pharmaceutical substance is administered separately or in partial combination of the said ingredients of the said composition.

In further embodiment of the invention, the synergistic effect as defined above has been adapted to increase the bioavailability by almost 1.3 times to 12 times relative to the therapeutic effect when pharmaceutical substance is administered separately and/or in partial combination of the said ingredients of the said composition administered through various routes, preferably intra nasal and ocular route. Increasing the bioavailability plays a very important role in the toxicity of the drugs. The composition can help in reduction in the dosage or the frequency of the dosages in the patients due to its higher bioavailability while reducing side effect of the drugs. In an object, the bioavailability of the pharmaceutically active substances is enhanced by at least 1.3 times to 12 times. In another object, the active pharmaceutical substance such as olanzapine when administered to the nasal cavity of a subject establishes a high bioavailability by at least 5 to 6 times in therapeutic plasma concentration within 5 to 10 minutes and bioavailability of 10 to 12 times in brain with in 10 to 30 minutes. The table shows drug efficiency of olanzapine through intra nasal route by almost 1.3 times or by 25% in reaching the brain concentration in 5 to 10 minutes and 1.78 times or 45% in attaining the plasma concentration within minutes when compared to intramuscular route of administration. Similarly, when compared to standard oral route of administration using the same drug olanzapine with the current invention through nasal route, the brain concentration was 5.31 times or 80% better and plasma concentration was almost 10.69 times or 91% higher in.

In a further embodiment, the composition with ondansetron also showed higher bioavailability of therapeutic plasma concentration by at least 8 to 10 times within a mean duration of about less than one hour. As shown in table the plasma concentration was almost 8.29 times or 87% higher than oral route of delivery.

In a further embodiment, as seen in the examples listed below and in table the composition has a drug loading capability of between about 10 mg/ml and about 80 mg/ml, preferably between 12 mg/ml to 75 mg/ml.

Bioavailability of a drug in this context means the mount of dose that reaches the site of action (brain and eye in the instant case) in an unchanged form (and usually active) at a particular time. The area under the time versus plasma and brain concentration curve provided in the results below is reflective of the amount of drug that has been absorbed in the brain and plasma using the compositions of the composition provided herein.

In another embodiment, the invention relates to a nasal spray for treatment of pain associated with migraine, headache, cluster headache, psychosis, nausea and vomiting or chemotherapy induced nausea and vomiting, autonomic cephalgia, agitation, sleep disorder, disturbance of mental state and ocular solution for reduction in ocular pressure.

In one embodiment, the method relates to a method of treatment of a mammal suffering from or susceptible to pain associated with migraine, comprising administering an effective amount of a composition according to the invention, wherein the pharmaceutically active ingredient is, or comprises, olanzapine or a pharmaceutically acceptable salt thereof. Preferably, the method involves administration of the composition nasally. Dosing may be once per day (for example, at the onset of symptoms), or may be several times per day as per the requirements. Preferably, the amount is from 0.01 to 20 mg depending upon the severity of symptoms.

In one embodiment, the method relates to a method of treatment of a mammal suffering from or susceptible to pain associated with migraine, comprising administering an effective amount of a composition according to the invention, wherein the pharmaceutically active ingredient is, or comprises, olanzapine or a pharmaceutically acceptable salt thereof. Preferably, the method involves administration of the composition nasally. Dosing may be once per day (for example, at the onset of symptoms), or may be several times per day as per the requirements. Preferably, the amount is from 0.01 to 20 mg depending upon the severity of symptoms.

In one embodiment, the method relates to a method of treatment of a mammal suffering from antipsychotic related symptoms including schizophrenia and bipolar disorders, comprising administering an effective amount of a composition according to the invention, wherein the pharmaceutically active ingredient is, or comprises, respiridone or a pharmaceutically acceptable salt thereof. Preferably, the method involves administration of the composition nasally. Dosing may be once per day (for example, at the onset of symptoms), or may be several times per day as per the requirements. Preferably, the amount is from 0.01 to 16 mg depending upon the severity of symptoms.

In one embodiment, the method relates to a method of treatment of a mammal suffering from nausea and vomiting that may be caused by surgery or by medicine, comprising administering an effective amount of a composition according to the invention, wherein the pharmaceutically active ingredient is, or comprises, ondansetron or a pharmaceutically acceptable salt thereof. Preferably, the method involves administration of the composition nasally. Dosing may be once per day (for example, at the onset of symptoms), or may be several times per day as per the requirements. Preferably, the amount is from 0.01 to 24 mg depending upon the severity of symptoms.

In one aspect, the method relates to a method of treatment of a mammal suffering from high intraocular pressure, comprising administering an effective amount of a composition according to the invention, wherein the pharmaceutically active ingredient is, or comprises, paracetamol or a pharmaceutically acceptable salt thereof. Preferably, the method involves administrating of the composition through ophthalmic route. Dosing may be once per day (for example, at the onset of symptoms), or may be several times per day.

Preferably, the method of treatment involves delivery of a predetermined amount of therapeutic agent (e.g. olanzapine, ondansetron, respiridone) by means of a metered actuation. Preferably, the method involves administration of from 0.01 to 100 mg of active agent, most preferably 0.1 to 20 mg per metered actuation.

The methods of the invention in some embodiments involve a second therapeutic agent of known efficacy in the treatment of migraine, for simultaneous, separate or sequential administration with the compositions described (particularly those of olanzapine). Preferred second therapeutic agents are selected from the group of almotriptan, eletriptan, flovatriptan, naratriptan, rizatriptan, sumatriptan, zolmitriptan, ergotamine, dihydroergotamine, bosentan and lanepitant.

Accordingly the present invention provides a pharmaceutical oil-in-water nano-emulsion, comprising: a pharmaceutically active substance, encased in monounsaturated fatty acid droplets, the droplets having an average particle size in the range of 60 to 200 nm; a non-ionic surfactant system comprising a mixture of polyethers, macrogolglycerides and polysaccharides; and pharmaceutically acceptable adjuvants.

The present invention also provides a process for the preparation of an oil-in-water emulsion composition, by initially forming an oil phase in the presence of a monounsaturated fatty acid, a polyether surfactant, a macrogolglyceride surfactant and a polysaccharide surfactant, under stirring at an ambient temperature; and adding a therapeutically amount pharmaceutically active substance to the oil phase, under constant stirring and at an ambient temperature, to encase said active substance, in the monounsaturated fatty acid droplets, the droplets with particle size in the range of 60 to 200 nm, to obtain a homogenous oil phase; and adding an aqueous medium to the homogenous oil phase, under stirring to obtain the oil-in-water emulsion.

The preferred embodiments of the present invention are now described by the following examples. These examples are illustrative in nature and will make it possible to understand the invention better and shall not be considered as limiting the scope of the invention.

EXAMPLES

Preparation of the Micro-Emulsion of the Composition Using Olanzapine

Example 1: Composition 1

To 7.5% (w/w) of oleic acid, 2.5% (w/w) of transcutol, 22.5% (w/w) of Labrasol along with 22.5% (w/w) of tween 80 and 15% (w/w) PEG 400 were added sequentially under constant stirring. To this 5% (w/w) Kolliphor HS 15. followed by 3.846% (w/w) of Olanzapine was added and mixed slowly into the above oil-surfactant mixture under constant stirring at 600-1000 rpm using a magnetic stirrer or overhead stirrer at room temperature (20 to 25° C.) for about 30 minutes or until the entire amount of drug was dissolved. Subsequently, 0.1% BHT along with 0.05% (w/w) EDTA and 0.1% (w/w) tochopherol were added consecutively under constant stirring at around 600-1000 rpm using a magnetic stirrer at room temperature (20 to 25° C.) until a homogeneous phase was formed.

Sufficient quantity of 4.5 pH buffered water was slowly added under stirring (600-1000 rpm on magnetic stirrer or any suitable stirrer at room temperature) to the above drug solution to get 100% product weight.

Example 2: Composition 2

To 7.5% (w/w) of oleic acid, 2.5% (w/w) of transcutol, 22.5% (w/w) of Labrasol along with 22.5% (w/w) of tween 80 and 15% (w/w) PEG 400 were added sequentially under constant stirring. To this 5% (w/w) Kolliphor HS 15 followed by 3.846% (w/w) of Olanzapine was added and mixed slowly into the above oil-surfactant mixture under constant stirring at 600-1000 rpm using a magnetic stirrer or overhead stirrer at room temperature (20 to 25° C.) for about 30 minutes or until the entire amount of drug was dissolved. Subsequently, 0.1% BHT along with 0.05% (w/w) EDTA and 0.05% (w/w) tochopherol were added consecutively under constant stirring at around 600-1000 rpm using a magnetic stirrer at room temperature (20 to 25° C.) until a homogeneous phase was formed.

Sufficient quantity of water was slowly added under stirring (600-1000 rpm on magnetic stirrer or any suitable stirrer at room temperature) to the above drug solution to get 100% product weight.

Example 3: Composition 3

To 7.5% (w/w) of oleic acid, 1% (w/w) of benzyl alcohol was added followed by 3.846% (w/w) of Olanzapine and mixed slowly into the above oil-surfactant mixture under constant stirring at 600-1000 rpm using a magnetic stirrer or any suitable stirrer at room temperature (20 to 25° C.) for about 30 minutes or until the entire amount of drug was dissolved. Thereafter, to this, 10% (w/w) of transcutol, and 22.5% (w/w) of Labrasol along with 15% (w/w) of tween 80, 15% (w/w) PEG 400, 5% (w/w) Kolliphor HS 15 and 5% (w/w) SPAN 80 were added sequentially under constant stirring. Subsequently, 0.1% BHT along with 0.05% (w/w) EDTA and 0.05% (w/w) tochopherol were added one after the other consecutively under constant stirring at around 600-1000 rpm using a magnetic stirrer at room temperature (20 to 25° C.) until a homogeneous phase was formed.

Sufficient quantity of 7 pH buffered water was slowly added under stirring (600-1000 rpm on magnetic stirrer or any suitable stirrer at room temperature) to the above drug solution to get 100% product weight.

Example 4: Composition 4

To 7.5% (w/w) of oleic acid, 2.5% (w/w) of transcutol, 22.5% (w/w) of Labrasol along with 22.5% (w/w) of tween 80, 15% (w/w) PEG 400 were added sequentially under constant stirring. To this 5% (w/w) Kolliphor HS 15 followed by 3.846% (w/w) of Olanzapine was added and mixed slowly into the above oil-surfactant mixture under constant stirring at 600-1000 rpm using a magnetic stirrer or any suitable stirrer at room temperature (20 to 25° C.) for about 30 minutes or until the entire amount of drug was dissolved. Subsequently, 0.1% BHT along with 0.05% (w/w) EDTA and 0.1% (w/w) tochopherol were added consecutively under constant stirring at around 600-1000 rpm using a magnetic stirrer at room temperature (20 to 25° C.) until a homogeneous phase was formed.

Sufficient quantity of water was slowly added under stirring (600-1000 rpm on magnetic stirrer or any suitable stirrer at room temperature) to the above drug solution to get 100% product weight.

Example 5: Composition 5

To 7.5% (w/w) of oleic acid, 2.5% (w/w) of transcutol, 22.5% (w/w) of Labrasol along with 22.5% (w/w) of tween 80, 15% (w/w) PEG 400 were added sequentially under constant stirring. To this 5% (w/w) Kolliphor HS 15 followed by 3.846% (w/w) of Olanzapine was added and mixed slowly into the above oil-surfactant mixture under constant stirring at 600-1000 rpm using a magnetic stirrer or any suitable stirrer at room temperature (20 to 25° C.) for about 30 minutes or until the entire amount of drug was dissolved. Subsequently, 0.1% BHT along with 0.05% (w/w) EDTA, 0.1% (w/w) tochopherol and 0.1% (w/w) ascorbic acid were added consecutively under constant stirring at around 600-1000 rpm using a magnetic stirrer at room temperature (20 to 25° C.) until a homogeneous phase was formed.

Sufficient quantity of water was slowly added under stirring (600-1000 rpm on magnetic stirrer or any suitable stirrer at room temperature) to the above drug solution to get 100% product weight.

Example 6: Composition 6

To 7.5% (w/w) of oleic acid, 2.5% (w/w) of transcutol, 22.5% (w/w) of Labrasol along with 22.5% (w/w) of tween 80, 15% (w/w) PEG 400 were added sequentially under constant stirring. To this 5% (w/w) Kolliphor HS 15 followed by 3.846% (w/w) of Olanzapine was added and mixed slowly into the above oil-surfactant mixture under constant stirring at 600-1000 rpm using a magnetic stirrer or any suitable stirrer at room temperature (20 to 25° C.) for about 30 minutes or until the entire amount of drug was dissolved. Subsequently, 0.1% BHT along with 0.05% (w/w) EDTA, 0.1% (w/w) tochopherol and 0.15% (w/w) ascorbic acid were added consecutively under constant stirring at around 600-1000 rpm using a magnetic stirrer at room temperature (20 to 25° C.) until a homogeneous phase was formed.

Sufficient quantity of water was slowly added under stirring (600-1000 rpm on magnetic stirrer or any suitable stirrer at room temperature) to the above drug solution to get 100% product weight.

Example 7: Composition 7

To 7.5% (w/w) of oleic acid, 15% (w/w) of Labrasol along with 15% (w/w) of tween 80 and 15% (w/w) PEG 400 were added sequentially under constant stirring. To this 5% (w/w) Kolliphor HS 15 followed by 3.846% (w/w) of Olanzapine was added and mixed slowly into the above oil-surfactant mixture under constant stirring at 600-1000 rpm using a magnetic stirrer or any suitable stirrer at room temperature (20 to 25° C.) for about 30 minutes or until the entire amount of drug was dissolved. Subsequently, 0.05% (w/w) of EDTA and 0.1% (w/w) of tochopherol was after the other consecutively under constant stirring at around 600-1000 rpm using a magnetic stirrer at room temperature (20 to 25° C.) until a homogeneous phase was formed.

Sufficient quantity of water was slowly added under stirring (600-1000 rpm on magnetic stirrer or any suitable stirrer at room temperature) to the above drug solution to get 100% product weight.

Example 8: Composition 8

To 10% (w/w) of oleic acid, 22.5% (w/w) of Labrasol along with 22.5% (w/w) of tween 20 and 15% (w/w) PEG 200 was added. To this 0.01% (w/w) each of BHA and BHT along with 0.1% (w/w) ascorbic acid was added one after another under constant stirring at around 600-1000 rpm on magnetic stirrer or any suitable stirrer at room temperature (20 to 25° C.) until a homogeneous phase was formed.

38.46 mg olanzapine per gram of emulsion was mixed slowly into the above oil-surfactant mixture under constant stirring at 600-1000 rpm on magnetic stirrer at room temperature (20 to 25° C.) for about 30 minutes or until the entire amount of drug was dissolved.

Sufficient quantity of water was slowly added under stirring (600-1000 rpm) on magnetic stirrer at room temperature) to the above drug solution to get 100% product weight.

Example 9: Composition 9

To 10% (w/w) of oleic acid, 22.5% (w/w) of Labrasol along with 22.5% (w/w) of tween 20 and 15% (w/w) PEG 200 were added. To this, 5% (w/w) Kolliphor HS, 0.01% (w/w) each of BHA and BHT along with 0.1% (w/w) ascorbic acid were added sequentially under constant stirring at around 600-1000 rpm on magnetic stirrer or any suitable stirrer at room temperature (20 to 25° C.) until a homogeneous phase was formed.

38.46 mg of olanzapine per gram of emulsion was mixed slowly into the above oil-surfactant mixture under constant stirring at 600-800 rpm using magnetic stirrer at room temperature (20 to 25° C.) for about 30 minutes or until the entire amount of drug was dissolved.

Sufficient quantity of water was slowly added under stirring (600-1000 rpm) using a magnetic stirrer at room temperature) to the above drug solution to get 100% product weight.

Example 10: Composition 10

To 10% (w/w) of oleic acid, 22.5% (w/w) of Labrasol along with 22.5% (w/w) of tween 20 and 15% (w/w) PEG 200 were added. To this 1% (w/w) sodium glycocholate, 0.01% (w/w) each of BHA and BHT along with 0.1% (w/w) ascorbic acid were added sequentially under constant stirring at around 600-1000 rpm on magnetic stirrer or any suitable stirrer at room temperature (20 to 25° C.) until a homogeneous phase was formed.

38.46 mg of olanzapine per gram of emulsion was mixed slowly into the above oil-surfactant mixture under constant stirring at 600-1000 rpm using a magnetic stirrer at room temperature (20 to 25° C.) for about 30 minutes or until the entire amount of drug was dissolved.

Sufficient quantity of water was slowly added under stirring (600-800 rpm on magnetic stirrer at room temperature) to the above drug solution to get 100% product weight.

Example 11: Composition 11

To 10% (w/w) of oleic acid, 22.5% (w/w) of Labrasol along with 22.5% (w/w) of tween 20 and 15% (w/w) PEG 200 were added. To this 1% (w/w) sodium caprylate, 0.01% (w/w) each of BHA and BHT along with 0.1% ascorbic acid were added sequentially under constant stirring at around 600-1000 rpm on magnetic stirrer or any suitable stirrer at room temperature (20 to 25° C.) until a homogeneous phase was formed.

38.46 mg of olanzapine per gram of emulsion was mixed slowly into the above oil-surfactant mixture under constant stirring at 600-1000 rpm using a magnetic stirrer at room temperature (20 to 25° C.) for about 30 minutes or until the entire amount of drug was dissolved.

Sufficient quantity of water was slowly added under stirring (600-1000 rpm on magnetic stirrer at room temperature) to the above drug solution to get 100% product weight.

Example 12: Composition 12

To 10% (w/w) of oleic acid, 22.5% (w/w) of Labrasol along with 22.5% (w/w) of tween 20 and 15% (w/w) Acconon CC 6 were added. To this 0.01% (w/w) each of BHA and BHT along with 0.1% (w/w) ascorbic acid was added one after another under constant stirring at around 600-1000 rpm on magnetic stirrer or any suitable stirrer at room temperature (20 to 25° C.) until a homogeneous phase was formed.

38.46 mg olanzapine per gram of emulsion was mixed slowly into the above oil-surfactant mixture under constant stirring at 600-1000 rpm on magnetic stirrer at room temperature (20 to 25° C.) for about 30 minutes or until the entire amount of drug was dissolved.

Sufficient quantity of water was slowly added under stirring (600-1000 rpm) on magnetic stirrer at room temperature) to the above drug solution to get 100% product weight.

Preparation of the Micro-Emulsion of the Composition Using Paracetamol

Example 13: Composition 13

To 10% (w/w) of oleic acid, 22.5% (w/w) of Labrasol along with 22.5% (w/w) of tween 20 and 15% (w/w) PEG 200 was added. The ingredients were added sequentially under constant stirring at around 600-800 rpm using a magnetic stirrer at room temperature (20 to 25° C.) until a homogeneous phase was formed.

7.5% (w/w) of paracetamol was mixed slowly into the above oil-surfactant mixture followed by addition of 0.5% (w/w) sodium citrate under constant stirring at 600-1000 rpm using a magnetic stirrer at room temperature (20 to 25° C.) for about 30 minutes or until the entire amount of drug was dissolved.

Sufficient quantity of water was slowly added under stirring (600-1000 rpm) on magnetic or any other suitable stirrer at room temperature to the above drug solution to get 100% product weight.

Example 14: Composition 14

To 10% (w/w) of oleic acid, 22.5% (w/w) of Labrasol along with 22.5% (w/w) of tween 20, 15% (w/w) PEG 200 and 1% (w/w) sodium glycoholate was added. The ingredients were added sequentially under constant stirring at around 600-1000 rpm using a magnetic or any other suitable stirrer at room temperature (20 to 25° C.) until a homogeneous phase was formed.

7.5% of paracetamol was mixed slowly into the above oil-surfactant mixture followed by addition of 0.5% (w/w) sodium citrate under constant stirring at 600-1000 rpm using a magnetic or any other suitable stirrer at room temperature (20 to 25° C.) for about 30 minutes or until the entire amount of drug was dissolved.

Sufficient quantity of water was slowly added under stirring (600-1000 rpm) on magnetic or any other suitable stirrer at room temperature to the above drug solution to get 100% product weight.

Preparation of the Micro-Emulsion of the Composition Using Risperidone

Example 15: Composition 15

To 10% (w/w) of oleic acid, 22.5% (w/w) of Labrasol along with 22.5% (w/w) of tween 20 and 15% (w/w) PEG 200 was added. To this 5% (w/w) Kolliphor HS 15 and 0.01% (w/w) each of BHA and BHT were added sequentially under constant stirring at around 600-800 rpm using a magnetic stirrer at room temperature (20 to 25° C.) until a homogeneous phase was formed.

2.5% (w/w) of Resperidone was mixed slowly into the above oil-surfactant mixture followed by addition of 0.1% (w/w) ascorbic acid dissolved in water under constant stirring at 600-1000 rpm using a magnetic stirrer at room temperature (20 to 25° C.) for about 30 minutes or until the entire amount of drug was dissolved.

Sufficient quantity of water was slowly added under stirring (600-800 rpm on magnetic stirrer at room temperature) to the above drug solution to get 100% product weight.

Example 16: Composition 16

To 10% (w/w) of oleic acid, 22.5% (w/w) of Labrasol along with 22.5% (w/w) of tween 20 and 15% (w/w)

Acconon CC6 were added. To this 0.01% (w/w) each of BHA and BHT were added sequentially under constant stirring at around 600-800 rpm using a magnetic stirrer at room temperature (20 to 25° C.) until a homogeneous phase was formed.

2.5% (w/w) of Resperidone was mixed slowly into the above oil-surfactant mixture followed by addition of 0.1% (w/w) ascorbic acid dissolved in water under constant stirring at 600-1000 rpm using a magnetic stirrer at room temperature (20 to 25° C.) for about 30 minutes or until the entire amount of drug was dissolved.

Sufficient quantity of water was slowly added under stirring (600-1000 rpm) on magnetic stirrer at room temperature to the above drug solution to get 100% product weight.

Preparation of the Micro-Emulsion of the Composition Using Ondansetron

Example 17: Composition 17

To 10% (w/w) of oleic acid, 0.01% (w/w) each of BHA and BHT were added, followed by 1.2% (w/w) of Ondansetron sequentially under constant stirring. To this 22.5% (w/w) of Labrasol along with 22.5% (w/w) of tween 20 and 15% (w/w) of PEG 200 were added and was mixed slowly into the above oil-surfactant mixture under constant stirring at 600-1000 rpm using a magnetic stirrer at room temperature (20 to 25° C.) for about 30 minutes or until the entire amount of drug was dissolved. Subsequently, 0.1% (w/w) of ascorbic acid and 0.5% of sodium citrate were added sequentially under constant stirring at around 600-800 rpm using a magnetic stirrer at room temperature (20 to 25° C.) until a homogeneous phase was formed.

Sufficient quantity of water was slowly added under stirring (600-1000 rpm on magnetic stirrer at room temperature) to the above drug solution to get 100% product weight.

Example 18: Composition 18

To 10% (w/w) of oleic acid, 0.01% (w/w) each of BHA and BHT were added, followed by 1.2% (w/w) of Ondansetron sequentially under constant stirring. To this 22.5% (w/w) of Labrasol along with 22.5% (w/w) of tween 20 and 15% (w/w) of PEG 200 were added and was mixed slowly into the above oil-surfactant mixture under constant stirring at 600-1000 rpm using a magnetic stirrer at room temperature (20 to 25° C.) for about 30 minutes or until the entire amount of drug was dissolved. Subsequently, 1% sodium glycocholate, 0.1% (w/w) of ascorbic acid and 0.5% of sodium citrate were added sequentially under constant stirring at around 600-800 rpm using a magnetic stirrer at room temperature (20 to 25° C.) until a homogeneous phase was formed.

Sufficient quantity of water was slowly added under stirring (600-1000 rpm on magnetic stirrer at room temperature) to the above drug solution to get 100% product weight.

Physiochemical Characterisation of the Micro Emulsion

In another embodiment of the present invention, physiochemical properties such as Particle size distribution and the droplet size of all the emulsions along with polydispersity and Zeta potential was measured and assessed by dynamic light scattering also referred to as photon correlation spectroscopy using a particle size analyser. In an embodiment, 1 mL of the diluted composition sample was placed in a clear disposable zeta cuvette. The zeta potential analysis at 25° C. in Malvern Zetasizer instrument was performed. The zeta potential and polydispersity indices were calculated using the inbuilt software. The primary feature of the nano or micro emulsions is the droplet size, which must be in the nanometer range and is a crucial factor indicating their performance because it determines the rate and extent of drug release as well as drug absorption. Therefore, in the advantageous composition of the present invention, the average droplet size of emulsion was found to be around 150 nm. Polydispersity index (PDI) indicates uniformity of droplet size within the composition and its stability. The value of PDI was found to be less than 0.3. Low value of PDI indicated uniform distribution of nano droplets within the composition, leading to more rapid absorption and improved bioavailability of the drug.

Figure 14:
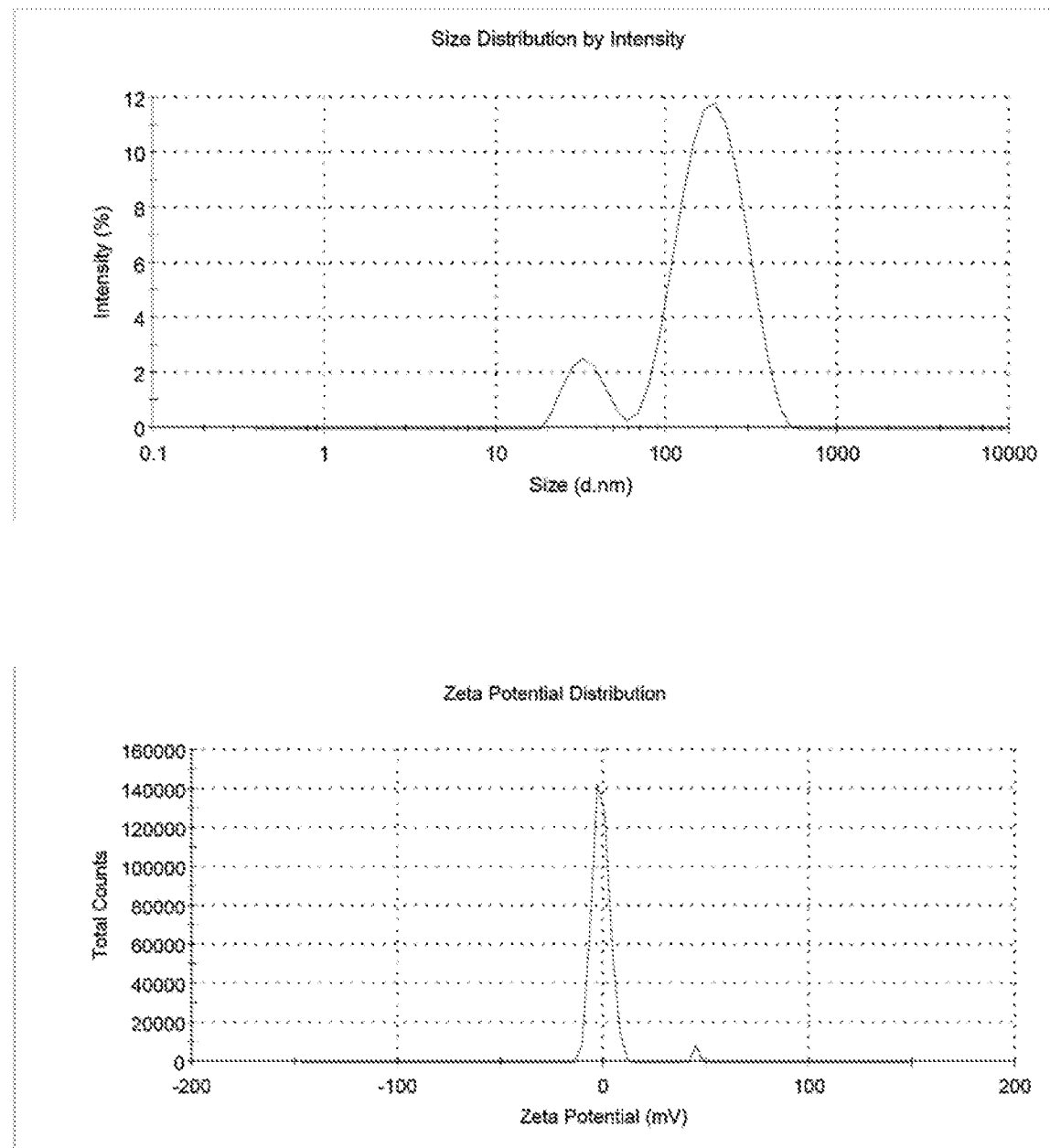
FIG. 14A to FIG. 14D depict particle size distribution in nanometre (nm), polydispersity index (PDI) and zeta potential (MV) of the exemplary composition No. 14 of the present invention under various conditions.
Figure 14B:
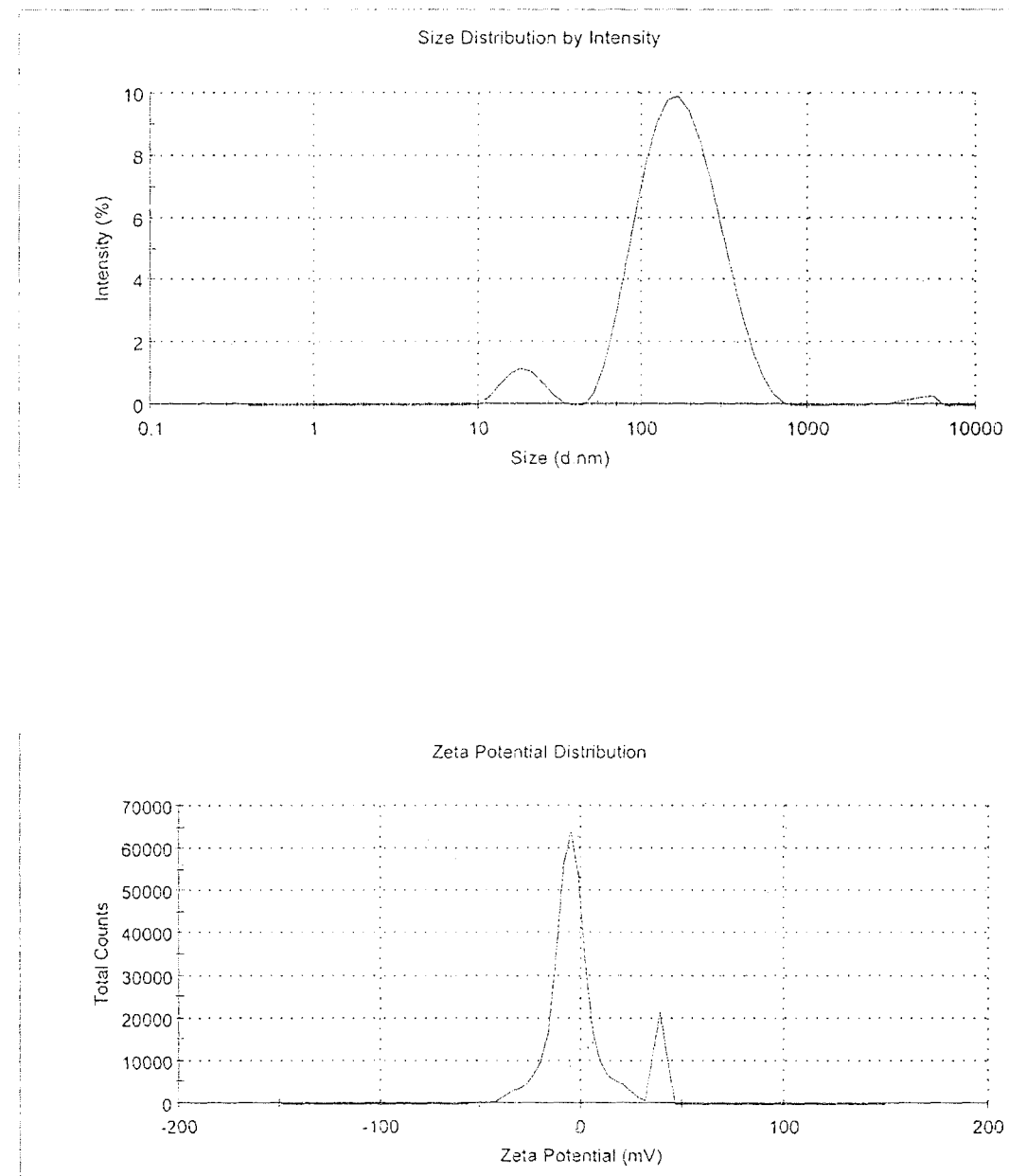
Figure 14C:
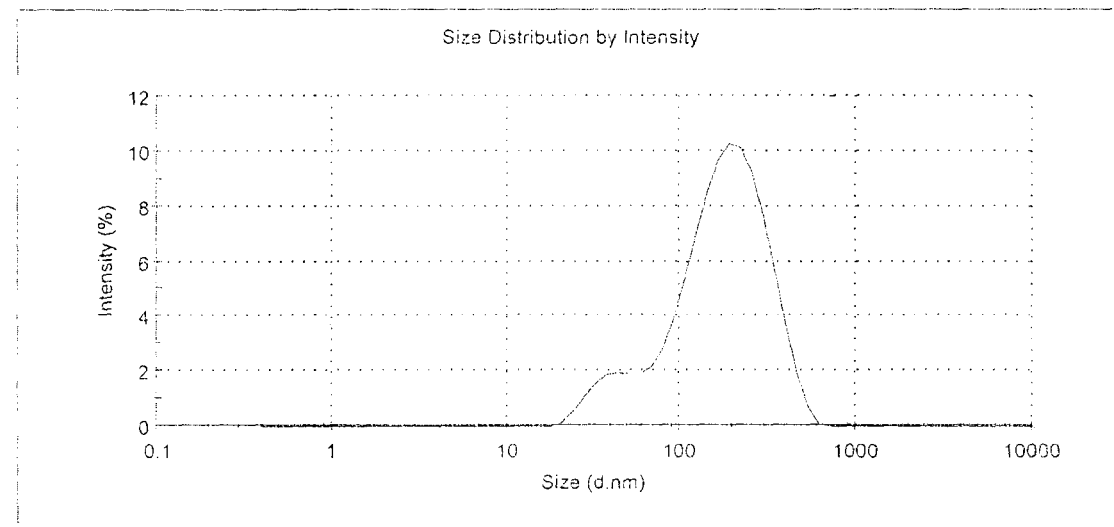
Figure 14C:
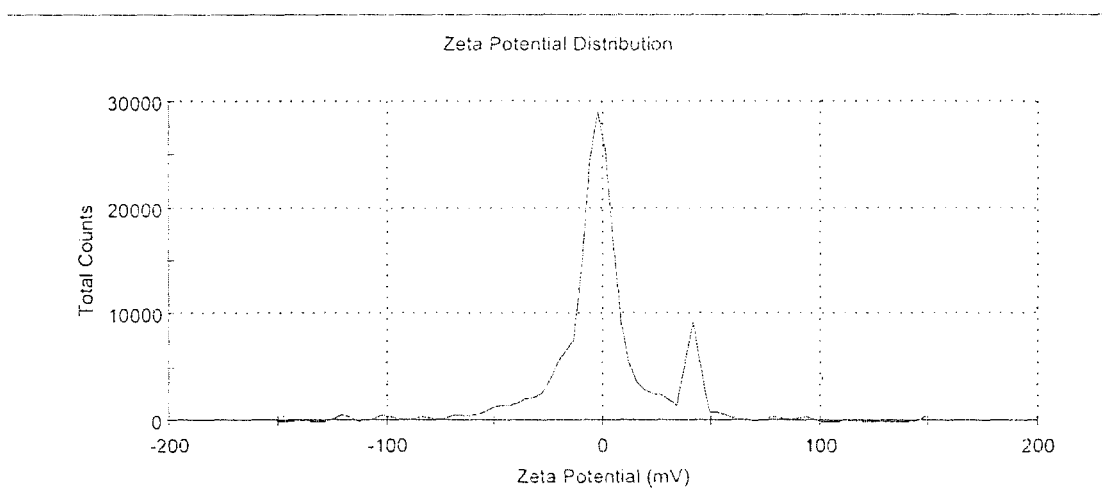
Figure 14D:
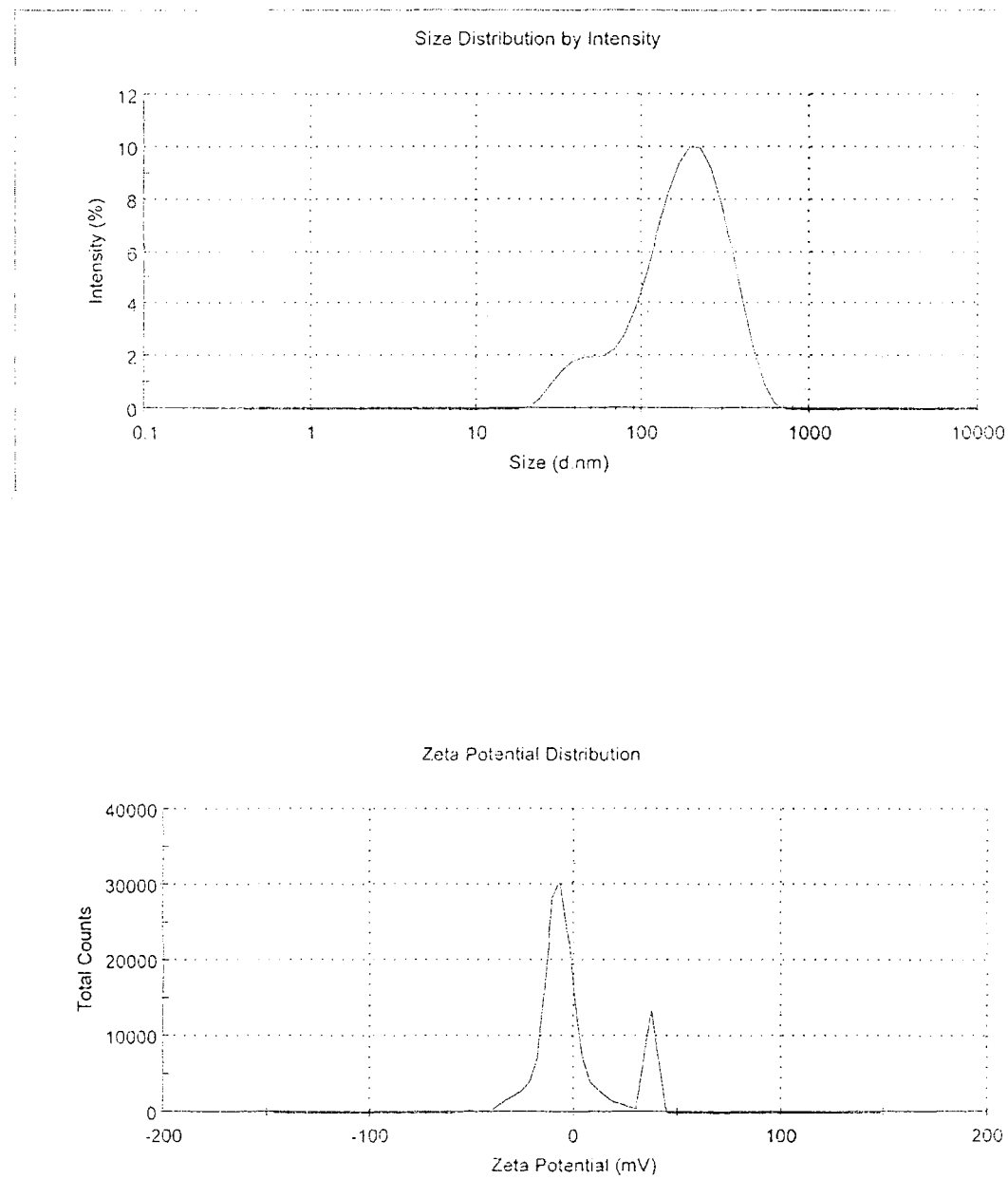
Figure 15:
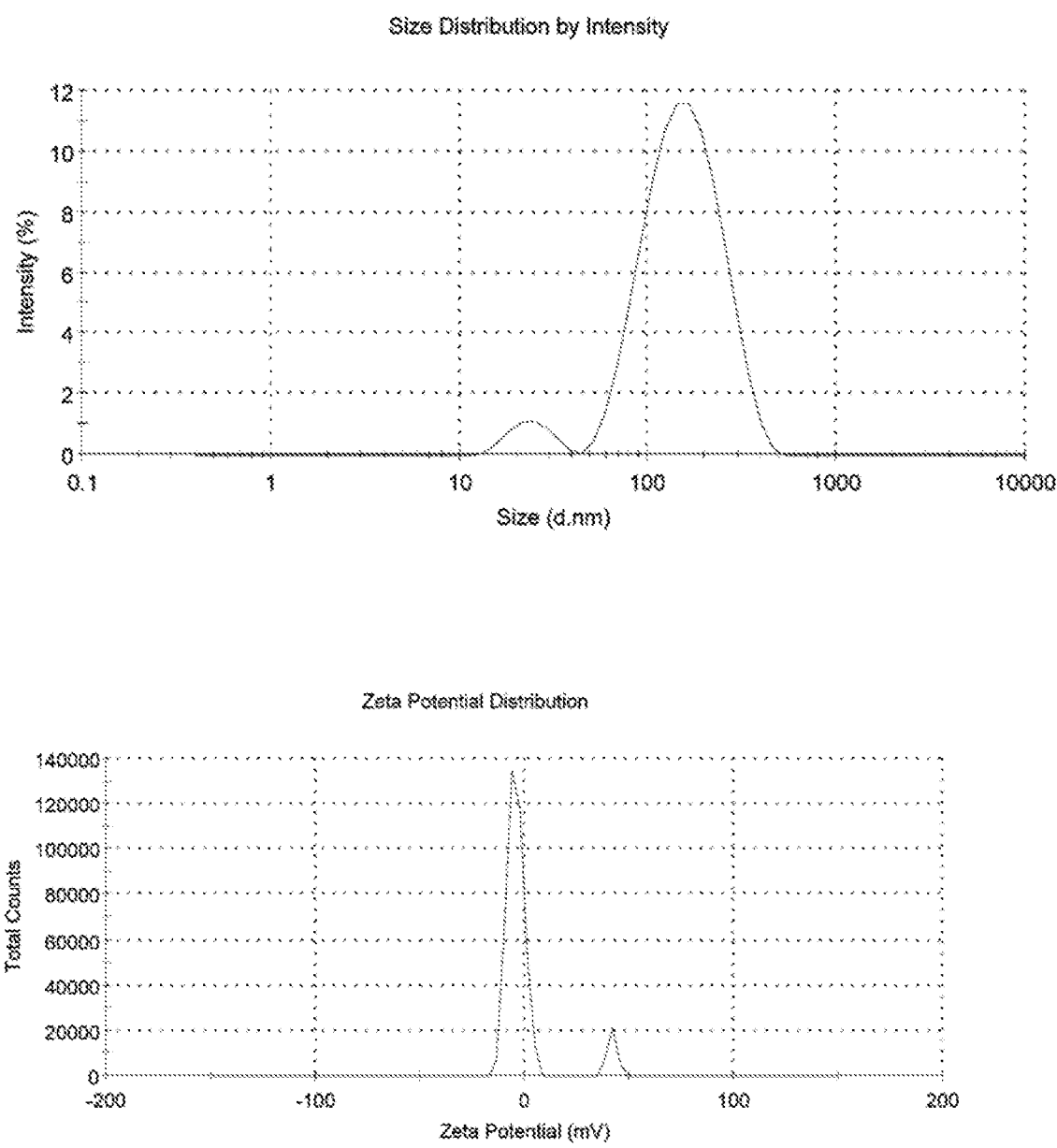
FIG. 15A to FIG. 15D depict particle size distribution in nanometre (nm), polydispersity index (PDI) and zeta potential (MV) of the exemplary composition No. 15 of the present invention under various conditions.
Figure 15B:
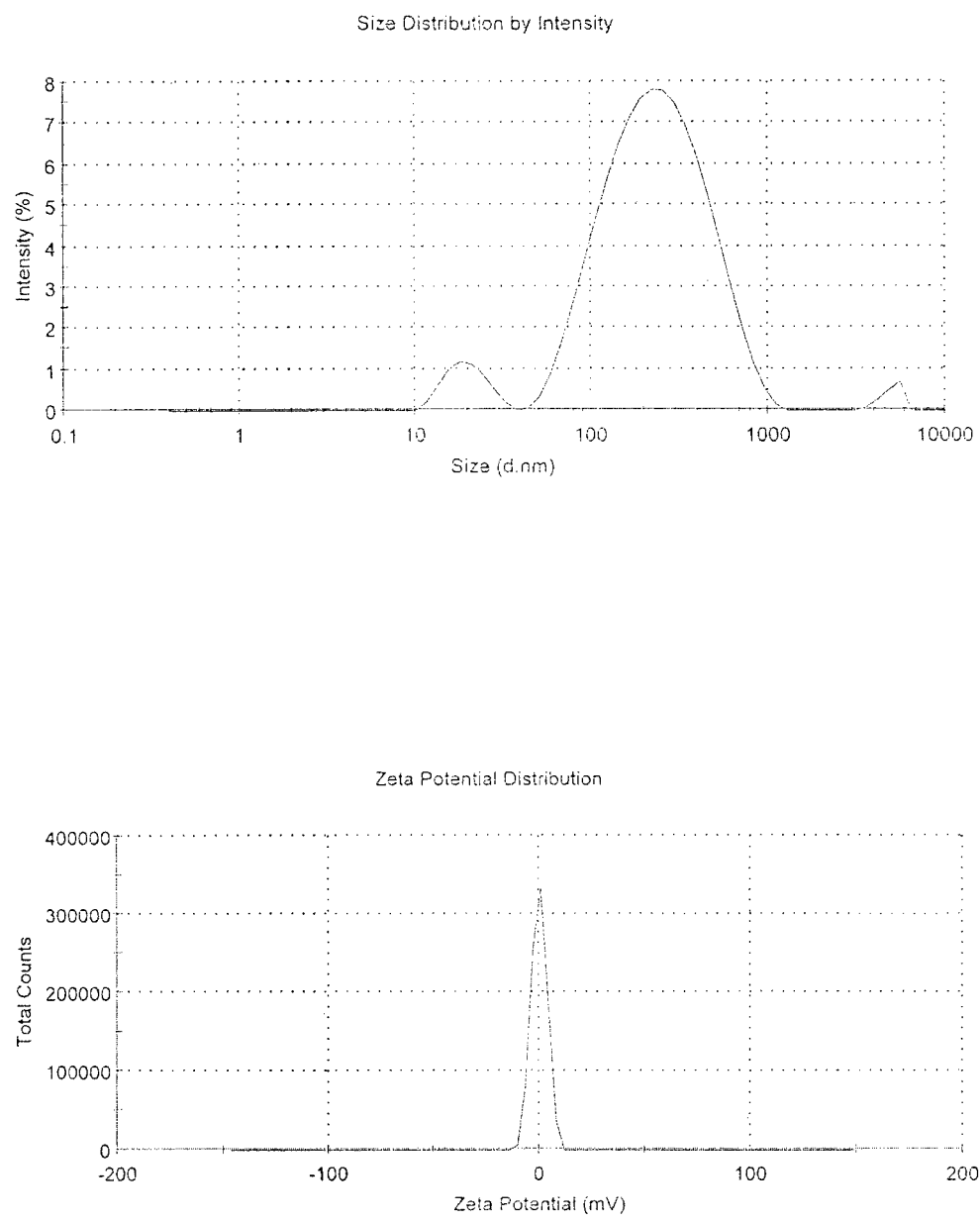
Figure 15:
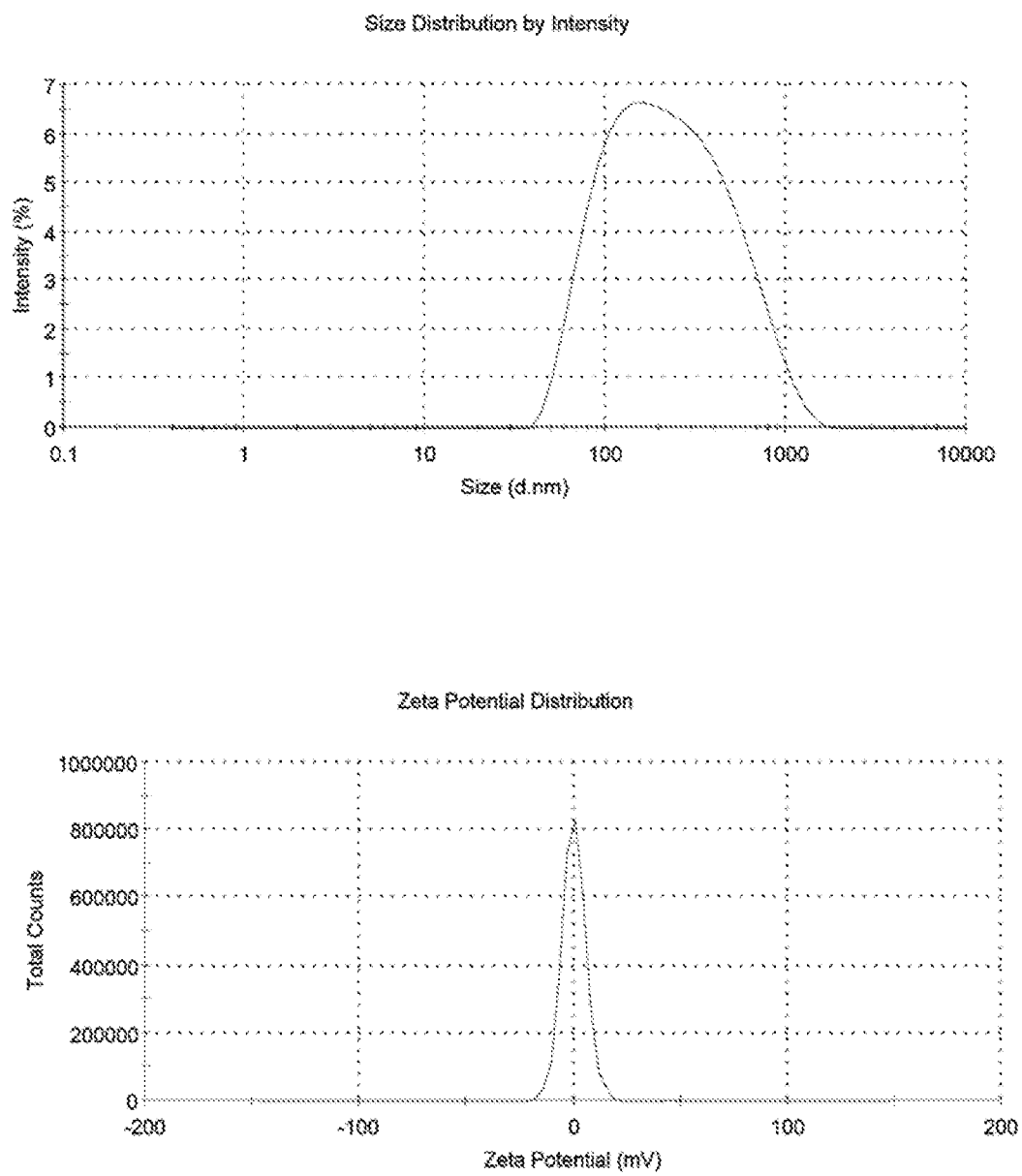
Figure 15D:
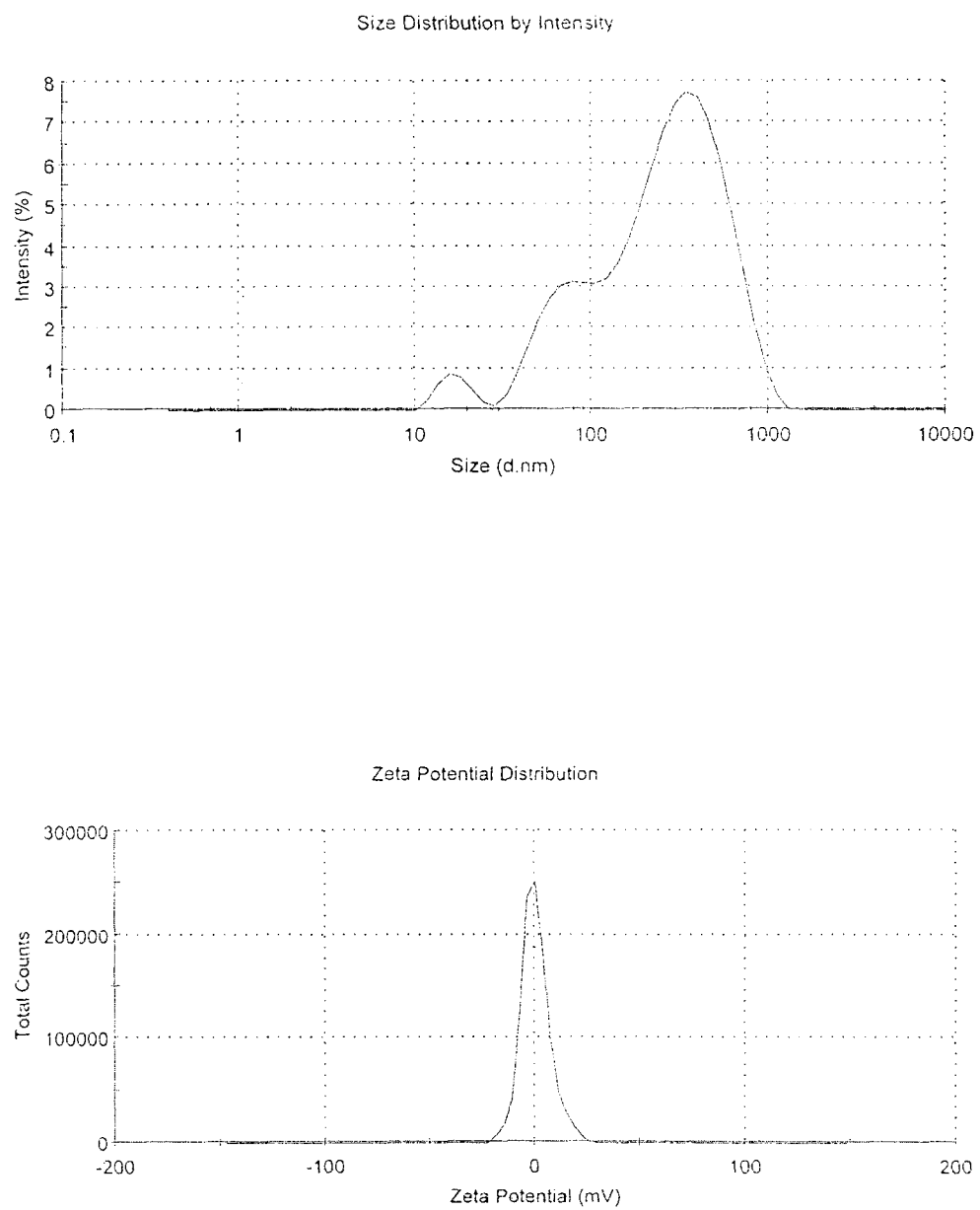
Figure 16A:
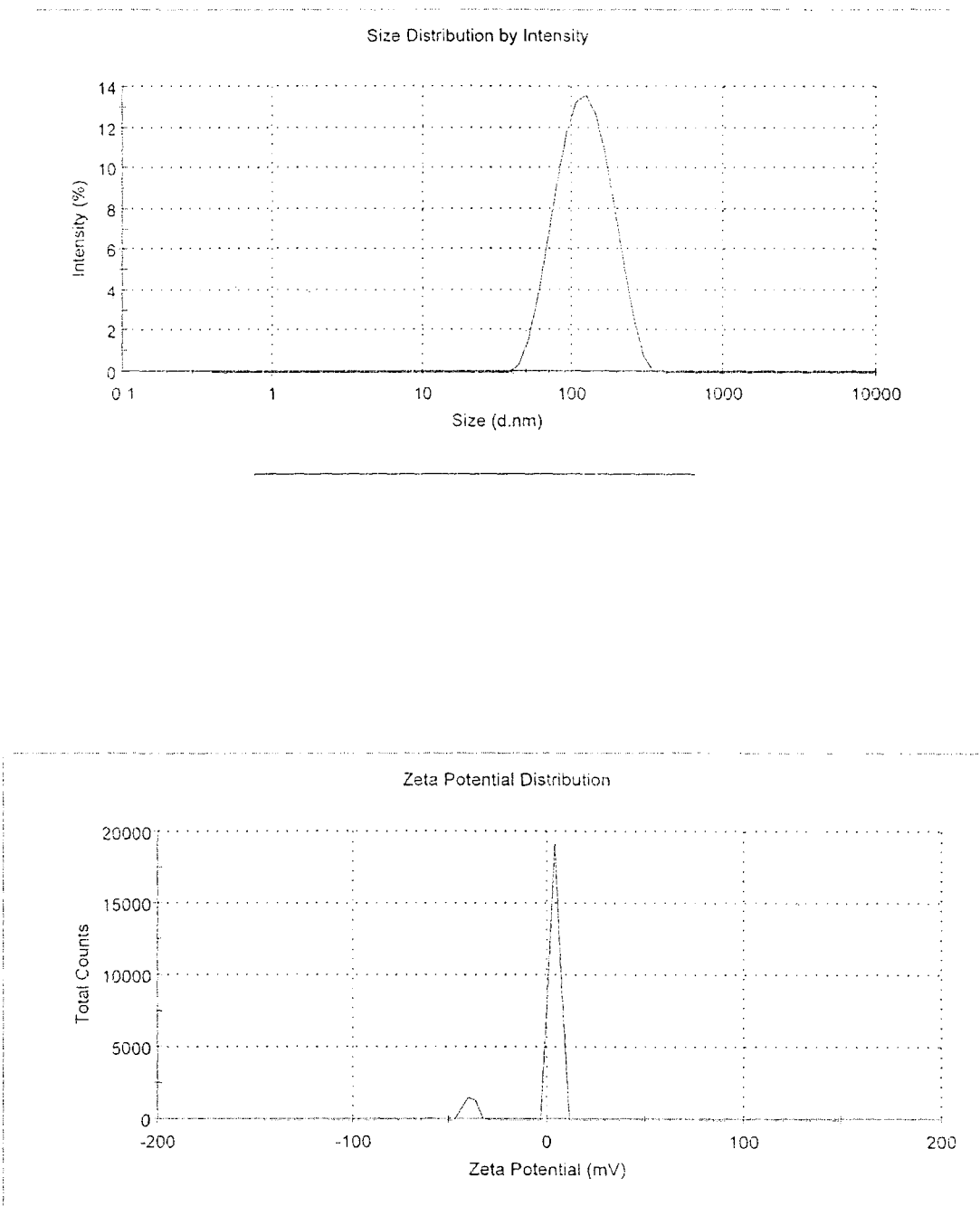
FIG. 16A to FIG. 16D depict particle size distribution in nanometre (nm), polydispersity index (PDI) and zeta potential (MV) of the exemplary composition No. 16 of the present invention under various conditions.
Figure 16B:
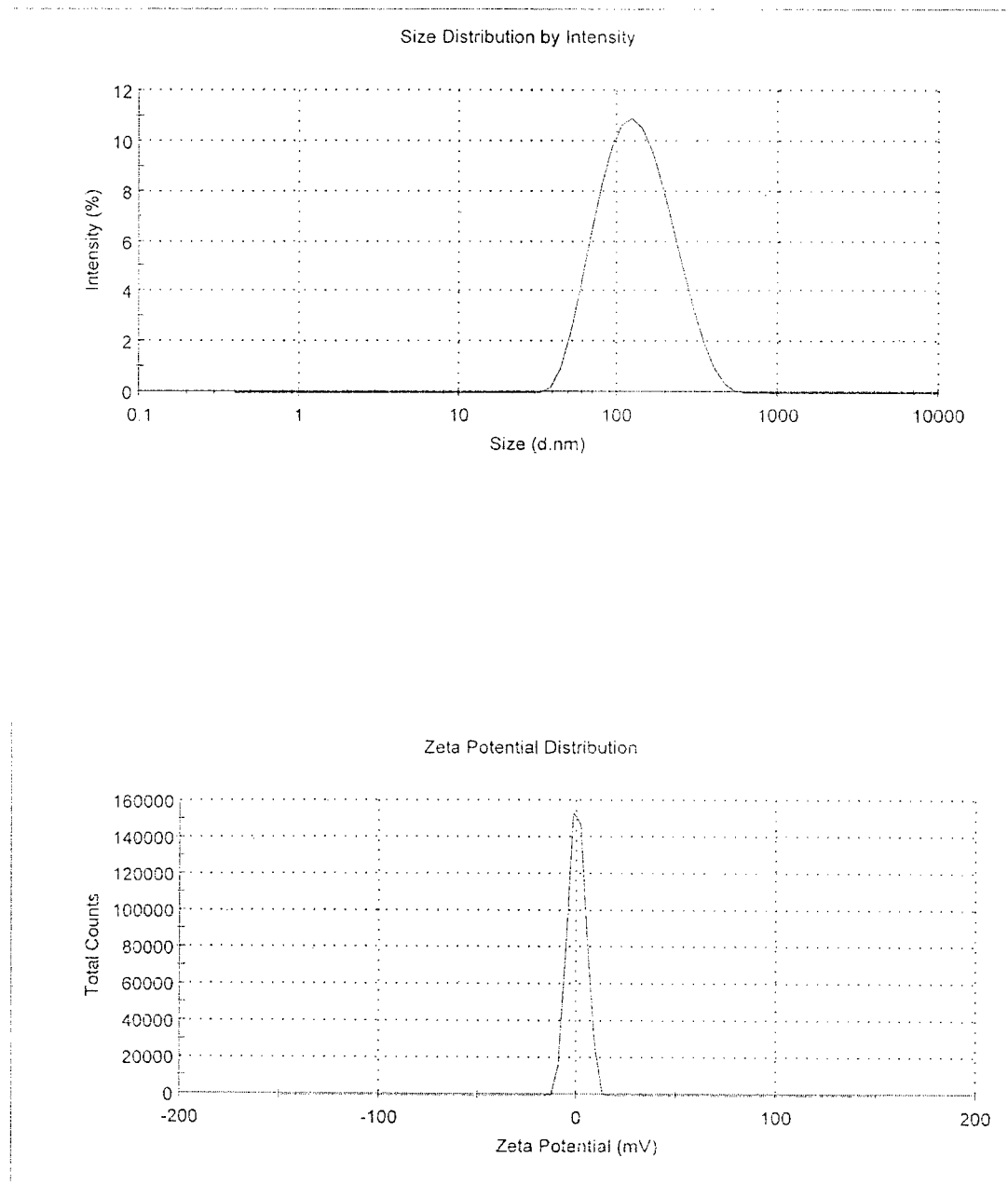
Figure 16C:
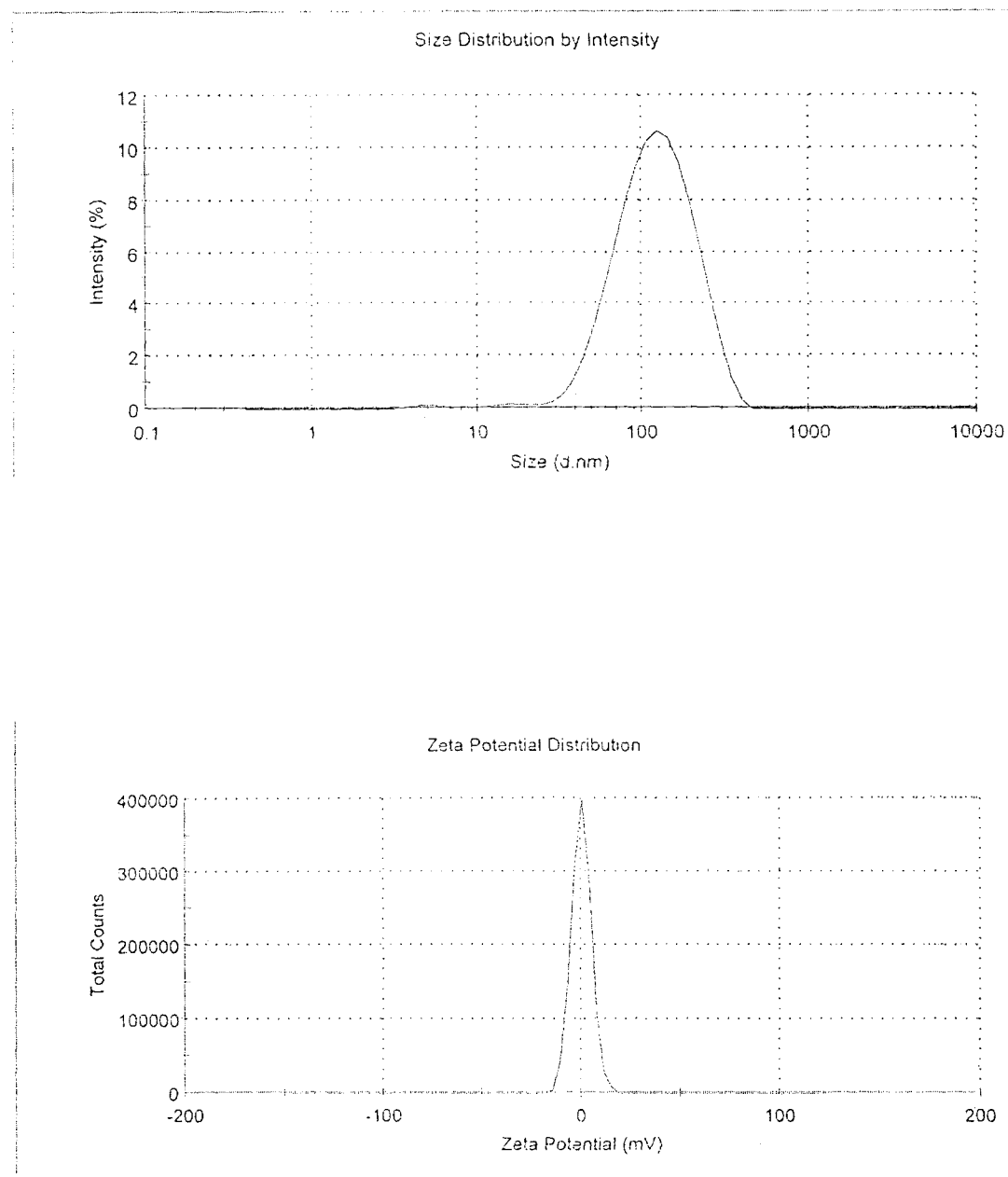
Figure 16:
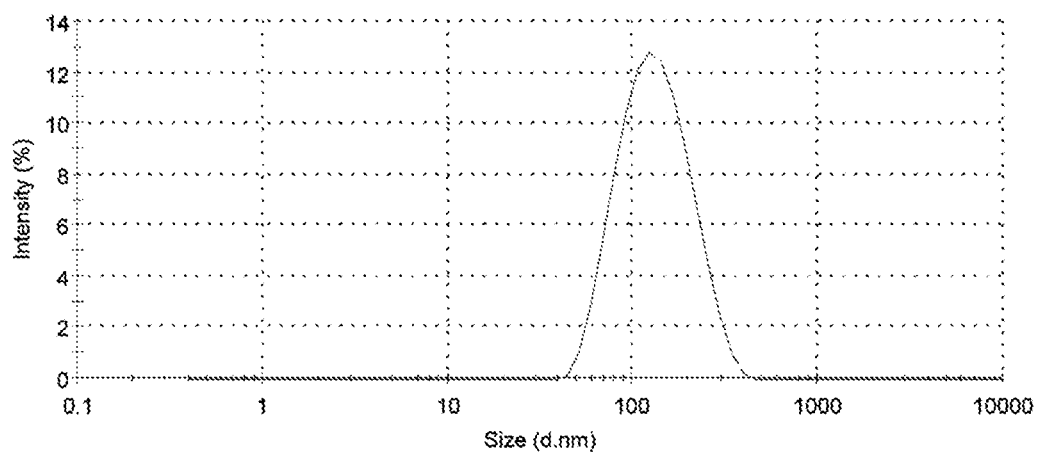
Figure 16:
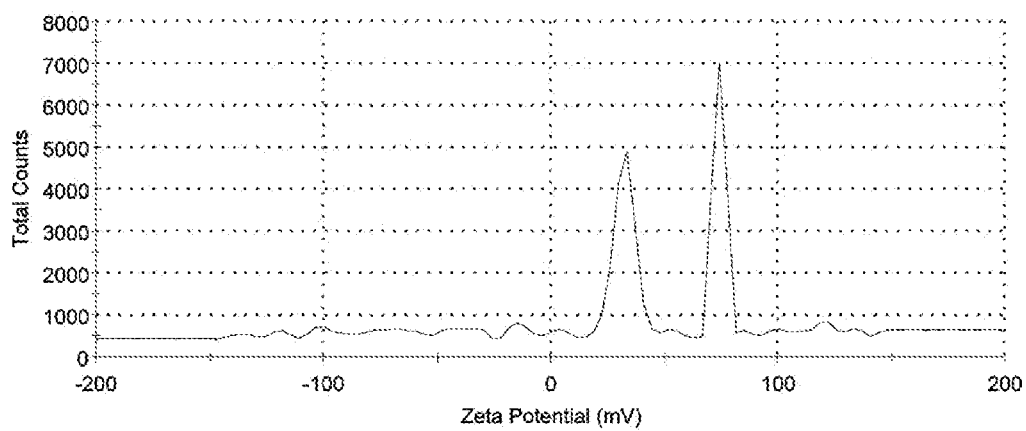
Figure 17:
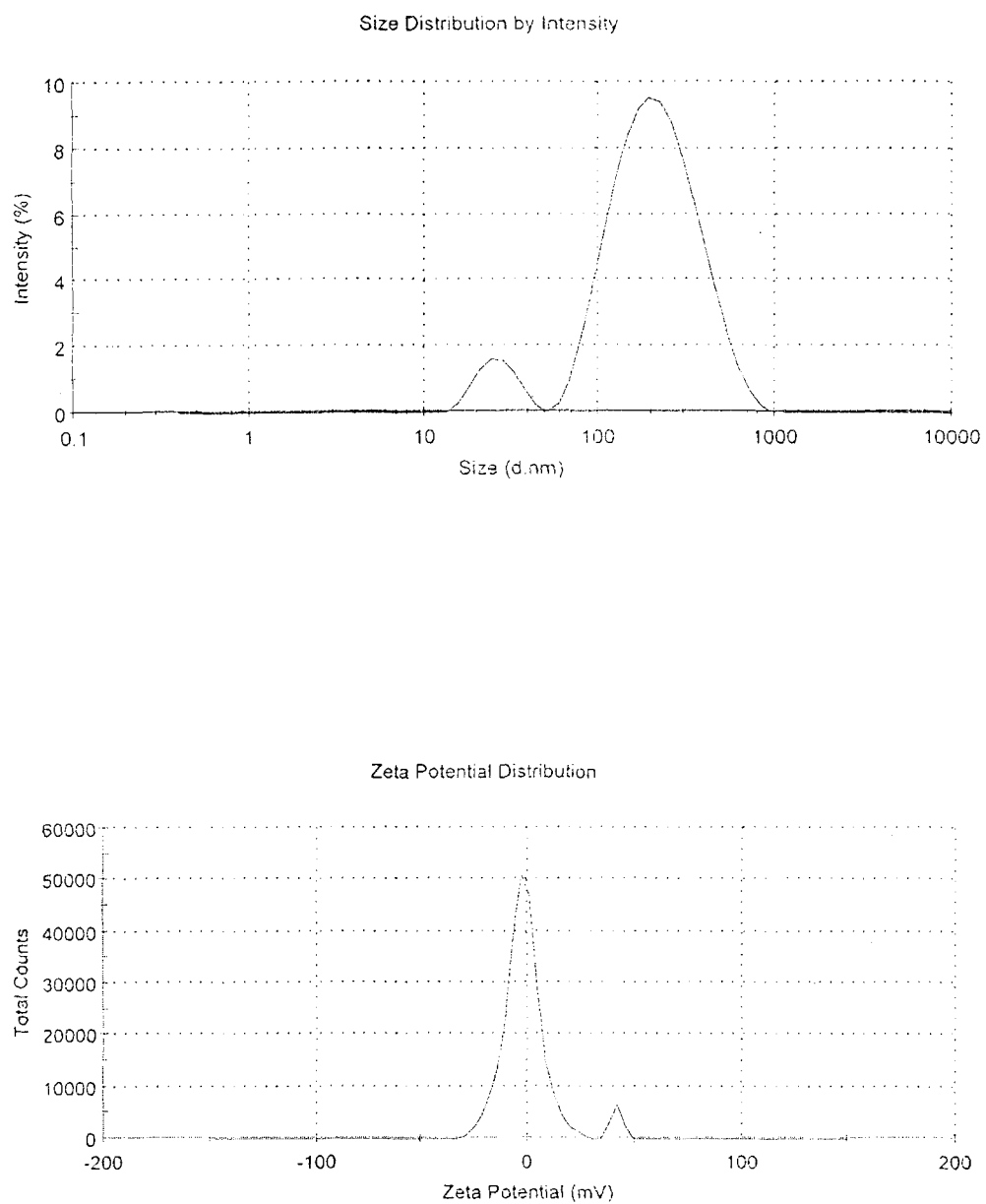
FIG. 17A to FIG. 17D depict particle size distribution in nanometre (nm), polydispersity index (PDI) and zeta potential (MV) of the exemplary composition No. 17 of the present invention under various conditions.
Figure 17B:
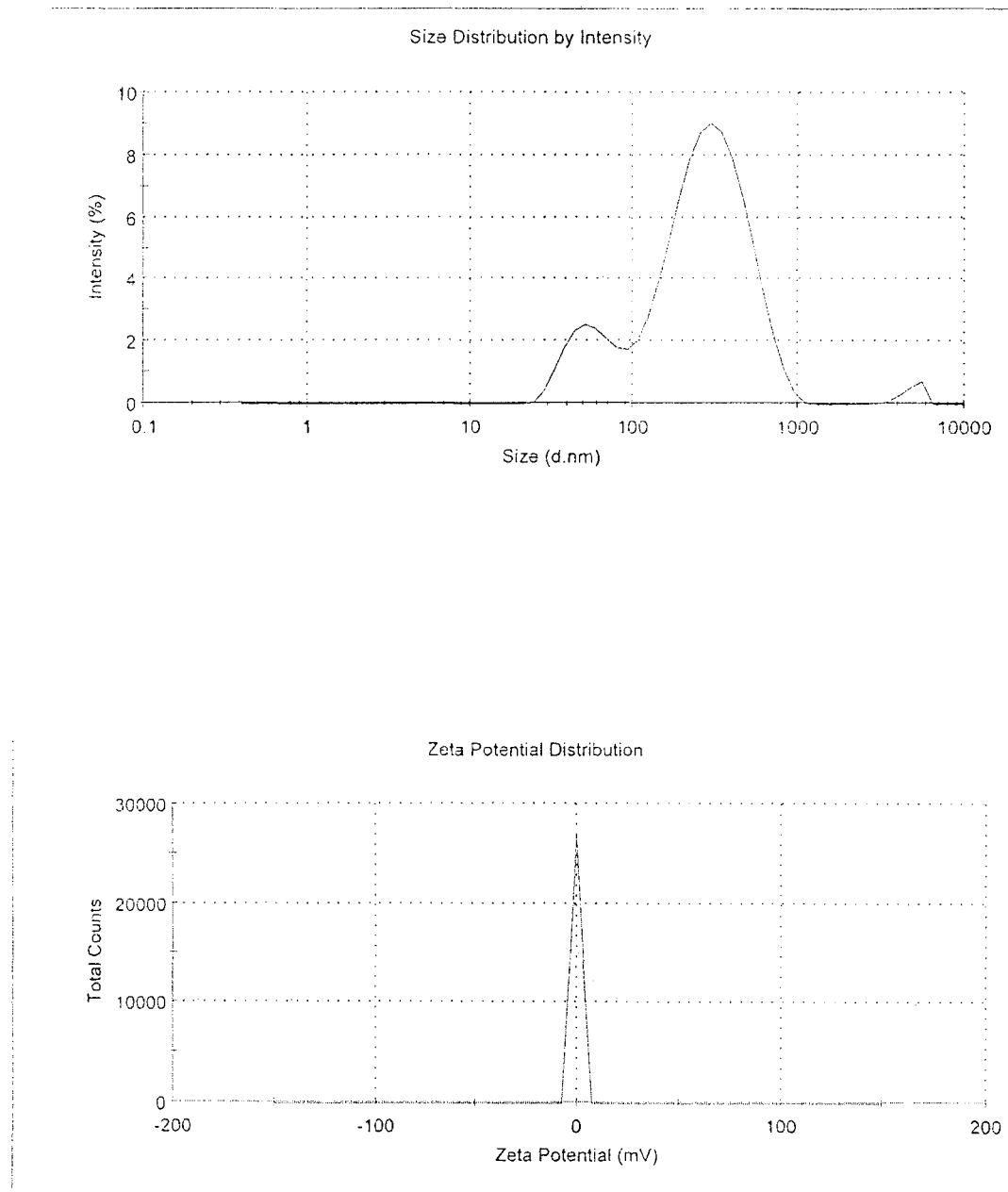
Figure 17C:
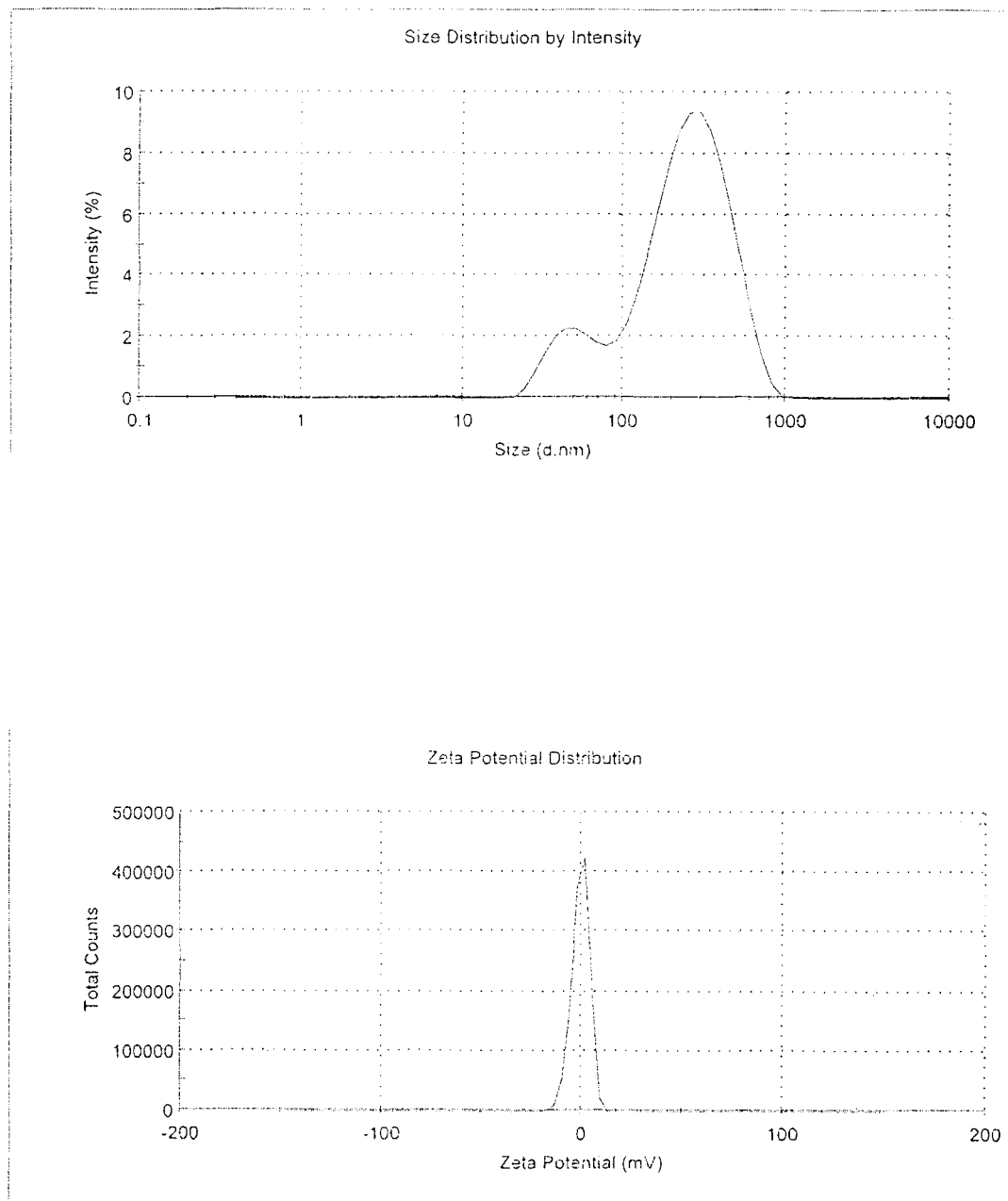
Figure 17D:
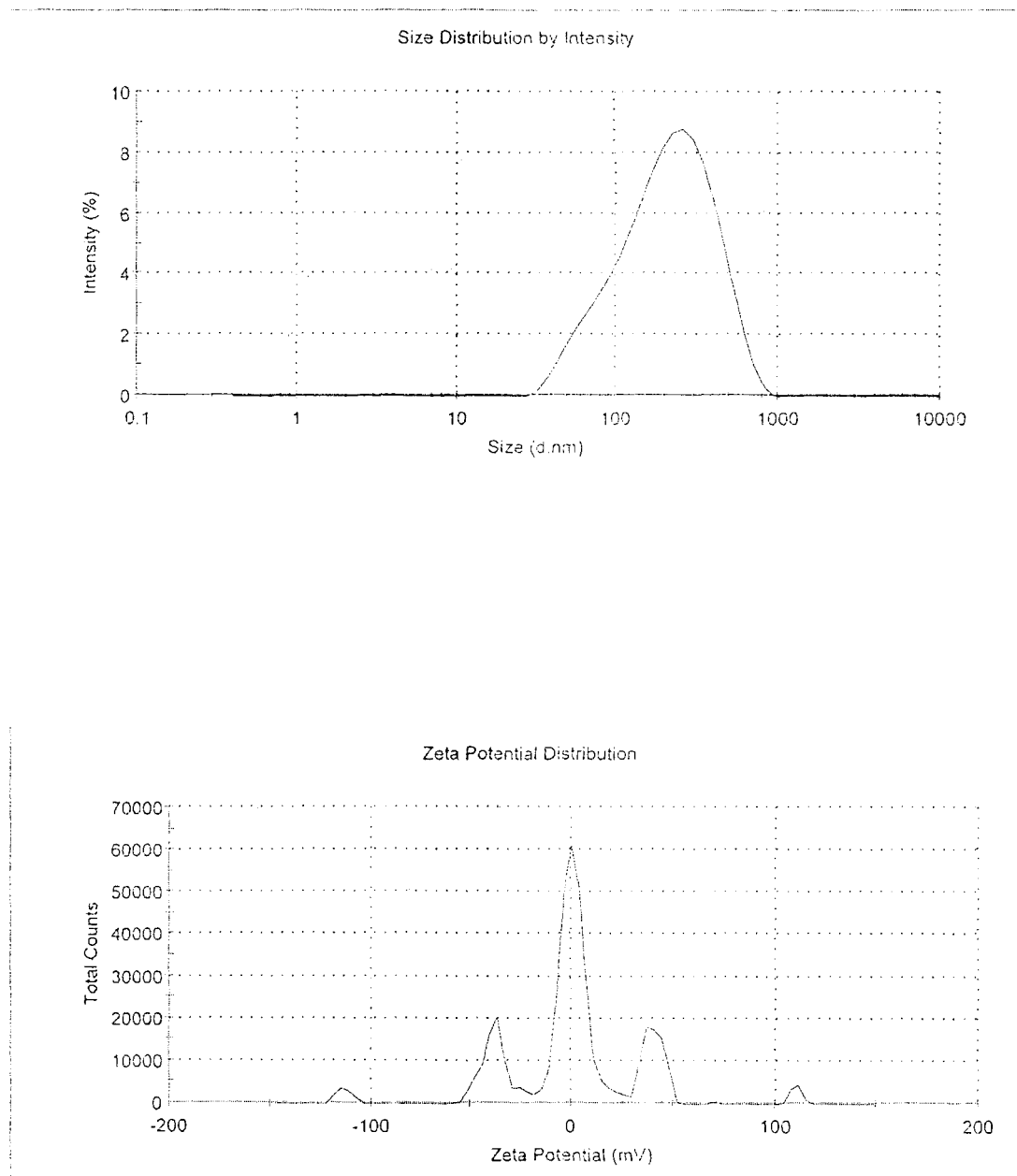
Figure 18A:
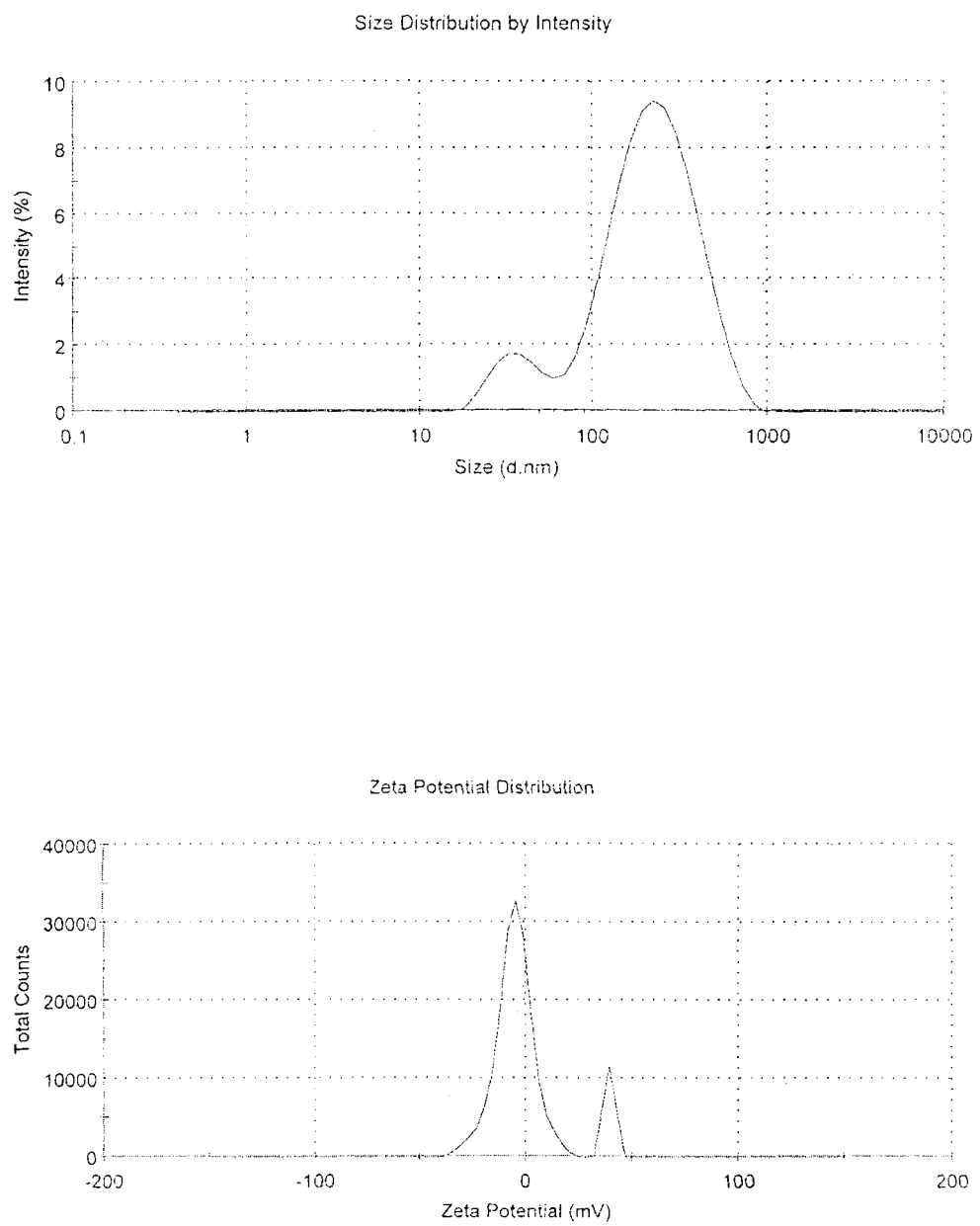
FIG. 18A to FIG. 18D depict particle size distribution in nanometre(nm), polydispersity index(PDI) and zeta potential (MV) of the exemplary composition No. 18 of the present invention under various conditions.
Figure 18B:
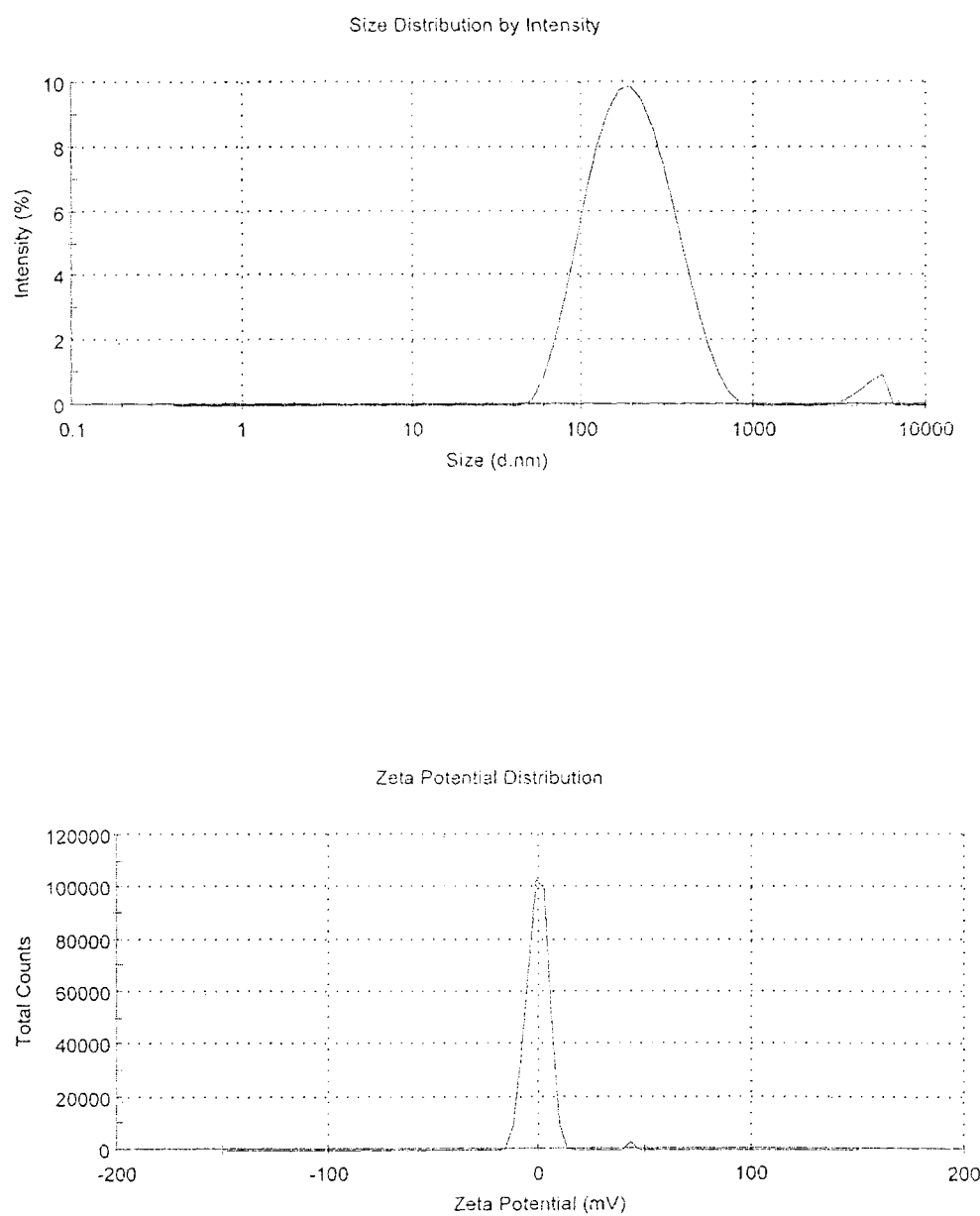
Figure 18C:
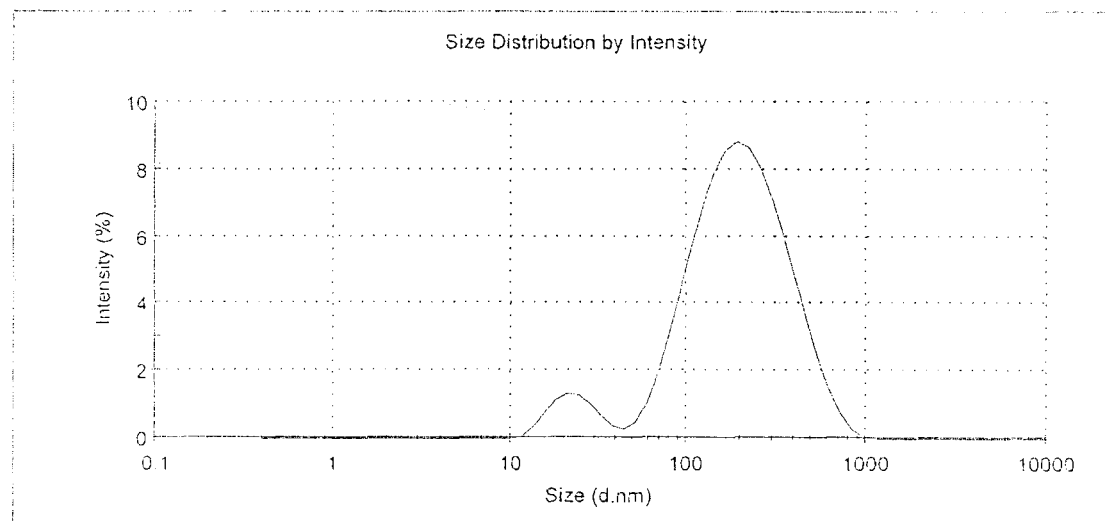
Figure 18C:
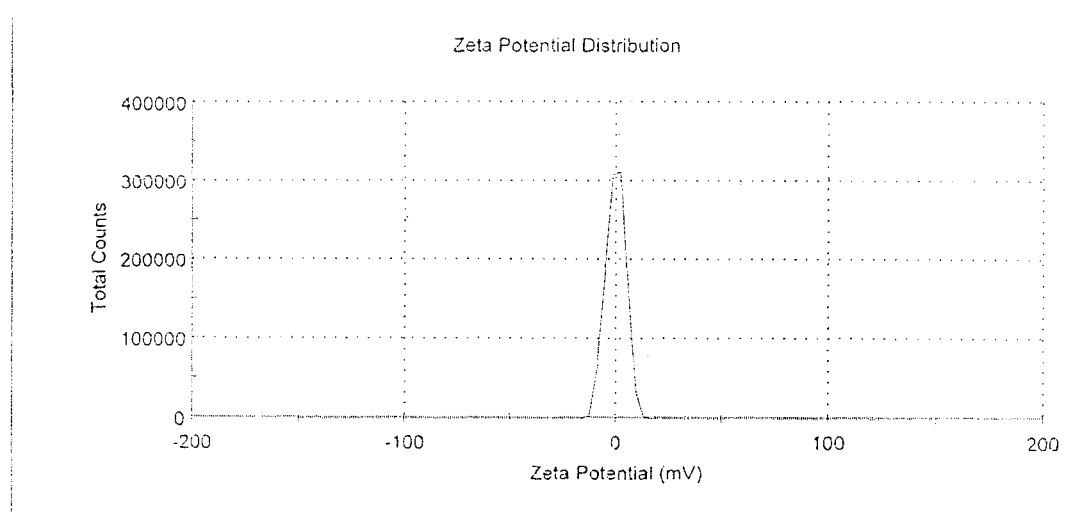
Figure 18D:
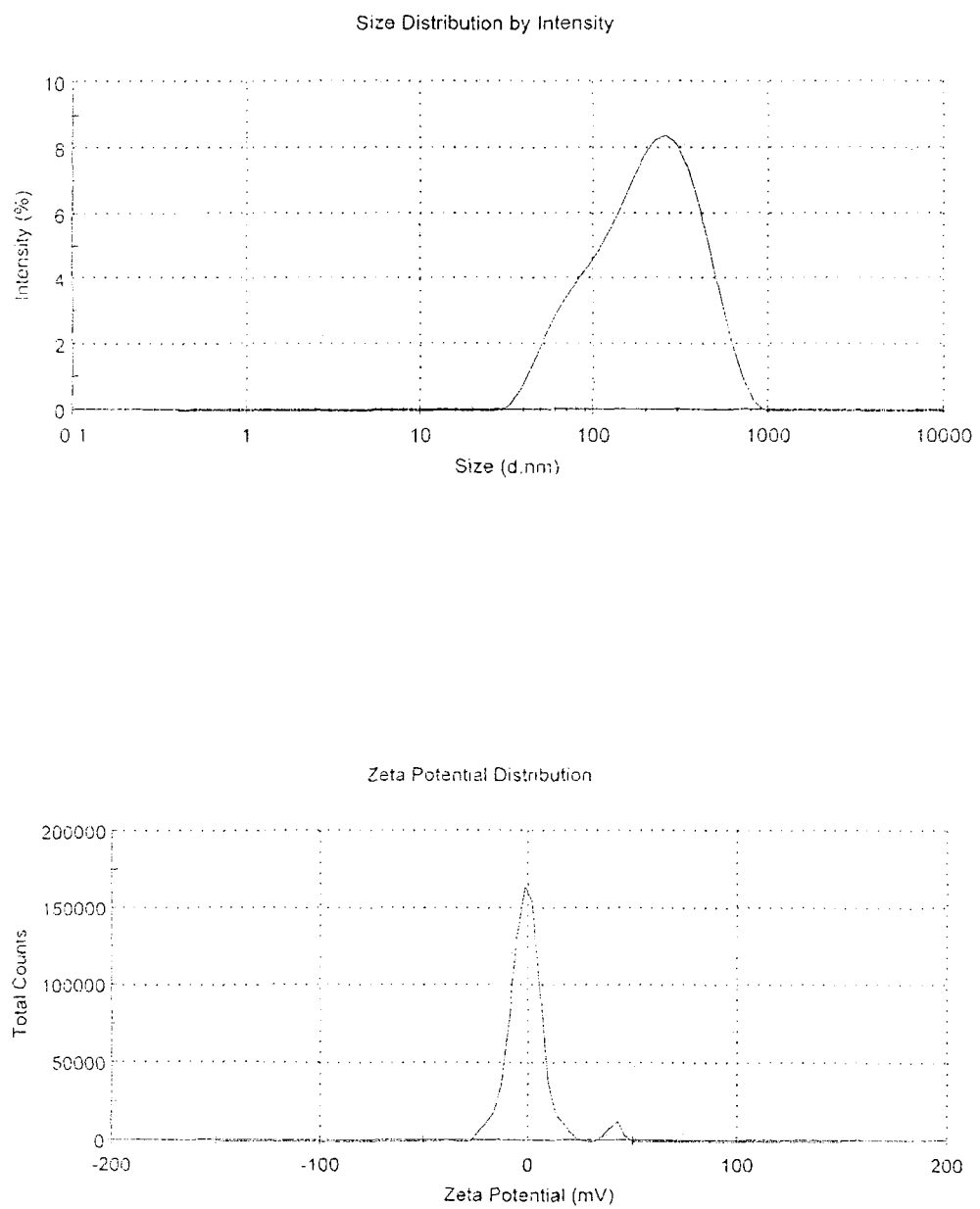

In a further embodiment, FIGS. 1 to 11 for Olanzipine, FIGS. 13 and 14 of Paracetamol, FIGS. 15 & 16 for Resperidone and FIGS. 17 & 18 for ondansetron respectively indicates small and uniform particle size of the emulsion droplets under various conditions such as initial, 2-80 C, 25° C./60% RH, 30° C./65% RH, 30° C./75% RH, 40° C./75% RH respectively.

Determination of Emulsion Stability

In a further embodiment, different test samples of the composition containing olanzapine, Paracetomol, Risperidone, Ondansetron were prepared according to the examples above, and the emulsion was used to determine the stability of the composition and to check any phase separation or turbidity. The compositions were stored and maintained at two different temperatures. The amount of drug degraded and remaining in the compositions were determined by withdrawing samples at regular intervals and analysing for drug content by analytical HPLC methods at 0 day and 30 day time interval. The results are as described in the table below.

Long term (room temperature) −25° C.±2° C./60% RH±5% RH; (Intermediate conditions) 30° C.±2° C./65% RH±5% RH; 30° C.±2° C./75% RH±5% RH; (accelerated conditions) 40° C.±2° C./75% RH±5% RH Long term (refrigerator) −5° C.±3° C.

RH indicates relative humidity

| Table 1 for Olanzipine compositions at 0 day and 30 day time period period | | | | | | | |
|---|---|---|---|---|---|---|---|
| Batch No | Test | Initial (RT) | 2-8° C. | 25° C./ 60% RH | 30° C./ 65% RH | 30° C./ 75% RH | 40° C./ 75% RH |
| Composition 1 | % Assay: | 108.8 | 102.7 | 94.9 | 88.4 | 97.7 | 76.9 |
| | pH: | 7.291 | 7.378 | 7.318 | 7.278 | 7.324 | 7.346 |
| | Particle size (nm) | 66.36 | 82.76 | 83.37 | 92.7 | 75.02 | 81.41 |
| | PDI | 0.408 | 0.286 | 0.289 | 0.285 | 0.313 | 0.29 |
| | Zeta potential (mV): | −0.0793 | −0.152 | 0.0278 | 0.0657 | −0.0999 | 0.00659 |

Table 1 for Olanzipine compositions at 0 day and 30 day time period period

| Batch No | Test | Initial (RT) | 2-8° C. | 25° C./ 60% RH | 30° C./ 65% RH | 30° C./ 75% RH | 40° C./ 75% RH |
|---|---|---|---|---|---|---|---|
| | Viscosity (cP): | 141.5 | 185.6 | 194 | 95.6 | 197.8 | 168.7 |
| Composition 2 | % Assay: | 105.5 | 107.6 | 101.4 | 95.5 | 92.9 | 85.7 |
| | pH: | 7.488 | 7.594 | 7.291 | 7.466 | 7.337 | 7.426 |
| | Particle size (nm) | 64.32 | 64.57 | 82.5 | 80.25 | 68.05 | 49.78 |
| | PDI | 0.372 | 0.28 | 0.284 | 0.438 | 0.294 | 0.224 |
| | Zeta potential (mV): | −0.0981 | −0.301 | −0.0702 | −0.171 | −0.0437 | 0.0591 |
| | Viscosity (cP) | 139.6 | 160.3 | 186.5 | 190.3 | 209 | 191.2 |
| Composition 3 | % Assay: | 107.2 | 103.2 | 100.2 | 98.2 | 99.6 | 84.3 |
| | pH: | 7.48 | 7.457 | 7.452 | 7.406 | 7.484 | 7.432 |
| | Particle size (nm) | 164.4 | 164.6 | 162 | 165.3 | 169.5 | 147.3 |
| | PDI | 0.418 | 0.375 | 0.286 | 0.289 | 0.293 | 0.252 |
| | Zeta potential (mV) | 0.0991 | 0.0743 | −0.0841 | 0.127 | 0.211 | 0.209 |
| | Viscosity (cP): | 128.4 | 147.1 | 110.6 | 129.3 | 106.8 | 65.6 |
| Composition 4 | % Assay: | 106.9 | 108.5 | 94.1 | 95.8 | 86.8 | 77.3 |
| | pH: | 7.324 | 7.525 | 7.411 | 7.304 | 7.36 | 7.481 |
| | Particle size (nm) | 73.55 | 71.1 | 84.47 | 97.15 | 77.79 | 80.43 |
| | PDI | 0.304 | 0.322 | 0.283 | 0.276 | 0.289 | 0.293 |
| | Zeta potential (mV) | −0.4 | 0.175 | 0.0954 | 0.0148 | 0.129 | 0.0134 |
| | Viscosity (cP): | 102.1 | 187.5 | 159.3 | 180 | 172.5 | 150.9 |
| Composition 7 | % Assay: | 104 | 101.5 | 93.1 | 92.9 | 91.8 | 66.6 |
| | pH: | 7.095 | 6.936 | 6.988 | 7.034 | 6.998 | 7.223 |
| | Particle size (nm) | 143.5 | 144.9 | 158.6 | 163.8 | 170.4 | 156.5 |
| | PDI | 0.266 | 0.255 | 0.276 | 0.276 | 0.306 | 0.282 |
| | Zeta potential (mV): | 0.0327 | −0.0155 | 0.0863 | 0.28 | 0.495 | −0.0123 |

Table 2 for Olanzapine compositions at 0 day and 30 day time period

| Batch No | Test | Initial | 2-8° C. | 25° C./ 60% RH | 40° C./ 75% RH |
|---|---|---|---|---|---|
| Composition 8 | % Assay: | 99.92 | 96.43 | 92.6 | 64.59 |
| | pH: | 6.84 | 6.62 | 6.5 | 6.74 |
| | Particle size (nm) | 98.72 | 97.17 | 109.4 | 107.2 |
| | PDI | 0.243 | 0.31 | 0.412 | 0.438 |
| | Zeta potential (mV) | −0.101 | −0.526 | −0.376 | −0.298 |
| | Viscosity (cP) | 62.35 | 79.93 | 75.45 | 70.26 |
| Composition 9 | % Assay: | 100.63 | 97.53 | 92.22 | 64.59 |
| | pH: | 6.94 | 6.6 | 6.55 | 6.74 |
| | Particle size (nm) | 96.11 | 87.26 | 74.91 | 91.65 |
| | PDI | 0.245 | 0.306 | 0.284 | 0.388 |
| | Zeta potential (mV) | −0.00741 | −0.0881 | −0.432 | −0.0307 |
| | Viscosity (cP) | 96.74 | 92.83 | 86.66 | 70.26 |
| Composition 10 | % Assay: | 100.63 | 99.19 | 92.7 | 66.59 |
| | pH: | 7.02 | 6.75 | 6.86 | 7 |
| | Particle size (nm) | 79.6 | 84.8 | 55.79 | 88.8 |
| | PDI | 0.279 | 0.292 | 0.241 | 0.315 |
| | Zeta potential (mV) | 0.161 | 0.00795 | −0.2 | 0.00409 |
| | Viscosity (cP): | 60.5 | 96.56 | 89.84 | 84.54 |
| Composition 11 | % Assay: | 100.23 | 95.21 | 92.36 | 70.09 |
| | pH: | 7.4 | 7.15 | 7.19 | 7.25 |
| | Particle size (nm) | 87.53 | 87.68 | 85.85 | 87.61 |
| | PDI | 0.242 | 0.295 | 0.298 | 0.395 |
| | Zeta potential (mV) | −0.176 | −0.0151 | −0.506 | −0.112 |
| | Viscosity (cP): | 58.51 | 109.9 | 103.5 | 97.6 |
| Composition 12 | % Assay: | 100.85 | 97.87 | 92.52 | 68.88 |
| | pH: | 6.73 | 6.39 | 6.5 | 6.57 |
| | Particle size (nm) | 92.01 | 56.99 | 63.26 | 70.92 |
| | PDI | — | — | — | — |

Table 2 for Olanzapine compositions at 0 day and 30 day time period

| Batch No | Test | Initial | 2-8° C. | 25° C./ 60% RH | 40° C./ 75% RH |
|---|---|---|---|---|---|
| | Zeta potential (mV): | −0.162 | −0.152 | −0.335 | −0.254 |
| | Viscosity (cP): | 94.44 | 70.9 | 66.03 | 64.36 |

Table 3 for Olanzapine compositions at 30 day time period

| Batch No | Test | 2-8° C. | 25° C./ 60% RH | 30° C./ 75% RH | 40° C./ 75% RH |
|---|---|---|---|---|---|
| Composition 5 | % Assay: | 98.1 | 93.6 | 91.7 | 87.5 |
| | Particle size (nm) | — | 98.77 | 87.18 | 84.34 |
| | PDI | — | 0.408 | 0.31 | 0.349 |
| | Zeta potential (mV): | — | −0.198 | 0.24 | 0.0726 |
| Composition 6 | % Assay: | 106 | 96.2 | 96 | 84 |
| | Particle size (nm) | — | 79.66 | 87.65 | 86.37 |
| | PDI | — | 0.418 | 0.311 | 0.351 |
| | Zeta potential (mV): | — | −0.111 | −0.0981 | 0.0412 |

Table 4 for Paracetamol

| Batch No | Test | Initial | 2-8° C. | 25° C./ 60% RH | 40° C./ 75% RH |
|---|---|---|---|---|---|
| Composition 13 | % Assay: | 99.35 | 100.28 | 101.66 | 99.84 |
| | pH: | 6.12 | 6.29 | 6.07 | 6.16 |
| | Particle size (nm) | 121.5 | 135.3 | 146.3 | 136.8 |
| | PDI | 0.252 | 0.431 | 0.407 | 0.287 |
| | Zeta potential (mV): | −0.592 | −0.583 | −0.309 | −0.361 |
| | Viscosity (cP): | 60.81 | 61.57 | 62.65 | 60.45 |
| Composition 14 | % Assay: | 100.64 | 101.05 | 99.1 | 99.91 |
| | pH: | 6.17 | 6.27 | 6.27 | 6.14 |
| | Particle size (nm) | 125.3 | 123.6 | 127.7 | 130.2 |
| | PDI | 0.311 | 0.387 | 0.317 | 0.319 |
| | Zeta potential (mV): | −0.341 | −0.219 | −0.00259 | −0.364 |
| | Viscosity (cP): | 58.97 | 60.65 | 59.86 | 60.27 |

Table 5 for Risperidone emulsions

| Batch No | Test | Initial | 2-8° C. | 25° C./ 60% RH | 40° C./ 75% RH |
|---|---|---|---|---|---|
| Composition 15 | % Assay: | 99.78 | 100.44 | 98.02 | 97.77 |
| | pH: | 6.14 | 5.58 | 5.72 | 5.46 |
| | Particle size (nm) | 117.5 | 161 | 148.3 | 158.3 |
| | PDI | 0.274 | 0.488 | 0.446 | 0.514 |
| | Zeta potential (mV): | −0.588 | 0.0531 | 0.115 | 0.157 |
| | Viscosity (cP): | 56.2 | 67.95 | 65.19 | 65.24 |
| Composition 16 | % Assay: | 99.38 | 99.99 | 98.14 | 97.19 |
| | pH: | 5.66 | 5.98 | 5.87 | 5.78 |
| | Particle size (nm) | 103.5 | 107 | 100.6 | 107.5 |
| | PDI | 0.194 | 0.251 | 0.233 | 0.228 |
| | Zeta potential (mV): | −0.139 | 0.139 | 0.00712 | 0.973 |
| | Viscosity (cP): | 63.57 | 66.57 | 64.71 | 64.21 |

Table 6 for Ondansetron emulsions

| Batch No | Test | Initial | 2-8° C. | 25° C./ 60% RH | 40° C./ 75% RH |
|---|---|---|---|---|---|
| Composition 17 | % Assay: | 101.51 | 100.7 | 100.57 | 100.11 |
| | pH: | 5.86 | 5.4 | 5.78 | 5.35 |
| | Particle size (nm) | 146.6 | 166.7 | 151.5 | 154.3 |
| | PDI | 0.332 | 0.522 | 0.462 | 0.318 |
| | Zeta potential (mV): | −0.254 | −0.175 | −0.233 | −0.0449 |
| | Viscosity (cP): | 66.69 | 70.02 | 67.98 | 69.1 |
| Composition 18 | % Assay: | 100.77 | 98.71 | 98.67 | 100.8 |
| | pH: | 6.08 | 5.9 | 5.9 | 5.85 |
| | Particle size (nm) | 142.5 | 146.7 | 131.4 | 144.9 |
| | PDI | 0.449 | 0.405 | 0.447 | 0.331 |
| | Zeta potential (mV): | −0.248 | −0.389 | −0.361 | −0.229 |
| | Viscosity (cP): | 65.48 | 65.95 | 65.98 | 67.68 |

As can been seen from the results in Table 1 to 4, the emulsions showed high stability, observed during a 1 month stability study. The zeta potential was estimated using Zetasizer instrument from Malvern and the percentage drug content was determined using HPLC.

In a further embodiment, the pH of the emulsions according to the invention is an important determinant of how well they are tolerated or favourable when administered into the nasal cavity, ophthalmic or any other preferred route. The emulsion may cause irritation and stinging if the pH is too high or low. Therefore, the pH of the aqueous phase of an emulsion according to the invention is preferably in the range pH 4.5 to 8.0, more preferably 5 to 7.5. The pH of the aqueous phase of the emulsions according to the invention may be adjusted and controlled by means well known to those skilled in the art, such as buffer salts, acids and bases selected from various organic acids or/and alkali metal salts thereof.

Thermodynamic Stability and Phase Separation Tests

In a further embodiment, temperature cycling, centrifugation and freeze-thaw cycle stress tests were performed to evaluate the thermodynamic stability of all the drug loaded compositions. Heating-cooling cycle of three cycles between refrigerator temperature 5° C. and 40° C. with storage at each temperature of not less than 48 h was studied. The values of the particle size, zeta potential and the pH did not vary significantly after the end of the heating-cooling cycle from the initial as per the results in table 8 below, which showed the stability of the compositions. Furthermore, since all the compositions were stable at these temperatures, they were further subjected to centrifugation test to check for any phase separation or turbidity.

In a further embodiment, the compositions were centrifuged at 5000 rpm for 30 min. After centrifugation, no phase separation or precipitation of the drug was observed which further confirmed the stability of the emulsion. Subsequently, the compositions were further subjected to freeze thaw stress test. Three freeze thaw cycles between □20° C. and −15° C. with storage at each temperature between 24 h and 48 h was conducted for the compositions. The values of the particle size, zeta potential and the pH did not vary significantly after the end of the freeze thaw cycle from the initial as per the results in table 7 below, which shows the stability of the composition. Further, the positive results indicated that all the compositions are thermodynamically stable systems and are formed at a particular concentration of oil, surfactant and cosurfactant, with no phase separation, creaming or cracking.

TABLE 7

Freeze-Thaw Study Results

| Batch No | Particle Size (d · nm) | Polydispersity Index (PdI) | Zeta Potential (mV) | Viscosity (cps at 200 rpm) | pH |
|---|---|---|---|---|---|
| Composition 1 | 70.69 | 0.306 | −0.234 | 213.7 | 7.518 |
| Composition 2 | 94.31 | 0.280 | −0.535 | 205.3 | 7.450 |
| Composition 3 | 239.2 | 0.485 | −0.107 | 138.7 | 7.167 |
| Composition 4 | 91.33 | 0.307 | −0.186 | 143.4 | 7.388 |
| Composition 5 | 77.47 | 0.291 | 0.006 | 180.0 | 7.365 |
| Composition 6 | 90.76 | 0.290 | −0.358 | 190.3 | 7.318 |

| Batch No | Particle Size (d · nm) | Polydispersity Index (PdI) | Zeta Potential (mV) | pH |
|---|---|---|---|---|
| Composition 8 | 92.71 | 0.390 | −0.0462 | 6.75 |
| Composition 9 | 82.68 | 0.239 | −0.0868 | 6.72 |
| Composition 10 | 74.27 | 0.363 | −0.106 | 7.02 |
| Composition 11 | 77.41 | 0.281 | −0.0777 | 6.98 |

TABLE 8

Heat Cool Cycle Study Results

| Batch No | Particle Size (d · nm) | Polydispersity Index (PdI) | Zeta Potential (mV) | Viscosity (cps at 200 rpm) | pH |
|---|---|---|---|---|---|
| Composition 1 | 59.78 | 0.415 | −0.180 | 196.8 | 7.468 |
| Composition 2 | 75.25 | 0.367 | −0.286 | 212.8 | 7.401 |
| Composition 3 | 215.4 | 0.474 | +0.141 | 142.5 | 7.103 |
| Composition 4 | 77.02 | 0.410 | −0.184 | 182.8 | 7.476 |
| Composition 5 | 61.73 | 0.410 | −0.169 | 209 | 7.200 |
| Composition 6 | 78.76 | 0.461 | −0.158 | 216.5 | 7.223 |

TABLE 8

Heat Cool Cycle Study Results

| Batch No | Particle Size (d · nm) | Polydispersity Index (PdI) | Zeta Potential (mV) | pH |
|---|---|---|---|---|
| Composition 8 | 86.24 | 0.400 | −0.136 | 6.79 |
| Composition 9 | 93.43 | 0.368 | −0.175 | 6.87 |

TABLE 8-continued

Heat Cool Cycle Study Results

| Batch No | Particle Size (d · nm) | Polydispersity Index (PdI) | Zeta Potential (mV) | pH |
|---|---|---|---|---|
| Composition 10 | 70.13 | 0.298 | 0.0311 | 6.98 |
| Composition 11 | 78.52 | 0.268 | 0.0101 | 6.92 |

Determination of Solubility of Olanzipine

In yet another embodiment, the components used in the delivery system should have high solubilisation capacity for the drug in order to ensure its solubilisation in the resultant dispersion. As an example, the solubility of the drug olanzapine was studied using different unsaturated fatty acids. The results of the solubility studies have been provided below.

It is also observed that the solubility of olanzapine in other unsaturated fatty acids was also studied. An accurately weighed quantity of olanzapine (40 mg) was added in 1 mL of oil and vortex mixed for 2 hrs. at 37° C. and observed visually for solubilisation. In case solubilisation was observed with the 40 mg of olanzapine in that particular oil, then subsequently 10 mg quantities of olanzapine were added to determine the exact solubility of the drug in that oil until the drug remained in its insolubilized form. Olanzapine has its maximum solubility in oleic acid. Olanzapine has solubility of less than 40 mg/mL in Labrafil(tradename), Capryol 90(tradename), Acconon CC6(tradename) and Kolliphor HS(tradename). Acconon CC6 and Kolliphor HS are miscible with water and hence were not used as oil in the development of the micro-emulsions. Olanzapine has a solubility of 60 mg/ml in Capryol 90 but it is lower than oleic acid. The solubility of olanzapine in oleic acid is ≈200 mg/ml.

As seen from the above results, oleic acid showed highest solubilisation capacity as compared to other unsaturated fatty acids.

Pharmacokinetics of Microemulsions

Animal Studies: Olanzapine

Experiments were performed on male Sprague-Dawley (S.D.) rats weighing 270-330 g, which fasted overnight before dosing. The emulsions were administered intra-nasally and intramuscularly at dose of 2.0 and 6.0 mg/kg olanzapine, respectively. Blood and brain samples were collected for analysis. The following pharmacokinetic parameters were evaluated and the results were captured.

Micro-emulsions were formulated and their in vivo pharmacokinetic performance was evaluated upon intranasal delivery in comparison to oral delivery. Further, the micro-emulsions were explored for relative bioavailability compared with intramuscular administration. Higher drug concentrations were observed in the target organ which is the brain. Direct nose to brain transport indicated more effective and best brain targeting of the micro-emulsions (Drug delivery system). The percentage of relative bioavailability indicated the amount of drug available in the systemic circulation for re-uptake by the brain for prolonged effect. Pharmacokinetic studies conclusively demonstrated rapid brain uptake of drug when compared with intramuscular and oral solutions. The results indicated that, the developed micro-emulsion compositions were effective for target organ delivery.

Derived pharmacokinetic parameters of olanzapine micro-emulsions following intranasal administration were compared with oral and intramuscular administration. The results are tabulated and provided in the following Table 9

The relative bioavailability of IN G7 olanzapine composition in plasma was found to be 57%.

TABLE 9

Comparison of pharmacokinetic parameters of olanzapine following intranasal administration of olanzapine micro-emulsions with control group of oral and intramuscular administration in male Sprague Dawley rats.

| Route/Composition (Dose) | Matrix | Tmax (h) | Cmax (ng/ml) | AUClast (ng · h/ml) | AUCinf (ng · h/ml) | T½ (h) | T/P ratio | % Relative bioavailability in relation to IM | AUC tissues ratio in relation to IM |
|---|---|---|---|---|---|---|---|---|---|
| IN/Composition 8 (2 mg/kg) | Plasma | 0.08 | 780.00 | 866.00 | 867.00 | 3.03 | 5.00 | 71.00 | NA |
| | Brain | 0.50 | 2024.00 | 4217.00 | 4336.00 | 1.57 | | NA | 0.61 |
| IN/Composition 9 (2 mg/kg) | Plasma | 0.16 | 678.00 | 691.00 | 745.00 | 2.67 | 5.59 | 57.00 | NA |
| | Brain | 0.25 | 1926.00 | 3863.00 | 4193.00 | 2.60 | | NA | 0.55 |
| IN/Composition 10 (2 mg/kg) | Plasma | 0.08 | 566.00 | 573.00 | 597.00 | 1.88 | 5.43 | 47.00 | NA |
| | Brain | 0.16 | 2495.00 | 3113.00 | 3252.00 | 1.98 | | NA | 0.44 |
| IN/Composition 11 (2 mg/kg) | Plasma | 0.08 | 596.00 | 637.00 | 649.00 | 1.30 | 5.05 | 52.00 | NA |
| | Brain | 0.25 | 1785.00 | 3217.00 | 3283.00 | 1.47 | | NA | 0.46 |
| IM Composition (6 mg/kg) | Plasma | 0.50 | 1319.00 | 3645.00 | 3650.00 | 2.78 | 5.81 | NA | NA |
| | Brain | 1.00 | 5615.00 | 21172.00 | 21236.00 | 3.19 | | NA | NA |
| PO Composition (6 mg/kg) | Plasma | 1.00 | 218.91 | 1177.88 | 1178.57 | 2.12 | 5.93 | 32.00 | NA |
| | Brain | 1.00 | 1408.36 | 6983.72 | 6988.47 | 2.19 | | NA | 0.33 |

IN—intranasal;
IM—intramuscular;
PO—per-oral,
NA—not applicable.
IM & Oral compositions are control group taken for comparison of pK parameters.

Results:
Intranasal Administration (2 mg/kg) Composition 1

Following the intranasal administration of olanzapine emulsion to rats at 2 mg/kg, mean time to reach peak plasma concentration ($T_{max}$) for olanzapine was found to be 0.08 h. The mean exposure ($C_{max}$ and $AUC_{last}$) of olanzapine was found to be 780 ng/ml and 866 ng·h/ml, respectively. Olanzapine was eliminated with mean elimination half-life of 3.03 h.
Brain (Including Olfactory Tubercle):

Following intranasal administration of olanzapine emulsion to rats at 2 mg/kg, the mean exposure $C_{max}$ and $AUC_{last}$ of olanzapine was found to be 2024 ng/ml and 4217 ng·h/ml for brain tissue. Olanzapine was eliminated with mean brain elimination half-life of 1.57 h for brain tissue.

The relative bioavailability of intra nasal olanzapine composition in plasma was found to be 71%.

AUC is the area under the plasma concentration versus time curve from time 0 to time x after nasal route. The relative bioavailability was determined by comparing the AUC of nasal administration and oral and intramuscular administration.
Intranasal Administration (2 mg/kg) Composition 2
Plasma:

Following intranasal administration of olanzapine emulsion to rats at 2 mg/kg, mean time to reach peak plasma concentration ($T_{max}$) for olanzapine was found to be 0.16 h. The mean exposure $C_{max}$ and $AUC_{last}$ of olanzapine was found to be 678 ng/ml and 691 ng·h/ml, respectively. Olanzapine was eliminated with mean elimination half-life of 2.67 h.
Brain (Including Olfactory Tubercle):

Following intranasal administration of olanzapine emulsion to rats at 2 mg/kg, the mean exposure $C_{max}$ and $AUC_{last}$ of olanzapine was found to be 1926 ng/ml and 3863 ng·h/ml for brain tissue. Olanzapine was eliminated with mean elimination half-life of 2.60 h for brain tissue.

Intranasal Administration (2 mg/kg) Composition 3
Plasma:

Following intranasal administration of olanzapine emulsion to rats at 2 mg/kg, mean time to reach peak plasma concentration ($T_{max}$) for olanzapine was found to be 0.08 h. The mean exposure ($C_{max}$ and $AUC_{last}$) of olanzapine was found to be 566 ng/ml and 573 ng·h/ml, respectively. Olanzapine was eliminated with mean elimination half-life of 1.88 h.
Brain (Including Olfactory Tubercle):

Following intranasal administration of olanzapine emulsion to rats at 2 mg/kg, the mean exposure $C_{max}$ and $AUC_{last}$ of olanzapine was found to be 2495 ng/ml and 3113 ng·h/ml for brain tissue. Olanzapine was eliminated with mean elimination half-life of 1.98 h for brain tissue.

The relative bioavailability of olanzapine composition in plasma was found to be 47%.
Intranasal Administration (2 mg/kg) Composition 4
Plasma:

Following intranasal administration of olanzapine emulsion to rats at 2 mg/kg, mean time to reach peak plasma concentration ($T_{max}$) for olanzapine was found to be 0.08 h. The mean exposure ($C_{max}$ and $AUC_{last}$) of olanzapine was found to be 596 ng/ml and 637 ng·h/mL, respectively. Olanzapine was eliminated with mean elimination half-life of 1.30 h.
Brain (Including Olfactory Tubercle):

Following intranasal administration of olanzapine emulsion to rats at 2 mg/kg, the mean exposure ($C_{max}$ and $AUC_{last}$) of olanzapine was found to be 1785 ng/ml and 3217 ng·h/ml for brain tissue. Olanzapine was eliminated with mean elimination half-life of 1.47 h for brain tissue.

The relative bioavailability of Olanzapine composition in plasma was found to be 52%.

Additionally, from the table above it can be observed that the Cmax in the brain when given through the IN route was 2495 ng/g with a dose administration of 2 mg/kg, but with respect to IM and oral administered dose of 6 mg/kg, it was 5615 ng/g and 1408.36 ng/g respectively. Therefore, in order to achieve the same concentrations reaching the brain one can reduce the dose of administration through the nasal route by 25% vis a vis IM and 80% vis a vis oral. Furthermore, the Tmax i.e., the time taken to reach the maximum concentration in brain by the nasal composition was attained within 10 mins when compared to 60 mins through the conventional routes of administration. Similarly, the time taken to reach the maximum concentration in plasma, via the nasal composition was 5 mins when compared to 30 mins and 60 mins through the intra muscular and oral routes of administration respectively.

Ondansetron

Comparative pharmacokinetics evaluation of three different compositions of ondansetron following intranasal, intramuscular and oral administration in sprague dawley rats. The objective of this study was to to evaluate and compare the plasma pharmacokinetic profile of Ondansetron Composition with marketed standards in Sprague Dawley rats following single Intranasal and per oral administration.

Sprague Dawley rat were randomly allotted to different groups. The Ondansetron Composition with marketed standards was administered. Approximately 0.5 mL of blood was collected from the retroorbital plexus of each rat into pre-labeled tubes containing $K_2EDTA$ at 0, 10 mins, 20 mins, 0.5, 1, 2 and 4 hr post dosing. Blood samples was centrifuged at approximately 5000 rpm for 10 min in refrigerated centrifuge at 4° C. and plasma samples was harvested and stored in deep freezer (−80° C.) until the analysis. At the end of experimental sample collection, plasma samples were transferred in to analytical department for analysis.

The results are provided in table 10 below.

Comparison of pharmacokinetic parameters of olanzapine following intranasal administration of Ondansetron micro-emulsions with control group of oral and intramuscular administration in male Sprague Dawley rats.

TABLE 10

| Route/ Composition (Dose) | Matrix | Tmax (h) | Cmax (ng/ml) | AUCinf (ng · h/ml) | T½ (h) | T/P ratio |
|---|---|---|---|---|---|---|
| IN/Composition (0.82 mg/kg) | Plasma | 0.50 | 15.59 | 20.63 | 2.22 | 0.90 |
|  | Brain | 0.17 | 19.63 | 18.61 | 0.43 |  |
| PO Composition (0.82 mg/kg) | Plasma | 1.00 | 1.88 | 6.97 | 2.30 | 0.00 |
|  | Brain | 0.00 | 0.00 | 0.00 | 0.00 |  |

IN—intranasal;
IM—intramuscular;
PO—per-oral,
NA—not applicable.
IM & Oral compositions are control group taken for comparison of pK parameters.

Results:

Intranasal Administration (0.82 mg/kg) Composition Developed

Plasma:

Following the intranasal administration of Ondansetron emulsion to rats at 0.82 mg/kg, mean time to reach peak plasma concentration ($T_{max}$) for Ondansetron was found to be 0.50 h. The mean exposure ($C_{max}$ and $AUC_{last}$) of Ondansetron was found to be 15.59 ng/ml and 20.63 ng·h/ml, respectively. Ondansetron was eliminated with mean elimination half-life of 2.22 h.

Brain:

Following intranasal administration of Ondansetron emulsion to rats at 0.82 mg/kg, the mean exposure $C_{max}$ and $AUC_{last}$ of Ondansetron was found to be 19.63 ng/ml and 18.61 ng·h/ml for brain tissue. Ondansetron was eliminated with mean brain elimination half-life of 0.43 h for brain tissue.

The results in the table above shows that with the intra nasal route of administration of the sample composition there is a marked decrease in the Tmax and a prolongation in half-life when compared with other conventional routes using the marketed salt form of the drug. i.e. for the intra nasal the maximum concentration in plasma was observed within 30 mins when compared with the oral route which took 60 mins for the same. No significant brain concentration was detected in case of oral route of administration whereas for the intra nasal route a concentration of 19.63 ng/ml was observed. With respect to the plasma concentrations achieved, the intranasal administration is comparable with that of the intra muscular route of administration.

Paracetamol

Intraocular pressure lowering activity of paracetamol composition 2% and paracetamol solution 2% with pilocar 2% in New Zealand white rabbits was performed.

Healthy male New Zealand White Rabbits were randomly allotted in to four groups after intraocular pressure (TOP) measurement in both the eyes. On experimental day, before and after treatment basal intraocular pressure was measured using a Tonometer (Make: HS Climent Clarke International, Model: MK2) and recorded for all the animals of the 4 groups.

Ophthalmological examination by indirect method was performed once during the acclimatization period and 24 hr post instillation of test item. All animals were observed once daily for clinical signs of toxicity and twice daily for mortality and morbidity during experimental period.

Based on the results obtained from the experiment, there were no significant treatment related changes in intraocular pressure up to 24 hrs on single dose administration with Paracetamol solution 2%, Paracetamol composition 2% and Pilocarpine 2% in New Zealand White Rabbits. However, a statistical significant (ie 0.05 level) decrease in intraocular pressure from 12.0 to 9.3 mm Hg was observed for the Paracetamol composition 2% treated group at 2 hr time point. However, the same was not observed with Pilocarpine 2% or the Paracetamol solution treated groups.

Ex Vivo Corneal Permeation of Paracetamol Solution 2% on Bovine Corneas Using the Franz Diffusion Instrument The bovine corneas, free of defects were used for the conduct of ex-vivo corneal permeation study. Permeation studies of Paracetamol composition 2% and Paracetamol solution 2% on bovine corneas was done by using the Franz diffusion instrument. 1 mL of each test item composition was added to the separate donor chamber in which the corneas are mounted. 1 mL of placebo was added to one donor chamber in which the cornea was mounted and was served as control. After the start of treatment of each test item and control, 500 μL of receptor fluid was collected at 0, 0.25, 0.5, 1, 2 and 4 hours (±5 minutes) and the same amount of receptor fluid was replaced at each time point. The collected samples were analyzed immediately for the content of Paracetamol by the HPLC method., the results are provided in table 11 below The analysis of Paracetamol composition 2% and Paracetamol solution 2% was calculated at the $4^{th}$ hour sample collection for the calculation of permeated amount (mg) and % permeation of Paracetamol content. At the end of the experiment each cornea (freed from adhering sclera) washed with receptor fluid and homogenized with 5 mL of receptor fluid and the contents were analyzed by the analytical method.

TABLE 11

| Treatment | | | Basal IOP | | 0.5 h | | 1 h | | 2 h | | 4 h | | 8 h | | 12 h | | 24 h | |
|---|---|---|---|---|---|---|---|---|---|---|---|---|---|---|---|---|---|---|
| Left Eye | Right Eye | | Left Eye | Right Eye | Left Eye | Right Eye | Left Eye | Right Eye | Left Eye | Right Eye | Left Eye | Right Eye | Left Eye | Right Eye | Left Eye | Right Eye | Left Eye | Right Eye |
| 50 µL of Placebo | 50 µL of Paracetamol solution 2% | Mean ±SD | 12.2 2 | 12.4 2.7 | 11.3 1.8 | 10.9 2.1 | 11.2 2.7 | 10.9 2.1 | 12.4 1.5 | 11.3 2.4 | 12.2 0.8 | 11.8 0.8 | 12.7 0.7 | 2.2 1.4 | 11.1 1 | 11.1 1 | 11.1 1 | 11.1 1 |
| 50 µL of Placebo | 50 µl of Paracetamol formulation 2% | Mean ±SD | 11.8 1.5 | 12 1.8 | 10.4 1.9 | 10.4 0.8 | 10.4 1.9 | 10.4 0.8 | 9.8 1.4 | 9.3* 1.8 | 10 1.2 | 10 1.2 | 9.8 0.8 | 9.8 0.4 | 10.9 0.4 | 10.4 0.4 | 10.9 0.4 | 10.4 0.4 |
| 50 µL of sterile water | 50 µL of Pilocar 2% | Mean ±SD | 11.1 1 | 10.9 1 | 11.1 1 | 9.8 1.7 | 11.3 1.2 | 9.8 1.7 | 11.6 1.4 | 10.7 1.2 | 10.7 1.2 | 10.4 1.4 | 11.6 1 | 10.9 1.5 | 11.8 1.5 | 11.8 1.5 | 11.8 1.5 | 11.8 1.5 |
| 50 µL of sterile water | 50 µL of Paracetamol formulation 2% | Mean ±SD | 11.8 1.7 | 11.8 1.5 | 12 2 | 11.1 0.4 | 11.6 1 | 11.1 0.4 | 11.8 1.7 | 10.7 2 | 12.4 0.4 | 12 1.8 | 12 0.7 | 11.8 1 | 12.7 0.7 | 11.8 0.8 | 12.7 0.7 | 11.8 0.8 |

*The mean difference is significant at the 0.05 level.

Note:
The statistical analysis was performed Basal IOP vs 0.5 hr, 1 hr, 2 hr, 4 hr, 8 hr, 12 hr and 24 hr IOP of each eye of each group

TABLE 12

Corneal penetration studies

| Time (h) | Amount Permeated (mg) for Composition 2% | Amount Permeated (mg) for Simple solution 2% |
|---|---|---|
| 0 | 0 | 0 |
| 0.25 | 0 | 0 |
| 0.5 | 0.006 | 0.006 |
| 1 | 0.060 | 0.083 |
| 2 | 0.409 | 0.455 |
| 4 | 1.164 | 2.134 |

TABLE 13

Corneal membrane homogenization

| Composition | Average in mg |
|---|---|
| Composition 2% | 0.621 |
| Simple solution 2% | 1.318 |

CONCLUSION

From the sample analysis it is observed that the permeation observed in Paracetamol composition 2% was 1.164 mg and Paracetamol solution 2% was 2.134 mg at 4 hour as per the results in table 12 above The results obtained from the corneal homogenized sample for Paracetamol composition 2% was found to be 0.621 mg and Paracetamol solution 2% was 1.318 mg as per the results in table 13 above.

The permeation study shows that the simple solution is able to permeate the drug much more than composition but fails in lowering the IOP significantly. This might be because of the synergistic effect of the composition of the composition that makes the effect.

ADVANTAGES OF THE INVENTION

The competitive advantage of the invention described lies in its enhanced drug delivery mechanism, ease of use, enhanced access, reduced dosage of administration leading to reduced side effects and high drug loading, which leads to better patient acceptance and compliance and increased bioavailability.

In particular, the composition of this invention helps in solubilizing higher amounts of drug. This invention also provides increased absorption of pharmaceutical agents through endothelial or epithelial membranes. Furthermore, the invention with nano-sized oil droplets and the drug dissolved in it, surrounded by surfactant layer aids the lipophilic compounds to be stable in aqueous environment. The invention presents a stable composition by preventing oxidation and hydrolysis. This invention also improves the mucous absorption and bioavailability.

This invention offers clinical advantages over competitor products in a large market of considerable unmet need. The drug delivery system is able to enhance the rapid onset of action for lipophilic drugs than the conventional or existing delivery systems. Furthermore, the nasal route not only improves the bioavailability by preventing extensive first-pass metabolism but also targets the receptor site and passes through the blood-brain barrier (BBB). Direct transport of drugs to the brain circumventing the brain barriers following intranasal administration provides a unique feature and better option to target the site of action and to reduce the side effects.

This invention also offers the advantages of the drug being administered simply, non-invasively, cost-effectively, and conveniently. One such example showing the ease of treatment is demonstrated by easy sprayability and ease of self-administration with reduced side effects. The composition demonstrates improved bioavailability, rapid drug absorption via highly vascularized mucosa, thus demonstrating a superior mode of delivery to the existing treatment options.

This invention is superior in at least one of the criteria from the similar compositions described in the literature i.e., higher drug loading, better in vivo performance, rapid onset of action etc. Even at this higher drug content, the developed systems show suitable physicochemical characteristics. A benefit of the invention is to prepare a composition of higher drug concentration for lipophilic and moderately lipophilic compounds, at concentrations of around 10-80 mg/ml.

We claim:

1. A pharmaceutical oil-in-water nano-emulsion composition, comprising:
   a pharmaceutically active substance, encased in monounsaturated fatty acid droplets, wherein said monounsaturated fatty acid is present in an amount of about 5-25% w/w based on the weight of the total composition
   said droplets having an average particle size in the range of 60 to 200 nm;
   a non-ionic surfactant system comprising a mixture of polyethers, macrogolglycerides and polysaccharides
   wherein the polyethers are present in an amount ranging from about 2-25% w/w based on the total weight of the composition,
   wherein the macrogolglycerides are present in an amount ranging from 10-30% w/w based on the total weight of the composition,
   wherein the polysaccharides are present in an amount ranging from 2-30% w/w based on the total weight of the composition;
   water present in an amount of between 15 and 50% w/w; and
   pharmaceutically acceptable adjuvants,
   wherein the composition is highly stable having a drug loading capacity of the pharmaceutically active substance of up to 100 mg/mL.

2. The composition as claimed in claim 1, wherein said pharmaceutically active substance is lipophilic or partially lipophilic and is selected from a group consisting of antipsychotics, antiemetics, analgesics, antipyretics, anti-inflammatory agents or any lipophilic-based drugs.

3. The composition as claimed in claim 2, wherein said antipsychotics are selected from the group consisting of ziprasidone, fluphenazine, haloperidol, olanzapine, chlorpromazine, risperidone, aripiprazole, molindone, loxapine, and sulpiride and pharmaceutically acceptable salts thereof.

4. The composition as claimed in claim 2, wherein said antiemetics are diphenhydrinate, diphenhydramine, doxylamine, meclizine, ondansetron, promethazine, prochlorperazine, or pharmaceutically acceptable salts thereof.

5. The composition as claimed in claim 2, wherein said analgesics, antipyretics, and anti-inflammatory agents are selected from the group consisting of paracetamol, methadone, diamorphine, fentanyl, buprenorphine, temazepam, piracetam, sufentanil, mefenamic acid, naproxen, piroxicam, indomethacin, valdecoxib, celecoxib, probenecid, nabumetone, ibuprofen, flurbiprofen, isoxicam, meclofenamic acid, fenclozic acid, and phenyl butazone.

6. The composition as claimed in claim 1, wherein said monounsaturated fatty acid is an oleic acid.

7. The composition as claimed in claim 1, wherein said polyether surfactant is a combination of polyethylene glycol and diethylene glycol monoethyl ether.

8. The composition as claimed in claim 1, wherein said polyether surfactant is polyethylene glycol and is present in an amount ranging from about 2.5% to 20% w/w based on the total weight of the composition.

9. The composition as claimed in claim 1, wherein said macrogolglyceride surfactant is caprylocaproyl macrogol-8 glyceride, acconon CC 6, or a combination thereof.

10. The composition as claimed in claim 1, wherein said polysaccharide surfactant is polyoxyethylene sorbitan fatty acid esters.

11. The composition as claimed in claim 1, further comprising a solvent selected from the group consisting of benzyl alcohol, phenyl ethyl alcohol, and chloro butanol.

12. The composition as claimed in claim 1, wherein said adjuvants are selected from the group consisting of stabilizers, antioxidants, preservatives, mucoadhesive agents, buffering agents, absorption enhancers, and pH adjusting agents.

13. The composition according to claim 12, wherein said antioxidant is selected from butylated hydroxytoluene, butylated hydroxyanisole, ascorbic acid and tocopherol, or a combination thereof in the range of 0.01% to 0.2% w/w of the total composition.

14. The composition according to claim 12, wherein said absorption enhancers are selected from macrogol-15-hydroxystearate, sodium glycocholate, sodium caprylate, and a combination thereof.

15. The composition as claimed in claim 1, wherein
   the pharmaceutically active substance is selected from the group consisting of olanzapine, ondansetron, risperidone and pharmaceutically acceptable salts thereof;
   the mononunsaturated fatty acid is oleic acid; and
   the non-ionic surfactant system comprises a mixture of polyethylene glycol, caprylocaproyl macrogol-8 glyceride, and polyoxyethylene (20) sorbitan monolaurate.

16. A method for the treatment of migraine, nausea, cluster headache, schizophrenia, bipolar disorder, vomiting, psychosis, or sleep disorders, said method comprising nasal administration of the composition of claim 15.

17. A process for the preparation of an oil-in-water emulsion composition as claimed in claim 1, comprising the steps of
   i) forming an oil phase in the presence of a monounsaturated fatty acid, a polyether surfactant, a macrogolglyceride surfactant, and a polysaccharide surfactant, under stirring at an ambient temperature; and
   ii) adding a therapeutic amount of pharmaceutically active substance to said oil phase, under constant stirring and at an ambient temperature, to encase said active substance, in said monounsaturated fatty acid droplets, said droplets with particle size in the range of 60 to 200 nm, to obtain a homogenous oil phase; and
   iii) adding an aqueous medium to said homogenous oil phase, under stirring to obtain the oil-in-water emulsion.

18. The composition of claim 3, wherein said antipsychotics are olanzapine or risperidone, or pharmaceutically acceptable salts thereof.

19. The composition of claim 10, wherein said polyoxyethylene sorbitan fatty acid ester is selected from the group consisting of polyoxyethylene (20) sorbitan monolaurate, polyoxyethylene (80) sorbitan monooleate, sorbitan monooleate, and a combination thereof.

* * * * *